US008198081B2

(12) United States Patent
Ono et al.

(10) Patent No.: US 8,198,081 B2
(45) Date of Patent: Jun. 12, 2012

(54) DOPAMINERGIC NEURON PROGENITOR CELL MARKER 187A5

(75) Inventors: Yuichi Ono, Kobe (JP); Yoshimasa Sakamoto, Kobe (JP)

(73) Assignee: Eisai R&D Management Co., Ltd., Tokyo (JP)

(*) Notice: Subject to any disclaimer, the term of this patent is extended or adjusted under 35 U.S.C. 154(b) by 623 days.

(21) Appl. No.: 12/296,915

(22) PCT Filed: Apr. 11, 2007

(86) PCT No.: PCT/JP2007/058009

§ 371 (c)(1), (2), (4) Date: Oct. 10, 2008

(87) PCT Pub. No.: WO2007/119759

PCT Pub. Date: Oct. 25, 2007

(65) Prior Publication Data

US 2011/0008769 A1 Jan. 13, 2011

(30) Foreign Application Priority Data

Apr. 11, 2006 (JP) ................................ 2006-108786

(51) Int. Cl.
*C07K 16/28* (2006.01)
*C12N 5/079* (2010.01)

(52) U.S. Cl. ...................... 435/325; 530/387.9; 530/810

(58) Field of Classification Search ........................ None
See application file for complete search history.

(56) References Cited

U.S. PATENT DOCUMENTS

2001/0053519 A1* 12/2001 Fodor et al. ....................... 435/6

FOREIGN PATENT DOCUMENTS

| | | | |
|---|---|---|---|
| EP | 1447413 | A2 | 8/2004 |
| WO | WO 2004/005458 | A2 | 1/2004 |
| WO | WO 2004/038018 | A1 | 5/2004 |
| WO | WO 2004/048511 | A2 | 6/2004 |
| WO | WO 2004/048938 | A2 | 6/2004 |
| WO | WO 2004/065599 | A1 | 8/2004 |
| WO | WO 2004/094598 | A2 | 11/2004 |
| WO | WO 2004/094651 | A2 | 11/2004 |
| WO | WO 2005/052190 | A1 | 6/2005 |
| WO | WO 2006/009241 | A1 | 1/2006 |
| WO | WO 2007/021003 | A1 | 2/2007 |
| WO | WO 2007/021004 | A1 | 2/2007 |

OTHER PUBLICATIONS

"Affymetrix GeneChip Human Genome U95 Version [1 or 2] Set HG-U95A," GEO Expression, 2 pgs. (Mar. 11, 2002).
"Affymetrix GeneChip Human Genome U133 Array Set HG-U133A," GEO Expression, 2 pgs. (Mar. 11, 2002).
Stamatoyannopoulos, JA, et al., DATABASE Geneseq [Online], "Diagnosis and therapy associated functional site SEQ ID 11873,", Database Accession No. AGH79117, 1 pg. (Oct. 18, 2007).
Bentwich, I., DATABASE Geneseq [Online] "Viral regulatory mlRNA SEQ ID No. 116234," Database Accession No. AJI63913, 1 pg. (Dec. 28, 2007).
English Translation of International Preliminary Report on Patentability from PCT/JP2007/058009 (9 pages).
Office Action issued Jan. 10, 2012, for Japanese Application No. 2008-510971, 12 pgs.
Office Action issued Apr. 3, 2012, for Japanese Application No. 2008-510971, 6 pgs.

* cited by examiner

*Primary Examiner* — Daniel E Kolker
(74) *Attorney, Agent, or Firm* — Kilpatrick Townsend & Stockton LLP

(57) ABSTRACT

An object of the present invention is to provide a probe, a primer, a primer set and an antibody for use in the detection or selection of a dopaminergic neuron progenitor cell. The present invention provides a probe, a primer and a primer set for use in the detection or selection of a mesencephalon dopaminergic neuron progenitor cell, and preferably a dopaminergic neuron proliferative progenitor cell, which can hybridize with a nucleotide sequence of a 187A5 gene, or a complementary sequence thereto, and an antibody for use in the detection or selection of a mesencephalon dopaminergic neuron progenitor cell, and preferably a dopaminergic neuron progenitor cell, which is capable of binding to a 187A5 protein.

2 Claims, 13 Drawing Sheets

METENCEPHALON

187A5

MESENCEPHALON

187A5

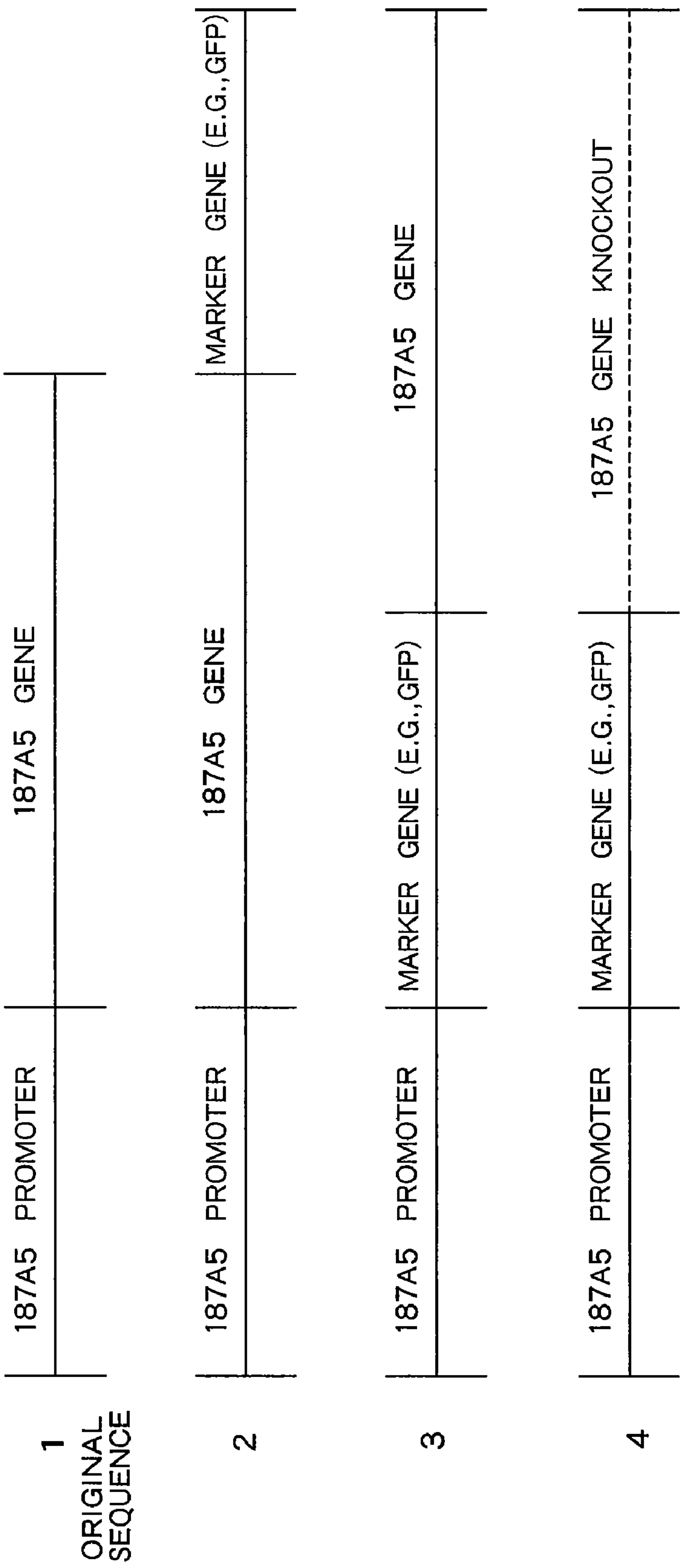
F I G. 15

SEQUENCE LISTING

```
<160> NUMBER OF SEQ ID NOS: 52

<210> SEQ ID NO 1
<211> LENGTH: 3402
<212> TYPE: DNA
<213> ORGANISM: Homo sapiens
<220> FEATURE:
<221> NAME/KEY: CDS
<222> LOCATION: (31)..(3357)
<223> OTHER INFORMATION:

<400> SEQUENCE: 1

ggcgggctgc gtgagcggcc gggacgcagg atg cgc tcc gag ggt gcg gcc ccc       54
                                 Met Arg Ser Glu Gly Ala Ala Pro
                                 1               5

ggg ccg gcg gcg ccg ctg tgc ggg gcg ctg agc ctg ctg ctg ggc gcg       102
Gly Pro Ala Ala Pro Leu Cys Gly Ala Leu Ser Leu Leu Leu Gly Ala
    10                  15                  20

ctg ctg ggc aaa gtg ata gag ggt cac ggg gtc aca gac aac ata cag       150
Leu Leu Gly Lys Val Ile Glu Gly His Gly Val Thr Asp Asn Ile Gln
25                  30                  35                  40

aga ttc tcc tca ctg cca cct tac cta cct gtg agc tac cac atc ctc       198
Arg Phe Ser Ser Leu Pro Pro Tyr Leu Pro Val Ser Tyr His Ile Leu
                45                  50                  55

aga gca gag acc tcc ttc ttc ctc aag gaa gcc aac cag gac ctg ctg       246
Arg Ala Glu Thr Ser Phe Phe Leu Lys Glu Ala Asn Gln Asp Leu Leu
            60                  65                  70
```

```
cgg aac tcc agc ctg cag gcg agg gtg gag tcc ttc ttt acc tac aaa      294
Arg Asn Ser Ser Leu Gln Ala Arg Val Glu Ser Phe Phe Thr Tyr Lys
        75                  80                  85

acc agg cag ccc cca gtg ctc aat gcc agc tat gga ccc ttt tct gtg      342
Thr Arg Gln Pro Pro Val Leu Asn Ala Ser Tyr Gly Pro Phe Ser Val
    90                  95                  100

gag aag gtt gtg cct ctg gac ttg atg ttg act tca aac ttt tta ggt      390
Glu Lys Val Val Pro Leu Asp Leu Met Leu Thr Ser Asn Phe Leu Gly
105                 110                 115                 120

cca acc aat aag ttt agt ttt gat tgg aaa cta aaa gcc cac atc ctg      438
Pro Thr Asn Lys Phe Ser Phe Asp Trp Lys Leu Lys Ala His Ile Leu
                125                 130                 135

cgg gac aaa gtc tac ctg agc cgg ccc aaa gtg cag gtt ctt ttc cac      486
Arg Asp Lys Val Tyr Leu Ser Arg Pro Lys Val Gln Val Leu Phe His
            140                 145                 150

atc atg ggc aga gac tgg gat gac cgc ggc gcc ggg gag aag ctg cca      534
Ile Met Gly Arg Asp Trp Asp Asp Arg Gly Ala Gly Glu Lys Leu Pro
        155                 160                 165

tgc ctg agg gtc ttt gct ttc cga gaa acc aga gag gtg cgg ggc agc      582
Cys Leu Arg Val Phe Ala Phe Arg Glu Thr Arg Glu Val Arg Gly Ser
    170                 175                 180

tgc cgg ctg aag ggg gac ctg ggg ctg tgt gtg gct gag ctg gag ctc      630
Cys Arg Leu Lys Gly Asp Leu Gly Leu Cys Val Ala Glu Leu Glu Leu
185                 190                 195                 200

ctg tcc agc tgg ttc agt gcc ccg acg gtg ggt gcc ggg agg aag aag      678
Leu Ser Ser Trp Phe Ser Ala Pro Thr Val Gly Ala Gly Arg Lys Lys
                205                 210                 215

tcc atg gac cag ccg gag ggg acc cct gtg gag ctc tac tac acc gtg      726
Ser Met Asp Gln Pro Glu Gly Thr Pro Val Glu Leu Tyr Tyr Thr Val
            220                 225                 230

cac cca gga aac gag cga ggg gac tgt gcc ggg ggt gac ttc agg aag      774
His Pro Gly Asn Glu Arg Gly Asp Cys Ala Gly Gly Asp Phe Arg Lys
        235                 240                 245

ggc aac gcc atc cgt cca gga aag gat ggg ctg gag gaa acc acg tcc      822
Gly Asn Ala Ile Arg Pro Gly Lys Asp Gly Leu Glu Glu Thr Thr Ser
    250                 255                 260

cac ctg cag agg atc ggc acc gtc ggc ctt tac cgg gcc cag gac agc      870
His Leu Gln Arg Ile Gly Thr Val Gly Leu Tyr Arg Ala Gln Asp Ser
265                 270                 275                 280

gcc cag ctc agc gag ctg cgt ttg gat ggt aac gtg gtc atc tgg ctg      918
Ala Gln Leu Ser Glu Leu Arg Leu Asp Gly Asn Val Val Ile Trp Leu
                285                 290                 295

cct tcc agg cca gtc aag cag gga gag gtg gtc acg gcc tat gtc acc      966
Pro Ser Arg Pro Val Lys Gln Gly Glu Val Val Thr Ala Tyr Val Thr
            300                 305                 310

atc tcg agc aat tcc tct gtg gac ctc ttc atc ttg aga gcc aag gtg     1014
Ile Ser Ser Asn Ser Ser Val Asp Leu Phe Ile Leu Arg Ala Lys Val
        315                 320                 325

aag aag ggg gtg aac atc ctg agt gct cag acc cgt gag ccc cgg cag     1062
Lys Lys Gly Val Asn Ile Leu Ser Ala Gln Thr Arg Glu Pro Arg Gln
    330                 335                 340

tgg ggc gtc aag cag gag gtg ggc agc ggc gga aag cac gtg acg gcc     1110
Trp Gly Val Lys Gln Glu Val Gly Ser Gly Gly Lys His Val Thr Ala
345                 350                 355                 360

acc gtg gcc tgc cag cgc ctg ggg ccc agc cca cgc aac agg agc agc     1158
Thr Val Ala Cys Gln Arg Leu Gly Pro Ser Pro Arg Asn Arg Ser Ser
                365                 370                 375

agt tta ttc aat gag gtt gtg cag atg aac ttt gaa ata gcc agt ttc     1206
Ser Leu Phe Asn Glu Val Val Gln Met Asn Phe Glu Ile Ala Ser Phe
            380                 385                 390
```

-continued

```
agc agc ctt tca ggg act cag ccc atc acg tgg cag gtg gag tac cca     1254
Ser Ser Leu Ser Gly Thr Gln Pro Ile Thr Trp Gln Val Glu Tyr Pro
        395                 400                 405

cgg aag ggg acc aca gac atc gcc gtg tcc gag atc ttt gtc agc cag     1302
Arg Lys Gly Thr Thr Asp Ile Ala Val Ser Glu Ile Phe Val Ser Gln
    410                 415                 420

aag gac ctg gtg ggc atc gtt ccc ttg gct atg gac act gaa att ctg     1350
Lys Asp Leu Val Gly Ile Val Pro Leu Ala Met Asp Thr Glu Ile Leu
425                 430                 435                 440

aac acc gcc gta ctc aca gga aag aca gtt gcc atg cct atc aag gtg     1398
Asn Thr Ala Val Leu Thr Gly Lys Thr Val Ala Met Pro Ile Lys Val
                445                 450                 455

gtc tct gtg gag gag aac agt gcc gtg atg gac atc tca gag tcg gtg     1446
Val Ser Val Glu Glu Asn Ser Ala Val Met Asp Ile Ser Glu Ser Val
            460                 465                 470

gag tgc aag tcc aca gac gag gac gtt atc aaa gtg tct gag cgc tgt     1494
Glu Cys Lys Ser Thr Asp Glu Asp Val Ile Lys Val Ser Glu Arg Cys
        475                 480                 485

gac tac atc ttt gtc aat ggc aaa gag atc aaa gga aag atg gat gcg     1542
Asp Tyr Ile Phe Val Asn Gly Lys Glu Ile Lys Gly Lys Met Asp Ala
    490                 495                 500

gtg gtg aac ttc aca tac cag tac ctg agc gcc ccc ctg tgt gtc acc     1590
Val Val Asn Phe Thr Tyr Gln Tyr Leu Ser Ala Pro Leu Cys Val Thr
505                 510                 515                 520

gtg tgg gtg ccc cgg ctg ccc ctg cag atc gag gtc tct gac acg gag     1638
Val Trp Val Pro Arg Leu Pro Leu Gln Ile Glu Val Ser Asp Thr Glu
                525                 530                 535

ctc agc cag ata aag ggc tgg agg gtc ccc att gtg acc aat aag agg     1686
Leu Ser Gln Ile Lys Gly Trp Arg Val Pro Ile Val Thr Asn Lys Arg
            540                 545                 550

ccc act cgt gag agc gag gat gag gac gag gag gag cgg cgg ggc cgg     1734
Pro Thr Arg Glu Ser Glu Asp Glu Asp Glu Glu Glu Arg Arg Gly Arg
        555                 560                 565

ggc tgc gca ctg caa tac cag cac gcc acc gtg cgg gtc ctc acc cag     1782
Gly Cys Ala Leu Gln Tyr Gln His Ala Thr Val Arg Val Leu Thr Gln
    570                 575                 580

ttt gtg tct gag ggc gcc ggt cca tgg ggc cag ccg aac tac ctg ctt     1830
Phe Val Ser Glu Gly Ala Gly Pro Trp Gly Gln Pro Asn Tyr Leu Leu
585                 590                 595                 600

agt cct aac tgg cag ttc gac atc act cac ctg gtg gca gac ttc atg     1878
Ser Pro Asn Trp Gln Phe Asp Ile Thr His Leu Val Ala Asp Phe Met
                605                 610                 615

aag ctg gag gaa cct cac gtg gcc acc ctc cag gac agc cgg gtc ctg     1926
Lys Leu Glu Glu Pro His Val Ala Thr Leu Gln Asp Ser Arg Val Leu
            620                 625                 630

gtt ggg cga gag gtt ggg atg acg acc atc cag gtg ttg tct cca ctg     1974
Val Gly Arg Glu Val Gly Met Thr Thr Ile Gln Val Leu Ser Pro Leu
        635                 640                 645

tct gac tcc atc ctg gca gag aag acg ata acc gtg cta gat gac aaa     2022
Ser Asp Ser Ile Leu Ala Glu Lys Thr Ile Thr Val Leu Asp Asp Lys
    650                 655                 660

gtg tcg gtg aca gac ttg gcc atc cag ctc gtg gct ggg ctg tct gtc     2070
Val Ser Val Thr Asp Leu Ala Ile Gln Leu Val Ala Gly Leu Ser Val
665                 670                 675                 680

gcc ctt tac ccc aac gca gaa aac agc aag gcc gta aca gct gtg gtc     2118
Ala Leu Tyr Pro Asn Ala Glu Asn Ser Lys Ala Val Thr Ala Val Val
                685                 690                 695

aca gct gag gag gtg ctg cgg acc ccc aaa cag gag gct gta ttc agc     2166
Thr Ala Glu Glu Val Leu Arg Thr Pro Lys Gln Glu Ala Val Phe Ser
            700                 705                 710
```

```
acg tgg ctg cag ttc agt gat ggc tct gtg acg ccc ctg gac atc tac      2214
Thr Trp Leu Gln Phe Ser Asp Gly Ser Val Thr Pro Leu Asp Ile Tyr
        715                 720                 725

gac acc aag gac ttc tcc ctg gca gcc acc tcc cag gac gag gct gtc      2262
Asp Thr Lys Asp Phe Ser Leu Ala Ala Thr Ser Gln Asp Glu Ala Val
    730                 735                 740

gtg tca gtc ccc cag ccc cgc tct ccc agg tgg ccc gtt gtg gtg gcc      2310
Val Ser Val Pro Gln Pro Arg Ser Pro Arg Trp Pro Val Val Val Ala
745                 750                 755                 760

gaa ggg gaa ggc cag ggc cca ctg atc cga gtg gac atg acg atc gcc      2358
Glu Gly Glu Gly Gln Gly Pro Leu Ile Arg Val Asp Met Thr Ile Ala
                765                 770                 775

gag gcc tgc cag aaa tct aaa cgc aag agc atc ctg gct gtg ggc gtc      2406
Glu Ala Cys Gln Lys Ser Lys Arg Lys Ser Ile Leu Ala Val Gly Val
            780                 785                 790

ggc aac gtc agg gtc aag ttc gga cag aac gat gct gac tcc agc ccc      2454
Gly Asn Val Arg Val Lys Phe Gly Gln Asn Asp Ala Asp Ser Ser Pro
        795                 800                 805

ggc agg gac tat gag gaa gat gag atc aag aac cac gcc agc gac cgc      2502
Gly Arg Asp Tyr Glu Glu Asp Glu Ile Lys Asn His Ala Ser Asp Arg
    810                 815                 820

cgg cag aag ggc cag cac cat gag cgc aca ggc cag gat ggg cac ctc      2550
Arg Gln Lys Gly Gln His His Glu Arg Thr Gly Gln Asp Gly His Leu
825                 830                 835                 840

tat ggc agc tct ccc gtg gag cgt gag gaa ggg gct ctc cga aga gcc      2598
Tyr Gly Ser Ser Pro Val Glu Arg Glu Glu Gly Ala Leu Arg Arg Ala
                845                 850                 855

act acc acg gcc agg tcc ctg ctg gac aac aaa gtg gtg aag aac agt      2646
Thr Thr Thr Ala Arg Ser Leu Leu Asp Asn Lys Val Val Lys Asn Ser
            860                 865                 870

cgg gca gac ggg ggc agg ctg gca gga gag ggg cag ctg cag aac atc      2694
Arg Ala Asp Gly Gly Arg Leu Ala Gly Glu Gly Gln Leu Gln Asn Ile
        875                 880                 885

ccc att gac ttc acc aac ttc cct gcc cac gtg gac ctc ccc aag gcc      2742
Pro Ile Asp Phe Thr Asn Phe Pro Ala His Val Asp Leu Pro Lys Ala
    890                 895                 900

ggg agt ggg ctg gag gaa aac gac ctg gtg cag act ccg cgg ggc ctg      2790
Gly Ser Gly Leu Glu Glu Asn Asp Leu Val Gln Thr Pro Arg Gly Leu
905                 910                 915                 920

agt gat ctg gag ata ggg atg tac gcc ctc ctg ggg gtg ttc tgc ctg      2838
Ser Asp Leu Glu Ile Gly Met Tyr Ala Leu Leu Gly Val Phe Cys Leu
                925                 930                 935

gcc atc ctc gtc ttc ctg atc aac tgc gcc acc ttt gcc ctg aag tac      2886
Ala Ile Leu Val Phe Leu Ile Asn Cys Ala Thr Phe Ala Leu Lys Tyr
            940                 945                 950

agg cac aag caa gtg ccc ctg gaa ggt cag gcc tcc atg acc cac tct      2934
Arg His Lys Gln Val Pro Leu Glu Gly Gln Ala Ser Met Thr His Ser
        955                 960                 965

cac gac tgg gtg tgg ctt ggc aat gag gcc gaa ctc ctg gag agc atg      2982
His Asp Trp Val Trp Leu Gly Asn Glu Ala Glu Leu Leu Glu Ser Met
    970                 975                 980

ggg gat gca ccg ccg ccc cag gac gag cac acc acc atc ata gac cgc      3030
Gly Asp Ala Pro Pro Pro Gln Asp Glu His Thr Thr Ile Ile Asp Arg
985                 990                 995                 1000

gga ccg ggg gcc tgc  gag gag agc aac cat  ctc ctg ctc aat ggt       3075
Gly Pro Gly Ala Cys  Glu Glu Ser Asn His  Leu Leu Leu Asn Gly
                1005                 1010                 1015

ggc tcc cac aag cac  gtg cag agc cag att  cac agg tca gcc gac       3120
Gly Ser His Lys His  Val Gln Ser Gln Ile  His Arg Ser Ala Asp
                1020                 1025                 1030
```

```
tcc ggg ggg cgg cag  ggc aga gaa cag aag  cag gac ccc ctg cac       3165
Ser Gly Gly Arg Gln  Gly Arg Glu Gln Lys  Gln Asp Pro Leu His
                1035                 1040                 1045

tcg ccc acc tcc aag  agg aag aag gtg aaa  ttt acc acc ttt acc       3210
Ser Pro Thr Ser Lys  Arg Lys Lys Val Lys  Phe Thr Thr Phe Thr
                1050                 1055                 1060

acc atc ccc ccg gac  gac agc tgc ccc acg  gtg aac tcc atc gtc       3255
Thr Ile Pro Pro Asp  Asp Ser Cys Pro Thr  Val Asn Ser Ile Val
                1065                 1070                 1075

agc agc aat gat gag  gac atc aaa tgg gtg  tgt caa gac gtg gct       3300
Ser Ser Asn Asp Glu  Asp Ile Lys Trp Val  Cys Gln Asp Val Ala
                1080                 1085                 1090

gtg ggt gcc ccc aag  gaa ctt aga aac tat  ctg gag aaa ctc aaa       3345
Val Gly Ala Pro Lys  Glu Leu Arg Asn Tyr  Leu Glu Lys Leu Lys
                1095                 1100                 1105

gat aag gct tag gcccctctag ccaaagggcc ctgcccagat gccttccttg tactg   3402
Asp Lys Ala


<210> SEQ ID NO 2
<211> LENGTH: 1108
<212> TYPE: PRT
<213> ORGANISM: Homo sapiens

<400> SEQUENCE: 2

Met Arg Ser Glu Gly Ala Ala Pro Gly Pro Ala Ala Pro Leu Cys Gly
1               5                   10                  15

Ala Leu Ser Leu Leu Leu Gly Ala Leu Leu Gly Lys Val Ile Glu Gly
            20                  25                  30

His Gly Val Thr Asp Asn Ile Gln Arg Phe Ser Ser Leu Pro Pro Tyr
        35                  40                  45

Leu Pro Val Ser Tyr His Ile Leu Arg Ala Glu Thr Ser Phe Phe Leu
    50                  55                  60

Lys Glu Ala Asn Gln Asp Leu Leu Arg Asn Ser Ser Leu Gln Ala Arg
65                  70                  75                  80

Val Glu Ser Phe Phe Thr Tyr Lys Thr Arg Gln Pro Pro Val Leu Asn
                85                  90                  95

Ala Ser Tyr Gly Pro Phe Ser Val Glu Lys Val Val Pro Leu Asp Leu
            100                 105                 110

Met Leu Thr Ser Asn Phe Leu Gly Pro Thr Asn Lys Phe Ser Phe Asp
        115                 120                 125

Trp Lys Leu Lys Ala His Ile Leu Arg Asp Lys Val Tyr Leu Ser Arg
    130                 135                 140

Pro Lys Val Gln Val Leu Phe His Ile Met Gly Arg Asp Trp Asp Asp
145                 150                 155                 160

Arg Gly Ala Gly Glu Lys Leu Pro Cys Leu Arg Val Phe Ala Phe Arg
                165                 170                 175

Glu Thr Arg Glu Val Arg Gly Ser Cys Arg Leu Lys Gly Asp Leu Gly
            180                 185                 190

Leu Cys Val Ala Glu Leu Glu Leu Leu Ser Ser Trp Phe Ser Ala Pro
        195                 200                 205

Thr Val Gly Ala Gly Arg Lys Lys Ser Met Asp Gln Pro Glu Gly Thr
    210                 215                 220

Pro Val Glu Leu Tyr Tyr Thr Val His Pro Gly Asn Glu Arg Gly Asp
225                 230                 235                 240

Cys Ala Gly Gly Asp Phe Arg Lys Gly Asn Ala Ile Arg Pro Gly Lys
                245                 250                 255
```

-continued

```
Asp Gly Leu Glu Glu Thr Thr Ser His Leu Gln Arg Ile Gly Thr Val
            260                 265                 270

Gly Leu Tyr Arg Ala Gln Asp Ser Ala Gln Leu Ser Glu Leu Arg Leu
        275                 280                 285

Asp Gly Asn Val Val Ile Trp Leu Pro Ser Arg Pro Val Lys Gln Gly
    290                 295                 300

Glu Val Val Thr Ala Tyr Val Thr Ile Ser Ser Asn Ser Ser Val Asp
305                 310                 315                 320

Leu Phe Ile Leu Arg Ala Lys Val Lys Lys Gly Val Asn Ile Leu Ser
                325                 330                 335

Ala Gln Thr Arg Glu Pro Arg Gln Trp Gly Val Lys Gln Glu Val Gly
            340                 345                 350

Ser Gly Gly Lys His Val Thr Ala Thr Val Ala Cys Gln Arg Leu Gly
        355                 360                 365

Pro Ser Pro Arg Asn Arg Ser Ser Ser Leu Phe Asn Glu Val Val Gln
    370                 375                 380

Met Asn Phe Glu Ile Ala Ser Phe Ser Ser Leu Ser Gly Thr Gln Pro
385                 390                 395                 400

Ile Thr Trp Gln Val Glu Tyr Pro Arg Lys Gly Thr Thr Asp Ile Ala
                405                 410                 415

Val Ser Glu Ile Phe Val Ser Gln Lys Asp Leu Val Gly Ile Val Pro
            420                 425                 430

Leu Ala Met Asp Thr Glu Ile Leu Asn Thr Ala Val Leu Thr Gly Lys
        435                 440                 445

Thr Val Ala Met Pro Ile Lys Val Val Ser Val Glu Glu Asn Ser Ala
    450                 455                 460

Val Met Asp Ile Ser Glu Ser Val Glu Cys Lys Ser Thr Asp Glu Asp
465                 470                 475                 480

Val Ile Lys Val Ser Glu Arg Cys Asp Tyr Ile Phe Val Asn Gly Lys
                485                 490                 495

Glu Ile Lys Gly Lys Met Asp Ala Val Val Asn Phe Thr Tyr Gln Tyr
            500                 505                 510

Leu Ser Ala Pro Leu Cys Val Thr Val Trp Val Pro Arg Leu Pro Leu
        515                 520                 525

Gln Ile Glu Val Ser Asp Thr Glu Leu Ser Gln Ile Lys Gly Trp Arg
    530                 535                 540

Val Pro Ile Val Thr Asn Lys Arg Pro Thr Arg Glu Ser Glu Asp Glu
545                 550                 555                 560

Asp Glu Glu Glu Arg Arg Gly Arg Gly Cys Ala Leu Gln Tyr Gln His
                565                 570                 575

Ala Thr Val Arg Val Leu Thr Gln Phe Val Ser Glu Gly Ala Gly Pro
            580                 585                 590

Trp Gly Gln Pro Asn Tyr Leu Leu Ser Pro Asn Trp Gln Phe Asp Ile
        595                 600                 605

Thr His Leu Val Ala Asp Phe Met Lys Leu Glu Glu Pro His Val Ala
    610                 615                 620

Thr Leu Gln Asp Ser Arg Val Leu Val Gly Arg Glu Val Gly Met Thr
625                 630                 635                 640

Thr Ile Gln Val Leu Ser Pro Leu Ser Asp Ser Ile Leu Ala Glu Lys
                645                 650                 655

Thr Ile Thr Val Leu Asp Asp Lys Val Ser Val Thr Asp Leu Ala Ile
            660                 665                 670

Gln Leu Val Ala Gly Leu Ser Val Ala Leu Tyr Pro Asn Ala Glu Asn
        675                 680                 685
```

```
Ser Lys Ala Val Thr Ala Val Val Thr Ala Glu Glu Val Leu Arg Thr
    690                 695                 700

Pro Lys Gln Glu Ala Val Phe Ser Thr Trp Leu Gln Phe Ser Asp Gly
705                 710                 715                 720

Ser Val Thr Pro Leu Asp Ile Tyr Asp Thr Lys Asp Phe Ser Leu Ala
                725                 730                 735

Ala Thr Ser Gln Asp Glu Ala Val Val Ser Val Pro Gln Pro Arg Ser
            740                 745                 750

Pro Arg Trp Pro Val Val Val Ala Glu Gly Glu Gly Gln Gly Pro Leu
        755                 760                 765

Ile Arg Val Asp Met Thr Ile Ala Glu Ala Cys Gln Lys Ser Lys Arg
    770                 775                 780

Lys Ser Ile Leu Ala Val Gly Val Gly Asn Val Arg Val Lys Phe Gly
785                 790                 795                 800

Gln Asn Asp Ala Asp Ser Ser Pro Gly Arg Asp Tyr Glu Glu Asp Glu
                805                 810                 815

Ile Lys Asn His Ala Ser Asp Arg Arg Gln Lys Gly Gln His His Glu
            820                 825                 830

Arg Thr Gly Gln Asp Gly His Leu Tyr Gly Ser Ser Pro Val Glu Arg
        835                 840                 845

Glu Glu Gly Ala Leu Arg Arg Ala Thr Thr Thr Ala Arg Ser Leu Leu
    850                 855                 860

Asp Asn Lys Val Val Lys Asn Ser Arg Ala Asp Gly Gly Arg Leu Ala
865                 870                 875                 880

Gly Glu Gly Gln Leu Gln Asn Ile Pro Ile Asp Phe Thr Asn Phe Pro
                885                 890                 895

Ala His Val Asp Leu Pro Lys Ala Gly Ser Gly Leu Glu Glu Asn Asp
            900                 905                 910

Leu Val Gln Thr Pro Arg Gly Leu Ser Asp Leu Glu Ile Gly Met Tyr
        915                 920                 925

Ala Leu Leu Gly Val Phe Cys Leu Ala Ile Leu Val Phe Leu Ile Asn
    930                 935                 940

Cys Ala Thr Phe Ala Leu Lys Tyr Arg His Lys Gln Val Pro Leu Glu
945                 950                 955                 960

Gly Gln Ala Ser Met Thr His Ser His Asp Trp Val Trp Leu Gly Asn
                965                 970                 975

Glu Ala Glu Leu Leu Glu Ser Met Gly Asp Ala Pro Pro Pro Gln Asp
            980                 985                 990

Glu His Thr Thr Ile Ile Asp Arg  Gly Pro Gly Ala Cys  Glu Glu Ser
        995                 1000                1005

Asn His  Leu Leu Leu Asn Gly  Gly Ser His Lys His  Val Gln Ser
    1010                1015                1020

Gln Ile  His Arg Ser Ala Asp  Ser Gly Gly Arg Gln  Gly Arg Glu
    1025                1030                1035

Gln Lys  Gln Asp Pro Leu His  Ser Pro Thr Ser Lys  Arg Lys Lys
    1040                1045                1050

Val Lys  Phe Thr Thr Phe Thr  Thr Ile Pro Pro Asp  Asp Ser Cys
    1055                1060                1065

Pro Thr  Val Asn Ser Ile Val  Ser Ser Asn Asp Glu  Asp Ile Lys
    1070                1075                1080

Trp Val  Cys Gln Asp Val Ala  Val Gly Ala Pro Lys  Glu Leu Arg
    1085                1090                1095

Asn Tyr  Leu Glu Lys Leu Lys  Asp Lys Ala
```

```
    1100                1105


<210> SEQ ID NO 3
<211> LENGTH: 5961
<212> TYPE: DNA
<213> ORGANISM: Homo sapiens
<220> FEATURE:
<221> NAME/KEY: CDS
<222> LOCATION: (1)..(4347)
<223> OTHER INFORMATION:

<400> SEQUENCE: 3

atg tct ctg ggc ctt atc tcc ata ttt cag aaa cca agt tca ggg tca       48
Met Ser Leu Gly Leu Ile Ser Ile Phe Gln Lys Pro Ser Ser Gly Ser
1               5                   10                  15

gtc aca ggg aag tca cct gaa ccg gac agc aag gtc tgt gac tgc ctt       96
Val Thr Gly Lys Ser Pro Glu Pro Asp Ser Lys Val Cys Asp Cys Leu
            20                  25                  30

atc cac agg cag atc ccg ctc gcc ctg ccc tgg cat cac cac cac tgg      144
Ile His Arg Gln Ile Pro Leu Ala Leu Pro Trp His His His His Trp
        35                  40                  45

gca gct ttg cct ctc act aga tat gaa aaa agt gga aaa gca aaa cag      192
Ala Ala Leu Pro Leu Thr Arg Tyr Glu Lys Ser Gly Lys Ala Lys Gln
    50                  55                  60

aaa cta aag gtg aca act ctg cag agc tgg gca cgt tgg aaa ggc caa      240
Lys Leu Lys Val Thr Thr Leu Gln Ser Trp Ala Arg Trp Lys Gly Gln
65                  70                  75                  80

gcc tta acc ctg tct ctc tct ctc tcc cat ctt cat ccc cac aga gcc      288
Ala Leu Thr Leu Ser Leu Ser Leu Ser His Leu His Pro His Arg Ala
                85                  90                  95

aag gtg aag aag ggg gtg aac atc ctg agt gct cag acc cgt gag ccc      336
Lys Val Lys Lys Gly Val Asn Ile Leu Ser Ala Gln Thr Arg Glu Pro
            100                 105                 110

cgg cag tgg ggc gtc aag cag gag gtg ggc agc ggc gga aag cac gtg      384
Arg Gln Trp Gly Val Lys Gln Glu Val Gly Ser Gly Gly Lys His Val
        115                 120                 125

acg gcc acc gtg gcc tgc cag cgc ctg ggg ccc agc cca cgc aac aga      432
Thr Ala Thr Val Ala Cys Gln Arg Leu Gly Pro Ser Pro Arg Asn Arg
    130                 135                 140

acc cac tcc tct gtc ctt cct tta atg tgt aat gag aaa aag aaa atc      480
Thr His Ser Ser Val Leu Pro Leu Met Cys Asn Glu Lys Lys Lys Ile
145                 150                 155                 160

tgg tgt ccc aaa cag ttc aca aac tca aat gcc aac cgt cac cat cat      528
Trp Cys Pro Lys Gln Phe Thr Asn Ser Asn Ala Asn Arg His His His
                165                 170                 175

tac ccc aag aag gat ttt agt gca tct ggc gga gga agc atc ttc cgc      576
Tyr Pro Lys Lys Asp Phe Ser Ala Ser Gly Gly Gly Ser Ile Phe Arg
            180                 185                 190

ctc ccc ctt cat ctc ctt tcc tcg gtc tgc atc ttt ttt caa aac cag      624
Leu Pro Leu His Leu Leu Ser Ser Val Cys Ile Phe Phe Gln Asn Gln
        195                 200                 205

gtg tcc ggc tcc ggg ggt gtc tgt gcc cag gac tgg tta cgg gcc atg      672
Val Ser Gly Ser Gly Gly Val Cys Ala Gln Asp Trp Leu Arg Ala Met
    210                 215                 220

tgg gag act ttc act tta acc tca aaa ctt cta aaa gaa tct aaa aag      720
Trp Glu Thr Phe Thr Leu Thr Ser Lys Leu Leu Lys Glu Ser Lys Lys
225                 230                 235                 240

gaa aca ctt tct gtc cac gtg att caa cct tac tca agg gat gca cgt      768
Glu Thr Leu Ser Val His Val Ile Gln Pro Tyr Ser Arg Asp Ala Arg
                245                 250                 255

tgc ctt ttg gaa acc ttt cct ggg ata ctt cat cag tcc cct aga ggg      816
Cys Leu Leu Glu Thr Phe Pro Gly Ile Leu His Gln Ser Pro Arg Gly
```

-continued

```
            260                 265                 270

gct gtc act gac act tgt aca gag ttt gca gca aaa cag ctg tct ggg      864
Ala Val Thr Asp Thr Cys Thr Glu Phe Ala Ala Lys Gln Leu Ser Gly
        275                 280                 285

aac tcg act gtg cct ctt ttg gag gga ctt aga aag aag gcc agc tgt      912
Asn Ser Thr Val Pro Leu Leu Glu Gly Leu Arg Lys Lys Ala Ser Cys
    290                 295                 300

ttc aaa gac tca gct gcc cct cat ttt cac cac acg agc cct cct aaa      960
Phe Lys Asp Ser Ala Ala Pro His Phe His His Thr Ser Pro Pro Lys
305                 310                 315                 320

cag agc aca tcg cac aga cgc tcc tgt att tcc agc aga tgc tat aaa     1008
Gln Ser Thr Ser His Arg Arg Ser Cys Ile Ser Ser Arg Cys Tyr Lys
                325                 330                 335

cac gca tct gag ctc cgg ttc tta tgg cta agc agc tgc tgc atc ccc     1056
His Ala Ser Glu Leu Arg Phe Leu Trp Leu Ser Ser Cys Cys Ile Pro
            340                 345                 350

aag ctc ctt aat tca aga gcc agc atc gtg ctt cag gga ctc tct gct     1104
Lys Leu Leu Asn Ser Arg Ala Ser Ile Val Leu Gln Gly Leu Ser Ala
        355                 360                 365

gca ggg gag aaa agt aaa tca ggc agg aat tcc agt tca acc atg atg     1152
Ala Gly Glu Lys Ser Lys Ser Gly Arg Asn Ser Ser Ser Thr Met Met
    370                 375                 380

ttt tct gat tct tac atc aac cct gag ata tgg gta cga tgg gtc cca     1200
Phe Ser Asp Ser Tyr Ile Asn Pro Glu Ile Trp Val Arg Trp Val Pro
385                 390                 395                 400

tat tcc aga aaa caa tgt gac atg aag aca gag ccc aca cta gag cgg     1248
Tyr Ser Arg Lys Gln Cys Asp Met Lys Thr Glu Pro Thr Leu Glu Arg
                405                 410                 415

ctt gtg gag aga gta gta aaa cct gac agg ctc ctt agc acc aga gag     1296
Leu Val Glu Arg Val Val Lys Pro Asp Arg Leu Leu Ser Thr Arg Glu
            420                 425                 430

gag tgg aaa ggt gaa aga aag aaa att caa ggg ctg aaa aat atc tac     1344
Glu Trp Lys Gly Glu Arg Lys Lys Ile Gln Gly Leu Lys Asn Ile Tyr
        435                 440                 445

acc tcc cca ccc ccg cac ccc cca cac act cac act gtg gtc aca ttg     1392
Thr Ser Pro Pro Pro His Pro Pro His Thr His Thr Val Val Thr Leu
    450                 455                 460

aga aaa gat gca aga cgc att ctg aca ctt aga ttg cga tgt gga gac     1440
Arg Lys Asp Ala Arg Arg Ile Leu Thr Leu Arg Leu Arg Cys Gly Asp
465                 470                 475                 480

act cac aca gcc aat cca tgg agc tca ggc ttt gac ctg gat atg cct     1488
Thr His Thr Ala Asn Pro Trp Ser Ser Gly Phe Asp Leu Asp Met Pro
                485                 490                 495

gat tcc tgc atg gga att gga gtt gag ttg gtc tgg gtt ccg gtc ctg     1536
Asp Ser Cys Met Gly Ile Gly Val Glu Leu Val Trp Val Pro Val Leu
            500                 505                 510

ctc cag cag ctc tgt gca ctg ggg cag gtc ctg att ctg cag gag gcc     1584
Leu Gln Gln Leu Cys Ala Leu Gly Gln Val Leu Ile Leu Gln Glu Ala
        515                 520                 525

ggt gcc tac ttt acg aac agc tac ggc ctc agt gcc tgt gat ttg aaa     1632
Gly Ala Tyr Phe Thr Asn Ser Tyr Gly Leu Ser Ala Cys Asp Leu Lys
    530                 535                 540

aat gcc cct agc tgt ccg tcc cgg ctg ctg aag gga acg agc ttc ggt     1680
Asn Ala Pro Ser Cys Pro Ser Arg Leu Leu Lys Gly Thr Ser Phe Gly
545                 550                 555                 560

ggt gac tgc atc cct cac atc cga gga ggg tcc tgg tac aga ggc agc     1728
Gly Asp Cys Ile Pro His Ile Arg Gly Gly Ser Trp Tyr Arg Gly Ser
                565                 570                 575

agg gct tca ctg atc ccg ttt tct gtc cat cac act ggg ctg ccc ctt     1776
Arg Ala Ser Leu Ile Pro Phe Ser Val His His Thr Gly Leu Pro Leu
```

-continued

```
        580                 585                 590

tcg cag gtc ctg gta cag agg tgg cac ggc ttg act gat ccc gtg ttc     1824
Ser Gln Val Leu Val Gln Arg Trp His Gly Leu Thr Asp Pro Val Phe
        595                 600                 605

tct cca tca cac tgg gct gcc cct ttc gca ggt cct gtg ggc tgc ccc     1872
Ser Pro Ser His Trp Ala Ala Pro Phe Ala Gly Pro Val Gly Cys Pro
    610                 615                 620

ttt cgc agg tct tgg tac aga ggt ggc agg gct tca ctg atc cca tgt     1920
Phe Arg Arg Ser Trp Tyr Arg Gly Gly Arg Ala Ser Leu Ile Pro Cys
625                 630                 635                 640

tct ctc cgt cac act ggg ctg ccc ctt ttg cag gtc ctg gta cag agg     1968
Ser Leu Arg His Thr Gly Leu Pro Leu Leu Gln Val Leu Val Gln Arg
                645                 650                 655

cgg cag ggc ttc act gat ccc tgt tct gtc cat cgc act ggg ctg ccc     2016
Arg Gln Gly Phe Thr Asp Pro Cys Ser Val His Arg Thr Gly Leu Pro
            660                 665                 670

ctt ttg cag gtc ctg gta cag agg cac cag ggc ttc act gat ccc atg     2064
Leu Leu Gln Val Leu Val Gln Arg His Gln Gly Phe Thr Asp Pro Met
        675                 680                 685

tcc tct cca tca cac tgg gct gcc cct ttc gca ggt cct gat cct cgc     2112
Ser Ser Pro Ser His Trp Ala Ala Pro Phe Ala Gly Pro Asp Pro Arg
    690                 695                 700

cta aga cag ctg gtg gtc aag aac cac ctg agc agc agt tta ttc aat     2160
Leu Arg Gln Leu Val Val Lys Asn His Leu Ser Ser Ser Leu Phe Asn
705                 710                 715                 720

gag gtt gtg cag atg aac ttt gaa ata gcc agt ttc agc agc ctt tca     2208
Glu Val Val Gln Met Asn Phe Glu Ile Ala Ser Phe Ser Ser Leu Ser
                725                 730                 735

ggg act cag ccc atc acg tgg cag gtg gag tac cca cgg aag ggg acc     2256
Gly Thr Gln Pro Ile Thr Trp Gln Val Glu Tyr Pro Arg Lys Gly Thr
            740                 745                 750

aca gac atc gcc gtg tcc gag atc ttt gtc agc cag aag gac ctg gtg     2304
Thr Asp Ile Ala Val Ser Glu Ile Phe Val Ser Gln Lys Asp Leu Val
        755                 760                 765

ggc atc gtt ccc ttg gct atg gac act gaa att ctg aac acc gcc gta     2352
Gly Ile Val Pro Leu Ala Met Asp Thr Glu Ile Leu Asn Thr Ala Val
    770                 775                 780

ctc aca gga aag aca gtt gcc atg cct atc aag gtg gtc tct gtg gag     2400
Leu Thr Gly Lys Thr Val Ala Met Pro Ile Lys Val Val Ser Val Glu
785                 790                 795                 800

gag aac agt gcc gtg atg gac atc tca gag tcg gtg gag tgc aag tcc     2448
Glu Asn Ser Ala Val Met Asp Ile Ser Glu Ser Val Glu Cys Lys Ser
                805                 810                 815

aca gac gag gac gtt atc aaa gtg tct gag cgc tgt gac tac atc ttt     2496
Thr Asp Glu Asp Val Ile Lys Val Ser Glu Arg Cys Asp Tyr Ile Phe
            820                 825                 830

gtc aat ggc aaa gag atc aaa gga aag atg gat gcg gtg gtg aac ttc     2544
Val Asn Gly Lys Glu Ile Lys Gly Lys Met Asp Ala Val Val Asn Phe
        835                 840                 845

aca tac cag tac ctg agc gcc ccc ctg tgt gtc acc gtg tgg gtg ccc     2592
Thr Tyr Gln Tyr Leu Ser Ala Pro Leu Cys Val Thr Val Trp Val Pro
    850                 855                 860

cgg ctg ccc ctg cag atc gag gtc tct gac acg gag ctc agc cag ata     2640
Arg Leu Pro Leu Gln Ile Glu Val Ser Asp Thr Glu Leu Ser Gln Ile
865                 870                 875                 880

aag ggc tgg agg gtc ccc att gtg acc aat aag agg ccc act cgt gag     2688
Lys Gly Trp Arg Val Pro Ile Val Thr Asn Lys Arg Pro Thr Arg Glu
                885                 890                 895

agc gag gat gag gac gag gag gag cgg cgg ggc cgg ggc tgc gca ctg     2736
Ser Glu Asp Glu Asp Glu Glu Glu Arg Arg Gly Arg Gly Cys Ala Leu
```

```
            900                 905                 910

caa tac cag cac gcc acc gtg cgg gtc ctc acc cag ttt gtg tct gag      2784
Gln Tyr Gln His Ala Thr Val Arg Val Leu Thr Gln Phe Val Ser Glu
        915                 920                 925

ggc gcc ggt cca tgg ggc cag ccg aac tac ctg ctt agt cct aac tgg      2832
Gly Ala Gly Pro Trp Gly Gln Pro Asn Tyr Leu Leu Ser Pro Asn Trp
    930                 935                 940

cag ttc gac atc act cac ctg gtg gca gac ttc atg aag ctg gag gaa      2880
Gln Phe Asp Ile Thr His Leu Val Ala Asp Phe Met Lys Leu Glu Glu
945                 950                 955                 960

cct cac gtg gcc acc ctc cag gac agc cgg gtc ctg gtt ggg cga gag      2928
Pro His Val Ala Thr Leu Gln Asp Ser Arg Val Leu Val Gly Arg Glu
                965                 970                 975

gtt ggg atg acg acc atc cag gtg ttg tct cca ctg tct gac tcc atc      2976
Val Gly Met Thr Thr Ile Gln Val Leu Ser Pro Leu Ser Asp Ser Ile
            980                 985                 990

ctg gca gag aag aca ata acc gtg  cta gat gac aaa gta  tcg gtg aca    3024
Leu Ala Glu Lys Thr Ile Thr Val  Leu Asp Asp Lys Val  Ser Val Thr
        995                 1000                1005

gac ttg  gcc atc cag ctc gtg  gct ggg ctg tct gtc  gcc ctt tac      3069
Asp Leu  Ala Ile Gln Leu Val  Ala Gly Leu Ser Val  Ala Leu Tyr
    1010                1015                1020

ccc aac  gca gaa aac agc aag  gcc gta aca gct gtg  gtc aca gct      3114
Pro Asn  Ala Glu Asn Ser Lys  Ala Val Thr Ala Val  Val Thr Ala
    1025                1030                1035

gag gag  gtg ctg cgg acc ccc  aaa cag gag gct gta  ttc agc acg      3159
Glu Glu  Val Leu Arg Thr Pro  Lys Gln Glu Ala Val  Phe Ser Thr
    1040                1045                1050

tgg ctg  cag ttc agt gat ggc  tct gtg acg ccc ctg  gac atc tac      3204
Trp Leu  Gln Phe Ser Asp Gly  Ser Val Thr Pro Leu  Asp Ile Tyr
    1055                1060                1065

gac acc  aag gac ttc tcc ctg  gca gcc acc tcc cag  gac gag gct      3249
Asp Thr  Lys Asp Phe Ser Leu  Ala Ala Thr Ser Gln  Asp Glu Ala
    1070                1075                1080

gtc gtg  tca gtc ccc cag ccc  cgc tct ccc agg tgg  ccc gtt gtg      3294
Val Val  Ser Val Pro Gln Pro  Arg Ser Pro Arg Trp  Pro Val Val
    1085                1090                1095

gtg gcc  gaa ggg gaa ggc cag  ggc cca ctg atc cga  gtg gac atg      3339
Val Ala  Glu Gly Glu Gly Gln  Gly Pro Leu Ile Arg  Val Asp Met
    1100                1105                1110

acg atc  gcc gag gcc tgc cag  aaa tct aaa cgc aag  agc atc ctg      3384
Thr Ile  Ala Glu Ala Cys Gln  Lys Ser Lys Arg Lys  Ser Ile Leu
    1115                1120                1125

gct gtg  ggc gtc ggc aac gtc  agg gtc aag ttc gga  cag aac gat      3429
Ala Val  Gly Val Gly Asn Val  Arg Val Lys Phe Gly  Gln Asn Asp
    1130                1135                1140

gct gac  tcc agc ccc ggc ggg  gac tat gag gaa gat  gag atc aag      3474
Ala Asp  Ser Ser Pro Gly Gly  Asp Tyr Glu Glu Asp  Glu Ile Lys
    1145                1150                1155

aac cac  gcc agc gac cgc cgg  cag aag ggc cag cac  cat gag cgc      3519
Asn His  Ala Ser Asp Arg Arg  Gln Lys Gly Gln His  His Glu Arg
    1160                1165                1170

aca ggc  caa gat ggg cac ctc  tat ggc agc tct ccc  gtg gag cgt      3564
Thr Gly  Gln Asp Gly His Leu  Tyr Gly Ser Ser Pro  Val Glu Arg
    1175                1180                1185

gag gaa  ggg gct ctc cga aga  gcc act acc acg gcc  agg tcc ctg      3609
Glu Glu  Gly Ala Leu Arg Arg  Ala Thr Thr Thr Ala  Arg Ser Leu
    1190                1195                1200

ctg gac  aac aaa gtg gtg aag  aac agt cgg gca gac  ggg ggc agg      3654
Leu Asp  Asn Lys Val Val Lys  Asn Ser Arg Ala Asp  Gly Gly Arg
```

-continued

```
    1205                1210                1215

ctg gca  gga gag ggg cag ctg  cag aac atc ccc att  gac ttc acc      3699
Leu Ala  Gly Glu Gly Gln Leu  Gln Asn Ile Pro Ile  Asp Phe Thr
    1220                1225                1230

aac ttc  cct gcc cac gtg gac  ctc ccc aag gcc ggg  agt ggg ctg      3744
Asn Phe  Pro Ala His Val Asp  Leu Pro Lys Ala Gly  Ser Gly Leu
    1235                1240                1245

gag gaa  aac gac ctg gtg cag  act ccg cgg ggc ctg  agt gat ctg      3789
Glu Glu  Asn Asp Leu Val Gln  Thr Pro Arg Gly Leu  Ser Asp Leu
    1250                1255                1260

gag ata  ggg atg tac gcc ctc  ctg ggg gtg ttc tgc  ctg gcc atc      3834
Glu Ile  Gly Met Tyr Ala Leu  Leu Gly Val Phe Cys  Leu Ala Ile
    1265                1270                1275

ctc gtc  ttc ctg atc aac tgc  gcc acc ttt gcc ctg  aag tac agg      3879
Leu Val  Phe Leu Ile Asn Cys  Ala Thr Phe Ala Leu  Lys Tyr Arg
    1280                1285                1290

cac aag  caa gtg ccc ctg gaa  ggt cag gcc tcc atg  acc cac tct      3924
His Lys  Gln Val Pro Leu Glu  Gly Gln Ala Ser Met  Thr His Ser
    1295                1300                1305

cac gac  tgg gtg tgg ctt ggc  aat gag gcc gaa ctc  ctg gag agc      3969
His Asp  Trp Val Trp Leu Gly  Asn Glu Ala Glu Leu  Leu Glu Ser
    1310                1315                1320

atg ggg  gat gcg ccg ccg ccc  cag gac gag cac acc  acc atc ata      4014
Met Gly  Asp Ala Pro Pro Pro  Gln Asp Glu His Thr  Thr Ile Ile
    1325                1330                1335

gac cgc  gga ccg ggg gcc tgc  gag gag agc aac cat  ctc ctg ctc      4059
Asp Arg  Gly Pro Gly Ala Cys  Glu Glu Ser Asn His  Leu Leu Leu
    1340                1345                1350

aat ggt  ggc tcc cac aag cac  gtg cag agc cag att  cac agg tca      4104
Asn Gly  Gly Ser His Lys His  Val Gln Ser Gln Ile  His Arg Ser
    1355                1360                1365

gcc gac  tcc ggg ggg cgg cag  ggc aga gaa cag aag  cag gac ccc      4149
Ala Asp  Ser Gly Gly Arg Gln  Gly Arg Glu Gln Lys  Gln Asp Pro
    1370                1375                1380

ctg cac  tcg ccc acc tcc aag  agg aag aag gtg aaa  ttt acc acc      4194
Leu His  Ser Pro Thr Ser Lys  Arg Lys Lys Val Lys  Phe Thr Thr
    1385                1390                1395

ttt acc  acc atc ccc ccg gac  gac agc tgc ccc acg  gtg aac tcc      4239
Phe Thr  Thr Ile Pro Pro Asp  Asp Ser Cys Pro Thr  Val Asn Ser
    1400                1405                1410

atc gtc  agc agc aat gat gag  gac atc aaa tgg gtg  tgt caa gac      4284
Ile Val  Ser Ser Asn Asp Glu  Asp Ile Lys Trp Val  Cys Gln Asp
    1415                1420                1425

gtg gct  gtg ggt gcc ccc aag  gaa ctt aga aac tat  ctg gag aaa      4329
Val Ala  Val Gly Ala Pro Lys  Glu Leu Arg Asn Tyr  Leu Glu Lys
    1430                1435                1440

ctc aaa  gat aag gct tag gcccctctag ccaaagggcc ctgcccagat          4377
Leu Lys  Asp Lys Ala
    1445

gccttccttg tactggaaac tggcccaagt ggggcagaag gcgttgtcag tggggttaag   4437

aagggacggt cccagggtcc atgctagacc agttggaaag ttttgaagtc aggaaaagac   4497

gtttttgtat caagggattt ttagcagtta atggtggtgg atttttaaag gtcaggggaa   4557

taaagtctgg ggcatgggga gtgcagacca agttactgaa ctgcacaggc aaaattagga   4617

aggttatttt atgagtcaaa acatactaca gacaagctac caaaaattat ttgttaaaaa   4677

atgcaacaag acaaataaaa agagaaataa tcatctgttt atatttctaa taaaggagca   4737

aaatataaaa ataggacctg ctaagagaca ttttccattc taattcacga ttcacttttc   4797
```

-continued

```
caaggacagc cttcaactgt caccacacag ctgggggga gtcatttctt aacaagggat   4857

gcctcttggg atagaactag ggagttttaa atctttactt gatcatcttt tattttcttt   4917

tccacttttt ccttttttct ctctctctgt gtcctagact tccattgcat ttatatttaa   4977

tgtttatttc tgagaatcaa gcagtatatt tttcctaaat gaaacataaa ttatattcct   5037

attcattaga taggttccta ggaacaatgc caattaatcc attgtttaag tagtaacttg   5097

aatgtttttc tatatccctc cagctttgtt gatagtggcg ggttttgtac aattggaggg   5157

agccctcaga gccttctggg ggaggagagg aactgtcctt aatccatcac cactaccata   5217

gggcaaagcc agcaggtgtg gccctgtgag ggctgtaca gacgggatgt ggccaggaga   5277

acagagcccc acctggacca cctgacccct cgggattcca cccctgtcat cgtggggatg   5337

ttcctatatg ggagaaagtt gggttaaatc aaaaaagagg ccacgcccag gtgtaatcag   5397

agccaacctg gtgggcttgg tctatcacaa gacataactg atgctgaaca tgaacaaaga   5457

taaaaactgt ttggagggtt tttgagttgt ttttcttatg ttgttgggtg gggtatacca   5517

gcataaactc taaagataaa atctatgtta gattgtcaat caactgtgtt tttgaacagc   5577

ataattgtgt agcagcacat tgcaaaaatg cattcatcca aagcgacaca tgtggcaacg   5637

tagaccacgc cagtgaaata agccccttcg tgatcacctg actccagttc tccgtgtgct   5697

ccattggctg cggctgcagg aggaagatgc ctgacagccc tcatgctctc cgcagggggg   5757

cgctcacaaa gatgccaggg gtgtttattg tgtttatttt tttaattact aaaatcagta   5817

gctaagaaag ggtccttgaa gcctcctaac ctgggttgga cctttgaaaa atatatttgt   5877

agcacatatt atagatggaa agaagaagat atttatttat acctgtgatg ccaattgtca   5937

ttaaaaggct tttcatggct tgac                                          5961
```

<210> SEQ ID NO 4
<211> LENGTH: 1448
<212> TYPE: PRT
<213> ORGANISM: Homo sapiens

<400> SEQUENCE: 4

```
Met Ser Leu Gly Leu Ile Ser Ile Phe Gln Lys Pro Ser Ser Gly Ser
1               5                   10                  15

Val Thr Gly Lys Ser Pro Glu Pro Asp Ser Lys Val Cys Asp Cys Leu
            20                  25                  30

Ile His Arg Gln Ile Pro Leu Ala Leu Pro Trp His His His His Trp
        35                  40                  45

Ala Ala Leu Pro Leu Thr Arg Tyr Glu Lys Ser Gly Lys Ala Lys Gln
    50                  55                  60

Lys Leu Lys Val Thr Thr Leu Gln Ser Trp Ala Arg Trp Lys Gly Gln
65                  70                  75                  80

Ala Leu Thr Leu Ser Leu Ser Leu Ser His Leu His Pro His Arg Ala
                85                  90                  95

Lys Val Lys Lys Gly Val Asn Ile Leu Ser Ala Gln Thr Arg Glu Pro
            100                 105                 110

Arg Gln Trp Gly Val Lys Gln Glu Val Gly Ser Gly Gly Lys His Val
        115                 120                 125

Thr Ala Thr Val Ala Cys Gln Arg Leu Gly Pro Ser Pro Arg Asn Arg
    130                 135                 140

Thr His Ser Ser Val Leu Pro Leu Met Cys Asn Glu Lys Lys Lys Ile
145                 150                 155                 160

Trp Cys Pro Lys Gln Phe Thr Asn Ser Asn Ala Asn Arg His His His
                165                 170                 175
```

-continued

```
Tyr Pro Lys Lys Asp Phe Ser Ala Ser Gly Gly Gly Ser Ile Phe Arg
            180                 185                 190

Leu Pro Leu His Leu Leu Ser Ser Val Cys Ile Phe Phe Gln Asn Gln
        195                 200                 205

Val Ser Gly Ser Gly Gly Val Cys Ala Gln Asp Trp Leu Arg Ala Met
    210                 215                 220

Trp Glu Thr Phe Thr Leu Thr Ser Lys Leu Leu Lys Glu Ser Lys Lys
225                 230                 235                 240

Glu Thr Leu Ser Val His Val Ile Gln Pro Tyr Ser Arg Asp Ala Arg
                245                 250                 255

Cys Leu Leu Glu Thr Phe Pro Gly Ile Leu His Gln Ser Pro Arg Gly
            260                 265                 270

Ala Val Thr Asp Thr Cys Thr Glu Phe Ala Ala Lys Gln Leu Ser Gly
        275                 280                 285

Asn Ser Thr Val Pro Leu Leu Glu Gly Leu Arg Lys Lys Ala Ser Cys
    290                 295                 300

Phe Lys Asp Ser Ala Ala Pro His Phe His His Thr Ser Pro Pro Lys
305                 310                 315                 320

Gln Ser Thr Ser His Arg Arg Ser Cys Ile Ser Ser Arg Cys Tyr Lys
                325                 330                 335

His Ala Ser Glu Leu Arg Phe Leu Trp Leu Ser Ser Cys Cys Ile Pro
            340                 345                 350

Lys Leu Leu Asn Ser Arg Ala Ser Ile Val Leu Gln Gly Leu Ser Ala
        355                 360                 365

Ala Gly Glu Lys Ser Lys Ser Gly Arg Asn Ser Ser Ser Thr Met Met
    370                 375                 380

Phe Ser Asp Ser Tyr Ile Asn Pro Glu Ile Trp Val Arg Trp Val Pro
385                 390                 395                 400

Tyr Ser Arg Lys Gln Cys Asp Met Lys Thr Glu Pro Thr Leu Glu Arg
                405                 410                 415

Leu Val Glu Arg Val Val Lys Pro Asp Arg Leu Leu Ser Thr Arg Glu
            420                 425                 430

Glu Trp Lys Gly Glu Arg Lys Lys Ile Gln Gly Leu Lys Asn Ile Tyr
        435                 440                 445

Thr Ser Pro Pro Pro His Pro Pro His Thr His Thr Val Val Thr Leu
    450                 455                 460

Arg Lys Asp Ala Arg Arg Ile Leu Thr Leu Arg Leu Arg Cys Gly Asp
465                 470                 475                 480

Thr His Thr Ala Asn Pro Trp Ser Ser Gly Phe Asp Leu Asp Met Pro
                485                 490                 495

Asp Ser Cys Met Gly Ile Gly Val Glu Leu Val Trp Val Pro Val Leu
            500                 505                 510

Leu Gln Gln Leu Cys Ala Leu Gly Gln Val Leu Ile Leu Gln Glu Ala
        515                 520                 525

Gly Ala Tyr Phe Thr Asn Ser Tyr Gly Leu Ser Ala Cys Asp Leu Lys
    530                 535                 540

Asn Ala Pro Ser Cys Pro Ser Arg Leu Leu Lys Gly Thr Ser Phe Gly
545                 550                 555                 560

Gly Asp Cys Ile Pro His Ile Arg Gly Gly Ser Trp Tyr Arg Gly Ser
                565                 570                 575

Arg Ala Ser Leu Ile Pro Phe Ser Val His His Thr Gly Leu Pro Leu
            580                 585                 590

Ser Gln Val Leu Val Gln Arg Trp His Gly Leu Thr Asp Pro Val Phe
```

-continued

```
        595                 600                 605

Ser Pro Ser His Trp Ala Ala Pro Phe Ala Gly Pro Val Gly Cys Pro
    610                 615                 620

Phe Arg Arg Ser Trp Tyr Arg Gly Gly Arg Ala Ser Leu Ile Pro Cys
625                 630                 635                 640

Ser Leu Arg His Thr Gly Leu Pro Leu Leu Gln Val Leu Val Gln Arg
                645                 650                 655

Arg Gln Gly Phe Thr Asp Pro Cys Ser Val His Arg Thr Gly Leu Pro
            660                 665                 670

Leu Leu Gln Val Leu Val Gln Arg His Gln Gly Phe Thr Asp Pro Met
        675                 680                 685

Ser Ser Pro Ser His Trp Ala Ala Pro Phe Ala Gly Pro Asp Pro Arg
    690                 695                 700

Leu Arg Gln Leu Val Val Lys Asn His Leu Ser Ser Ser Leu Phe Asn
705                 710                 715                 720

Glu Val Val Gln Met Asn Phe Glu Ile Ala Ser Phe Ser Ser Leu Ser
                725                 730                 735

Gly Thr Gln Pro Ile Thr Trp Gln Val Glu Tyr Pro Arg Lys Gly Thr
            740                 745                 750

Thr Asp Ile Ala Val Ser Glu Ile Phe Val Ser Gln Lys Asp Leu Val
        755                 760                 765

Gly Ile Val Pro Leu Ala Met Asp Thr Glu Ile Leu Asn Thr Ala Val
    770                 775                 780

Leu Thr Gly Lys Thr Val Ala Met Pro Ile Lys Val Val Ser Val Glu
785                 790                 795                 800

Glu Asn Ser Ala Val Met Asp Ile Ser Glu Ser Val Glu Cys Lys Ser
                805                 810                 815

Thr Asp Glu Asp Val Ile Lys Val Ser Glu Arg Cys Asp Tyr Ile Phe
            820                 825                 830

Val Asn Gly Lys Glu Ile Lys Gly Lys Met Asp Ala Val Val Asn Phe
        835                 840                 845

Thr Tyr Gln Tyr Leu Ser Ala Pro Leu Cys Val Thr Val Trp Val Pro
    850                 855                 860

Arg Leu Pro Leu Gln Ile Glu Val Ser Asp Thr Glu Leu Ser Gln Ile
865                 870                 875                 880

Lys Gly Trp Arg Val Pro Ile Val Thr Asn Lys Arg Pro Thr Arg Glu
                885                 890                 895

Ser Glu Asp Glu Asp Glu Glu Glu Arg Arg Gly Arg Gly Cys Ala Leu
            900                 905                 910

Gln Tyr Gln His Ala Thr Val Arg Val Leu Thr Gln Phe Val Ser Glu
        915                 920                 925

Gly Ala Gly Pro Trp Gly Gln Pro Asn Tyr Leu Leu Ser Pro Asn Trp
    930                 935                 940

Gln Phe Asp Ile Thr His Leu Val Ala Asp Phe Met Lys Leu Glu Glu
945                 950                 955                 960

Pro His Val Ala Thr Leu Gln Asp Ser Arg Val Leu Val Gly Arg Glu
                965                 970                 975

Val Gly Met Thr Thr Ile Gln Val Leu Ser Pro Leu Ser Asp Ser Ile
            980                 985                 990

Leu Ala Glu Lys Thr Ile Thr Val  Leu Asp Asp Lys Val  Ser Val Thr
        995                 1000                1005

Asp Leu  Ala Ile Gln Leu Val  Ala Gly Leu Ser Val  Ala Leu Tyr
    1010                 1015                1020
```

-continued

```
Pro Asn  Ala Glu Asn Ser Lys  Ala Val Thr Ala Val  Val Thr Ala
    1025                 1030                 1035

Glu Glu  Val Leu Arg Thr Pro  Lys Gln Glu Ala Val  Phe Ser Thr
    1040                 1045                 1050

Trp Leu  Gln Phe Ser Asp Gly  Ser Val Thr Pro Leu  Asp Ile Tyr
    1055                 1060                 1065

Asp Thr  Lys Asp Phe Ser Leu  Ala Ala Thr Ser Gln  Asp Glu Ala
    1070                 1075                 1080

Val Val  Ser Val Pro Gln Pro  Arg Ser Pro Arg Trp  Pro Val Val
    1085                 1090                 1095

Val Ala  Glu Gly Glu Gly Gln  Gly Pro Leu Ile Arg  Val Asp Met
    1100                 1105                 1110

Thr Ile  Ala Glu Ala Cys Gln  Lys Ser Lys Arg Lys  Ser Ile Leu
    1115                 1120                 1125

Ala Val  Gly Val Gly Asn Val  Arg Val Lys Phe Gly  Gln Asn Asp
    1130                 1135                 1140

Ala Asp  Ser Ser Pro Gly Gly  Asp Tyr Glu Glu Asp  Glu Ile Lys
    1145                 1150                 1155

Asn His  Ala Ser Asp Arg Arg  Gln Lys Gly Gln His  His Glu Arg
    1160                 1165                 1170

Thr Gly  Gln Asp Gly His Leu  Tyr Gly Ser Ser Pro  Val Glu Arg
    1175                 1180                 1185

Glu Glu  Gly Ala Leu Arg Arg  Ala Thr Thr Thr Ala  Arg Ser Leu
    1190                 1195                 1200

Leu Asp  Asn Lys Val Val Lys  Asn Ser Arg Ala Asp  Gly Gly Arg
    1205                 1210                 1215

Leu Ala  Gly Glu Gly Gln Leu  Gln Asn Ile Pro Ile  Asp Phe Thr
    1220                 1225                 1230

Asn Phe  Pro Ala His Val Asp  Leu Pro Lys Ala Gly  Ser Gly Leu
    1235                 1240                 1245

Glu Glu  Asn Asp Leu Val Gln  Thr Pro Arg Gly Leu  Ser Asp Leu
    1250                 1255                 1260

Glu Ile  Gly Met Tyr Ala Leu  Leu Gly Val Phe Cys  Leu Ala Ile
    1265                 1270                 1275

Leu Val  Phe Leu Ile Asn Cys  Ala Thr Phe Ala Leu  Lys Tyr Arg
    1280                 1285                 1290

His Lys  Gln Val Pro Leu Glu  Gly Gln Ala Ser Met  Thr His Ser
    1295                 1300                 1305

His Asp  Trp Val Trp Leu Gly  Asn Glu Ala Glu Leu  Leu Glu Ser
    1310                 1315                 1320

Met Gly  Asp Ala Pro Pro Pro  Gln Asp Glu His Thr  Thr Ile Ile
    1325                 1330                 1335

Asp Arg  Gly Pro Gly Ala Cys  Glu Glu Ser Asn His  Leu Leu Leu
    1340                 1345                 1350

Asn Gly  Gly Ser His Lys His  Val Gln Ser Gln Ile  His Arg Ser
    1355                 1360                 1365

Ala Asp  Ser Gly Gly Arg Gln  Gly Arg Glu Gln Lys  Gln Asp Pro
    1370                 1375                 1380

Leu His  Ser Pro Thr Ser Lys  Arg Lys Lys Val Lys  Phe Thr Thr
    1385                 1390                 1395

Phe Thr  Thr Ile Pro Pro Asp  Asp Ser Cys Pro Thr  Val Asn Ser
    1400                 1405                 1410

Ile Val  Ser Ser Asn Asp Glu  Asp Ile Lys Trp Val  Cys Gln Asp
    1415                 1420                 1425
```

```
Val Ala  Val Gly Ala Pro Lys  Glu Leu Arg Asn Tyr  Leu Glu Lys
    1430                1435                1440

Leu Lys  Asp Lys Ala
    1445


<210> SEQ ID NO 5
<211> LENGTH: 3810
<212> TYPE: DNA
<213> ORGANISM: Homo sapiens
<220> FEATURE:
<221> NAME/KEY: CDS
<222> LOCATION: (1)..(2196)
<223> OTHER INFORMATION:

<400> SEQUENCE: 5

tta ttc aat gag gtt gtg cag atg aac ttt gaa ata gcc agt ttc agc       48
Leu Phe Asn Glu Val Val Gln Met Asn Phe Glu Ile Ala Ser Phe Ser
1               5                   10                  15

agc ctt tca ggg act cag ccc atc acg tgg cag gtg gag tac cca cgg       96
Ser Leu Ser Gly Thr Gln Pro Ile Thr Trp Gln Val Glu Tyr Pro Arg
            20                  25                  30

aag ggg acc aca gac atc gcc ttg tcc gag atc ttt gtc agc cag aag      144
Lys Gly Thr Thr Asp Ile Ala Leu Ser Glu Ile Phe Val Ser Gln Lys
        35                  40                  45

gac ctg gtg ggc atc gtt ccc ttg gct atg gac act gaa att ctg aac      192
Asp Leu Val Gly Ile Val Pro Leu Ala Met Asp Thr Glu Ile Leu Asn
    50                  55                  60

acc gcc gta ctc aca gga aag aca gtt gcc atg cct atc aag gtg gtc      240
Thr Ala Val Leu Thr Gly Lys Thr Val Ala Met Pro Ile Lys Val Val
65                  70                  75                  80

tct gtg gag gag aac agt gcc gtg atg gac atc tca gag tcg gtg gag      288
Ser Val Glu Glu Asn Ser Ala Val Met Asp Ile Ser Glu Ser Val Glu
                85                  90                  95

tgc aag tcc aca gac gag gac gtt atc aaa gtg tct gag cgc tgt gac      336
Cys Lys Ser Thr Asp Glu Asp Val Ile Lys Val Ser Glu Arg Cys Asp
            100                 105                 110

tac atc ttt gtc aat ggc aaa gag atc aaa gga aag atg gat gcg gtg      384
Tyr Ile Phe Val Asn Gly Lys Glu Ile Lys Gly Lys Met Asp Ala Val
        115                 120                 125

gtg aac ttc aca tac cag tac ctg agc gcc ccc ctg tgt gtc acc gtg      432
Val Asn Phe Thr Tyr Gln Tyr Leu Ser Ala Pro Leu Cys Val Thr Val
    130                 135                 140

tgg gtg ccc cgg ctg ccc ctg cag atc gag gtc tct gac acg gag ctc      480
Trp Val Pro Arg Leu Pro Leu Gln Ile Glu Val Ser Asp Thr Glu Leu
145                 150                 155                 160

agc cag ata aag ggc tgg agg gtc ccc att gtg acc aat aag agg ccc      528
Ser Gln Ile Lys Gly Trp Arg Val Pro Ile Val Thr Asn Lys Arg Pro
                165                 170                 175

act cgt gag agc gag gat gag gac gag gag gag cgg cgg ggc cgg ggc      576
Thr Arg Glu Ser Glu Asp Glu Asp Glu Glu Glu Arg Arg Gly Arg Gly
            180                 185                 190

tgc gca ctg caa tac cag cac gcc acc gtg cgg gtc ctc acc cag ttt      624
Cys Ala Leu Gln Tyr Gln His Ala Thr Val Arg Val Leu Thr Gln Phe
        195                 200                 205

gtg tct gag ggc gcc ggt cca tgg ggc cag ccg aac tac ctg ctt agt      672
Val Ser Glu Gly Ala Gly Pro Trp Gly Gln Pro Asn Tyr Leu Leu Ser
    210                 215                 220

cct aac tgg cag ttc gac atc act cac ctg gtg gca gac ttc atg aag      720
Pro Asn Trp Gln Phe Asp Ile Thr His Leu Val Ala Asp Phe Met Lys
225                 230                 235                 240

ctg gag gaa cct cac gtg gcc acc ctc cag gac agc cgg gtc ctg gtt      768
```

```
Leu Glu Glu Pro His Val Ala Thr Leu Gln Asp Ser Arg Val Leu Val
                245                 250                 255

ggg cga gag gtt ggg atg acg acc atc cag gtg ttg tct cca ctg tct      816
Gly Arg Glu Val Gly Met Thr Thr Ile Gln Val Leu Ser Pro Leu Ser
            260                 265                 270

gac tcc atc ctg gca gag aag acg ata acc gtg cta gat gac aaa gtg      864
Asp Ser Ile Leu Ala Glu Lys Thr Ile Thr Val Leu Asp Asp Lys Val
        275                 280                 285

tcg gtg aca gac ttg gcc atc cag ctc gtg gct ggg ctg tct gtc gcc      912
Ser Val Thr Asp Leu Ala Ile Gln Leu Val Ala Gly Leu Ser Val Ala
    290                 295                 300

ctt tac ccc aac gca gaa aac agc aag gcc gta aca gct gtg gtc aca      960
Leu Tyr Pro Asn Ala Glu Asn Ser Lys Ala Val Thr Ala Val Val Thr
305                 310                 315                 320

gct gag gag gtg ctg cgg acc ccc aaa cag gag gct gta ttc agc acg     1008
Ala Glu Glu Val Leu Arg Thr Pro Lys Gln Glu Ala Val Phe Ser Thr
                325                 330                 335

tgg ctg cag ttc agt gat ggc tct gtg acg ccc ctg gac atc tac gac     1056
Trp Leu Gln Phe Ser Asp Gly Ser Val Thr Pro Leu Asp Ile Tyr Asp
            340                 345                 350

acc aag gac ttc tcc ctg gca gcc atc tcc cag gac ggg gct gtc gtg     1104
Thr Lys Asp Phe Ser Leu Ala Ala Ile Ser Gln Asp Gly Ala Val Val
        355                 360                 365

tca gtc ccc cag ccc cgc tct ccc agg tgg ccc gtt gtg gtg gcc gaa     1152
Ser Val Pro Gln Pro Arg Ser Pro Arg Trp Pro Val Val Val Ala Glu
    370                 375                 380

ggg gaa ggc cag ggc cca ctg atc cga gtg gac atg acg atc gcc gag     1200
Gly Glu Gly Gln Gly Pro Leu Ile Arg Val Asp Met Thr Ile Ala Glu
385                 390                 395                 400

gcc tgc cag aaa tct aaa cgc aag agc atc ctg gct gtg ggc gtc ggc     1248
Ala Cys Gln Lys Ser Lys Arg Lys Ser Ile Leu Ala Val Gly Val Gly
                405                 410                 415

aac gtc agg gtc aag ttc gga cag aac gat gct gac tcc agc ccc ggc     1296
Asn Val Arg Val Lys Phe Gly Gln Asn Asp Ala Asp Ser Ser Pro Gly
            420                 425                 430

agg gac tat gag gaa gat gag atc aag aac cac gcc agc gac cgc cgg     1344
Arg Asp Tyr Glu Glu Asp Glu Ile Lys Asn His Ala Ser Asp Arg Arg
        435                 440                 445

cag aag ggc cag cac cat gag cgc aca ggc cag gat ggg cac ctc tat     1392
Gln Lys Gly Gln His His Glu Arg Thr Gly Gln Asp Gly His Leu Tyr
    450                 455                 460

ggc agc tct ccc gtg gag cgt gag gaa ggg gct ctc cga aga gcc act     1440
Gly Ser Ser Pro Val Glu Arg Glu Glu Gly Ala Leu Arg Arg Ala Thr
465                 470                 475                 480

acc acg gcc agg tcc ctg ctg gac aac aaa gtg gtg aag aac agt cgg     1488
Thr Thr Ala Arg Ser Leu Leu Asp Asn Lys Val Val Lys Asn Ser Arg
                485                 490                 495

gca gac ggg ggc agg ctg gca gga gag ggg cag ctg cag aac atc ccc     1536
Ala Asp Gly Gly Arg Leu Ala Gly Glu Gly Gln Leu Gln Asn Ile Pro
            500                 505                 510

att gac ttc acc aac ttc cct gcc cac gtg gac ctc ccc aag gcc ggg     1584
Ile Asp Phe Thr Asn Phe Pro Ala His Val Asp Leu Pro Lys Ala Gly
        515                 520                 525

agt ggg ctg gag gaa aac gac ctg gtg cag act ccg cgg ggc ctg agt     1632
Ser Gly Leu Glu Glu Asn Asp Leu Val Gln Thr Pro Arg Gly Leu Ser
    530                 535                 540

gat ctg gag ata ggg atg tac gcc ctc ctg ggg gtg ttc tgc ctg gcc     1680
Asp Leu Glu Ile Gly Met Tyr Ala Leu Leu Gly Val Phe Cys Leu Ala
545                 550                 555                 560

atc ctc gtc ttc ctg atc aac tgc gcc acc ttt gcc ctg aag tac agg     1728
```

-continued

```
Ile Leu Val Phe Leu Ile Asn Cys Ala Thr Phe Ala Leu Lys Tyr Arg
                565                 570                 575

cac aag caa gtg ccc ctg gaa ggt cag gcc tcc atg acc cac tct cac     1776
His Lys Gln Val Pro Leu Glu Gly Gln Ala Ser Met Thr His Ser His
            580                 585                 590

gac tgg gtg tgg ctt ggc aat gag gcc gaa ctc ctg gag agc atg ggg     1824
Asp Trp Val Trp Leu Gly Asn Glu Ala Glu Leu Leu Glu Ser Met Gly
        595                 600                 605

gat gca ccg ccg ccc cag gac gag cac acc acc atc ata gac cgc gga     1872
Asp Ala Pro Pro Pro Gln Asp Glu His Thr Thr Ile Ile Asp Arg Gly
    610                 615                 620

ccg ggg gcc tgc gag gag agc aac cat ctc ctg ctc aat ggt ggc tcc     1920
Pro Gly Ala Cys Glu Glu Ser Asn His Leu Leu Leu Asn Gly Gly Ser
625                 630                 635                 640

cac aag cac gtg cag agc cag att cac agg tca gcc gac tcc ggg ggg     1968
His Lys His Val Gln Ser Gln Ile His Arg Ser Ala Asp Ser Gly Gly
                645                 650                 655

cgg cag ggc aga gaa cag aag cag gac ccc ctg cac tcg ccc acc tcc     2016
Arg Gln Gly Arg Glu Gln Lys Gln Asp Pro Leu His Ser Pro Thr Ser
            660                 665                 670

aag agg aag aag gtg aaa ttt acc acc ttt acc acc atc ccc ccg gac     2064
Lys Arg Lys Lys Val Lys Phe Thr Thr Phe Thr Thr Ile Pro Pro Asp
        675                 680                 685

gac agc tgc ccc acg gtg aac tcc atc gtc agc agc aat gat gag gac     2112
Asp Ser Cys Pro Thr Val Asn Ser Ile Val Ser Ser Asn Asp Glu Asp
    690                 695                 700

atc aaa tgg gtg tgt caa gac gtg gct gtg ggt gcc ccc aag gaa ctt     2160
Ile Lys Trp Val Cys Gln Asp Val Ala Val Gly Ala Pro Lys Glu Leu
705                 710                 715                 720

aga aac tat ctg gag aaa ctc aaa gat aag gct tag gcccctctag          2206
Arg Asn Tyr Leu Glu Lys Leu Lys Asp Lys Ala
                725                 730

ccaaagggcc ctgcccagat gccttccttg tactggaaac tggcccaagt ggggcagaag   2266

gcgttgtcag tggggttaag aagggacggt cccagggtcc atgctagacc agttggaaag   2326

ttttgaagtc aggaaaagac gtttttgtat caagggattt ttagcagtta atggtggtgg   2386

atttttaaag gtcaggggaa taaagtctgg ggcatgggga gtgcagacca agttactgaa   2446

ctgcacaggc aaaattagga aggttatttt atgagtcaaa acatactaca gacaagctac   2506

caaaaattat ttgttaaaaa atgcaacaag acaaataaaa agagaaataa tcatctgttt   2566

atatttctaa taaaggagca aaatataaaa ataggacctg ctaagagaca ttttccattc   2626

taattcacga ttcacttttc caaggacagc cttcaactgt caccacacag ctgggggga    2686

gtcatttctt aacaagggat gcctcttggg atagaactag ggagttttaa atctttactt   2746

gatcatcttt tattttcttt tccacttttt ccttttctct ctctctctgt gtcctagact   2806

tccattgcat ttatatttaa tgtttatttc tgagaatcaa gcagtatatt tttcctaaat   2866

gaaacataaa ttatattcct attcattaga taggttccta ggaacaatgc caattaatcc   2926

attgtttaag tagtaacttg aatgtttttc tatatccctc cagctttgtt gatagtggcg   2986

ggttttgtac aattggaggg agccctcaga gccttctggg ggaggagagg aactgtcctt   3046

aatccatcac cactaccata gggcaaagcc agcaggtgtg gccctgtgag ggctgtaca    3106

gacgggatgt ggccaggaga acagagcccc acctggacca cctgacccct cgggattcca   3166

cccctgtcat cgtggggatg ttcctatata ggagaaagtt gggttaaatc aaaaaagagg   3226

ccacgcccag gtgtaatcag agccaacctg gtgggctggg tctatcacaa gacataactg   3286

atgctgaaca tgaacaaaga taaaaactgt ttggagggtt tttgagttgt ttttcttatg   3346
```

-continued

```
ttgttgggtg gggtatacca gcataaactc taaagataaa atctatgtta gattgtcaat   3406

caactgtgtt tttgaacagc ataattgtgt agcagcacat tgcaaaaatg cattcatcca   3466

aagcgacaca tgtggcaacg tagaccacgc cagtgaaata agccccttcg tgatcacctg   3526

actccagttc tccgtgtgct ccattggctg cggctgcagg aggaagatgc ctgacagccc   3586

tcatgctctc cgcagggggg cgctcacaaa gatgccaggg gtgtttattg tgtttatttt   3646

tttaattact aaaatcagta gctaagaaag ggtccttgaa gcctcctaac ctgggttgga   3706

cctttgaaaa atatatttgt agcacatatt atagatggaa agaagaagat atttatttat   3766

acctgtgatg ccaattgtca ttaaaaggct tttcatggct tgac                    3810


<210> SEQ ID NO 6
<211> LENGTH: 731
<212> TYPE: PRT
<213> ORGANISM: Homo sapiens

<400> SEQUENCE: 6

Leu Phe Asn Glu Val Val Gln Met Asn Phe Glu Ile Ala Ser Phe Ser
1               5                   10                  15

Ser Leu Ser Gly Thr Gln Pro Ile Thr Trp Gln Val Glu Tyr Pro Arg
            20                  25                  30

Lys Gly Thr Thr Asp Ile Ala Leu Ser Glu Ile Phe Val Ser Gln Lys
        35                  40                  45

Asp Leu Val Gly Ile Val Pro Leu Ala Met Asp Thr Glu Ile Leu Asn
    50                  55                  60

Thr Ala Val Leu Thr Gly Lys Thr Val Ala Met Pro Ile Lys Val Val
65                  70                  75                  80

Ser Val Glu Glu Asn Ser Ala Val Met Asp Ile Ser Glu Ser Val Glu
                85                  90                  95

Cys Lys Ser Thr Asp Glu Asp Val Ile Lys Val Ser Glu Arg Cys Asp
            100                 105                 110

Tyr Ile Phe Val Asn Gly Lys Glu Ile Lys Gly Lys Met Asp Ala Val
        115                 120                 125

Val Asn Phe Thr Tyr Gln Tyr Leu Ser Ala Pro Leu Cys Val Thr Val
    130                 135                 140

Trp Val Pro Arg Leu Pro Leu Gln Ile Glu Val Ser Asp Thr Glu Leu
145                 150                 155                 160

Ser Gln Ile Lys Gly Trp Arg Val Pro Ile Val Thr Asn Lys Arg Pro
                165                 170                 175

Thr Arg Glu Ser Glu Asp Glu Asp Glu Glu Glu Arg Arg Gly Arg Gly
            180                 185                 190

Cys Ala Leu Gln Tyr Gln His Ala Thr Val Arg Val Leu Thr Gln Phe
        195                 200                 205

Val Ser Glu Gly Ala Gly Pro Trp Gly Gln Pro Asn Tyr Leu Leu Ser
    210                 215                 220

Pro Asn Trp Gln Phe Asp Ile Thr His Leu Val Ala Asp Phe Met Lys
225                 230                 235                 240

Leu Glu Glu Pro His Val Ala Thr Leu Gln Asp Ser Arg Val Leu Val
                245                 250                 255

Gly Arg Glu Val Gly Met Thr Thr Ile Gln Val Leu Ser Pro Leu Ser
            260                 265                 270

Asp Ser Ile Leu Ala Glu Lys Thr Ile Thr Val Leu Asp Asp Lys Val
        275                 280                 285

Ser Val Thr Asp Leu Ala Ile Gln Leu Val Ala Gly Leu Ser Val Ala
```

```
    290                 295                 300

Leu Tyr Pro Asn Ala Glu Asn Ser Lys Ala Val Thr Ala Val Val Thr
305                 310                 315                 320

Ala Glu Glu Val Leu Arg Thr Pro Lys Gln Glu Ala Val Phe Ser Thr
                325                 330                 335

Trp Leu Gln Phe Ser Asp Gly Ser Val Thr Pro Leu Asp Ile Tyr Asp
            340                 345                 350

Thr Lys Asp Phe Ser Leu Ala Ala Ile Ser Gln Asp Gly Ala Val Val
        355                 360                 365

Ser Val Pro Gln Pro Arg Ser Pro Arg Trp Pro Val Val Val Ala Glu
    370                 375                 380

Gly Glu Gly Gln Gly Pro Leu Ile Arg Val Asp Met Thr Ile Ala Glu
385                 390                 395                 400

Ala Cys Gln Lys Ser Lys Arg Lys Ser Ile Leu Ala Val Gly Val Gly
                405                 410                 415

Asn Val Arg Val Lys Phe Gly Gln Asn Asp Ala Asp Ser Ser Pro Gly
            420                 425                 430

Arg Asp Tyr Glu Glu Asp Glu Ile Lys Asn His Ala Ser Asp Arg Arg
        435                 440                 445

Gln Lys Gly Gln His His Glu Arg Thr Gly Gln Asp Gly His Leu Tyr
    450                 455                 460

Gly Ser Ser Pro Val Glu Arg Glu Glu Gly Ala Leu Arg Arg Ala Thr
465                 470                 475                 480

Thr Thr Ala Arg Ser Leu Leu Asp Asn Lys Val Val Lys Asn Ser Arg
                485                 490                 495

Ala Asp Gly Gly Arg Leu Ala Gly Glu Gly Gln Leu Gln Asn Ile Pro
            500                 505                 510

Ile Asp Phe Thr Asn Phe Pro Ala His Val Asp Leu Pro Lys Ala Gly
        515                 520                 525

Ser Gly Leu Glu Glu Asn Asp Leu Val Gln Thr Pro Arg Gly Leu Ser
    530                 535                 540

Asp Leu Glu Ile Gly Met Tyr Ala Leu Leu Gly Val Phe Cys Leu Ala
545                 550                 555                 560

Ile Leu Val Phe Leu Ile Asn Cys Ala Thr Phe Ala Leu Lys Tyr Arg
                565                 570                 575

His Lys Gln Val Pro Leu Glu Gly Gln Ala Ser Met Thr His Ser His
            580                 585                 590

Asp Trp Val Trp Leu Gly Asn Glu Ala Glu Leu Leu Glu Ser Met Gly
        595                 600                 605

Asp Ala Pro Pro Pro Gln Asp Glu His Thr Thr Ile Ile Asp Arg Gly
    610                 615                 620

Pro Gly Ala Cys Glu Glu Ser Asn His Leu Leu Leu Asn Gly Gly Ser
625                 630                 635                 640

His Lys His Val Gln Ser Gln Ile His Arg Ser Ala Asp Ser Gly Gly
                645                 650                 655

Arg Gln Gly Arg Glu Gln Lys Gln Asp Pro Leu His Ser Pro Thr Ser
            660                 665                 670

Lys Arg Lys Lys Val Lys Phe Thr Thr Phe Thr Thr Ile Pro Pro Asp
        675                 680                 685

Asp Ser Cys Pro Thr Val Asn Ser Ile Val Ser Ser Asn Asp Glu Asp
    690                 695                 700

Ile Lys Trp Val Cys Gln Asp Val Ala Val Gly Ala Pro Lys Glu Leu
705                 710                 715                 720
```

```
Arg Asn Tyr Leu Glu Lys Leu Lys Asp Lys Ala
                725                 730


<210> SEQ ID NO 7
<211> LENGTH: 3804
<212> TYPE: DNA
<213> ORGANISM: Homo sapiens
<220> FEATURE:
<221> NAME/KEY: CDS
<222> LOCATION: (3)..(2174)
<223> OTHER INFORMATION:

<400> SEQUENCE: 7

tg aac ttt gaa ata gcc agt ttc agc agc ctt tca ggg act cag ccc          47
   Asn Phe Glu Ile Ala Ser Phe Ser Ser Leu Ser Gly Thr Gln Pro
   1               5                   10                  15

atc acg tgg cag gtg gag tac cca cgg aag ggg acc aca gac atc gcc         95
Ile Thr Trp Gln Val Glu Tyr Pro Arg Lys Gly Thr Thr Asp Ile Ala
                20                  25                  30

gtg tcc gag atc ttt gtc agc cag aag gac ctg gtg ggc atc gtt ccc        143
Val Ser Glu Ile Phe Val Ser Gln Lys Asp Leu Val Gly Ile Val Pro
            35                  40                  45

ttg gct atg gac act gaa att ctg aac acc gcc gta ctc aca gga aag        191
Leu Ala Met Asp Thr Glu Ile Leu Asn Thr Ala Val Leu Thr Gly Lys
        50                  55                  60

aca gtt gcc atg cct atc aag gtg gtc tct gtg gag gag aac agt gcc        239
Thr Val Ala Met Pro Ile Lys Val Val Ser Val Glu Glu Asn Ser Ala
    65                  70                  75

gtg atg gac atc tca gag tcg gtg gag tgc aag tcc aca gac gag gac        287
Val Met Asp Ile Ser Glu Ser Val Glu Cys Lys Ser Thr Asp Glu Asp
80                  85                  90                  95

gtt atc aaa gtg tct gag cgc tgt gac tac atc ttt gtc aat ggc aaa        335
Val Ile Lys Val Ser Glu Arg Cys Asp Tyr Ile Phe Val Asn Gly Lys
                100                 105                 110

gag atc aaa gga aag atg gat gcg gtg gtg aac ttc aca tac cag tac        383
Glu Ile Lys Gly Lys Met Asp Ala Val Val Asn Phe Thr Tyr Gln Tyr
            115                 120                 125

ctg agc gcc ccc ctg tgt gtc acc gtg tgg gtg ccc cgg ctg ccc ctg        431
Leu Ser Ala Pro Leu Cys Val Thr Val Trp Val Pro Arg Leu Pro Leu
        130                 135                 140

cag atc gag gtc tct gac acg gag ctc agc cag ata aag ggc tgg agg        479
Gln Ile Glu Val Ser Asp Thr Glu Leu Ser Gln Ile Lys Gly Trp Arg
    145                 150                 155

gtc ccc att gtg acc aat aag agg ccc act cgt gag agc gag gat gag        527
Val Pro Ile Val Thr Asn Lys Arg Pro Thr Arg Glu Ser Glu Asp Glu
160                 165                 170                 175

gac gag gag gag cgg cgg ggc cgg ggc tgc gca ctg caa tac cag cac        575
Asp Glu Glu Glu Arg Arg Gly Arg Gly Cys Ala Leu Gln Tyr Gln His
                180                 185                 190

gcc acc gtg cgg gtc ctc acc cag ttt gtg tct gag ggc gcc ggt cca        623
Ala Thr Val Arg Val Leu Thr Gln Phe Val Ser Glu Gly Ala Gly Pro
            195                 200                 205

tgg ggc cag ccg aac tac ctg ctt agt cct aac tgg cag ttc gac atc        671
Trp Gly Gln Pro Asn Tyr Leu Leu Ser Pro Asn Trp Gln Phe Asp Ile
        210                 215                 220

act cac ctg gtg gca gac ttc atg aag ctg gag gaa cct cac gtg gcc        719
Thr His Leu Val Ala Asp Phe Met Lys Leu Glu Glu Pro His Val Ala
    225                 230                 235

acc ctc cag gac agc cgg gtc ctg gtt ggg cga gag gtt ggg atg acg        767
Thr Leu Gln Asp Ser Arg Val Leu Val Gly Arg Glu Val Gly Met Thr
240                 245                 250                 255

acc atc cag gtg ttg tct cca ctg tct gac tcc atc ctg gca gag aag        815
```

-continued

```
Thr Ile Gln Val Leu Ser Pro Leu Ser Asp Ser Ile Leu Ala Glu Lys
                260                 265                 270

acg ata acc gtg cta gat gac aaa gtg tcg gtg aca gac ttg gcc atc      863
Thr Ile Thr Val Leu Asp Asp Lys Val Ser Val Thr Asp Leu Ala Ile
            275                 280                 285

cag ctc gtg gct ggg ctg tct gtc gcc ctt tac ccc aac gca gaa aac      911
Gln Leu Val Ala Gly Leu Ser Val Ala Leu Tyr Pro Asn Ala Glu Asn
        290                 295                 300

agc aag gcc gta aca gct gtg gtc aca gct gag gag gtg ctg cgg acc      959
Ser Lys Ala Val Thr Ala Val Val Thr Ala Glu Glu Val Leu Arg Thr
    305                 310                 315

ccc aaa cag gag gct gta ttc agc acg tgg ctg cag ttc agt gat ggc     1007
Pro Lys Gln Glu Ala Val Phe Ser Thr Trp Leu Gln Phe Ser Asp Gly
320                 325                 330                 335

tct gtg acg ccc ctg gac atc tac gac acc aag gac ttc tcc ctg gca     1055
Ser Val Thr Pro Leu Asp Ile Tyr Asp Thr Lys Asp Phe Ser Leu Ala
                340                 345                 350

gcc acc tcc cag gac gag gct gtc gtg tca gtc ccc cag ccc cgc tct     1103
Ala Thr Ser Gln Asp Glu Ala Val Val Ser Val Pro Gln Pro Arg Ser
            355                 360                 365

ccc agg tgg ccc gtt gtg gtg gcc gaa ggg gaa ggc cag ggc cca ctg     1151
Pro Arg Trp Pro Val Val Val Ala Glu Gly Glu Gly Gln Gly Pro Leu
        370                 375                 380

atc cga gtg gac atg acg atc gcc gag gcc tgc cag aaa tct aaa cgc     1199
Ile Arg Val Asp Met Thr Ile Ala Glu Ala Cys Gln Lys Ser Lys Arg
    385                 390                 395

aag agc atc ctg gct gtg ggc gtc ggc aac gtc agg gtc aag ttc gga     1247
Lys Ser Ile Leu Ala Val Gly Val Gly Asn Val Arg Val Lys Phe Gly
400                 405                 410                 415

cag aac gat gct gac tcc agc ccc ggc agg gac tat gag gaa gat gag     1295
Gln Asn Asp Ala Asp Ser Ser Pro Gly Arg Asp Tyr Glu Glu Asp Glu
                420                 425                 430

atc aag aac cac gcc agc gac cgc cgg cag aag ggc cag cac cat gag     1343
Ile Lys Asn His Ala Ser Asp Arg Arg Gln Lys Gly Gln His His Glu
            435                 440                 445

cgc aca ggc cag gat ggg cac ctc tat ggc agc tct ccc gtg gag cgt     1391
Arg Thr Gly Gln Asp Gly His Leu Tyr Gly Ser Ser Pro Val Glu Arg
        450                 455                 460

gag gaa ggg gct ctc cga aga gcc act acc acg gcc agg tcc ctg ctg     1439
Glu Glu Gly Ala Leu Arg Arg Ala Thr Thr Thr Ala Arg Ser Leu Leu
    465                 470                 475

gac aac aaa gtg gtg aag aac agt cgg gca gac ggg ggc agg ctg gca     1487
Asp Asn Lys Val Val Lys Asn Ser Arg Ala Asp Gly Gly Arg Leu Ala
480                 485                 490                 495

gga gag ggg cag ctg cag aac atc ccc att gac ttc acc aac ttc cct     1535
Gly Glu Gly Gln Leu Gln Asn Ile Pro Ile Asp Phe Thr Asn Phe Pro
                500                 505                 510

gcc cac gtg gac ctc ccc aag gcc ggg agt ggg ctg gag gaa aac gac     1583
Ala His Val Asp Leu Pro Lys Ala Gly Ser Gly Leu Glu Glu Asn Asp
            515                 520                 525

ctg gtg cag act ccg cgg ggc ctg agt gat ctg gag ata ggg atg tac     1631
Leu Val Gln Thr Pro Arg Gly Leu Ser Asp Leu Glu Ile Gly Met Tyr
        530                 535                 540

gcc ctc ctg ggg gtg ttc tgc ctg gcc atc ctc gtc ttc ctg atc aac     1679
Ala Leu Leu Gly Val Phe Cys Leu Ala Ile Leu Val Phe Leu Ile Asn
    545                 550                 555

tgc gcc acc ttt gcc ctg aag tac agg cac aag caa gtg ccc ctg gaa     1727
Cys Ala Thr Phe Ala Leu Lys Tyr Arg His Lys Gln Val Pro Leu Glu
560                 565                 570                 575

ggt cag gcc tcc atg acc cac tct cac gac tgg gtg tgg ctt ggc aat     1775
```

```
Gly Gln Ala Ser Met Thr His Ser His Asp Trp Val Trp Leu Gly Asn
                580                 585                 590

gag gcc gaa ctc ctg gag agc atg ggg gat gca ccg ccg ccc cag gac     1823
Glu Ala Glu Leu Leu Glu Ser Met Gly Asp Ala Pro Pro Pro Gln Asp
            595                 600                 605

gag cac acc acc atc ata gac cgc gga ccg ggg gcc tgc gag gag agc     1871
Glu His Thr Thr Ile Ile Asp Arg Gly Pro Gly Ala Cys Glu Glu Ser
        610                 615                 620

aac cat ctc ctg ctc aat ggt ggc tcc cac aag cac gtg cag agc cag     1919
Asn His Leu Leu Leu Asn Gly Gly Ser His Lys His Val Gln Ser Gln
    625                 630                 635

att cac agg tca gcc gac tcc ggg ggg cgg cag ggc aga gaa cag aag     1967
Ile His Arg Ser Ala Asp Ser Gly Gly Arg Gln Gly Arg Glu Gln Lys
640                 645                 650                 655

cag gac ccc ctg cac tcg ccc acc tcc aag agg aag aag gtg aaa ttt     2015
Gln Asp Pro Leu His Ser Pro Thr Ser Lys Arg Lys Lys Val Lys Phe
                660                 665                 670

acc acc ttt acc acc atc ccc ccg gac gac agc tgc ccc acg gtg aac     2063
Thr Thr Phe Thr Thr Ile Pro Pro Asp Asp Ser Cys Pro Thr Val Asn
            675                 680                 685

tcc atc gtc agc agc aat gat gag gac atc aaa tgg gtg tgt caa gac     2111
Ser Ile Val Ser Ser Asn Asp Glu Asp Ile Lys Trp Val Cys Gln Asp
        690                 695                 700

gtg gct gtg ggt gcc ccc aag gaa ctt aga aac tat ctg gag aaa ctc     2159
Val Ala Val Gly Ala Pro Lys Glu Leu Arg Asn Tyr Leu Glu Lys Leu
    705                 710                 715

aaa gat aag gct tag gcccctctag ccaaagggcc ctgcccagat gccttccttg     2214
Lys Asp Lys Ala
720

tactggaaac tggcccaagt ggggcagaag gcgttgtcag tggggttaag aagggacggt   2274

cccagggtcc atgctagacc agttggaaag ttttgaagtc aggaaaagac gtttttgtat   2334

caagggattt ttagcagtta atggtggtgg atttttaaag gtcaggggaa taaagtctgg   2394

ggcatgggga gtgcagacca agttactgaa ctgcacaggc aaaattagga aggttatttt   2454

atgagtcaaa acatactaca gacaagctac caaaaattat ttgttaaaaa atgcaacaag   2514

acaaataaaa agagaaataa tcatctgttt atatttctaa taaaggagca aaatataaaa   2574

ataggacctg ctaagagaca ttttccattc taattcacga ttcacttttc caaggacagc   2634

cttcaactgt caccacacag ctgggggga gtcatttctt aacaagggat gcctcttggg   2694

atagaactag ggagttttaa atctttactt gatcatcttt tattttcttt tccacttttt   2754

ccttttctct ctctctctgt gtcctagact tccattgcat ttatatttaa tgtttatttc   2814

tgagaatcaa gcagtatatt tttcctaaat gaaacataaa ttatattcct attcattaga   2874

taggttccta ggaacaatgc caattaatcc attgtttaag tagtaacttg aatgtttttc   2934

tatatccctc cagctttgtt gatagtggcg ggttttgtac aattggaggg agccctcaga   2994

gccttctggg ggaggagagg aactgtcctt aatccatcac cactaccata gggcaaagcc   3054

agcaggtgtg gccctgtgag ggctgtaca gacgggatgt ggccaggaga acagagcccc   3114

acctggacca cctgacccct cgggattcca cccctgtcat cgtggggatg ttcctatata   3174

ggagaaagtt gggttaaatc aaaaaagagg ccacgcccag gtgtaatcag agccaacctg   3234

gtgggctggg tctatcacaa gacataactg atgctgaaca tgaacaaaga taaaaactgt   3294

ttggagggtt tttgagttgt ttttcttatg ttgttgggtg gggtatacca gcataaactc   3354

taaagataaa atctatgtta gattgtcaat caactgtgtt tttgaacagc ataattgtgt   3414

agcagcacat tgcaaaaatg cattcatcca aagcgacaca tgtggcaacg tagaccacgc   3474
```

```
cagtgaaata agccccttcg tgatcacctg actccagttc tccgtgtgct ccattggctg   3534

cggctgcagg aggaagatgc ctgacagccc tcatgctctc cgcagggggg cgctcacaaa   3594

gatgccaggg gtgtttattg tgtttatttt tttaattact aaaatcagta gctaagaaag   3654

ggtccttgaa gcctcctaac ctgggttgga cctttgaaaa atatatttgt agcacatatt   3714

atagatggaa agaagaagat atttatttat acctgtgatg ccaattgtca ttaaaaggct   3774

tttcatggct taaaaaaaaa aaaaaaaaaa                                     3804


<210> SEQ ID NO 8
<211> LENGTH: 723
<212> TYPE: PRT
<213> ORGANISM: Homo sapiens

<400> SEQUENCE: 8

Asn Phe Glu Ile Ala Ser Phe Ser Ser Leu Ser Gly Thr Gln Pro Ile
1               5                   10                  15

Thr Trp Gln Val Glu Tyr Pro Arg Lys Gly Thr Thr Asp Ile Ala Val
            20                  25                  30

Ser Glu Ile Phe Val Ser Gln Lys Asp Leu Val Gly Ile Val Pro Leu
        35                  40                  45

Ala Met Asp Thr Glu Ile Leu Asn Thr Ala Val Leu Thr Gly Lys Thr
    50                  55                  60

Val Ala Met Pro Ile Lys Val Val Ser Val Glu Glu Asn Ser Ala Val
65                  70                  75                  80

Met Asp Ile Ser Glu Ser Val Glu Cys Lys Ser Thr Asp Glu Asp Val
                85                  90                  95

Ile Lys Val Ser Glu Arg Cys Asp Tyr Ile Phe Val Asn Gly Lys Glu
            100                 105                 110

Ile Lys Gly Lys Met Asp Ala Val Val Asn Phe Thr Tyr Gln Tyr Leu
        115                 120                 125

Ser Ala Pro Leu Cys Val Thr Val Trp Val Pro Arg Leu Pro Leu Gln
    130                 135                 140

Ile Glu Val Ser Asp Thr Glu Leu Ser Gln Ile Lys Gly Trp Arg Val
145                 150                 155                 160

Pro Ile Val Thr Asn Lys Arg Pro Thr Arg Glu Ser Glu Asp Glu Asp
                165                 170                 175

Glu Glu Glu Arg Arg Gly Arg Gly Cys Ala Leu Gln Tyr Gln His Ala
            180                 185                 190

Thr Val Arg Val Leu Thr Gln Phe Val Ser Glu Gly Ala Gly Pro Trp
        195                 200                 205

Gly Gln Pro Asn Tyr Leu Leu Ser Pro Asn Trp Gln Phe Asp Ile Thr
    210                 215                 220

His Leu Val Ala Asp Phe Met Lys Leu Glu Glu Pro His Val Ala Thr
225                 230                 235                 240

Leu Gln Asp Ser Arg Val Leu Val Gly Arg Glu Val Gly Met Thr Thr
                245                 250                 255

Ile Gln Val Leu Ser Pro Leu Ser Asp Ser Ile Leu Ala Glu Lys Thr
            260                 265                 270

Ile Thr Val Leu Asp Asp Lys Val Ser Val Thr Asp Leu Ala Ile Gln
        275                 280                 285

Leu Val Ala Gly Leu Ser Val Ala Leu Tyr Pro Asn Ala Glu Asn Ser
    290                 295                 300

Lys Ala Val Thr Ala Val Val Thr Ala Glu Glu Val Leu Arg Thr Pro
305                 310                 315                 320
```

```
Lys Gln Glu Ala Val Phe Ser Thr Trp Leu Gln Phe Ser Asp Gly Ser
                325                 330                 335

Val Thr Pro Leu Asp Ile Tyr Asp Thr Lys Asp Phe Ser Leu Ala Ala
            340                 345                 350

Thr Ser Gln Asp Glu Ala Val Val Ser Val Pro Gln Pro Arg Ser Pro
        355                 360                 365

Arg Trp Pro Val Val Val Ala Glu Gly Glu Gly Gln Gly Pro Leu Ile
    370                 375                 380

Arg Val Asp Met Thr Ile Ala Glu Ala Cys Gln Lys Ser Lys Arg Lys
385                 390                 395                 400

Ser Ile Leu Ala Val Gly Val Gly Asn Val Arg Val Lys Phe Gly Gln
                405                 410                 415

Asn Asp Ala Asp Ser Ser Pro Gly Arg Asp Tyr Glu Glu Asp Glu Ile
            420                 425                 430

Lys Asn His Ala Ser Asp Arg Arg Gln Lys Gly Gln His His Glu Arg
        435                 440                 445

Thr Gly Gln Asp Gly His Leu Tyr Gly Ser Ser Pro Val Glu Arg Glu
    450                 455                 460

Glu Gly Ala Leu Arg Arg Ala Thr Thr Thr Ala Arg Ser Leu Leu Asp
465                 470                 475                 480

Asn Lys Val Val Lys Asn Ser Arg Ala Asp Gly Gly Arg Leu Ala Gly
                485                 490                 495

Glu Gly Gln Leu Gln Asn Ile Pro Ile Asp Phe Thr Asn Phe Pro Ala
            500                 505                 510

His Val Asp Leu Pro Lys Ala Gly Ser Gly Leu Glu Glu Asn Asp Leu
        515                 520                 525

Val Gln Thr Pro Arg Gly Leu Ser Asp Leu Glu Ile Gly Met Tyr Ala
    530                 535                 540

Leu Leu Gly Val Phe Cys Leu Ala Ile Leu Val Phe Leu Ile Asn Cys
545                 550                 555                 560

Ala Thr Phe Ala Leu Lys Tyr Arg His Lys Gln Val Pro Leu Glu Gly
                565                 570                 575

Gln Ala Ser Met Thr His Ser His Asp Trp Val Trp Leu Gly Asn Glu
            580                 585                 590

Ala Glu Leu Leu Glu Ser Met Gly Asp Ala Pro Pro Pro Gln Asp Glu
        595                 600                 605

His Thr Thr Ile Ile Asp Arg Gly Pro Gly Ala Cys Glu Glu Ser Asn
    610                 615                 620

His Leu Leu Leu Asn Gly Gly Ser His Lys His Val Gln Ser Gln Ile
625                 630                 635                 640

His Arg Ser Ala Asp Ser Gly Gly Arg Gln Gly Arg Glu Gln Lys Gln
                645                 650                 655

Asp Pro Leu His Ser Pro Thr Ser Lys Arg Lys Lys Val Lys Phe Thr
            660                 665                 670

Thr Phe Thr Thr Ile Pro Pro Asp Asp Ser Cys Pro Thr Val Asn Ser
        675                 680                 685

Ile Val Ser Ser Asn Asp Glu Asp Ile Lys Trp Val Cys Gln Asp Val
    690                 695                 700

Ala Val Gly Ala Pro Lys Glu Leu Arg Asn Tyr Leu Glu Lys Leu Lys
705                 710                 715                 720

Asp Lys Ala

<210> SEQ ID NO 9
```

```
<211> LENGTH: 3558
<212> TYPE: DNA
<213> ORGANISM: Homo sapiens
<220> FEATURE:
<221> NAME/KEY: CDS
<222> LOCATION: (2)..(1801)
<223> OTHER INFORMATION:

<400> SEQUENCE: 9

a tac cag tac ctg agc gcc ccc ctg tgt gtc acc gtg tgg gtg ccc cgg      49
  Tyr Gln Tyr Leu Ser Ala Pro Leu Cys Val Thr Val Trp Val Pro Arg
  1               5                   10                  15

ctg ccc ctg cag atc gag gtc tct gac acg gag ctc agc cag ata aag       97
Leu Pro Leu Gln Ile Glu Val Ser Asp Thr Glu Leu Ser Gln Ile Lys
            20                  25                  30

ggc tgg agg gtc ccc att gtg acc aat aag agg ccc act cgt gag agc      145
Gly Trp Arg Val Pro Ile Val Thr Asn Lys Arg Pro Thr Arg Glu Ser
        35                  40                  45

gag gat gag gac gag gag gag cgg cgg ggc cgg ggc tgc gca ctg caa      193
Glu Asp Glu Asp Glu Glu Glu Arg Arg Gly Arg Gly Cys Ala Leu Gln
    50                  55                  60

tac cag cac gcc acc gtg cgg gtc ctc acc cag ttt gtg tct gag ggc      241
Tyr Gln His Ala Thr Val Arg Val Leu Thr Gln Phe Val Ser Glu Gly
65                  70                  75                  80

gcc ggt cca tgg ggc cag ccg aac tac ctg ctt agt cct aac tgg cag      289
Ala Gly Pro Trp Gly Gln Pro Asn Tyr Leu Leu Ser Pro Asn Trp Gln
                85                  90                  95

ttc gac atc act cac ctg gtg gca gac ttc atg aag ctg gag gaa cct      337
Phe Asp Ile Thr His Leu Val Ala Asp Phe Met Lys Leu Glu Glu Pro
            100                 105                 110

cac gtg gcc acc ctc cag gac agc cgg gtc ctg gtt ggg cga gag gtt      385
His Val Ala Thr Leu Gln Asp Ser Arg Val Leu Val Gly Arg Glu Val
        115                 120                 125

ggg atg acg acc atc cag gtg ttg tct cca ctg tct gac tcc atc ctg      433
Gly Met Thr Thr Ile Gln Val Leu Ser Pro Leu Ser Asp Ser Ile Leu
    130                 135                 140

gca gag aag acg ata acc gtg cta gat gac aaa gtg tcg gtg aca gac      481
Ala Glu Lys Thr Ile Thr Val Leu Asp Asp Lys Val Ser Val Thr Asp
145                 150                 155                 160

ttg gcc atc cag ctc gtg gct ggg ctg tct gtc gcc ctt tac ccc aac      529
Leu Ala Ile Gln Leu Val Ala Gly Leu Ser Val Ala Leu Tyr Pro Asn
                165                 170                 175

gca gaa aac agc aag gcc gta aca gct gtg gtc aca gct gag gag gtg      577
Ala Glu Asn Ser Lys Ala Val Thr Ala Val Val Thr Ala Glu Glu Val
            180                 185                 190

ctg cgg acc ccc aaa cag gag gct gta ttc agc acg tgg ctg cag ttc      625
Leu Arg Thr Pro Lys Gln Glu Ala Val Phe Ser Thr Trp Leu Gln Phe
        195                 200                 205

agt gat ggc tct gtg acg ccc ctg gac atc tac gac acc aag gac ttc      673
Ser Asp Gly Ser Val Thr Pro Leu Asp Ile Tyr Asp Thr Lys Asp Phe
    210                 215                 220

tcc ctg gca gcc acc tcc cag gac gag gct gtc gtg tca gtc ccc cag      721
Ser Leu Ala Ala Thr Ser Gln Asp Glu Ala Val Val Ser Val Pro Gln
225                 230                 235                 240

ccc agc tct ccc agg tgg ccc gtt gtg gtg gcc gaa ggg gaa ggc cag      769
Pro Ser Ser Pro Arg Trp Pro Val Val Val Ala Glu Gly Glu Gly Gln
                245                 250                 255

ggc cca ctg atc cga gtg gac atg acg atc gcc gag gcc tgc cag aaa      817
Gly Pro Leu Ile Arg Val Asp Met Thr Ile Ala Glu Ala Cys Gln Lys
            260                 265                 270

tct aaa cgc aag agc atc ctg gct gtg ggc gtc ggc aac gtc agg gtc      865
Ser Lys Arg Lys Ser Ile Leu Ala Val Gly Val Gly Asn Val Arg Val
```

-continued

```
        275                 280                 285

aag ttc gga cag aac gat gct gac tcc agc ccc ggc ggg gac tat gag      913
Lys Phe Gly Gln Asn Asp Ala Asp Ser Ser Pro Gly Gly Asp Tyr Glu
    290                 295                 300

gaa gat gag atc aag aac cac gcc agc gac cgc cgg cag aag ggc cag      961
Glu Asp Glu Ile Lys Asn His Ala Ser Asp Arg Arg Gln Lys Gly Gln
305                 310                 315                 320

cac cat gag cgc aca ggc cag gat ggg cac ctc tat ggc agc tct ccc     1009
His His Glu Arg Thr Gly Gln Asp Gly His Leu Tyr Gly Ser Ser Pro
                325                 330                 335

gtg gag cgt gag gaa ggg gct ctc cga aga gcc act acc acg gcc agg     1057
Val Glu Arg Glu Glu Gly Ala Leu Arg Arg Ala Thr Thr Thr Ala Arg
            340                 345                 350

tcc ctg ctg gac aac aaa gtg gtg aag aac agt cgg gca gac ggg ggc     1105
Ser Leu Leu Asp Asn Lys Val Val Lys Asn Ser Arg Ala Asp Gly Gly
        355                 360                 365

agg ctg gca gga gag ggg cag ctg cag aac atc ccc att gac ttc acc     1153
Arg Leu Ala Gly Glu Gly Gln Leu Gln Asn Ile Pro Ile Asp Phe Thr
    370                 375                 380

aac ttc cct gcc cac gtg gac ctc ccc aag gcc ggg agt ggg ctg gag     1201
Asn Phe Pro Ala His Val Asp Leu Pro Lys Ala Gly Ser Gly Leu Glu
385                 390                 395                 400

gaa aac gac ctg gtg cag act ccg cgg ggc ctg agt gat ctg gag ata     1249
Glu Asn Asp Leu Val Gln Thr Pro Arg Gly Leu Ser Asp Leu Glu Ile
                405                 410                 415

ggg atg tac gcc ctc ctg ggg gtg ttc tgc ctg gcc atc ctc gtc ttc     1297
Gly Met Tyr Ala Leu Leu Gly Val Phe Cys Leu Ala Ile Leu Val Phe
            420                 425                 430

ctg atc aac tgc gcc acc ttt gcc ctg aag tac agg cac aag caa gtg     1345
Leu Ile Asn Cys Ala Thr Phe Ala Leu Lys Tyr Arg His Lys Gln Val
        435                 440                 445

ccc ctg gaa ggt cag gcc tcc atg acc cac tct cac gac tgg gtg tgg     1393
Pro Leu Glu Gly Gln Ala Ser Met Thr His Ser His Asp Trp Val Trp
    450                 455                 460

ctt ggc aat gag gcc gaa ctc ctg gag agc atg ggg gat gcg ccg ccg     1441
Leu Gly Asn Glu Ala Glu Leu Leu Glu Ser Met Gly Asp Ala Pro Pro
465                 470                 475                 480

ccc cag gac gag cac acc acc atc ata gac cgc gga ccg ggg gcc tgc     1489
Pro Gln Asp Glu His Thr Thr Ile Ile Asp Arg Gly Pro Gly Ala Cys
                485                 490                 495

gag gag agc aac cat ctc ctg ctc aat ggt ggc tcc cac aag cac gtg     1537
Glu Glu Ser Asn His Leu Leu Leu Asn Gly Gly Ser His Lys His Val
            500                 505                 510

cag agc cag att cac agg tca gcc gac tcc ggg ggg cgg cag ggc aga     1585
Gln Ser Gln Ile His Arg Ser Ala Asp Ser Gly Gly Arg Gln Gly Arg
        515                 520                 525

gaa cag aag cag gac ccc ctg cac tcg ccc acc tcc aag agg aag aag     1633
Glu Gln Lys Gln Asp Pro Leu His Ser Pro Thr Ser Lys Arg Lys Lys
    530                 535                 540

gtg aaa ttt acc acc ttt acc acc atc ccc ccg gac gac agc tgc ccc     1681
Val Lys Phe Thr Thr Phe Thr Thr Ile Pro Pro Asp Asp Ser Cys Pro
545                 550                 555                 560

acg gtg aac tcc atc gtc agc agc aat gat gag gac atc aaa tgg gtg     1729
Thr Val Asn Ser Ile Val Ser Ser Asn Asp Glu Asp Ile Lys Trp Val
                565                 570                 575

tgt caa gac gtg gct gtg ggt gcc ccc aag gaa ctt aga aac tat ctg     1777
Cys Gln Asp Val Ala Val Gly Ala Pro Lys Glu Leu Arg Asn Tyr Leu
            580                 585                 590

gag aaa ctc aaa gat aag gct tag gcccctctag ccaaagggcc ctgcccagat    1831
Glu Lys Leu Lys Asp Lys Ala
```

-continued

595 gccttccttg tactggaaac tggcccaagt ggggcagaag gcgttgtcag tggggttaag 1891 aagggacggt cccagggtcc atgctagacc agttggaaag ttttgaagtc aggaaaagac 1951 gtttttgtat caagggattt ttagcagtta atggtggtgg atttttaaag gtcaggggaa 2011 taaagtctgg ggcatgggga gtgcagacca agttactgaa ctgcacaggc aaaattagga 2071 aggttatttt atgagtcaaa acatactaca gacaagctac caaaaattat ttgttaaaaa 2131 atgcaacaag acaaataaaa agagaaataa tcatctgttt atatttctaa taaaggagca 2191 aaatataaaa ataggacctg ctaagagaca ttttccattc taattcacga ttcacttttc 2251 caaggacagc cttcaactgt caccacacag ctgggggga gtcatttctt aacaagggat 2311 gcctcttggg atagaactag ggagttttaa atctttactt gatcatcttt tattttcttt 2371 tccacttttt cctttttct ctctctctgt gtcctagact tccattgcat ttatatttaa 2431 tgtttatttc tgagaatcaa gcagtatatt tttcctaaat gaaacataaa ttatattcct 2491 attcattaga taggttccta ggaacaatgc caattaatcc attgtttaag tagtaacttg 2551 aatgtttttc tatatccctc cagctttgtt gatagtggcg ggttttgtac aattggaggg 2611 agccctcaga gccttctggg ggaggagagg aactgtcctt aatccatcac cactaccata 2671 gggcaaagcc agcaggtgtg gccctgtgag ggctgtaca gatgggatgt ggccaggaga 2731 acagagcccc acctggacca cctgacccct cgggattcca cccctgtcat cgtggggatg 2791 ttcctatatg ggagaaagtt gggttaaatc aaaaaagagg ccacgcccag gtgtaatcag 2851 agccaacctg gtgggctggg tctatcacaa gacataactg atgctgaaca tgaacaaaga 2911 taaaaactgt ttggagggtt tttgagttgt ttttcttatg ttgttgggtg gggtatacca 2971 gcataaactc taaagataaa atctatgtta gattgtcaat caactgtgtt tttgaacagc 3031 ataattgtgt agcagcacat tgcaaaaatg cattcatcca aagcgacaca tgtggcaacg 3091 tagaccacgc cagtgaaata agccccttcg tgatcacctg actccagttc tccgtgtgct 3151 ccattggctg cggctgcagg aggaagatgc ctgacagccc tcatgctctc cgcagggggg 3211 cgctcacaaa gatgccaggg gtgtttattg tgtttatttt tttaattact aaaatcagta 3271 gctaagaaag ggtccttgaa gcctcctaac ctgggttgga cctttgaaaa atatatttgt 3331 agcacatatt atagatggaa agaagaagat atttatttat acctgtgatg ccaattgtca 3391 ttaaaaggct tttcatggct tgacaaaaaa aaaaaaaaaa aaaaaaaaaa aaaaaaaaaa 3451 aaaaaaaaaa aaaaaaaaaa aaaaaaaaaa aaaaaaaaaa aaaaaaaaaa aaaaaaaaaa 3511 aaaaaaaaaa aaaaaaaaaa aaaaaaaaaa aaaaaaaaaa aaaaaaa 3558

<210> SEQ ID NO 10
<211> LENGTH: 599
<212> TYPE: PRT
<213> ORGANISM: Homo sapiens

<400> SEQUENCE: 10

Tyr Gln Tyr Leu Ser Ala Pro Leu Cys Val Thr Val Trp Val Pro Arg
1 5 10 15

Leu Pro Leu Gln Ile Glu Val Ser Asp Thr Glu Leu Ser Gln Ile Lys
20 25 30

Gly Trp Arg Val Pro Ile Val Thr Asn Lys Arg Pro Thr Arg Glu Ser
35 40 45

Glu Asp Glu Asp Glu Glu Glu Arg Arg Gly Arg Gly Cys Ala Leu Gln
50 55 60

-continued

```
Tyr Gln His Ala Thr Val Arg Val Leu Thr Gln Phe Val Ser Glu Gly
65                  70                  75                  80

Ala Gly Pro Trp Gly Gln Pro Asn Tyr Leu Leu Ser Pro Asn Trp Gln
                85                  90                  95

Phe Asp Ile Thr His Leu Val Ala Asp Phe Met Lys Leu Glu Glu Pro
            100                 105                 110

His Val Ala Thr Leu Gln Asp Ser Arg Val Leu Val Gly Arg Glu Val
        115                 120                 125

Gly Met Thr Thr Ile Gln Val Leu Ser Pro Leu Ser Asp Ser Ile Leu
    130                 135                 140

Ala Glu Lys Thr Ile Thr Val Leu Asp Asp Lys Val Ser Val Thr Asp
145                 150                 155                 160

Leu Ala Ile Gln Leu Val Ala Gly Leu Ser Val Ala Leu Tyr Pro Asn
                165                 170                 175

Ala Glu Asn Ser Lys Ala Val Thr Ala Val Val Thr Ala Glu Glu Val
            180                 185                 190

Leu Arg Thr Pro Lys Gln Glu Ala Val Phe Ser Thr Trp Leu Gln Phe
        195                 200                 205

Ser Asp Gly Ser Val Thr Pro Leu Asp Ile Tyr Asp Thr Lys Asp Phe
    210                 215                 220

Ser Leu Ala Ala Thr Ser Gln Asp Glu Ala Val Val Ser Val Pro Gln
225                 230                 235                 240

Pro Ser Ser Pro Arg Trp Pro Val Val Val Ala Glu Gly Glu Gly Gln
                245                 250                 255

Gly Pro Leu Ile Arg Val Asp Met Thr Ile Ala Glu Ala Cys Gln Lys
            260                 265                 270

Ser Lys Arg Lys Ser Ile Leu Ala Val Gly Val Gly Asn Val Arg Val
        275                 280                 285

Lys Phe Gly Gln Asn Asp Ala Asp Ser Ser Pro Gly Gly Asp Tyr Glu
    290                 295                 300

Glu Asp Glu Ile Lys Asn His Ala Ser Asp Arg Arg Gln Lys Gly Gln
305                 310                 315                 320

His His Glu Arg Thr Gly Gln Asp Gly His Leu Tyr Gly Ser Ser Pro
                325                 330                 335

Val Glu Arg Glu Glu Gly Ala Leu Arg Arg Ala Thr Thr Thr Ala Arg
            340                 345                 350

Ser Leu Leu Asp Asn Lys Val Val Lys Asn Ser Arg Ala Asp Gly Gly
        355                 360                 365

Arg Leu Ala Gly Glu Gly Gln Leu Gln Asn Ile Pro Ile Asp Phe Thr
    370                 375                 380

Asn Phe Pro Ala His Val Asp Leu Pro Lys Ala Gly Ser Gly Leu Glu
385                 390                 395                 400

Glu Asn Asp Leu Val Gln Thr Pro Arg Gly Leu Ser Asp Leu Glu Ile
                405                 410                 415

Gly Met Tyr Ala Leu Leu Gly Val Phe Cys Leu Ala Ile Leu Val Phe
            420                 425                 430

Leu Ile Asn Cys Ala Thr Phe Ala Leu Lys Tyr Arg His Lys Gln Val
        435                 440                 445

Pro Leu Glu Gly Gln Ala Ser Met Thr His Ser His Asp Trp Val Trp
    450                 455                 460

Leu Gly Asn Glu Ala Glu Leu Leu Glu Ser Met Gly Asp Ala Pro Pro
465                 470                 475                 480

Pro Gln Asp Glu His Thr Thr Ile Ile Asp Arg Gly Pro Gly Ala Cys
                485                 490                 495
```

```
Glu Glu Ser Asn His Leu Leu Leu Asn Gly Gly Ser His Lys His Val
            500                 505                 510

Gln Ser Gln Ile His Arg Ser Ala Asp Ser Gly Gly Arg Gln Gly Arg
        515                 520                 525

Glu Gln Lys Gln Asp Pro Leu His Ser Pro Thr Ser Lys Arg Lys Lys
    530                 535                 540

Val Lys Phe Thr Thr Phe Thr Thr Ile Pro Pro Asp Asp Ser Cys Pro
545                 550                 555                 560

Thr Val Asn Ser Ile Val Ser Ser Asn Asp Glu Asp Ile Lys Trp Val
                565                 570                 575

Cys Gln Asp Val Ala Val Gly Ala Pro Lys Glu Leu Arg Asn Tyr Leu
            580                 585                 590

Glu Lys Leu Lys Asp Lys Ala
        595


<210> SEQ ID NO 11
<211> LENGTH: 3820
<212> TYPE: DNA
<213> ORGANISM: Mus musculus
<220> FEATURE:
<221> NAME/KEY: CDS
<222> LOCATION: (1)..(3432)
<223> OTHER INFORMATION:

<400> SEQUENCE: 11

gaa ccc gag aaa agt tgt ccg gac ccg ttc agg agc agc cgc cgg agc       48
Glu Pro Glu Lys Ser Cys Pro Asp Pro Phe Arg Ser Ser Arg Arg Ser
1               5                   10                  15

cgg agc gct gcc ggg ggc ggc ccc ggg cat ggg gca acc ggc gcg gtc       96
Arg Ser Ala Ala Gly Gly Gly Pro Gly His Gly Ala Thr Gly Ala Val
            20                  25                  30

ccg ggg ctg gcg atg gat ggc gtg aca gcg gcc acg atg cgc tcc gag      144
Pro Gly Leu Ala Met Asp Gly Val Thr Ala Ala Thr Met Arg Ser Glu
        35                  40                  45

ggc gcg gcc ccg agg cgg gcg gcg cgg tac ggg gcg ctg agc ctg gtc      192
Gly Ala Ala Pro Arg Arg Ala Ala Arg Tyr Gly Ala Leu Ser Leu Val
    50                  55                  60

cta gcc acg cta ctg ggc caa gtg acc gaa agc cga ggg gtc atg gat      240
Leu Ala Thr Leu Leu Gly Gln Val Thr Glu Ser Arg Gly Val Met Asp
65                  70                  75                  80

aat ata cag aga ttc tct tca ttg ccg ccg tac ctg ccc gtg agc ttc      288
Asn Ile Gln Arg Phe Ser Ser Leu Pro Pro Tyr Leu Pro Val Ser Phe
                85                  90                  95

cac gtc ctc aga gcc gag act gca ttc ttc cta aag gag gcc aac ccc      336
His Val Leu Arg Ala Glu Thr Ala Phe Phe Leu Lys Glu Ala Asn Pro
            100                 105                 110

gac ccg ctg cgg aat gcc agc ctg cag tcc agg gtg gag tct ttc ttc      384
Asp Pro Leu Arg Asn Ala Ser Leu Gln Ser Arg Val Glu Ser Phe Phe
        115                 120                 125

atc tac aag gcc cag cag ccc ccg gta tta aac gtc agc tat ggg cct      432
Ile Tyr Lys Ala Gln Gln Pro Pro Val Leu Asn Val Ser Tyr Gly Pro
    130                 135                 140

tac tct gca gaa aag gtc atc cct ctg gac ttg atg ttg aac ccc aac      480
Tyr Ser Ala Glu Lys Val Ile Pro Leu Asp Leu Met Leu Asn Pro Asn
145                 150                 155                 160

ttt tta ggc cca acc agt aag ttt ccc ttt gac tgg agg ctg aag gcc      528
Phe Leu Gly Pro Thr Ser Lys Phe Pro Phe Asp Trp Arg Leu Lys Ala
                165                 170                 175

tac atc ctt caa gag aaa gtc tac ctg agc cat ccc aaa gta cag gtg      576
Tyr Ile Leu Gln Glu Lys Val Tyr Leu Ser His Pro Lys Val Gln Val
```

```
            180                 185                 190

ctc ttc cac atc gtg ggc cga gac tgg gat gac cac agg gac gag aaa       624
Leu Phe His Ile Val Gly Arg Asp Trp Asp Asp His Arg Asp Glu Lys
        195                 200                 205

ctg ccc tgc ctg cgg gtc ttt gcg ttc aga gac agc cgg gag gtt cga       672
Leu Pro Cys Leu Arg Val Phe Ala Phe Arg Asp Ser Arg Glu Val Arg
    210                 215                 220

ggc agc tgt cgt ctg ggt ggg ccc ctg gga ctg tgc gtg gcc cag ctg       720
Gly Ser Cys Arg Leu Gly Gly Pro Leu Gly Leu Cys Val Ala Gln Leu
225                 230                 235                 240

gag atg ctg cct ggc tgg ttc agt ccc cca gcg gtt gta tct ggg cgc       768
Glu Met Leu Pro Gly Trp Phe Ser Pro Pro Ala Val Val Ser Gly Arg
                245                 250                 255

agg agg cca gca gag cgg cca gag ggg agt ccg gtg gaa ctg tat tat       816
Arg Arg Pro Ala Glu Arg Pro Glu Gly Ser Pro Val Glu Leu Tyr Tyr
            260                 265                 270

gct gta cag cca ggg gac gag cgt ggt gac tgc act gga ggt gac acc       864
Ala Val Gln Pro Gly Asp Glu Arg Gly Asp Cys Thr Gly Gly Asp Thr
        275                 280                 285

agg aag gac aat gct att cgt cca gga aag gat gga cag gag ggc agg       912
Arg Lys Asp Asn Ala Ile Arg Pro Gly Lys Asp Gly Gln Glu Gly Arg
    290                 295                 300

aca tcc cac cta cag aag att ggc acc att agc ctt tac cgc gcc cag       960
Thr Ser His Leu Gln Lys Ile Gly Thr Ile Ser Leu Tyr Arg Ala Gln
305                 310                 315                 320

gac agc aac cag ctc agc gaa ctg cgc ctg gat ggc aat gtg gtc atc      1008
Asp Ser Asn Gln Leu Ser Glu Leu Arg Leu Asp Gly Asn Val Val Ile
                325                 330                 335

tgg ctg ccc tcc cag ccc gtc aag cag gga gac ata gtc acc gca tct      1056
Trp Leu Pro Ser Gln Pro Val Lys Gln Gly Asp Ile Val Thr Ala Ser
            340                 345                 350

gtc acc atc gcc aat aac tct act gtg gac cat ttc atc cta aga gcc      1104
Val Thr Ile Ala Asn Asn Ser Thr Val Asp His Phe Ile Leu Arg Ala
        355                 360                 365

aag gtg aag aag ggg gtg aac atc ctg acc gtg cag acc agc gag cct      1152
Lys Val Lys Lys Gly Val Asn Ile Leu Thr Val Gln Thr Ser Glu Pro
    370                 375                 380

cgg cag tgg gat gtg agg caa gag gtg ggc aat gga ggg aag cac acc      1200
Arg Gln Trp Asp Val Arg Gln Glu Val Gly Asn Gly Gly Lys His Thr
385                 390                 395                 400

acc acc tcg gtg gcc tgc cag cgc ctg ggc cct ggg gca cga aat agg      1248
Thr Thr Ser Val Ala Cys Gln Arg Leu Gly Pro Gly Ala Arg Asn Arg
                405                 410                 415

agc agc aat tta ttc agc gag gtc atg cag atg aat ttt gaa atc gcc      1296
Ser Ser Asn Leu Phe Ser Glu Val Met Gln Met Asn Phe Glu Ile Ala
            420                 425                 430

agc ttc agc agc ctc tcg ggg aca cag cct atc aca tgg cag gtg gag      1344
Ser Phe Ser Ser Leu Ser Gly Thr Gln Pro Ile Thr Trp Gln Val Glu
        435                 440                 445

tac ccg agg aag ggg gcc acg gac att gct gtg tcg gag atc ttc atc      1392
Tyr Pro Arg Lys Gly Ala Thr Asp Ile Ala Val Ser Glu Ile Phe Ile
    450                 455                 460

agc cag aag gac cta gtt gcc atc gtc ccc ctt gct atg gac act gaa      1440
Ser Gln Lys Asp Leu Val Ala Ile Val Pro Leu Ala Met Asp Thr Glu
465                 470                 475                 480

ctc ctg aac aca gcc atc ctc aca ggg aag acg gtg gcc atg cct gtc      1488
Leu Leu Asn Thr Ala Ile Leu Thr Gly Lys Thr Val Ala Met Pro Val
                485                 490                 495

agg gtg gtg tcg gtg gaa gag aat agc acc ctg agg gac atc tcg gag      1536
Arg Val Val Ser Val Glu Glu Asn Ser Thr Leu Arg Asp Ile Ser Glu
```

-continued

```
            500                 505                 510

ttg gtg gag tgc aag gcc aca gac gag aat gtc atc aag gtc tcg gac      1584
Leu Val Glu Cys Lys Ala Thr Asp Glu Asn Val Ile Lys Val Ser Asp
        515                 520                 525

cac tgt gac tat gtc ttt gtc aat ggt aaa gag atc aag ggc aag atg      1632
His Cys Asp Tyr Val Phe Val Asn Gly Lys Glu Ile Lys Gly Lys Met
    530                 535                 540

gac tct gtg gtg aac ttc acc tac cag cac ctg agc gca ccg ctg cat      1680
Asp Ser Val Val Asn Phe Thr Tyr Gln His Leu Ser Ala Pro Leu His
545                 550                 555                 560

gtc act gtg tgg gtg cca cgg ctt ccc ctg cag atc gag gtc tct gac      1728
Val Thr Val Trp Val Pro Arg Leu Pro Leu Gln Ile Glu Val Ser Asp
                565                 570                 575

aca gaa ctc agc cag gtt aag ggc tgg aga gtc ccc atc gtg gcc agc      1776
Thr Glu Leu Ser Gln Val Lys Gly Trp Arg Val Pro Ile Val Ala Ser
            580                 585                 590

aag agg ccc act cgg gac agt gag gag gaa gaa gag gaa gaa cag aaa      1824
Lys Arg Pro Thr Arg Asp Ser Glu Glu Glu Glu Glu Glu Glu Gln Lys
        595                 600                 605

ggc cgg ggt tgt acc ctg cag ttc cag cat gcc aca gtg cgc gtc ctc      1872
Gly Arg Gly Cys Thr Leu Gln Phe Gln His Ala Thr Val Arg Val Leu
    610                 615                 620

acc caa ttt gta tca gag ggt gct ggg ccc tgg ggc cag ctg agc cac      1920
Thr Gln Phe Val Ser Glu Gly Ala Gly Pro Trp Gly Gln Leu Ser His
625                 630                 635                 640

ctt ctc agt cca gac tgg cag ttt gac atc acc cac ctg gtg gct gac      1968
Leu Leu Ser Pro Asp Trp Gln Phe Asp Ile Thr His Leu Val Ala Asp
                645                 650                 655

ttt atg aag ctg gag tcc cca cac ata gcc acc ctg cag gac agc agg      2016
Phe Met Lys Leu Glu Ser Pro His Ile Ala Thr Leu Gln Asp Ser Arg
            660                 665                 670

gtc ttg gtt ggg cgg gaa gtc gga atg acc acc atc cag gtg ttg tct      2064
Val Leu Val Gly Arg Glu Val Gly Met Thr Thr Ile Gln Val Leu Ser
        675                 680                 685

ccc ctg tcc gac tcc atc ttg gcc gag aag aca gta act gtg ctg gat      2112
Pro Leu Ser Asp Ser Ile Leu Ala Glu Lys Thr Val Thr Val Leu Asp
    690                 695                 700

gac aaa gta tct gtg aca gac tta gct gtc cag gtg gtg gct ggg ctg      2160
Asp Lys Val Ser Val Thr Asp Leu Ala Val Gln Val Val Ala Gly Leu
705                 710                 715                 720

tct gtc acc cta cac ccc atc tca gag aac aac aag gcc acc tca gct      2208
Ser Val Thr Leu His Pro Ile Ser Glu Asn Asn Lys Ala Thr Ser Ala
                725                 730                 735

gtg gcc atg gca gaa gag ctg cta cgt gcc cca aaa aag gaa gct ata      2256
Val Ala Met Ala Glu Glu Leu Leu Arg Ala Pro Lys Lys Glu Ala Ile
            740                 745                 750

atc agc aca tgg ctc cag ttc agt gat ggc tca gtg aca ccc ctg gat      2304
Ile Ser Thr Trp Leu Gln Phe Ser Asp Gly Ser Val Thr Pro Leu Asp
        755                 760                 765

atc tac gac tcc aag gac ttc tcc ttg act gcc atc tct ttg gac gag      2352
Ile Tyr Asp Ser Lys Asp Phe Ser Leu Thr Ala Ile Ser Leu Asp Glu
    770                 775                 780

gct gtc gtg tcc atc ccc caa ccc ctc tcg cct tgg tgg ccc acc gtg      2400
Ala Val Val Ser Ile Pro Gln Pro Leu Ser Pro Trp Trp Pro Thr Val
785                 790                 795                 800

gta gct gaa gga gaa ggc cag ggc cca ctg ctc cgg gtc gat atg tcc      2448
Val Ala Glu Gly Glu Gly Gln Gly Pro Leu Leu Arg Val Asp Met Ser
                805                 810                 815

att gcc gaa gcc tgt cag aaa tcc aag cgc aag agt gtg ctg gct gtt      2496
Ile Ala Glu Ala Cys Gln Lys Ser Lys Arg Lys Ser Val Leu Ala Val
```

```
            820                 825                 830

ggc att ggc cac gtg ggg gtc aag ttt gga tgg gat gac gct gac tcc      2544
Gly Ile Gly His Val Gly Val Lys Phe Gly Trp Asp Asp Ala Asp Ser
        835                 840                 845

agc cag act gga gaa aag gat gag gag gag atc aag aac cat gcc agt      2592
Ser Gln Thr Gly Glu Lys Asp Glu Glu Glu Ile Lys Asn His Ala Ser
    850                 855                 860

gac cgt cgg cag aag att cag gac ctg gaa cgc cca ggc cag gat gaa      2640
Asp Arg Arg Gln Lys Ile Gln Asp Leu Glu Arg Pro Gly Gln Asp Glu
865                 870                 875                 880

cta tac cat ggc aac ttt cct ggg gat cgt gaa gaa gga gcg ctg agt      2688
Leu Tyr His Gly Asn Phe Pro Gly Asp Arg Glu Glu Gly Ala Leu Ser
                885                 890                 895

gct acc acc act acc aag tcc ctg ctg gat aac aac gtg ggg aag agt      2736
Ala Thr Thr Thr Thr Lys Ser Leu Leu Asp Asn Asn Val Gly Lys Ser
            900                 905                 910

ggc agg cgg gac ggg gct agg cta cac agc ata ccc att gac ttc acc      2784
Gly Arg Arg Asp Gly Ala Arg Leu His Ser Ile Pro Ile Asp Phe Thr
        915                 920                 925

aat ttc ccg gcc cat gtg gac ctc ccc aag gcc aag acc agg ggc aca      2832
Asn Phe Pro Ala His Val Asp Leu Pro Lys Ala Lys Thr Arg Gly Thr
    930                 935                 940

ctg gag gag aat ggt ctc atg cag aca gcc cat ggc ctg agt gac cta      2880
Leu Glu Glu Asn Gly Leu Met Gln Thr Ala His Gly Leu Ser Asp Leu
945                 950                 955                 960

gag att ggg atg tat gcc ctc cta ggt gtc ttc tgc ctg gcc atc ctt      2928
Glu Ile Gly Met Tyr Ala Leu Leu Gly Val Phe Cys Leu Ala Ile Leu
                965                 970                 975

gtc ttt ctc att aac tgc gcc acc ttt gcc ttc aag tac agg cac aaa      2976
Val Phe Leu Ile Asn Cys Ala Thr Phe Ala Phe Lys Tyr Arg His Lys
            980                 985                 990

cag gtg cct ctg gaa ggc cag gca  tcc atg acc cac tct  cat gac tgg    3024
Gln Val Pro Leu Glu Gly Gln Ala  Ser Met Thr His Ser  His Asp Trp
        995                 1000                 1005

gtc tgg  ctg ggc aat gag gcg  gag ctc ttg gag aac  att ggg gac      3069
Val Trp  Leu Gly Asn Glu Ala  Glu Leu Leu Glu Asn  Ile Gly Asp
    1010                 1015                 1020

ctg tcc  cca ccc cag gat gag  cac acg acc atc ata  gac cga ggg      3114
Leu Ser  Pro Pro Gln Asp Glu  His Thr Thr Ile Ile  Asp Arg Gly
    1025                 1030                 1035

ctg ggg  ggc tgt gag gag aac  aac cac tta ctt ctc  aac ggt ggc      3159
Leu Gly  Gly Cys Glu Glu Asn  Asn His Leu Leu Leu  Asn Gly Gly
    1040                 1045                 1050

tcc caa  aag ccc acg cag agc  cag gtt cac agg ccg  cca ggc tcc      3204
Ser Gln  Lys Pro Thr Gln Ser  Gln Val His Arg Pro  Pro Gly Ser
    1055                 1060                 1065

ggg gga  cgg cag acc agg gag  ccc agg cag gag cct  gca aac tca      3249
Gly Gly  Arg Gln Thr Arg Glu  Pro Arg Gln Glu Pro  Ala Asn Ser
    1070                 1075                 1080

ccc acc  tcc aag atg aag aag  gtc aag ttt gcc aca  ttc acc atc      3294
Pro Thr  Ser Lys Met Lys Lys  Val Lys Phe Ala Thr  Phe Thr Ile
    1085                 1090                 1095

cca cct  gag gaa agc tgc ccc  acg gtg aac tcc atc  ctc agt ggg      3339
Pro Pro  Glu Glu Ser Cys Pro  Thr Val Asn Ser Ile  Leu Ser Gly
    1100                 1105                 1110

gaa gat  gat atc aag tgg gtt  tgt caa gac ctg gac  gtg ggc gca      3384
Glu Asp  Asp Ile Lys Trp Val  Cys Gln Asp Leu Asp  Val Gly Ala
    1115                 1120                 1125

ccc aag  gaa ctc aga acc tac  ctg gag aaa ttc caa  gac agt gtg      3429
Pro Lys  Glu Leu Arg Thr Tyr  Leu Glu Lys Phe Gln  Asp Ser Val
```

1130 1135 1140 tag cgctctggcc tcctcgccaa cttgggacag tagcctcctt cccgacctcc 3482 ctcagcagag tagctgaacg gaaggagctc tcagtggact gagtgaggaa atctggggcc 3542 cacagaatac caggtagcag gttagaagct gggaagggat gtttttatac taaagcagtt 3602 tttttgttt tttgtttttt gttttttgtt ttttttagca gcaaaggatg gtaggtttcc 3662 agaagtttga gtctctgact cagcagcgag gcagagtgga tccgaaagag aactgctcag 3722 acatgagaga gttattttat gaatcaaacg acactgcaga caagctacca aaaatatttg 3782 ttaaaaaaaa tatataaaaa gacgaataaa aaaaacac 3820

<210> SEQ ID NO 12
<211> LENGTH: 1143
<212> TYPE: PRT
<213> ORGANISM: Mus musculus

<400> SEQUENCE: 12

Glu Pro Glu Lys Ser Cys Pro Asp Pro Phe Arg Ser Ser Arg Arg Ser
1 5 10 15

Arg Ser Ala Ala Gly Gly Gly Pro Gly His Gly Ala Thr Gly Ala Val
20 25 30

Pro Gly Leu Ala Met Asp Gly Val Thr Ala Ala Thr Met Arg Ser Glu
35 40 45

Gly Ala Ala Pro Arg Arg Ala Ala Arg Tyr Gly Ala Leu Ser Leu Val
50 55 60

Leu Ala Thr Leu Leu Gly Gln Val Thr Glu Ser Arg Gly Val Met Asp
65 70 75 80

Asn Ile Gln Arg Phe Ser Ser Leu Pro Pro Tyr Leu Pro Val Ser Phe
85 90 95

His Val Leu Arg Ala Glu Thr Ala Phe Phe Leu Lys Glu Ala Asn Pro
100 105 110

Asp Pro Leu Arg Asn Ala Ser Leu Gln Ser Arg Val Glu Ser Phe Phe
115 120 125

Ile Tyr Lys Ala Gln Gln Pro Pro Val Leu Asn Val Ser Tyr Gly Pro
130 135 140

Tyr Ser Ala Glu Lys Val Ile Pro Leu Asp Leu Met Leu Asn Pro Asn
145 150 155 160

Phe Leu Gly Pro Thr Ser Lys Phe Pro Phe Asp Trp Arg Leu Lys Ala
165 170 175

Tyr Ile Leu Gln Glu Lys Val Tyr Leu Ser His Pro Lys Val Gln Val
180 185 190

Leu Phe His Ile Val Gly Arg Asp Trp Asp Asp His Arg Asp Glu Lys
195 200 205

Leu Pro Cys Leu Arg Val Phe Ala Phe Arg Asp Ser Arg Glu Val Arg
210 215 220

Gly Ser Cys Arg Leu Gly Gly Pro Leu Gly Leu Cys Val Ala Gln Leu
225 230 235 240

Glu Met Leu Pro Gly Trp Phe Ser Pro Pro Ala Val Val Ser Gly Arg
245 250 255

Arg Arg Pro Ala Glu Arg Pro Glu Gly Ser Pro Val Glu Leu Tyr Tyr
260 265 270

Ala Val Gln Pro Gly Asp Glu Arg Gly Asp Cys Thr Gly Gly Asp Thr
275 280 285

Arg Lys Asp Asn Ala Ile Arg Pro Gly Lys Asp Gly Gln Glu Gly Arg
290 295 300

-continued

```
Thr Ser His Leu Gln Lys Ile Gly Thr Ile Ser Leu Tyr Arg Ala Gln
305                 310                 315                 320

Asp Ser Asn Gln Leu Ser Glu Leu Arg Leu Asp Gly Asn Val Val Ile
                325                 330                 335

Trp Leu Pro Ser Gln Pro Val Lys Gln Gly Asp Ile Val Thr Ala Ser
            340                 345                 350

Val Thr Ile Ala Asn Asn Ser Thr Val Asp His Phe Ile Leu Arg Ala
        355                 360                 365

Lys Val Lys Lys Gly Val Asn Ile Leu Thr Val Gln Thr Ser Glu Pro
    370                 375                 380

Arg Gln Trp Asp Val Arg Gln Glu Val Gly Asn Gly Gly Lys His Thr
385                 390                 395                 400

Thr Thr Ser Val Ala Cys Gln Arg Leu Gly Pro Gly Ala Arg Asn Arg
                405                 410                 415

Ser Ser Asn Leu Phe Ser Glu Val Met Gln Met Asn Phe Glu Ile Ala
            420                 425                 430

Ser Phe Ser Ser Leu Ser Gly Thr Gln Pro Ile Thr Trp Gln Val Glu
        435                 440                 445

Tyr Pro Arg Lys Gly Ala Thr Asp Ile Ala Val Ser Glu Ile Phe Ile
    450                 455                 460

Ser Gln Lys Asp Leu Val Ala Ile Val Pro Leu Ala Met Asp Thr Glu
465                 470                 475                 480

Leu Leu Asn Thr Ala Ile Leu Thr Gly Lys Thr Val Ala Met Pro Val
                485                 490                 495

Arg Val Val Ser Val Glu Glu Asn Ser Thr Leu Arg Asp Ile Ser Glu
            500                 505                 510

Leu Val Glu Cys Lys Ala Thr Asp Glu Asn Val Ile Lys Val Ser Asp
        515                 520                 525

His Cys Asp Tyr Val Phe Val Asn Gly Lys Glu Ile Lys Gly Lys Met
    530                 535                 540

Asp Ser Val Val Asn Phe Thr Tyr Gln His Leu Ser Ala Pro Leu His
545                 550                 555                 560

Val Thr Val Trp Val Pro Arg Leu Pro Leu Gln Ile Glu Val Ser Asp
                565                 570                 575

Thr Glu Leu Ser Gln Val Lys Gly Trp Arg Val Pro Ile Val Ala Ser
            580                 585                 590

Lys Arg Pro Thr Arg Asp Ser Glu Glu Glu Glu Glu Glu Glu Gln Lys
        595                 600                 605

Gly Arg Gly Cys Thr Leu Gln Phe Gln His Ala Thr Val Arg Val Leu
    610                 615                 620

Thr Gln Phe Val Ser Glu Gly Ala Gly Pro Trp Gly Gln Leu Ser His
625                 630                 635                 640

Leu Leu Ser Pro Asp Trp Gln Phe Asp Ile Thr His Leu Val Ala Asp
                645                 650                 655

Phe Met Lys Leu Glu Ser Pro His Ile Ala Thr Leu Gln Asp Ser Arg
            660                 665                 670

Val Leu Val Gly Arg Glu Val Gly Met Thr Thr Ile Gln Val Leu Ser
        675                 680                 685

Pro Leu Ser Asp Ser Ile Leu Ala Glu Lys Thr Val Thr Val Leu Asp
    690                 695                 700

Asp Lys Val Ser Val Thr Asp Leu Ala Val Gln Val Val Ala Gly Leu
705                 710                 715                 720

Ser Val Thr Leu His Pro Ile Ser Glu Asn Asn Lys Ala Thr Ser Ala
```

725 730 735

Val Ala Met Ala Glu Glu Leu Leu Arg Ala Pro Lys Lys Glu Ala Ile
740 745 750

Ile Ser Thr Trp Leu Gln Phe Ser Asp Gly Ser Val Thr Pro Leu Asp
755 760 765

Ile Tyr Asp Ser Lys Asp Phe Ser Leu Thr Ala Ile Ser Leu Asp Glu
770 775 780

Ala Val Val Ser Ile Pro Gln Pro Leu Ser Pro Trp Trp Pro Thr Val
785 790 795 800

Val Ala Glu Gly Glu Gly Gln Gly Pro Leu Leu Arg Val Asp Met Ser
805 810 815

Ile Ala Glu Ala Cys Gln Lys Ser Lys Arg Lys Ser Val Leu Ala Val
820 825 830

Gly Ile Gly His Val Gly Val Lys Phe Gly Trp Asp Asp Ala Asp Ser
835 840 845

Ser Gln Thr Gly Glu Lys Asp Glu Glu Glu Ile Lys Asn His Ala Ser
850 855 860

Asp Arg Arg Gln Lys Ile Gln Asp Leu Glu Arg Pro Gly Gln Asp Glu
865 870 875 880

Leu Tyr His Gly Asn Phe Pro Gly Asp Arg Glu Glu Gly Ala Leu Ser
885 890 895

Ala Thr Thr Thr Thr Lys Ser Leu Leu Asp Asn Asn Val Gly Lys Ser
900 905 910

Gly Arg Arg Asp Gly Ala Arg Leu His Ser Ile Pro Ile Asp Phe Thr
915 920 925

Asn Phe Pro Ala His Val Asp Leu Pro Lys Ala Lys Thr Arg Gly Thr
930 935 940

Leu Glu Glu Asn Gly Leu Met Gln Thr Ala His Gly Leu Ser Asp Leu
945 950 955 960

Glu Ile Gly Met Tyr Ala Leu Leu Gly Val Phe Cys Leu Ala Ile Leu
965 970 975

Val Phe Leu Ile Asn Cys Ala Thr Phe Ala Phe Lys Tyr Arg His Lys
980 985 990

Gln Val Pro Leu Glu Gly Gln Ala Ser Met Thr His Ser His Asp Trp
995 1000 1005

Val Trp Leu Gly Asn Glu Ala Glu Leu Leu Glu Asn Ile Gly Asp
1010 1015 1020

Leu Ser Pro Pro Gln Asp Glu His Thr Thr Ile Ile Asp Arg Gly
1025 1030 1035

Leu Gly Gly Cys Glu Glu Asn Asn His Leu Leu Leu Asn Gly Gly
1040 1045 1050

Ser Gln Lys Pro Thr Gln Ser Gln Val His Arg Pro Pro Gly Ser
1055 1060 1065

Gly Gly Arg Gln Thr Arg Glu Pro Arg Gln Glu Pro Ala Asn Ser
1070 1075 1080

Pro Thr Ser Lys Met Lys Lys Val Lys Phe Ala Thr Phe Thr Ile
1085 1090 1095

Pro Pro Glu Glu Ser Cys Pro Thr Val Asn Ser Ile Leu Ser Gly
1100 1105 1110

Glu Asp Asp Ile Lys Trp Val Cys Gln Asp Leu Asp Val Gly Ala
1115 1120 1125

Pro Lys Glu Leu Arg Thr Tyr Leu Glu Lys Phe Gln Asp Ser Val
1130 1135 1140

<210> SEQ ID NO 13
<211> LENGTH: 5114
<212> TYPE: DNA
<213> ORGANISM: Mus musculus

<400> SEQUENCE: 13
gggacccgtt caggagcagc cgccggagcc ggagcgctgc cgggggcggc cccgggcatg 60
gggcaaccgg cgcggtcccg gggctggcga tggatggcgt gacagcggcc acgatgcgct 120
ccgagggcgc ggccccgagg cgggcggcgc ggtacggggc gctgagcctg gtcctagcca 180
cgctactggg ccaagtgacc gaaagccgag ggggtcatgga taatatacag agattctctt 240
cattgccgcc gtacctgccc gtgagcttcc acgtcctcag agccgagact gcattcttcc 300
taaaggaggc caaccccgac ccgctgcgga atgccagcct gcagtccagg gtggagtctt 360
tcttcatcta caaggcccag cagcccccgg tattaaacgt cagctatggg ccttactctg 420
cagaaaaggt catccctctg gacttgatgt tgaaccccaa ctttttaggc ccaaccagta 480
agtttccctt tgactggagg ctgaaggcct acatccttca agagaaagtc tacctgagcc 540
atcccaaagt acaggtgctc ttccacatcg tgggccgaga ctgggatgac cacagggacg 600
agaaactgcc ctgcctgcgg gtctttgcgt tcagagacag ccgggaggtt cgaggcagct 660
gtcgtctggg tgggcccctg ggactgtgcg tggcccagct ggagatgctg cctggctggt 720
tcagtccccc agcggttgta tctgggcgca ggaggccagc agagcggcca gaggggagtc 780
cggtggaact gtattatgct gtacagccag ggacgagcg tggtgactgc actggaggtg 840
acaccaggaa ggacaatgct attcgtccag gaaaggatgg acaggagggc aggacatccc 900
acctacagaa gattggcacc attagccttt accgcgccca ggacagcacc cagcctcagc 960
gaactgcgcc tggatggcaa tgtggtcatc tggctgccct cccagcccgt caagcaggga 1020
gacatagtca ccgcatctgt caccatcgcc aataactcta ctgtggacca tttcatccta 1080
agagccaagg tgaagaaggg ggtgaacatc ctgaccgtgc agaccagcga gcctcggcag 1140
tgggatgtga ggcaagaggt gggcaatgga gggaagcaca ccaccacctc ggtggcctgc 1200
cagcgcctgg gccctggggc acgaaatagg agcagcaatt tattcagcga ggtcatgcag 1260
atgaattttg aaatcgccag cttcagcagc ctctcgggga cacagcctat cacatggcag 1320
gtggagtacc cgaggaaggg ggccacggac attgctgtgt cggagatctt catcagccag 1380
aaggacctag ttgccatcgt ccccccttgct atggacactg aactcctgaa cacagccatc 1440
ctcacaggga agacggtggc catgcctgtc agggtggtgt cggtggaaga gaatagcacc 1500
ctgagggaca tctcggagtt ggtggagtgc aaggccacag acgagaatgt catcaaggtc 1560
tcggaccact gtgactatgt ctttgtcaat ggtaaagaga tcaagggcaa gatggactct 1620
gtggtgaact tcacctacca gcacctgagc gcaccgctgc atgtcactgt gtgggtgcca 1680
cggcttcccc tgcagatcga ggtctctgac acagaactca gccaggttaa gggctggaga 1740
gtccccatcg tggccagcaa gaggcccact cgggacagtg aggaggaaga agaggaagaa 1800
cagaaaggcc ggggttgtac cctgcagttc cagcatgcca cagtgcgcgt cctcacccaa 1860
tttgtatcag agggtgctgg gccctggggc cagctgagcc accttctcag tccagactgg 1920
cagtttgaca tcacccacct ggtggctgac tttatgaagc tggagtcccc acacatagcc 1980
accctgcagg acagcagggt cttggttggg cgggaagtcg gaatgaccac catccaggtg 2040
ttgtctcccc tgtccgactc catcttggcc gagaagacag taactgtgct ggatgacaaa 2100
gtatctgtga cagacttagc tgtccaggtg gtggctgggc tgtctgtcac cctacacccc 2160

-continued atctcagaga acaacaaggc cacctcagct gtggccatgg cagaagagct gctacgtgcc 2220
ccaaaaaagg aagctataat cagcacatgg ctccagttca gtgatggctc agtgacaccc 2280
ctggatatct acgactccaa ggacttctcc ttgactgcca tctctttgga cgaggctgtc 2340
gtgtccatcc cccaacccct ctcgccttgg tggcccaccg tggtagctga aggagaaggc 2400
cagggcccac tgctccgggt cgatatgtcc attgccgaag cctgtcagaa atccaagcgc 2460
aagagtgtgc tggctgttgg cattggccac gtgggggtca agtttggatg ggatgacgct 2520
gactccagcc agactggaga aaaggatgag gaggagatca agaaccatgc cagtgaccgt 2580
cggcagaaga ttcaggacct ggaacgccca ggccaggatg aactatacca tggcaacttt 2640
cctggggatc gtgaagaagg agcgctgagt gctaccacca ctaccaagtc cctgctggat 2700
aacaacgtgg ggaagagtgg caggcgggac ggggctaggc tacacagcat acccattgac 2760
ttcaccaatt tcccggccca tgtggacctc cccaaggcca agaccagggg cacactggag 2820
gagaatggtc tcatgcagac agcccatggc ctgagtgacc tagagattgg gatgtatgcc 2880
ctcctaggtg tcttctgcct ggccatcctt gtctttctca ttaactgcgc cacctttgcc 2940
ttcaagtaca ggcacaaaca ggtgcctctg gaaggccagg catccatgac ccactctcat 3000
gactgggtct ggctgggcaa tgaggcggag ctcttggaga acattgggga cctgtcccca 3060
ccccaggatg agcacacgac catcatagac cgagggctgg ggggctgtga ggagaacaac 3120
cacttacttc tcaacggtgg ctcccaaaag cccacgcaga gccaggttca caggccgcca 3180
ggctccgggg gacggcagac cagggagccc aggcaggagc ctgcaaactc acccacctcc 3240
aagatgaaga aggtcaagtt tgccacattc accatcccac ctgaggaaag ctgccccacg 3300
gtgaactcca tcctcagtgg ggaagatgat atcaagtggg tttgtcaaga cctggacgtg 3360
ggcgcaccca aggaactcag aacctacctg gagaaattcc aagacagtgt gtagcgctct 3420
ggcctcctcg ccaacttggg acagtagcct ccttcccgac ctccctcagc agagtagctg 3480
aacggaagga gctctcagtg gactgagtga ggaaatctgg ggcccacaga ataccaggta 3540
gcaggttaga agctgggaag ggatgttttt atactaaagc agtttttttt gtttttttgtt 3600
ttttgttttt tgtttttttt agcagcaaag gatggtaggt ttccagaagt ttgagtctct 3660
gactcagcag cgaggcagag tggatccgaa agagaactgc tcagacatga gagagttatt 3720
ttatgaatca aacgacactg cagacaagct accaaaaaata tttgttaaaa aaaatatata 3780
aaaagacgaa taaaaaaaac acacaaatga ctgtcggttt atatttctaa taaaggaaca 3840
aaatgtaaga atagggcttg ctaaaagaag gcctacattt taattcagtc tttatgcttc 3900
tgaggacagt ccaggtctgt tagccttctg cccaaggaga ggcacatctg aacaatggtc 3960
acctcttagg aagaatgaga attttacatt ggattccatt atctctgttt gcttccatgt 4020
ttctttctaa ggtcctaagc ctccatttga ttcaatgtca tgtttatttc tgaggaccaa 4080
gtggtacatt ttcctaaatg aaatgtaaat tatatttcta ttcattagat agcttttttcc 4140
ccctcttttt aagaagatca tcaacgaatc cagtctttac gttgtaacat taacctgtct 4200
ttatattata catctcttgc tttgttaata ttttctggct tgtttgtaat tctttttgtt 4260
tttttgtttt gttttgtttt aacaatatag caagtgtgca gttccccaca tggggagagt 4320
gcaccccaca atctgtcatc agccgggtca ggccaatgag tggaataatg ttcacagcta 4380
tctgaatagg gtatggccaa gagaacagag tgcagcctgt gacacctggc cactccctat 4440
ggagacagag actcagtggg tgtctccggc agtttgggca tagggatgcc tctatgtgaa 4500
gagctgtgag tgaaatccat aaactcgagg tgtgcagagt caggcagatg ggccatgtct 4560

```
accacaagat acagccgacc ctgtactgaa caaacagaaa agacatgtgg gggaggggca   4620

ggctggagtt atctgatttt attactgggc aaggcgaacc agcatgaact caaaatgatt   4680

tttttaaaaa aaagaaatct atgttagatt gtcaatcaaa ctgcggcttt gaagagtatg   4740

gctgtgttaa cagcacaatg cagtatcata tccactcaaa acagagtgtt tacgcaaaaa   4800

gcaggaggga tcaaatgaac taggatgtcc ggagcctggc gctctccatc catcagctga   4860

gggagaggat gttgggcact gtgaccctca gcagagcagc attcacagag agaccagggg   4920

acggccattg tttgggtttt tttgtttttt ttctattact aaaatcagta gctgagaaaa   4980

ggtctcagaa gcctagtggc cttggttgga cctttgacac atatatttgt agcatttaca   5040

atagattaaa aaaaaaaaag ctatttattt atacctgtgg tggcagttgt cattaaaacg   5100

cttgccatgc ttcc                                                     5114


<210> SEQ ID NO 14
<211> LENGTH: 4226
<212> TYPE: DNA
<213> ORGANISM: Mus musculus
<220> FEATURE:
<221> NAME/KEY: CDS
<222> LOCATION: (91)..(3414)
<223> OTHER INFORMATION:

<400> SEQUENCE: 14

agggacccgt tcaggagcag ccgccggagc cggagcgctg ccgggggcgg ccccgggcat     60

ggggcaaccg gcgcggtccc ggggctggcg atg gat ggc gtg aca gcg gcc acg     114
                                 Met Asp Gly Val Thr Ala Ala Thr
                                 1               5

atg cgc tcc gag ggc gcg gcc ccg agg cgg gcg gcg cgg tac ggg gcg      162
Met Arg Ser Glu Gly Ala Ala Pro Arg Arg Ala Ala Arg Tyr Gly Ala
    10                  15                  20

ctg agc ctg gtc cta gcc acg cta ctg ggc caa gtg acc gaa agc cga      210
Leu Ser Leu Val Leu Ala Thr Leu Leu Gly Gln Val Thr Glu Ser Arg
25                  30                  35                  40

ggg gtc atg gat aat ata cag aga ttc tct tca ttg ccg ccg tac ctg      258
Gly Val Met Asp Asn Ile Gln Arg Phe Ser Ser Leu Pro Pro Tyr Leu
                45                  50                  55

ccc gtg agc ttc cac gtc ctc aga gcc gag act gca ttc ttc cta aag      306
Pro Val Ser Phe His Val Leu Arg Ala Glu Thr Ala Phe Phe Leu Lys
            60                  65                  70

gag gcc aac ccc gac ccg ctg cgg aat gcc agc ctg cag tcc agg gtg      354
Glu Ala Asn Pro Asp Pro Leu Arg Asn Ala Ser Leu Gln Ser Arg Val
        75                  80                  85

gag tct ttc ttc atc tac aag gcc cag cag ccc ccg gta tta aac gtc      402
Glu Ser Phe Phe Ile Tyr Lys Ala Gln Gln Pro Pro Val Leu Asn Val
    90                  95                  100

agc tat ggg cct tac tct gca gaa aag gtc atc cct ctg gac ttg atg      450
Ser Tyr Gly Pro Tyr Ser Ala Glu Lys Val Ile Pro Leu Asp Leu Met
105                 110                 115                 120

ttg aac ccc aac ttt tta ggc cca acc agt aag ttt ccc ttt gac tgg      498
Leu Asn Pro Asn Phe Leu Gly Pro Thr Ser Lys Phe Pro Phe Asp Trp
                125                 130                 135

agg ctg aag gcc tac atc ctt caa gag aaa gtc tac ctg agc cat ccc      546
Arg Leu Lys Ala Tyr Ile Leu Gln Glu Lys Val Tyr Leu Ser His Pro
            140                 145                 150

aaa gta cag gtg ctc ttc cac atc gtg ggc cga gac tgg gat gac cac      594
Lys Val Gln Val Leu Phe His Ile Val Gly Arg Asp Trp Asp Asp His
        155                 160                 165

agg gac gag aaa ctg ccc tgc ctg cgg gtc ttt gcg ttc aga gac agc      642
Arg Asp Glu Lys Leu Pro Cys Leu Arg Val Phe Ala Phe Arg Asp Ser
```

```
    170                 175                 180

cgg gag gtt cga ggc agc tgt cgt ctg ggt ggg ccc ctg gga ctg tgc      690
Arg Glu Val Arg Gly Ser Cys Arg Leu Gly Gly Pro Leu Gly Leu Cys
185                 190                 195                 200

gtg gcc cag ctg gag atg ctg cct ggc tgg ttc agt ccc cca gcg gtt      738
Val Ala Gln Leu Glu Met Leu Pro Gly Trp Phe Ser Pro Pro Ala Val
                205                 210                 215

gta tct ggg cgc agg agg cca gca gag cgg cca gag ggg agt ccg gtg      786
Val Ser Gly Arg Arg Arg Pro Ala Glu Arg Pro Glu Gly Ser Pro Val
            220                 225                 230

gaa ctg tat tat gct gta cag cca ggg gac gag cgt ggt gac tgc act      834
Glu Leu Tyr Tyr Ala Val Gln Pro Gly Asp Glu Arg Gly Asp Cys Thr
        235                 240                 245

gga ggt gac acc agg aag gac aat gct att cgt cca gga aag gat gga      882
Gly Gly Asp Thr Arg Lys Asp Asn Ala Ile Arg Pro Gly Lys Asp Gly
    250                 255                 260

cag gag ggc agg aca tcc cac cta cag aag att ggc acc att agc ctt      930
Gln Glu Gly Arg Thr Ser His Leu Gln Lys Ile Gly Thr Ile Ser Leu
265                 270                 275                 280

tac cgc gcc cag gac agc acc cag ctc agc gaa ctg cgc ctg gat ggc      978
Tyr Arg Ala Gln Asp Ser Thr Gln Leu Ser Glu Leu Arg Leu Asp Gly
                285                 290                 295

aat gtg gtc atc tgg ctg ccc tcc cag ccc gtc aag cag gga gac ata     1026
Asn Val Val Ile Trp Leu Pro Ser Gln Pro Val Lys Gln Gly Asp Ile
            300                 305                 310

gtc acc gca tct gtc acc atc gcc aat aac tct act gtg gac cat ttc     1074
Val Thr Ala Ser Val Thr Ile Ala Asn Asn Ser Thr Val Asp His Phe
        315                 320                 325

atc cta aga gcc aag gtg aag aag ggg gtg aac atc ctg acc gtg cag     1122
Ile Leu Arg Ala Lys Val Lys Lys Gly Val Asn Ile Leu Thr Val Gln
    330                 335                 340

acc agc gag cct cgg cag tgg gat gtg agg caa gag gtg ggc aat gga     1170
Thr Ser Glu Pro Arg Gln Trp Asp Val Arg Gln Glu Val Gly Asn Gly
345                 350                 355                 360

ggg aag cac acc acc acc tcg gtg gcc tgc cag cgc ctg ggc cct ggg     1218
Gly Lys His Thr Thr Thr Ser Val Ala Cys Gln Arg Leu Gly Pro Gly
                365                 370                 375

gca cga aat agg agc agc aat tta ttc agc gag gtc atg cag atg aat     1266
Ala Arg Asn Arg Ser Ser Asn Leu Phe Ser Glu Val Met Gln Met Asn
            380                 385                 390

ttt gaa atc gcc agc ttc agc aga ctc tcg ggg aca cag cct atc aca     1314
Phe Glu Ile Ala Ser Phe Ser Arg Leu Ser Gly Thr Gln Pro Ile Thr
        395                 400                 405

tgg cag gtg gag tac ccg agg aag ggg gcc acg gac att gct gtg tcg     1362
Trp Gln Val Glu Tyr Pro Arg Lys Gly Ala Thr Asp Ile Ala Val Ser
    410                 415                 420

gag atc ttc atc agc cag aag gac cta gtt gcc atc gtc ccc ctt gct     1410
Glu Ile Phe Ile Ser Gln Lys Asp Leu Val Ala Ile Val Pro Leu Ala
425                 430                 435                 440

atg gac act gaa ctc ctg aac aca gcc atc ctc aca ggg aag acg gtg     1458
Met Asp Thr Glu Leu Leu Asn Thr Ala Ile Leu Thr Gly Lys Thr Val
                445                 450                 455

gcc atg cct gtc agg gtg gtg tcg gtg gaa gag aat agc acc ctg agg     1506
Ala Met Pro Val Arg Val Val Ser Val Glu Glu Asn Ser Thr Leu Arg
            460                 465                 470

gac atc tcg gag ttg gtg gag tgc aag gcc aca gac gag aat gtc atc     1554
Asp Ile Ser Glu Leu Val Glu Cys Lys Ala Thr Asp Glu Asn Val Ile
        475                 480                 485

aag gtc tcg gac cac tgt gac tat gtc ttt gtc aat ggt aaa gag atc     1602
Lys Val Ser Asp His Cys Asp Tyr Val Phe Val Asn Gly Lys Glu Ile
```

-continued

```
    490                 495                 500

aag ggc aag atg gac tct gtg gtg aac ttc acc tac cag cac ctg agc      1650
Lys Gly Lys Met Asp Ser Val Val Asn Phe Thr Tyr Gln His Leu Ser
505                 510                 515                 520

gca ccg ctg cat gtc act gtg tgg gtg cca cgg ctt ccc ctg cag atc      1698
Ala Pro Leu His Val Thr Val Trp Val Pro Arg Leu Pro Leu Gln Ile
                525                 530                 535

gag gtc tct gac aca gaa ctc agc cag gtt aag ggc tgg aga gtc ccc      1746
Glu Val Ser Asp Thr Glu Leu Ser Gln Val Lys Gly Trp Arg Val Pro
            540                 545                 550

atc gtg gcc agc aag agg ccc act cgg gac agt gag gag gaa gaa gag      1794
Ile Val Ala Ser Lys Arg Pro Thr Arg Asp Ser Glu Glu Glu Glu Glu
        555                 560                 565

gaa gaa cag aaa ggc cgg ggt tgt acc ctg cag ttc cag cat gcc aca      1842
Glu Glu Gln Lys Gly Arg Gly Cys Thr Leu Gln Phe Gln His Ala Thr
    570                 575                 580

gtg cgc gtc ctc acc caa ttt gta tca gag ggt gct ggg ccc tgg ggc      1890
Val Arg Val Leu Thr Gln Phe Val Ser Glu Gly Ala Gly Pro Trp Gly
585                 590                 595                 600

cag ctg agc cac ctt ctc agt cca gac tgg cag ttt gac atc acc cac      1938
Gln Leu Ser His Leu Leu Ser Pro Asp Trp Gln Phe Asp Ile Thr His
                605                 610                 615

ctg gtg gct gac ttt atg aag ctg gag tcc cca cac ata gcc acc ctg      1986
Leu Val Ala Asp Phe Met Lys Leu Glu Ser Pro His Ile Ala Thr Leu
                620                 625                 630

cag gac agc agg gtc ttg gtt ggg cgg gaa gtc gga atg acc acc atc      2034
Gln Asp Ser Arg Val Leu Val Gly Arg Glu Val Gly Met Thr Thr Ile
        635                 640                 645

cag gtg ttg tct ccc ctg tcc gac tca atc ttg gcc gag aag aca gta      2082
Gln Val Leu Ser Pro Leu Ser Asp Ser Ile Leu Ala Glu Lys Thr Val
    650                 655                 660

act gtg ctg gat gac aaa gta tct gtg aca gac tta gct gtc cag gtg      2130
Thr Val Leu Asp Asp Lys Val Ser Val Thr Asp Leu Ala Val Gln Val
665                 670                 675                 680

gtg gct ggg ctg tct gtc acc cta cac ccc atc tca gag aac aac aag      2178
Val Ala Gly Leu Ser Val Thr Leu His Pro Ile Ser Glu Asn Asn Lys
                685                 690                 695

gcc acc tca gct gtg gcc atg gca gaa gag ctg cta cgt gcc cca aaa      2226
Ala Thr Ser Ala Val Ala Met Ala Glu Glu Leu Leu Arg Ala Pro Lys
            700                 705                 710

aag gaa gct ata atc agc aca tgg ctc cag ttc agt gat ggc tca gtg      2274
Lys Glu Ala Ile Ile Ser Thr Trp Leu Gln Phe Ser Asp Gly Ser Val
        715                 720                 725

aca ccc ctg gat atc tac gac tcc aag gac ttc tcc ttg act gcc atc      2322
Thr Pro Leu Asp Ile Tyr Asp Ser Lys Asp Phe Ser Leu Thr Ala Ile
    730                 735                 740

tct ttg gac gag gct gtc gtg tcc atc ccc caa ccc ctc tcg cct tgg      2370
Ser Leu Asp Glu Ala Val Val Ser Ile Pro Gln Pro Leu Ser Pro Trp
745                 750                 755                 760

tgg ccc acc gtg gta gct gaa gga gaa ggc cag ggc cca ctg ctc cgg      2418
Trp Pro Thr Val Val Ala Glu Gly Glu Gly Gln Gly Pro Leu Leu Arg
                765                 770                 775

gtc gat atg tcc att gcc gaa gcc tgt cag aaa tcc aag cgc aag agt      2466
Val Asp Met Ser Ile Ala Glu Ala Cys Gln Lys Ser Lys Arg Lys Ser
            780                 785                 790

gtg ctg gct gtt ggc att ggc cac gtg ggg gtc aag ttt gga tgg gat      2514
Val Leu Ala Val Gly Ile Gly His Val Gly Val Lys Phe Gly Trp Asp
        795                 800                 805

gac gct gac tcc agc cag act gga gaa aag gat gag gag gag atc aag      2562
Asp Ala Asp Ser Ser Gln Thr Gly Glu Lys Asp Glu Glu Glu Ile Lys
```

-continued

```
    810                 815                 820

aac cat gcc agt gac cgt cgg cag aag att cag gac ctg gaa cgc cca      2610
Asn His Ala Ser Asp Arg Arg Gln Lys Ile Gln Asp Leu Glu Arg Pro
825                 830                 835                 840

ggc cag gat gaa cta tac cat ggc aac ttt cct ggg gat cgt gaa gaa      2658
Gly Gln Asp Glu Leu Tyr His Gly Asn Phe Pro Gly Asp Arg Glu Glu
                845                 850                 855

gga gcg ctg agt gct acc acc act acc aag tcc ctg ctg gat aac aac      2706
Gly Ala Leu Ser Ala Thr Thr Thr Thr Lys Ser Leu Leu Asp Asn Asn
            860                 865                 870

gtg ggg aag agt ggc agg cgg gac ggg gct agg cta cac agc ata ccc      2754
Val Gly Lys Ser Gly Arg Arg Asp Gly Ala Arg Leu His Ser Ile Pro
        875                 880                 885

att gac ttc acc aat ttc ccg gcc cat gtg gac ctc ccc aag gcc aag      2802
Ile Asp Phe Thr Asn Phe Pro Ala His Val Asp Leu Pro Lys Ala Lys
    890                 895                 900

acc agg ggc aca ctg gag gag aat ggt ctc atg cag aca gcc cat ggc      2850
Thr Arg Gly Thr Leu Glu Glu Asn Gly Leu Met Gln Thr Ala His Gly
905                 910                 915                 920

ctg agt gac cta gag att ggg atg tat gcc ctc cta ggt gtc ttc tgc      2898
Leu Ser Asp Leu Glu Ile Gly Met Tyr Ala Leu Leu Gly Val Phe Cys
                925                 930                 935

ctg gcc atc ctt gtc ttt ctc att aac tgc gcc acc ttt gcc ttc aag      2946
Leu Ala Ile Leu Val Phe Leu Ile Asn Cys Ala Thr Phe Ala Phe Lys
            940                 945                 950

tac agg cac aaa cag gtg cct ctg gaa ggc cag gca tcc atg acc cac      2994
Tyr Arg His Lys Gln Val Pro Leu Glu Gly Gln Ala Ser Met Thr His
        955                 960                 965

tct cat gac tgg gtc tgg ctg ggc aat gag gcg gag ctc ttg gag aac      3042
Ser His Asp Trp Val Trp Leu Gly Asn Glu Ala Glu Leu Leu Glu Asn
    970                 975                 980

att ggg gac ctg tcc cca ccc cag gat gag cac acg acc atc ata gac      3090
Ile Gly Asp Leu Ser Pro Pro Gln Asp Glu His Thr Thr Ile Ile Asp
985                 990                 995                 1000

cga ggg ctg ggg ggc  tgt gag gag aac aac  cac tta ctt ctc aac      3135
Arg Gly Leu Gly Gly  Cys Glu Glu Asn Asn  His Leu Leu Leu Asn
                1005                 1010                 1015

ggt ggc tcc caa aag  ccc acg cag agc cag  gtt cac agg ccg cca      3180
Gly Gly Ser Gln Lys  Pro Thr Gln Ser Gln  Val His Arg Pro Pro
                1020                 1025                 1030

ggc tcc ggg gga cgg  cag acc agg gag ccc  agg cag gag cct gca      3225
Gly Ser Gly Gly Arg  Gln Thr Arg Glu Pro  Arg Gln Glu Pro Ala
                1035                 1040                 1045

aac tca ccc acc tcc  aag atg aag aag gtc  aag ttt gcc aca ttc      3270
Asn Ser Pro Thr Ser  Lys Met Lys Lys Val  Lys Phe Ala Thr Phe
                1050                 1055                 1060

acc atc cca cct gag  gaa agc tgc ccc acg  gtg aac tcc atc ctc      3315
Thr Ile Pro Pro Glu  Glu Ser Cys Pro Thr  Val Asn Ser Ile Leu
                1065                 1070                 1075

agt ggg gaa gat gat  atc aag tgg gtt tgt  caa gac ctg gac gtg      3360
Ser Gly Glu Asp Asp  Ile Lys Trp Val Cys  Gln Asp Leu Asp Val
                1080                 1085                 1090

ggc gca ccc aag gaa  ctc aga acc tac ctg  gag aaa ttc caa gac      3405
Gly Ala Pro Lys Glu  Leu Arg Thr Tyr Leu  Glu Lys Phe Gln Asp
                1095                 1100                 1105

agt gtg tag cgctctggcc tcctcgccaa cttgggacag tagcctcctt              3454
Ser Val

cccgacctcc ctcagcagag tagctgaacg gaaggagctc tcagtggact gagtgaggaa    3514

atctggggcc cacagaatac caggtagcag gttagaagct gggaagggat gtttttatac    3574
```

-continued

```
taaagcagtt ttttttgttt tttgtttttt gtttttttgtt ttttttagca gcaaaggatg   3634

gtaggtttcc agaagtttga gtctctgact cagcagcgag gcagagtgga tccgaaagag   3694

aactgctcag acatgagaga gttattttat gaatcaaacg acactgcaga caagctacca   3754

aaaatatttg ttaaaaaaaa tatataaaaa gacgaataaa aaaaacacac aaatgactgt   3814

cggtttatat ttctaataaa ggaacaaaat gtaaaaatag ggcttgctaa aagaaggcct   3874

acattttaat tcagtcttta tgcttctgag gacagtccag gtctgttagc cttctgccca   3934

aggagaggca catctgaaca atggtcacct cttaggaaga atgagaattt tacattggat   3994

tccattatct ctgtttgctt ccatgtttct ttctaaggtc ctaagcctcc atttgattca   4054

atgtcatgtt tatttctgag gaccaagtgg tacattttcc taaatgaaat gtaaattata   4114

tttctattca ttagatagct ttttccccct ctttttaaga agatcatcaa cgaatccagt   4174

ctttacgttg taacattaac ctgtctttat attatacatc tcttgctttg tt           4226


<210> SEQ ID NO 15
<211> LENGTH: 1107
<212> TYPE: PRT
<213> ORGANISM: Mus musculus

<400> SEQUENCE: 15

Met Asp Gly Val Thr Ala Ala Thr Met Arg Ser Glu Gly Ala Ala Pro
1               5                   10                  15

Arg Arg Ala Ala Arg Tyr Gly Ala Leu Ser Leu Val Leu Ala Thr Leu
            20                  25                  30

Leu Gly Gln Val Thr Glu Ser Arg Gly Val Met Asp Asn Ile Gln Arg
        35                  40                  45

Phe Ser Ser Leu Pro Pro Tyr Leu Pro Val Ser Phe His Val Leu Arg
    50                  55                  60

Ala Glu Thr Ala Phe Phe Leu Lys Glu Ala Asn Pro Asp Pro Leu Arg
65                  70                  75                  80

Asn Ala Ser Leu Gln Ser Arg Val Glu Ser Phe Phe Ile Tyr Lys Ala
                85                  90                  95

Gln Gln Pro Pro Val Leu Asn Val Ser Tyr Gly Pro Tyr Ser Ala Glu
            100                 105                 110

Lys Val Ile Pro Leu Asp Leu Met Leu Asn Pro Asn Phe Leu Gly Pro
        115                 120                 125

Thr Ser Lys Phe Pro Phe Asp Trp Arg Leu Lys Ala Tyr Ile Leu Gln
    130                 135                 140

Glu Lys Val Tyr Leu Ser His Pro Lys Val Gln Val Leu Phe His Ile
145                 150                 155                 160

Val Gly Arg Asp Trp Asp Asp His Arg Asp Glu Lys Leu Pro Cys Leu
                165                 170                 175

Arg Val Phe Ala Phe Arg Asp Ser Arg Glu Val Arg Gly Ser Cys Arg
            180                 185                 190

Leu Gly Gly Pro Leu Gly Leu Cys Val Ala Gln Leu Glu Met Leu Pro
        195                 200                 205

Gly Trp Phe Ser Pro Pro Ala Val Val Ser Gly Arg Arg Arg Pro Ala
    210                 215                 220

Glu Arg Pro Glu Gly Ser Pro Val Glu Leu Tyr Tyr Ala Val Gln Pro
225                 230                 235                 240

Gly Asp Glu Arg Gly Asp Cys Thr Gly Gly Asp Thr Arg Lys Asp Asn
                245                 250                 255

Ala Ile Arg Pro Gly Lys Asp Gly Gln Glu Gly Arg Thr Ser His Leu
```

-continued

```
            260                 265                 270

Gln Lys Ile Gly Thr Ile Ser Leu Tyr Arg Ala Gln Asp Ser Thr Gln
        275                 280                 285

Leu Ser Glu Leu Arg Leu Asp Gly Asn Val Val Ile Trp Leu Pro Ser
    290                 295                 300

Gln Pro Val Lys Gln Gly Asp Ile Val Thr Ala Ser Val Thr Ile Ala
305                 310                 315                 320

Asn Asn Ser Thr Val Asp His Phe Ile Leu Arg Ala Lys Val Lys Lys
                325                 330                 335

Gly Val Asn Ile Leu Thr Val Gln Thr Ser Glu Pro Arg Gln Trp Asp
            340                 345                 350

Val Arg Gln Glu Val Gly Asn Gly Gly Lys His Thr Thr Thr Ser Val
        355                 360                 365

Ala Cys Gln Arg Leu Gly Pro Gly Ala Arg Asn Arg Ser Ser Asn Leu
    370                 375                 380

Phe Ser Glu Val Met Gln Met Asn Phe Glu Ile Ala Ser Phe Ser Arg
385                 390                 395                 400

Leu Ser Gly Thr Gln Pro Ile Thr Trp Gln Val Glu Tyr Pro Arg Lys
                405                 410                 415

Gly Ala Thr Asp Ile Ala Val Ser Glu Ile Phe Ile Ser Gln Lys Asp
            420                 425                 430

Leu Val Ala Ile Val Pro Leu Ala Met Asp Thr Glu Leu Leu Asn Thr
        435                 440                 445

Ala Ile Leu Thr Gly Lys Thr Val Ala Met Pro Val Arg Val Val Ser
    450                 455                 460

Val Glu Glu Asn Ser Thr Leu Arg Asp Ile Ser Glu Leu Val Glu Cys
465                 470                 475                 480

Lys Ala Thr Asp Glu Asn Val Ile Lys Val Ser Asp His Cys Asp Tyr
                485                 490                 495

Val Phe Val Asn Gly Lys Glu Ile Lys Gly Lys Met Asp Ser Val Val
            500                 505                 510

Asn Phe Thr Tyr Gln His Leu Ser Ala Pro Leu His Val Thr Val Trp
        515                 520                 525

Val Pro Arg Leu Pro Leu Gln Ile Glu Val Ser Asp Thr Glu Leu Ser
    530                 535                 540

Gln Val Lys Gly Trp Arg Val Pro Ile Val Ala Ser Lys Arg Pro Thr
545                 550                 555                 560

Arg Asp Ser Glu Glu Glu Glu Glu Glu Glu Gln Lys Gly Arg Gly Cys
                565                 570                 575

Thr Leu Gln Phe Gln His Ala Thr Val Arg Val Leu Thr Gln Phe Val
            580                 585                 590

Ser Glu Gly Ala Gly Pro Trp Gly Gln Leu Ser His Leu Leu Ser Pro
        595                 600                 605

Asp Trp Gln Phe Asp Ile Thr His Leu Val Ala Asp Phe Met Lys Leu
    610                 615                 620

Glu Ser Pro His Ile Ala Thr Leu Gln Asp Ser Arg Val Leu Val Gly
625                 630                 635                 640

Arg Glu Val Gly Met Thr Thr Ile Gln Val Leu Ser Pro Leu Ser Asp
                645                 650                 655

Ser Ile Leu Ala Glu Lys Thr Val Thr Val Leu Asp Asp Lys Val Ser
            660                 665                 670

Val Thr Asp Leu Ala Val Gln Val Val Ala Gly Leu Ser Val Thr Leu
        675                 680                 685
```

```
His Pro Ile Ser Glu Asn Asn Lys Ala Thr Ser Ala Val Ala Met Ala
    690                 695                 700

Glu Glu Leu Leu Arg Ala Pro Lys Lys Glu Ala Ile Ile Ser Thr Trp
705                 710                 715                 720

Leu Gln Phe Ser Asp Gly Ser Val Thr Pro Leu Asp Ile Tyr Asp Ser
                725                 730                 735

Lys Asp Phe Ser Leu Thr Ala Ile Ser Leu Asp Glu Ala Val Val Ser
            740                 745                 750

Ile Pro Gln Pro Leu Ser Pro Trp Trp Pro Thr Val Val Ala Glu Gly
        755                 760                 765

Glu Gly Gln Gly Pro Leu Leu Arg Val Asp Met Ser Ile Ala Glu Ala
    770                 775                 780

Cys Gln Lys Ser Lys Arg Lys Ser Val Leu Ala Val Gly Ile Gly His
785                 790                 795                 800

Val Gly Val Lys Phe Gly Trp Asp Asp Ala Asp Ser Ser Gln Thr Gly
                805                 810                 815

Glu Lys Asp Glu Glu Glu Ile Lys Asn His Ala Ser Asp Arg Arg Gln
            820                 825                 830

Lys Ile Gln Asp Leu Glu Arg Pro Gly Gln Asp Glu Leu Tyr His Gly
        835                 840                 845

Asn Phe Pro Gly Asp Arg Glu Glu Gly Ala Leu Ser Ala Thr Thr Thr
    850                 855                 860

Thr Lys Ser Leu Leu Asp Asn Asn Val Gly Lys Ser Gly Arg Arg Asp
865                 870                 875                 880

Gly Ala Arg Leu His Ser Ile Pro Ile Asp Phe Thr Asn Phe Pro Ala
                885                 890                 895

His Val Asp Leu Pro Lys Ala Lys Thr Arg Gly Thr Leu Glu Glu Asn
            900                 905                 910

Gly Leu Met Gln Thr Ala His Gly Leu Ser Asp Leu Glu Ile Gly Met
        915                 920                 925

Tyr Ala Leu Leu Gly Val Phe Cys Leu Ala Ile Leu Val Phe Leu Ile
    930                 935                 940

Asn Cys Ala Thr Phe Ala Phe Lys Tyr Arg His Lys Gln Val Pro Leu
945                 950                 955                 960

Glu Gly Gln Ala Ser Met Thr His Ser His Asp Trp Val Trp Leu Gly
                965                 970                 975

Asn Glu Ala Glu Leu Leu Glu Asn Ile Gly Asp Leu Ser Pro Pro Gln
            980                 985                 990

Asp Glu His Thr Thr Ile Ile Asp  Arg Gly Leu Gly Gly  Cys Glu Glu
        995                 1000                1005

Asn Asn  His Leu Leu Leu Asn  Gly Gly Ser Gln Lys  Pro Thr Gln
    1010                1015                1020

Ser Gln  Val His Arg Pro Pro  Gly Ser Gly Gly Arg  Gln Thr Arg
    1025                1030                1035

Glu Pro  Arg Gln Glu Pro Ala  Asn Ser Pro Thr Ser  Lys Met Lys
    1040                1045                1050

Lys Val  Lys Phe Ala Thr Phe  Thr Ile Pro Pro Glu  Glu Ser Cys
    1055                1060                1065

Pro Thr  Val Asn Ser Ile Leu  Ser Gly Glu Asp Asp  Ile Lys Trp
    1070                1075                1080

Val Cys  Gln Asp Leu Asp Val  Gly Ala Pro Lys Glu  Leu Arg Thr
    1085                1090                1095

Tyr Leu  Glu Lys Phe Gln Asp  Ser Val
    1100                1105
```

-continued

<210> SEQ ID NO 16
<211> LENGTH: 3582
<212> TYPE: DNA
<213> ORGANISM: Mus musculus
<220> FEATURE:
<221> NAME/KEY: CDS
<222> LOCATION: (152)..(2311)
<223> OTHER INFORMATION:

<400> SEQUENCE: 16
gaacatcctg accgtgcaga ccagcgagcc tcggcagtgg gatgtgaggc aagaggtggg 60
caatggaggg aagcacacca ccacctcggt ggcctgccag cgcctgggcc ctggggcacg 120
aaataggagc agcaatttat tcagcgaggt c atg cag atg aat ttt gaa atc 172
Met Gln Met Asn Phe Glu Ile
1 5 gcc agc ttc agc agc ctc tcg ggg aca cag cct atc aca tgg cag gtg 220
Ala Ser Phe Ser Ser Leu Ser Gly Thr Gln Pro Ile Thr Trp Gln Val
10 15 20 gag tac ccg agg aag ggg gcc acg gac att gct gtg tcg gag atc ttc 268
Glu Tyr Pro Arg Lys Gly Ala Thr Asp Ile Ala Val Ser Glu Ile Phe
25 30 35 atc agc cag aag gac cta gtt gcc atc gtc ccc ctt gct atg gac act 316
Ile Ser Gln Lys Asp Leu Val Ala Ile Val Pro Leu Ala Met Asp Thr
40 45 50 55 gaa ctc ctg aac aca gcc atc ctc aca ggg aag acg gtg gcc atg cct 364
Glu Leu Leu Asn Thr Ala Ile Leu Thr Gly Lys Thr Val Ala Met Pro
60 65 70 gtc agg gtg gtg tcg gtg gaa gag aat agc acc ctg agg gac atc tcg 412
Val Arg Val Val Ser Val Glu Glu Asn Ser Thr Leu Arg Asp Ile Ser
75 80 85 gag ttg gtg gag tgc aag gcc aca gac gag aat gtc atc aag gtc tcg 460
Glu Leu Val Glu Cys Lys Ala Thr Asp Glu Asn Val Ile Lys Val Ser
90 95 100 gac cac tgt gac tat gtc ttt gtc aat ggt aaa gag atc aag ggc aag 508
Asp His Cys Asp Tyr Val Phe Val Asn Gly Lys Glu Ile Lys Gly Lys
105 110 115 atg gac tct gtg gtg aac ttc acc tac cag cac ctg agc gca ccg ctg 556
Met Asp Ser Val Val Asn Phe Thr Tyr Gln His Leu Ser Ala Pro Leu
120 125 130 135 cat gtc act gtg tgg gtg cca cgg ctt ccc ctg cag atc gag gtc tct 604
His Val Thr Val Trp Val Pro Arg Leu Pro Leu Gln Ile Glu Val Ser
140 145 150 gac aca gaa ctc agc cag gtt aag ggc tgg aga gtc ccc atc gtg gcc 652
Asp Thr Glu Leu Ser Gln Val Lys Gly Trp Arg Val Pro Ile Val Ala
155 160 165 agc aag agg ccc act cgg gac agt gag gag gaa gaa gag gaa gaa cag 700
Ser Lys Arg Pro Thr Arg Asp Ser Glu Glu Glu Glu Glu Glu Glu Gln
170 175 180 aaa ggc cgg ggt tgt acc ctg cag ttc cag cat gcc aca gtg cgc gtc 748
Lys Gly Arg Gly Cys Thr Leu Gln Phe Gln His Ala Thr Val Arg Val
185 190 195 ctc acc caa ttt gta tca gag ggt gct ggg ccc tgg ggc cag ctg agc 796
Leu Thr Gln Phe Val Ser Glu Gly Ala Gly Pro Trp Gly Gln Leu Ser
200 205 210 215 cac ctt ctc agt cca gac tgg cag ttt gac atc acc cac ctg gtg gct 844
His Leu Leu Ser Pro Asp Trp Gln Phe Asp Ile Thr His Leu Val Ala
220 225 230 gac ttt atg aag ctg gag tcc cca cac ata gcc acc ctg cag gac agc 892
Asp Phe Met Lys Leu Glu Ser Pro His Ile Ala Thr Leu Gln Asp Ser
235 240 245

```
agg gtc ttg gtt ggg cgg gaa gtc gga atg acc acc atc cag gtg ttg      940
Arg Val Leu Val Gly Arg Glu Val Gly Met Thr Thr Ile Gln Val Leu
        250                 255                 260

tct ccc ctg tcc gac tcc atc ttg gcc gag aag aca gta act gtg ctg      988
Ser Pro Leu Ser Asp Ser Ile Leu Ala Glu Lys Thr Val Thr Val Leu
    265                 270                 275

gat gac aaa gta tct gtg aca gac tta gct gtc cag gtg gtg gct ggg     1036
Asp Asp Lys Val Ser Val Thr Asp Leu Ala Val Gln Val Val Ala Gly
280                 285                 290                 295

ctg tct gtc acc cta cac ccc atc tca gag aac aac aag gcc acc tca     1084
Leu Ser Val Thr Leu His Pro Ile Ser Glu Asn Asn Lys Ala Thr Ser
                300                 305                 310

gct gtg gcc atg gca gaa gag ctg cta cgt gcc cca aaa aag gaa gct     1132
Ala Val Ala Met Ala Glu Glu Leu Leu Arg Ala Pro Lys Lys Glu Ala
            315                 320                 325

ata atc agc aca tgg ctc cag ttc agt gat ggc tca gtg aca ccc ctg     1180
Ile Ile Ser Thr Trp Leu Gln Phe Ser Asp Gly Ser Val Thr Pro Leu
        330                 335                 340

gat atc tac gac tcc aag gac ttc tcc ttg act gcc atc tct ttg gac     1228
Asp Ile Tyr Asp Ser Lys Asp Phe Ser Leu Thr Ala Ile Ser Leu Asp
    345                 350                 355

gag gct gtc gtg tcc atc ccc caa ccc ctc tcg cct tgg tgg ccc acc     1276
Glu Ala Val Val Ser Ile Pro Gln Pro Leu Ser Pro Trp Trp Pro Thr
360                 365                 370                 375

gtg gta gct gaa gga gaa ggc cag ggc cca ctg ctc cgg gtc gat atg     1324
Val Val Ala Glu Gly Glu Gly Gln Gly Pro Leu Leu Arg Val Asp Met
                380                 385                 390

tcc att gcc gaa gcc tgt cag aaa tcc aag cgc aag agt gtg ctg gct     1372
Ser Ile Ala Glu Ala Cys Gln Lys Ser Lys Arg Lys Ser Val Leu Ala
            395                 400                 405

gtt ggc att ggc cac gtg ggg gtc aag ttt gga tgg gat gac gct gac     1420
Val Gly Ile Gly His Val Gly Val Lys Phe Gly Trp Asp Asp Ala Asp
        410                 415                 420

tcc agc cag act gga gaa aag gat gag gag gag atc aag aac cat gcc     1468
Ser Ser Gln Thr Gly Glu Lys Asp Glu Glu Glu Ile Lys Asn His Ala
    425                 430                 435

agt gac cgt cgg cag aag att cag gac ctg gaa cgc cca ggc cag gat     1516
Ser Asp Arg Arg Gln Lys Ile Gln Asp Leu Glu Arg Pro Gly Gln Asp
440                 445                 450                 455

gaa cta tac cat ggc aac ttt cct ggg gat cgt gaa gaa gga gcg ctg     1564
Glu Leu Tyr His Gly Asn Phe Pro Gly Asp Arg Glu Glu Gly Ala Leu
                460                 465                 470

agt gct acc acc act acc aag tcc ctg ctg gat aac aac gtg ggg aag     1612
Ser Ala Thr Thr Thr Thr Lys Ser Leu Leu Asp Asn Asn Val Gly Lys
            475                 480                 485

agt ggc agg cgg gac ggg gct agg cta cac agc ata ccc att gac ttc     1660
Ser Gly Arg Arg Asp Gly Ala Arg Leu His Ser Ile Pro Ile Asp Phe
        490                 495                 500

acc aat ttc ccg gcc cat gtg gac ctc ccc aag gcc aag acc agg ggc     1708
Thr Asn Phe Pro Ala His Val Asp Leu Pro Lys Ala Lys Thr Arg Gly
    505                 510                 515

aca ctg gag gag aat ggt ctc atg cag aca gcc cat ggc ctg agt gac     1756
Thr Leu Glu Glu Asn Gly Leu Met Gln Thr Ala His Gly Leu Ser Asp
520                 525                 530                 535

cta gag att ggg atg tat gcc ctc cta ggt gtc ttc tgc ctg gcc atc     1804
Leu Glu Ile Gly Met Tyr Ala Leu Leu Gly Val Phe Cys Leu Ala Ile
                540                 545                 550

ctt gtc ttt ctc att aac tgc gcc acc ttt gcc ttc aag tac agg cac     1852
Leu Val Phe Leu Ile Asn Cys Ala Thr Phe Ala Phe Lys Tyr Arg His
            555                 560                 565
```

-continued

```
aaa cag gtg cct ctg gaa ggc cag gca tcc atg acc cac tct cat gac     1900
Lys Gln Val Pro Leu Glu Gly Gln Ala Ser Met Thr His Ser His Asp
        570                 575                 580

tgg gtc tgg ctg ggc aat gag gcg gag ctc ttg gag aac att ggg gac     1948
Trp Val Trp Leu Gly Asn Glu Ala Glu Leu Leu Glu Asn Ile Gly Asp
    585                 590                 595

ctg tcc cca ccc cag gat gag cac acg acc atc ata gac cga ggg ctg     1996
Leu Ser Pro Pro Gln Asp Glu His Thr Thr Ile Ile Asp Arg Gly Leu
600                 605                 610                 615

ggg ggc tgt gag gag aac aac cac tta ctt ctc aac ggt ggc tcc caa     2044
Gly Gly Cys Glu Glu Asn Asn His Leu Leu Leu Asn Gly Gly Ser Gln
                620                 625                 630

aag ccc acg cag agc cag gtt cac agg ccg cca ggc tcc ggg gga cgg     2092
Lys Pro Thr Gln Ser Gln Val His Arg Pro Pro Gly Ser Gly Gly Arg
            635                 640                 645

cag acc agg gag ccc agg cag gag cct gca aac tca ccc acc tcc aag     2140
Gln Thr Arg Glu Pro Arg Gln Glu Pro Ala Asn Ser Pro Thr Ser Lys
        650                 655                 660

atg aag aag gtc aag ttt gcc aca ttc acc atc cca cct gag gaa agc     2188
Met Lys Lys Val Lys Phe Ala Thr Phe Thr Ile Pro Pro Glu Glu Ser
    665                 670                 675

tgc ccc acg gtg aac tcc atc ctc agt ggg gaa gat gat atc aag tgg     2236
Cys Pro Thr Val Asn Ser Ile Leu Ser Gly Glu Asp Asp Ile Lys Trp
680                 685                 690                 695

gtt tgt caa gac ctg gac gtg ggc gca ccc aag gaa ctc aga acc tac     2284
Val Cys Gln Asp Leu Asp Val Gly Ala Pro Lys Glu Leu Arg Thr Tyr
                700                 705                 710

ctg gag aaa ttc caa gac agt gtg tag cgctctggcc tcctcgccaa           2331
Leu Glu Lys Phe Gln Asp Ser Val
            715

cttgggacag tagcctcctt cccgacctcc ctcagcagag tagctgaacg gaaggagctc   2391

tcagtggact gagtgaggaa atctggggcc cacagaatac caggtagcag gttagaagct   2451

gggaagggat gtttttatac taaagcagtt tttttgttt tttgtttttt gtttttttgtt   2511

ttttttagca gcaaaggatg gtaggtttcc agaagtttga gtctctgact cagcagcgag   2571

gcagagtgga tccgaaagag aactgctcag acatgagaga gttattttat gaatcaaacg   2631

acactgcaga caagctacca aaaatatttg ttaaaaaaaa tatataaaaa gacgaataaa   2691

aaaaacacac aaatgactgt cggtttatat ttctaataaa ggaacaaaat gtaaaaatag   2751

ggcttgctaa aagaaggcct acattttaat tcagtcttta tgcttctgag gacagtccag   2811

gtctgttagc cttctgccca aggagaggca catctgaaca atggtcacct cttaggaaga   2871

atgagaattt tacattggat tccattatct ctgtttgctt ccatgtttct ttctaaggtc   2931

ctaagcctcc atttgattca atgtcatgtt tatttctgag gaccaagtgg tacattttcc   2991

taaatgaaat gtaaattata tttctattca ttagatagct ttttccccct ctttttaaga   3051

agatcatcaa cgaatccagt ctttacgttg taacattaac ctgtctttat attatacatc   3111

tcttgctttg ttaatatttt ctggcttgtt tgtaattctt tttgtttttt tgttttgttt   3171

tgttttaaca atatagcaag tgtgcagttc cccacatggg gagagtgcac cccacaatct   3231

gtcatcagcc gggtcaggcc aatgagtgga ataatgttca cagctatctg aatagggtat   3291

ggccaagaga acagagtgca gcctgtgaca cctggccact ccctatggag acagagactc   3351

agtgggtgtc tccggcagtt tgggcatagg gatgcctcta tgtgaagagc tgtgagtgaa   3411

atccataaac tcgaggtgtg cagagtcagg cagatgggcc atgtctacca caagatacag   3471

ccgaccctgt actgaacaaa cagaaaagac atgtgggggga ggggcaggct ggagttatct   3531
```

gattttatta ctgggcaagg cgaaccagca tgaactcaaa atgatttttt t 3582

<210> SEQ ID NO 17
<211> LENGTH: 719
<212> TYPE: PRT
<213> ORGANISM: Mus musculus

<400> SEQUENCE: 17

```
Met Gln Met Asn Phe Glu Ile Ala Ser Phe Ser Ser Leu Ser Gly Thr
1               5                   10                  15

Gln Pro Ile Thr Trp Gln Val Glu Tyr Pro Arg Lys Gly Ala Thr Asp
            20                  25                  30

Ile Ala Val Ser Glu Ile Phe Ile Ser Gln Lys Asp Leu Val Ala Ile
        35                  40                  45

Val Pro Leu Ala Met Asp Thr Glu Leu Leu Asn Thr Ala Ile Leu Thr
    50                  55                  60

Gly Lys Thr Val Ala Met Pro Val Arg Val Val Ser Val Glu Glu Asn
65                  70                  75                  80

Ser Thr Leu Arg Asp Ile Ser Glu Leu Val Glu Cys Lys Ala Thr Asp
                85                  90                  95

Glu Asn Val Ile Lys Val Ser Asp His Cys Asp Tyr Val Phe Val Asn
            100                 105                 110

Gly Lys Glu Ile Lys Gly Lys Met Asp Ser Val Val Asn Phe Thr Tyr
        115                 120                 125

Gln His Leu Ser Ala Pro Leu His Val Thr Val Trp Val Pro Arg Leu
    130                 135                 140

Pro Leu Gln Ile Glu Val Ser Asp Thr Glu Leu Ser Gln Val Lys Gly
145                 150                 155                 160

Trp Arg Val Pro Ile Val Ala Ser Lys Arg Pro Thr Arg Asp Ser Glu
                165                 170                 175

Glu Glu Glu Glu Glu Glu Gln Lys Gly Arg Gly Cys Thr Leu Gln Phe
            180                 185                 190

Gln His Ala Thr Val Arg Val Leu Thr Gln Phe Val Ser Glu Gly Ala
        195                 200                 205

Gly Pro Trp Gly Gln Leu Ser His Leu Leu Ser Pro Asp Trp Gln Phe
    210                 215                 220

Asp Ile Thr His Leu Val Ala Asp Phe Met Lys Leu Glu Ser Pro His
225                 230                 235                 240

Ile Ala Thr Leu Gln Asp Ser Arg Val Leu Val Gly Arg Glu Val Gly
                245                 250                 255

Met Thr Thr Ile Gln Val Leu Ser Pro Leu Ser Asp Ser Ile Leu Ala
            260                 265                 270

Glu Lys Thr Val Thr Val Leu Asp Asp Lys Val Ser Val Thr Asp Leu
        275                 280                 285

Ala Val Gln Val Val Ala Gly Leu Ser Val Thr Leu His Pro Ile Ser
    290                 295                 300

Glu Asn Asn Lys Ala Thr Ser Ala Val Ala Met Ala Glu Glu Leu Leu
305                 310                 315                 320

Arg Ala Pro Lys Lys Glu Ala Ile Ile Ser Thr Trp Leu Gln Phe Ser
                325                 330                 335

Asp Gly Ser Val Thr Pro Leu Asp Ile Tyr Asp Ser Lys Asp Phe Ser
            340                 345                 350

Leu Thr Ala Ile Ser Leu Asp Glu Ala Val Val Ser Ile Pro Gln Pro
        355                 360                 365
```

```
Leu Ser Pro Trp Trp Pro Thr Val Val Ala Glu Gly Glu Gly Gln Gly
    370                 375                 380

Pro Leu Leu Arg Val Asp Met Ser Ile Ala Glu Ala Cys Gln Lys Ser
385                 390                 395                 400

Lys Arg Lys Ser Val Leu Ala Val Gly Ile Gly His Val Gly Val Lys
                405                 410                 415

Phe Gly Trp Asp Asp Ala Asp Ser Ser Gln Thr Gly Glu Lys Asp Glu
            420                 425                 430

Glu Glu Ile Lys Asn His Ala Ser Asp Arg Arg Gln Lys Ile Gln Asp
        435                 440                 445

Leu Glu Arg Pro Gly Gln Asp Glu Leu Tyr His Gly Asn Phe Pro Gly
    450                 455                 460

Asp Arg Glu Glu Gly Ala Leu Ser Ala Thr Thr Thr Thr Lys Ser Leu
465                 470                 475                 480

Leu Asp Asn Asn Val Gly Lys Ser Gly Arg Arg Asp Gly Ala Arg Leu
                485                 490                 495

His Ser Ile Pro Ile Asp Phe Thr Asn Phe Pro Ala His Val Asp Leu
            500                 505                 510

Pro Lys Ala Lys Thr Arg Gly Thr Leu Glu Glu Asn Gly Leu Met Gln
        515                 520                 525

Thr Ala His Gly Leu Ser Asp Leu Glu Ile Gly Met Tyr Ala Leu Leu
    530                 535                 540

Gly Val Phe Cys Leu Ala Ile Leu Val Phe Leu Ile Asn Cys Ala Thr
545                 550                 555                 560

Phe Ala Phe Lys Tyr Arg His Lys Gln Val Pro Leu Glu Gly Gln Ala
                565                 570                 575

Ser Met Thr His Ser His Asp Trp Val Trp Leu Gly Asn Glu Ala Glu
            580                 585                 590

Leu Leu Glu Asn Ile Gly Asp Leu Ser Pro Pro Gln Asp Glu His Thr
        595                 600                 605

Thr Ile Ile Asp Arg Gly Leu Gly Gly Cys Glu Glu Asn Asn His Leu
    610                 615                 620

Leu Leu Asn Gly Gly Ser Gln Lys Pro Thr Gln Ser Gln Val His Arg
625                 630                 635                 640

Pro Pro Gly Ser Gly Gly Arg Gln Thr Arg Glu Pro Arg Gln Glu Pro
                645                 650                 655

Ala Asn Ser Pro Thr Ser Lys Met Lys Lys Val Lys Phe Ala Thr Phe
            660                 665                 670

Thr Ile Pro Pro Glu Glu Ser Cys Pro Thr Val Asn Ser Ile Leu Ser
        675                 680                 685

Gly Glu Asp Asp Ile Lys Trp Val Cys Gln Asp Leu Asp Val Gly Ala
    690                 695                 700

Pro Lys Glu Leu Arg Thr Tyr Leu Glu Lys Phe Gln Asp Ser Val
705                 710                 715
```

<210> SEQ ID NO 18
<211> LENGTH: 5639
<212> TYPE: DNA
<213> ORGANISM: Mus musculus
<220> FEATURE:
<221> NAME/KEY: CDS
<222> LOCATION: (79)..(3936)
<223> OTHER INFORMATION:

<400> SEQUENCE: 18

```
aggagcagcc gccggagccg gagcgctgcc gggggcggcc ccgggcatgg ggcaaccggc      60
```

-continued

```
gcggtcccgg ggctggcg atg gat ggc gtg aca gcg gcc acg atg cgc tcc      111
                    Met Asp Gly Val Thr Ala Ala Thr Met Arg Ser
                    1               5                   10

gag ggc gcg gcc ccg agg cgg gcg gcg cgg tac ggg gcg ctg agc ctg      159
Glu Gly Ala Ala Pro Arg Arg Ala Ala Arg Tyr Gly Ala Leu Ser Leu
            15                  20                  25

gtc cta gcc acg cta ctg ggc caa gtg acc gaa agc cga ggg gtc atg      207
Val Leu Ala Thr Leu Leu Gly Gln Val Thr Glu Ser Arg Gly Val Met
        30                  35                  40

gat aat ata cag aga ttc tct tca ttg ccg ccg tac ctg ccc gtg agc      255
Asp Asn Ile Gln Arg Phe Ser Ser Leu Pro Pro Tyr Leu Pro Val Ser
    45                  50                  55

ttc cac gtc ctc aga gcc gag act gca ttc ttc cta aag gag gcc aac      303
Phe His Val Leu Arg Ala Glu Thr Ala Phe Phe Leu Lys Glu Ala Asn
60                  65                  70                  75

ccc gac ccg ctg cgg aat gcc agc ctg cag tcc agg gtg gag tct ttc      351
Pro Asp Pro Leu Arg Asn Ala Ser Leu Gln Ser Arg Val Glu Ser Phe
                80                  85                  90

ttc atc tac aag gcc cag cag ccc ccg gta tta aac gtc agc tat ggg      399
Phe Ile Tyr Lys Ala Gln Gln Pro Pro Val Leu Asn Val Ser Tyr Gly
            95                  100                 105

cct tac tct gca gaa aag gtc atc cct ctg gac ttg atg ttg aac ccc      447
Pro Tyr Ser Ala Glu Lys Val Ile Pro Leu Asp Leu Met Leu Asn Pro
        110                 115                 120

aac ttt tta ggc cca acc agt aag ttt ccc ttt gac tgg agg ctg aag      495
Asn Phe Leu Gly Pro Thr Ser Lys Phe Pro Phe Asp Trp Arg Leu Lys
    125                 130                 135

gcc tac atc ctt caa gag aaa gtc tac ctg agc cat ccc aaa gta cag      543
Ala Tyr Ile Leu Gln Glu Lys Val Tyr Leu Ser His Pro Lys Val Gln
140                 145                 150                 155

gtg ctc ttc cac atc gtg ggc cga gac tgg gat gac cac agg gac gag      591
Val Leu Phe His Ile Val Gly Arg Asp Trp Asp Asp His Arg Asp Glu
                160                 165                 170

aaa ctg ccc tgc ctg cgg gtc ttt gcg ttc aga gac agc cgg gag gtt      639
Lys Leu Pro Cys Leu Arg Val Phe Ala Phe Arg Asp Ser Arg Glu Val
            175                 180                 185

cga ggc agc tgt cgt ctg ggt ggg ccc ctg gga ctg tgc gtg gcc cag      687
Arg Gly Ser Cys Arg Leu Gly Gly Pro Leu Gly Leu Cys Val Ala Gln
        190                 195                 200

ctg gag atg ctg cct ggc tgg ttc agt ccc cca gcg gtt gta tct ggg      735
Leu Glu Met Leu Pro Gly Trp Phe Ser Pro Pro Ala Val Val Ser Gly
    205                 210                 215

cgc agg agg cca gca gag cgg cca gag ggg agt ccg gtg gaa ctg tat      783
Arg Arg Arg Pro Ala Glu Arg Pro Glu Gly Ser Pro Val Glu Leu Tyr
220                 225                 230                 235

tat gct gta cag cca ggg gac gag cgt ggt gac tgc act gga ggt gac      831
Tyr Ala Val Gln Pro Gly Asp Glu Arg Gly Asp Cys Thr Gly Gly Asp
                240                 245                 250

acc agg aag gac aat gct att cgt cca gga aag gat gga cag gag ggc      879
Thr Arg Lys Asp Asn Ala Ile Arg Pro Gly Lys Asp Gly Gln Glu Gly
            255                 260                 265

agg aca tcc cac cta cag aag att ggc acc att agc ctt tac cgc gcc      927
Arg Thr Ser His Leu Gln Lys Ile Gly Thr Ile Ser Leu Tyr Arg Ala
        270                 275                 280

cag gac agc acc cag ctc agc gaa ctg cgc ctg gat ggc aat gtg gtc      975
Gln Asp Ser Thr Gln Leu Ser Glu Leu Arg Leu Asp Gly Asn Val Val
    285                 290                 295

atc tgg ctg ccc tcc cag ccc gtc aag cag gga gac ata gtc acc gca     1023
Ile Trp Leu Pro Ser Gln Pro Val Lys Gln Gly Asp Ile Val Thr Ala
300                 305                 310                 315
```

-continued

```
tct gtc acc atc gcc aat aac tct act gtg gac cat ttc atc cta aga      1071
Ser Val Thr Ile Ala Asn Asn Ser Thr Val Asp His Phe Ile Leu Arg
                320                 325                 330

gcc aag gtg aag aag ggg gtg aac atc ctg acc gtg cag acc agc gag      1119
Ala Lys Val Lys Lys Gly Val Asn Ile Leu Thr Val Gln Thr Ser Glu
            335                 340                 345

cct cgg cag tgg gat gtg agg caa gag gtg ggc aat gga ggg aag cac      1167
Pro Arg Gln Trp Asp Val Arg Gln Glu Val Gly Asn Gly Gly Lys His
        350                 355                 360

acc acc acc tcg gtg gcc tgc cag cgc ctg ggc cct ggg gca cga aat      1215
Thr Thr Thr Ser Val Ala Cys Gln Arg Leu Gly Pro Gly Ala Arg Asn
    365                 370                 375

agg agc agc aat tta ttc agc gag gtc atg cag atg aat ttt gaa atc      1263
Arg Ser Ser Asn Leu Phe Ser Glu Val Met Gln Met Asn Phe Glu Ile
380                 385                 390                 395

gcc agc ttc agc agc ctc tcg ggg aca cag cct atc aca tgg cag gtg      1311
Ala Ser Phe Ser Ser Leu Ser Gly Thr Gln Pro Ile Thr Trp Gln Val
                400                 405                 410

gag tac ccg agg aag ggg gcc acg gac att gct gtg tcg gag atc ttc      1359
Glu Tyr Pro Arg Lys Gly Ala Thr Asp Ile Ala Val Ser Glu Ile Phe
            415                 420                 425

atc agc cag aag gac cta gtt gcc atc gtc ccc ctt gct atg aac gat      1407
Ile Ser Gln Lys Asp Leu Val Ala Ile Val Pro Leu Ala Met Asn Asp
        430                 435                 440

aag aca ttc aaa tgc ttt gaa aag caa aac cat tat aaa gac ata aga      1455
Lys Thr Phe Lys Cys Phe Glu Lys Gln Asn His Tyr Lys Asp Ile Arg
    445                 450                 455

tat tat tcc ggt cca ttg tca aca ctt tta cct cta gtg aat tcc gat      1503
Tyr Tyr Ser Gly Pro Leu Ser Thr Leu Leu Pro Leu Val Asn Ser Asp
460                 465                 470                 475

tgg ctt cat gcc atc atc aca gac aat gat gcc atc tcc aca gga cct      1551
Trp Leu His Ala Ile Ile Thr Asp Asn Asp Ala Ile Ser Thr Gly Pro
                480                 485                 490

gta gcc agg acc tgg aat tat tgc tgt gtg gct gtg agg cgc gca gag      1599
Val Ala Arg Thr Trp Asn Tyr Cys Cys Val Ala Val Arg Arg Ala Glu
            495                 500                 505

gtg tta gca tgt gtc ctc ggg gaa gga gag aaa ttt gct cag cta cct      1647
Val Leu Ala Cys Val Leu Gly Glu Gly Glu Lys Phe Ala Gln Leu Pro
        510                 515                 520

tcg gag agc agc agt aac tcc ctg gaa agg atg ggc cct atc tgg tat      1695
Ser Glu Ser Ser Ser Asn Ser Leu Glu Arg Met Gly Pro Ile Trp Tyr
    525                 530                 535

cga ctg aca tct ggg gtc atc tta gac aac ctg cag gaa ccg cag ggg      1743
Arg Leu Thr Ser Gly Val Ile Leu Asp Asn Leu Gln Glu Pro Gln Gly
540                 545                 550                 555

tct gaa act cat cca ctc ctg cat cca gcg agg acc ttt gtc cct cta      1791
Ser Glu Thr His Pro Leu Leu His Pro Ala Arg Thr Phe Val Pro Leu
                560                 565                 570

gag ata tcg gaa atg cct ctg ggg aca aaa ctg tcc ctg gtc agg atc      1839
Glu Ile Ser Glu Met Pro Leu Gly Thr Lys Leu Ser Leu Val Arg Ile
            575                 580                 585

ttc tgc att aaa aat ctg gct gct gtg atg aag gaa tgt aca gac agc      1887
Phe Cys Ile Lys Asn Leu Ala Ala Val Met Lys Glu Cys Thr Asp Ser
        590                 595                 600

tac aga aga gtc ttc tgc agc aag aag agg gga tgc aaa ggc cct gtg      1935
Tyr Arg Arg Val Phe Cys Ser Lys Lys Arg Gly Cys Lys Gly Pro Val
    605                 610                 615

gtc ctc atg gac agt gac cta atg ctg atc caa ttt tcc acc aag cat      1983
Val Leu Met Asp Ser Asp Leu Met Leu Ile Gln Phe Ser Thr Lys His
620                 625                 630                 635
```

-continued

```
tcg gct cac gtg cac agc cca ccg aca gag atg aaa aga ttc cga gaa      2031
Ser Ala His Val His Ser Pro Pro Thr Glu Met Lys Arg Phe Arg Glu
                640                 645                 650

aca cag cca atg ggc tgg aaa gat tcc tgc agg aat cag ttc ctt ttt      2079
Thr Gln Pro Met Gly Trp Lys Asp Ser Cys Arg Asn Gln Phe Leu Phe
            655                 660                 665

gtc tcg gac cac tgt gac tat gtc ttt gtc aat ggt aaa gag atc aag      2127
Val Ser Asp His Cys Asp Tyr Val Phe Val Asn Gly Lys Glu Ile Lys
        670                 675                 680

ggc aag atg gac tct gtg gtg aac ttc acc tac cag cac ctg agc gca      2175
Gly Lys Met Asp Ser Val Val Asn Phe Thr Tyr Gln His Leu Ser Ala
    685                 690                 695

ccg ctg cat gtc act gtg tgg gtg cca cgg ctt ccc ctg cag atc gag      2223
Pro Leu His Val Thr Val Trp Val Pro Arg Leu Pro Leu Gln Ile Glu
700                 705                 710                 715

gtc tct gac aca gaa ctc agc cag gtt aag ggc tgg aga gtc ccc atc      2271
Val Ser Asp Thr Glu Leu Ser Gln Val Lys Gly Trp Arg Val Pro Ile
                720                 725                 730

gtg gcc agc aag agg ccc act cgg gac agt gag gag gaa gaa gag gaa      2319
Val Ala Ser Lys Arg Pro Thr Arg Asp Ser Glu Glu Glu Glu Glu Glu
            735                 740                 745

gaa cag aaa ggc cgg ggt tgt acc ctg cag ttc cag cat gcc aca gtg      2367
Glu Gln Lys Gly Arg Gly Cys Thr Leu Gln Phe Gln His Ala Thr Val
        750                 755                 760

cgc gtc ctc acc caa ttt gta tca gag ggt gct ggg ccc tgg ggc cag      2415
Arg Val Leu Thr Gln Phe Val Ser Glu Gly Ala Gly Pro Trp Gly Gln
    765                 770                 775

ctg agc cac ctt ctc agt cca gac tgg cag ttt gac atc acc cac ctg      2463
Leu Ser His Leu Leu Ser Pro Asp Trp Gln Phe Asp Ile Thr His Leu
780                 785                 790                 795

gtg gct gac ttt atg aag ctg gag tcc cca cac ata gcc acc ctg cag      2511
Val Ala Asp Phe Met Lys Leu Glu Ser Pro His Ile Ala Thr Leu Gln
                800                 805                 810

gac agc agg gtc ttg gtt ggg cgg gaa gtc gga atg acc acc atc cag      2559
Asp Ser Arg Val Leu Val Gly Arg Glu Val Gly Met Thr Thr Ile Gln
            815                 820                 825

gtg ttg tct ccc ctg tcc gac tcc atc ttg gcc gag aag aca gta act      2607
Val Leu Ser Pro Leu Ser Asp Ser Ile Leu Ala Glu Lys Thr Val Thr
        830                 835                 840

gtg ctg gat gac aaa gta tct gtg aca gac tta gct gtc cag gtg gtg      2655
Val Leu Asp Asp Lys Val Ser Val Thr Asp Leu Ala Val Gln Val Val
    845                 850                 855

gct ggg ctg tct gtc acc cta cac ccc atc tca gag aac aac aag gcc      2703
Ala Gly Leu Ser Val Thr Leu His Pro Ile Ser Glu Asn Asn Lys Ala
860                 865                 870                 875

acc tca gct gtg gcc atg gca gaa gag ctg cta cgt gcc cca aaa aag      2751
Thr Ser Ala Val Ala Met Ala Glu Glu Leu Leu Arg Ala Pro Lys Lys
                880                 885                 890

gaa gct ata atc agc aca tgg ctc cag ttc agt gat ggc tca gtg aca      2799
Glu Ala Ile Ile Ser Thr Trp Leu Gln Phe Ser Asp Gly Ser Val Thr
            895                 900                 905

ccc ctg gat atc tac gac tcc aag gac ttc tcc ttg act gcc atc tct      2847
Pro Leu Asp Ile Tyr Asp Ser Lys Asp Phe Ser Leu Thr Ala Ile Ser
        910                 915                 920

ttg gac gag gct gtc gtg tcc atc ccc caa ccc ctc tcg cct tgg tgg      2895
Leu Asp Glu Ala Val Val Ser Ile Pro Gln Pro Leu Ser Pro Trp Trp
    925                 930                 935

ccc acc gtg gta gct gaa gga gaa ggc cag ggc cca ctg ctc cgg gtc      2943
Pro Thr Val Val Ala Glu Gly Glu Gly Gln Gly Pro Leu Leu Arg Val
940                 945                 950                 955
```

-continued

```
gat atg tcc att gcc gaa gcc tgt cag aaa tcc aag cgc aag agt gtg      2991
Asp Met Ser Ile Ala Glu Ala Cys Gln Lys Ser Lys Arg Lys Ser Val
                960                 965                 970

ctg gct gtt ggc att ggc cac gtg ggg gtc aag ttt gga tgg gat gac      3039
Leu Ala Val Gly Ile Gly His Val Gly Val Lys Phe Gly Trp Asp Asp
            975                 980                 985

gct gac tcc agc cag act gga gaa aag gat gag gag gag  atc aag aac     3087
Ala Asp Ser Ser Gln Thr Gly Glu Lys Asp Glu Glu Glu  Ile Lys Asn
        990                 995                 1000

cat gcc  agt gac cgt cgg cag  aag att cag gac ctg  gaa cgc cca      3132
His Ala  Ser Asp Arg Arg Gln  Lys Ile Gln Asp Leu  Glu Arg Pro
    1005                 1010                 1015

ggc cag  gat gaa cta tac cat  ggc aac ttt cct ggg  gat cgt gaa      3177
Gly Gln  Asp Glu Leu Tyr His  Gly Asn Phe Pro Gly  Asp Arg Glu
    1020                 1025                 1030

gaa gga  gcg ctg agt gct acc  acc act acc aag tcc  ctg ctg gat      3222
Glu Gly  Ala Leu Ser Ala Thr  Thr Thr Thr Lys Ser  Leu Leu Asp
    1035                 1040                 1045

aac aac  gtg ggg aag agt ggc  agg cgg gac ggg gct  agg cta cac      3267
Asn Asn  Val Gly Lys Ser Gly  Arg Arg Asp Gly Ala  Arg Leu His
    1050                 1055                 1060

agc ata  ccc att gac ttc acc  aat ttc ccg gcc cat  gtg gac ctc      3312
Ser Ile  Pro Ile Asp Phe Thr  Asn Phe Pro Ala His  Val Asp Leu
    1065                 1070                 1075

ccc aag  gcc aag acc agg ggc  aca ctg gag gag aat  ggt ctc atg      3357
Pro Lys  Ala Lys Thr Arg Gly  Thr Leu Glu Glu Asn  Gly Leu Met
    1080                 1085                 1090

cag aca  gcc cat ggc ctg agt  gac cta gag att ggg  atg tat gcc      3402
Gln Thr  Ala His Gly Leu Ser  Asp Leu Glu Ile Gly  Met Tyr Ala
    1095                 1100                 1105

ctc cta  ggt gtc ttc tgc ctg  gcc atc ctt gtc ttt  ctc att aac      3447
Leu Leu  Gly Val Phe Cys Leu  Ala Ile Leu Val Phe  Leu Ile Asn
    1110                 1115                 1120

tgc gcc  acc ttt gcc ttc aag  tac agg cac aaa cag  gtg cct ctg      3492
Cys Ala  Thr Phe Ala Phe Lys  Tyr Arg His Lys Gln  Val Pro Leu
    1125                 1130                 1135

gaa ggc  cag gca tcc atg acc  cac tct cat gac tgg  gtc tgg ctg      3537
Glu Gly  Gln Ala Ser Met Thr  His Ser His Asp Trp  Val Trp Leu
    1140                 1145                 1150

ggc aat  gag gcg gag ctc ttg  gag aac att ggg gac  ctg tcc cca      3582
Gly Asn  Glu Ala Glu Leu Leu  Glu Asn Ile Gly Asp  Leu Ser Pro
    1155                 1160                 1165

ccc cag  gat gag cac acg acc  atc ata gac cga ggg  ctg ggg ggc      3627
Pro Gln  Asp Glu His Thr Thr  Ile Ile Asp Arg Gly  Leu Gly Gly
    1170                 1175                 1180

tgt gag  gag aac aac cac tta  ctt ctc aac ggt ggc  tcc caa aag      3672
Cys Glu  Glu Asn Asn His Leu  Leu Leu Asn Gly Gly  Ser Gln Lys
    1185                 1190                 1195

ccc acg  cag agc cag gtt cac  agg ccg cca ggc tcc  ggg gga cgg      3717
Pro Thr  Gln Ser Gln Val His  Arg Pro Pro Gly Ser  Gly Gly Arg
    1200                 1205                 1210

cag acc  agg gag ccc agg cag  gag cct gca aac tca  ccc acc tcc      3762
Gln Thr  Arg Glu Pro Arg Gln  Glu Pro Ala Asn Ser  Pro Thr Ser
    1215                 1220                 1225

aag atg  aag aag gtc aag ttt  gcc aca ttc acc atc  cca cct gag      3807
Lys Met  Lys Lys Val Lys Phe  Ala Thr Phe Thr Ile  Pro Pro Glu
    1230                 1235                 1240

gaa agc  tgc ccc acg gtg aac  tcc atc ctc agt ggg  gaa gat gat      3852
Glu Ser  Cys Pro Thr Val Asn  Ser Ile Leu Ser Gly  Glu Asp Asp
    1245                 1250                 1255
```

```
atc aag  tgg gtt tgt caa gac  ctg gac gtg ggc gca  ccc aag gaa      3897
Ile Lys  Trp Val Cys Gln Asp  Leu Asp Val Gly Ala  Pro Lys Glu
    1260                 1265                 1270

ctc aga  acc tac ctg gag aaa  ttc caa gac agt gtg  tag cgctctggcc   3946
Leu Arg  Thr Tyr Leu Glu Lys  Phe Gln Asp Ser Val
    1275                 1280                 1285

tcctcgccaa cttgggacag tagcctcctt cccgacctcc ctcagcagag tagctgaacg   4006

gaaggagctc tcagtggact gagtgaggaa atctggggcc cacagaatac caggtagcag   4066

gttagaagct gggaagggat gtttttatac taaagcagtt ttttttgttt tttgtttttt   4126

gtttttttgtt ttttttagca gcaaaggatg gtaggtttcc agaagtttga gtctctgact   4186

cagcagcgag gcagagtgga tccgaaagag aactgctcag acatgagaga gttattttat   4246

gaatcaaacg acactgcaga caagctacca aaaatatttg ttaaaaaaaa tatataaaaa   4306

gacgaataaa aaaaacacac aaatgactgt cggtttatat ttctaataaa ggaacaaaat   4366

gtaaaaatag ggcttgctaa aagaaggcct acattttaat tcagtcttta tgcttctgag   4426

gacagtccag gtctgttagc cttctgccca aggagaggca catctgaaca atggtcacct   4486

cttaggaaga atgagaattt tacattggat tccattatct ctgtttgctt ccatgtttct   4546

ttctaaggtc ctaagcctcc atttgattca atgtcatgtt tatttctgag gaccaagtgg   4606

tacattttcc taaatgaaat gtaaattata tttctattca ttagatagct ttttccccct   4666

ctttttaaga agatcatcaa cgaatccagt ctttacgttg taacattaac ctgtctttat   4726

attatacatc tcttgctttg ttaatatttt ctggcttgtt tgtaattctt tttgtttttt   4786

tgttttgttt tgttttaaca atatagcaag tgtgcagttc cccacatggg gagagtgcac   4846

cccacaatct gtcatcagcc gggtcaggcc aatgagtgga ataatgttca cagctatctg   4906

aatagggtat ggccaagaga acagagtgca gcctgtgaca cctggccact ccctatggag   4966

acagagactc agtgggtgtc tccggcagtt tgggcatagg gatgcctcta tgtgaagagc   5026

tgtgagtgaa atccataaac tcgaggtgtg cagagtcagg cagatgggcc atgtctacca   5086

caagatacag ccgaccctgt actgaacaaa cagaaaagac atgtggggga ggggcaggct   5146

ggagttatct gattttatta ctgggcaagg cgaaccagca tgaactcaaa atgatttttt   5206

taaaaaaaag aaatctatgt tagattgtca atcaaactgc ggctttgaag agtatggctg   5266

tgttaacagc acaatgcagt atcatatcca ctcaaaacag agtgtttacg caaaaagcag   5326

gagggatcaa atgaactagg atgtccggag cctggcgctc tccatccatc agctgaggga   5386

gaggatgttg ggcactgtga ccctcagcag agcagcattc acagagagac caggggacgg   5446

ccattgtttg ggtttttttg ttttttttct attactaaaa tcagtagctg agaaaaggtc   5506

tcagaagcct agtggccttg gttggacctt tgacacatat atttgtagca tttacaatag   5566

attaaaaaaa aaaaagctat ttatttatac ctgtggtggc agttgtcatt aaaacgcttg   5626

ccatgcttcc aaa                                                      5639
```

<210> SEQ ID NO 19
<211> LENGTH: 1285
<212> TYPE: PRT
<213> ORGANISM: Mus musculus

<400> SEQUENCE: 19

```
Met Asp Gly Val Thr Ala Ala Thr Met Arg Ser Glu Gly Ala Ala Pro
1               5                   10                  15

Arg Arg Ala Ala Arg Tyr Gly Ala Leu Ser Leu Val Leu Ala Thr Leu
            20                  25                  30
```

```
Leu Gly Gln Val Thr Glu Ser Arg Gly Val Met Asp Asn Ile Gln Arg
        35                  40                  45

Phe Ser Ser Leu Pro Pro Tyr Leu Pro Val Ser Phe His Val Leu Arg
    50                  55                  60

Ala Glu Thr Ala Phe Phe Leu Lys Glu Ala Asn Pro Asp Pro Leu Arg
65                  70                  75                  80

Asn Ala Ser Leu Gln Ser Arg Val Glu Ser Phe Phe Ile Tyr Lys Ala
                85                  90                  95

Gln Gln Pro Pro Val Leu Asn Val Ser Tyr Gly Pro Tyr Ser Ala Glu
            100                 105                 110

Lys Val Ile Pro Leu Asp Leu Met Leu Asn Pro Asn Phe Leu Gly Pro
        115                 120                 125

Thr Ser Lys Phe Pro Phe Asp Trp Arg Leu Lys Ala Tyr Ile Leu Gln
    130                 135                 140

Glu Lys Val Tyr Leu Ser His Pro Lys Val Gln Val Leu Phe His Ile
145                 150                 155                 160

Val Gly Arg Asp Trp Asp Asp His Arg Asp Glu Lys Leu Pro Cys Leu
                165                 170                 175

Arg Val Phe Ala Phe Arg Asp Ser Arg Glu Val Arg Gly Ser Cys Arg
            180                 185                 190

Leu Gly Gly Pro Leu Gly Leu Cys Val Ala Gln Leu Glu Met Leu Pro
        195                 200                 205

Gly Trp Phe Ser Pro Pro Ala Val Val Ser Gly Arg Arg Arg Pro Ala
    210                 215                 220

Glu Arg Pro Glu Gly Ser Pro Val Glu Leu Tyr Tyr Ala Val Gln Pro
225                 230                 235                 240

Gly Asp Glu Arg Gly Asp Cys Thr Gly Gly Asp Thr Arg Lys Asp Asn
                245                 250                 255

Ala Ile Arg Pro Gly Lys Asp Gly Gln Glu Gly Arg Thr Ser His Leu
            260                 265                 270

Gln Lys Ile Gly Thr Ile Ser Leu Tyr Arg Ala Gln Asp Ser Thr Gln
        275                 280                 285

Leu Ser Glu Leu Arg Leu Asp Gly Asn Val Val Ile Trp Leu Pro Ser
    290                 295                 300

Gln Pro Val Lys Gln Gly Asp Ile Val Thr Ala Ser Val Thr Ile Ala
305                 310                 315                 320

Asn Asn Ser Thr Val Asp His Phe Ile Leu Arg Ala Lys Val Lys Lys
                325                 330                 335

Gly Val Asn Ile Leu Thr Val Gln Thr Ser Glu Pro Arg Gln Trp Asp
            340                 345                 350

Val Arg Gln Glu Val Gly Asn Gly Gly Lys His Thr Thr Thr Ser Val
        355                 360                 365

Ala Cys Gln Arg Leu Gly Pro Gly Ala Arg Asn Arg Ser Ser Asn Leu
    370                 375                 380

Phe Ser Glu Val Met Gln Met Asn Phe Glu Ile Ala Ser Phe Ser Ser
385                 390                 395                 400

Leu Ser Gly Thr Gln Pro Ile Thr Trp Gln Val Glu Tyr Pro Arg Lys
                405                 410                 415

Gly Ala Thr Asp Ile Ala Val Ser Glu Ile Phe Ile Ser Gln Lys Asp
            420                 425                 430

Leu Val Ala Ile Val Pro Leu Ala Met Asn Asp Lys Thr Phe Lys Cys
        435                 440                 445

Phe Glu Lys Gln Asn His Tyr Lys Asp Ile Arg Tyr Tyr Ser Gly Pro
    450                 455                 460
```

```
Leu Ser Thr Leu Leu Pro Leu Val Asn Ser Asp Trp Leu His Ala Ile
465                 470                 475                 480

Ile Thr Asp Asn Asp Ala Ile Ser Thr Gly Pro Val Ala Arg Thr Trp
                485                 490                 495

Asn Tyr Cys Cys Val Ala Val Arg Arg Ala Glu Val Leu Ala Cys Val
            500                 505                 510

Leu Gly Glu Gly Glu Lys Phe Ala Gln Leu Pro Ser Glu Ser Ser Ser
        515                 520                 525

Asn Ser Leu Glu Arg Met Gly Pro Ile Trp Tyr Arg Leu Thr Ser Gly
    530                 535                 540

Val Ile Leu Asp Asn Leu Gln Glu Pro Gln Gly Ser Glu Thr His Pro
545                 550                 555                 560

Leu Leu His Pro Ala Arg Thr Phe Val Pro Leu Glu Ile Ser Glu Met
                565                 570                 575

Pro Leu Gly Thr Lys Leu Ser Leu Val Arg Ile Phe Cys Ile Lys Asn
            580                 585                 590

Leu Ala Ala Val Met Lys Glu Cys Thr Asp Ser Tyr Arg Arg Val Phe
        595                 600                 605

Cys Ser Lys Lys Arg Gly Cys Lys Gly Pro Val Val Leu Met Asp Ser
    610                 615                 620

Asp Leu Met Leu Ile Gln Phe Ser Thr Lys His Ser Ala His Val His
625                 630                 635                 640

Ser Pro Pro Thr Glu Met Lys Arg Phe Arg Glu Thr Gln Pro Met Gly
                645                 650                 655

Trp Lys Asp Ser Cys Arg Asn Gln Phe Leu Phe Val Ser Asp His Cys
            660                 665                 670

Asp Tyr Val Phe Val Asn Gly Lys Glu Ile Lys Gly Lys Met Asp Ser
        675                 680                 685

Val Val Asn Phe Thr Tyr Gln His Leu Ser Ala Pro Leu His Val Thr
    690                 695                 700

Val Trp Val Pro Arg Leu Pro Leu Gln Ile Glu Val Ser Asp Thr Glu
705                 710                 715                 720

Leu Ser Gln Val Lys Gly Trp Arg Val Pro Ile Val Ala Ser Lys Arg
                725                 730                 735

Pro Thr Arg Asp Ser Glu Glu Glu Glu Glu Glu Glu Gln Lys Gly Arg
            740                 745                 750

Gly Cys Thr Leu Gln Phe Gln His Ala Thr Val Arg Val Leu Thr Gln
        755                 760                 765

Phe Val Ser Glu Gly Ala Gly Pro Trp Gly Gln Leu Ser His Leu Leu
    770                 775                 780

Ser Pro Asp Trp Gln Phe Asp Ile Thr His Leu Val Ala Asp Phe Met
785                 790                 795                 800

Lys Leu Glu Ser Pro His Ile Ala Thr Leu Gln Asp Ser Arg Val Leu
                805                 810                 815

Val Gly Arg Glu Val Gly Met Thr Thr Ile Gln Val Leu Ser Pro Leu
            820                 825                 830

Ser Asp Ser Ile Leu Ala Glu Lys Thr Val Thr Val Leu Asp Asp Lys
        835                 840                 845

Val Ser Val Thr Asp Leu Ala Val Gln Val Val Ala Gly Leu Ser Val
    850                 855                 860

Thr Leu His Pro Ile Ser Glu Asn Asn Lys Ala Thr Ser Ala Val Ala
865                 870                 875                 880

Met Ala Glu Glu Leu Leu Arg Ala Pro Lys Lys Glu Ala Ile Ile Ser
```

-continued

```
                885                 890                 895

Thr Trp Leu Gln Phe Ser Asp Gly Ser Val Thr Pro Leu Asp Ile Tyr
            900                 905                 910

Asp Ser Lys Asp Phe Ser Leu Thr Ala Ile Ser Leu Asp Glu Ala Val
        915                 920                 925

Val Ser Ile Pro Gln Pro Leu Ser Pro Trp Trp Pro Thr Val Val Ala
    930                 935                 940

Glu Gly Glu Gly Gln Gly Pro Leu Leu Arg Val Asp Met Ser Ile Ala
945                 950                 955                 960

Glu Ala Cys Gln Lys Ser Lys Arg Lys Ser Val Leu Ala Val Gly Ile
                965                 970                 975

Gly His Val Gly Val Lys Phe Gly Trp Asp Asp Ala Asp Ser Ser Gln
            980                 985                 990

Thr Gly Glu Lys Asp Glu Glu Glu  Ile Lys Asn His Ala  Ser Asp Arg
        995                 1000                1005

Arg Gln  Lys Ile Gln Asp Leu  Glu Arg Pro Gly Gln  Asp Glu Leu
    1010                1015                1020

Tyr His  Gly Asn Phe Pro Gly  Asp Arg Glu Glu Gly  Ala Leu Ser
    1025                1030                1035

Ala Thr  Thr Thr Thr Lys Ser  Leu Leu Asp Asn Asn  Val Gly Lys
    1040                1045                1050

Ser Gly  Arg Arg Asp Gly Ala  Arg Leu His Ser Ile  Pro Ile Asp
    1055                1060                1065

Phe Thr  Asn Phe Pro Ala His  Val Asp Leu Pro Lys  Ala Lys Thr
    1070                1075                1080

Arg Gly  Thr Leu Glu Glu Asn  Gly Leu Met Gln Thr  Ala His Gly
    1085                1090                1095

Leu Ser  Asp Leu Glu Ile Gly  Met Tyr Ala Leu Leu  Gly Val Phe
    1100                1105                1110

Cys Leu  Ala Ile Leu Val Phe  Leu Ile Asn Cys Ala  Thr Phe Ala
    1115                1120                1125

Phe Lys  Tyr Arg His Lys Gln  Val Pro Leu Glu Gly  Gln Ala Ser
    1130                1135                1140

Met Thr  His Ser His Asp Trp  Val Trp Leu Gly Asn  Glu Ala Glu
    1145                1150                1155

Leu Leu  Glu Asn Ile Gly Asp  Leu Ser Pro Pro Gln  Asp Glu His
    1160                1165                1170

Thr Thr  Ile Ile Asp Arg Gly  Leu Gly Gly Cys Glu  Glu Asn Asn
    1175                1180                1185

His Leu  Leu Leu Asn Gly Gly  Ser Gln Lys Pro Thr  Gln Ser Gln
    1190                1195                1200

Val His  Arg Pro Pro Gly Ser  Gly Gly Arg Gln Thr  Arg Glu Pro
    1205                1210                1215

Arg Gln  Glu Pro Ala Asn Ser  Pro Thr Ser Lys Met  Lys Lys Val
    1220                1225                1230

Lys Phe  Ala Thr Phe Thr Ile  Pro Pro Glu Glu Ser  Cys Pro Thr
    1235                1240                1245

Val Asn  Ser Ile Leu Ser Gly  Glu Asp Asp Ile Lys  Trp Val Cys
    1250                1255                1260

Gln Asp  Leu Asp Val Gly Ala  Pro Lys Glu Leu Arg  Thr Tyr Leu
    1265                1270                1275

Glu Lys  Phe Gln Asp Ser Val
    1280                1285
```

<210> SEQ ID NO 20
<211> LENGTH: 2683
<212> TYPE: DNA
<213> ORGANISM: Mus musculus

<400> SEQUENCE: 20

```
tgagctcttg ctcttgctcc tgctccttcg cctgcttgct gcgtgagact gagtaactgc     60
tagatccttg gacttccatt cacagctgcg actgaacaat tgttgggaat tgggctgccg    120
actgtctcgg accactgtga ctatgtcttt gtcaatggta aagagatcaa gggcaagatg    180
gactctgtgg tgaacttcac ctaccagcac ctgagcgcac cgctgcatgt cactgtgtgg    240
gtgccacggc ttcccctgca gatcgaggtc tctgacacag aactcagcca ggttaagggc    300
tggagagtcc ccatcgtggc cagcaagagg cccactcggg acagtgagga ggaagaagag    360
gaagaacaga aaggccgggg ttgtaccctg cagttccagc atgccacagt gcgcgtcctc    420
acccaatttg tatcagaggg tgctgggccc tggggccagc tgagccacct tctcagtcca    480
gactggcagt ttgacatcac ccacctggtg ggctgacttt atgaagctgg agtccccaca    540
catagccacc ctgcaggaca gcagggtctt ggttgggcgg gaagtcggaa tgaccaccat    600
ccaggtgttg tctcccctgt ccgactccat cttggccgag aagacagtaa ctgtgctgga    660
tgacaaagta tctgtgacag acttagctgt ccaggtggtg gctgggctgt ctgtcaccct    720
acaccccatc tcagagaaca acaaggccac ctcagctgtg gccatggcag aagagctgct    780
acgtgcccca aaaaaggaag ctataatcag cacatggctc cagttcagtg atggctcagt    840
gacacccctg gatatctacg actccaagga cttctccttg actgccatct ctttggacga    900
ggctgtcgtg tccatccccc aacccctctc gccttggtgg cccaccgtgg tagctgaagg    960
agaaggccag ggcccactgc tccgggtcga tatgtccatt gccgaagcct gtcagaaatc   1020
caagcgcaag agtgtgctgg ctgttggcat tggccacgtg ggggtcaagt ttggatggga   1080
tgacgctgac tccagccaga ctggagaaaa ggatgaggag gagatcaaga accatgccag   1140
tgaccgtcgg cagaagattc aggacctgga acgcccaggc caggatgaac tataccatgg   1200
caactttcct ggggatcgtg aagaaggagc gctgagtgct accaccacta ccaagtccct   1260
gctggataac aacgtgggga agagtggcag gcgggacggg gctaggctac acagcatacc   1320
cattgacttc accaatttcc cggcccatgt ggacctcccc aaggccaaga ccaggggcac   1380
actggaggag aatggtctca tgcagacagc ccatggcctg agtgacctag agattgggat   1440
gtatgccctc ctaggtgtct tctgcctggc catccttgtc tttctcatta actgcgccac   1500
ctttgccttc aagtacaggc acaaacaggt gcctctggaa ggccaggcat ccatgaccca   1560
ctctcatgac tgggtctggc tgggcaatga ggcggagctc ttggagaaca accacttact   1620
tctcaacggt ggctcccaaa agcccacgca gagccaggtt cacaggccgc caggctccgg   1680
gggacggcag accagggagc ccaggcagga gcctgcaaac tcacccacct ccaagatgaa   1740
gaaggtcaag tttgccacat tcaccatccc acctgaggaa agctgcccca cggtgaactc   1800
catcctcagt ggggaagatg atatcaagtg ggtttgtcaa gacctggacg tgggcgcacc   1860
caaggaactc agaacctacc tggagaaatt ccaagacagt gtgtagcgct ctggcctcct   1920
cgccaacttg ggacagtagc ctccttcccg acctccctca ccagagtagc tgaacggaag   1980
gagctctcag tggactgagt gaggaaatct ggggcccaca gaataccagg tagcaggtta   2040
gaagctggga agggatgttt ttatactaaa gcagtttttt ttgtttttttg ttttttgttt   2100
tttgtttttt ttagcagcaa aggatggtag gtttccagaa gtttgagtct ctgactcagc   2160
```

-continued

```
agcgaggcag agtggatccg aaagagaact gctcagacat gagagagtta ttttatgaat   2220

caaacgacac tgcagacaag ctaccaaaaa tatttgttaa aaaaaatata taaaaagacg   2280

aataaaaaaa acacacaaat gactgtcggt ttatatttct aataaaggaa caaaatgtaa   2340

aaatagggct tgctaaaaga aggcctacat tttaattcag tctttatgct tctgaggaca   2400

gtccaggtct gttagccttc tgcccaagga gaggcacatc tgaacaatgg tcacctctta   2460

ggaagaatga gaattttaca ttggattcca ttatctctgt ttgcttccat gtttctttct   2520

aaggtcctaa gcctccattt gattcaatgt catgtttatt tctgaggacc aagtggtaca   2580

ttttcctaaa tgaaatgtaa attatatttc tattcattag atagcttttt ccccctcttt   2640

ttaagaagat catcaacgaa tccagtcttt acgttgtaac atc                     2683


<210> SEQ ID NO 21
<211> LENGTH: 5112
<212> TYPE: DNA
<213> ORGANISM: Rattus norvegicus
<220> FEATURE:
<221> NAME/KEY: CDS
<222> LOCATION: (1)..(5112)
<223> OTHER INFORMATION:

<400> SEQUENCE: 21

atg cgc aga ctt aac tgt ctc atg act ctg gat ctg ggg ctc tta aca       48
Met Arg Arg Leu Asn Cys Leu Met Thr Leu Asp Leu Gly Leu Leu Thr
1               5                   10                  15

tta agt cca tcc cgg ggg tcc agc agg caa ttc ttt cag gct gca gac       96
Leu Ser Pro Ser Arg Gly Ser Ser Arg Gln Phe Phe Gln Ala Ala Asp
            20                  25                  30

gct gaa tcc aag tat cca gat gtc cac cat cca cca tct ctt att ctg      144
Ala Glu Ser Lys Tyr Pro Asp Val His His Pro Pro Ser Leu Ile Leu
        35                  40                  45

tgc cag ctg tgg act aac ccc cac ccc gct gtt tcc atc ctt act gcg      192
Cys Gln Leu Trp Thr Asn Pro His Pro Ala Val Ser Ile Leu Thr Ala
    50                  55                  60

ctg aga gtg ata gaa agc cga gga gtc atg gat aat gct cag aga ttc      240
Leu Arg Val Ile Glu Ser Arg Gly Val Met Asp Asn Ala Gln Arg Phe
65                  70                  75                  80

tct tcc ttg cct cca tac ctg ccg gta agc ttc cgt gtc ctc aga gcc      288
Ser Ser Leu Pro Pro Tyr Leu Pro Val Ser Phe Arg Val Leu Arg Ala
                85                  90                  95

gaa acc gcc ttt ttc cta agg gag gcc aac cct gac cca ttg cgg aat      336
Glu Thr Ala Phe Phe Leu Arg Glu Ala Asn Pro Asp Pro Leu Arg Asn
            100                 105                 110

gcc agc ctg cag tcc agg acg gag tct ttc ttc act tac aag gcc gag      384
Ala Ser Leu Gln Ser Arg Thr Glu Ser Phe Phe Thr Tyr Lys Ala Glu
        115                 120                 125

cag ccc ccg ata tta aat gtc agc tat ggg ccc tac tct gca gaa aag      432
Gln Pro Pro Ile Leu Asn Val Ser Tyr Gly Pro Tyr Ser Ala Glu Lys
    130                 135                 140

gtc atg cct ctg gac ttg atg ttg aac ccc aac ttt cta ggc cca acc      480
Val Met Pro Leu Asp Leu Met Leu Asn Pro Asn Phe Leu Gly Pro Thr
145                 150                 155                 160

aat aag ttt cct ttt gac tgg agg ctg aag gcc tac atc ctc caa gag      528
Asn Lys Phe Pro Phe Asp Trp Arg Leu Lys Ala Tyr Ile Leu Gln Glu
                165                 170                 175

aaa gtc tac ccg agc cat ccc aaa gtt cag gtg ctc ttc cac atc gtg      576
Lys Val Tyr Pro Ser His Pro Lys Val Gln Val Leu Phe His Ile Val
            180                 185                 190

ggc cga gac tgg gat aac cac agg gac gag aag cta ccc tgc ctt cgg      624
Gly Arg Asp Trp Asp Asn His Arg Asp Glu Lys Leu Pro Cys Leu Arg
```

-continued

```
        195                 200                 205

atc ttt gct ttc cga gat acc cgg gag gtt cga ggt agc tgc cgg ctg      672
Ile Phe Ala Phe Arg Asp Thr Arg Glu Val Arg Gly Ser Cys Arg Leu
    210                 215                 220

ggc ggg gcc ttg ggg ctg tgc gtg gcc cag ctg gag atg ctg ccg ggc      720
Gly Gly Ala Leu Gly Leu Cys Val Ala Gln Leu Glu Met Leu Pro Gly
225                 230                 235                 240

tgg ttc aat ccc cca ccg gtg gtg tct ggg cgc agg agg ccc acg gag      768
Trp Phe Asn Pro Pro Pro Val Val Ser Gly Arg Arg Arg Pro Thr Glu
                245                 250                 255

cag tca gag ggg agt ccc gtg gaa ctg tat tat tct gta cag cca ggg      816
Gln Ser Glu Gly Ser Pro Val Glu Leu Tyr Tyr Ser Val Gln Pro Gly
            260                 265                 270

gat gag cga ggg gac tgc acc gga ggt gac acc agg aag gac aat gcc      864
Asp Glu Arg Gly Asp Cys Thr Gly Gly Asp Thr Arg Lys Asp Asn Ala
        275                 280                 285

att cgt cca gga aag gac gga cag gag gac agg aca tcc cac ctg cag      912
Ile Arg Pro Gly Lys Asp Gly Gln Glu Asp Arg Thr Ser His Leu Gln
    290                 295                 300

aag att ggc tct att agc ctt tat cga acc cag gac agc acc cag ctc      960
Lys Ile Gly Ser Ile Ser Leu Tyr Arg Thr Gln Asp Ser Thr Gln Leu
305                 310                 315                 320

agc gaa ctg cga ctg gat ggg aat gtg gtc atc tgg ctg ccc tcc cag     1008
Ser Glu Leu Arg Leu Asp Gly Asn Val Val Ile Trp Leu Pro Ser Gln
                325                 330                 335

ccc gtc aag caa gga gac ata gtc acc gca tct gtc acc atc gcc aat     1056
Pro Val Lys Gln Gly Asp Ile Val Thr Ala Ser Val Thr Ile Ala Asn
            340                 345                 350

aac tct act gtg gac cat ttc atc cta agc aca ttt ggg ttc ctg gtt     1104
Asn Ser Thr Val Asp His Phe Ile Leu Ser Thr Phe Gly Phe Leu Val
        355                 360                 365

cct gga aaa gtc aat ctt ctg cat ttt gaa ttt ctg tgc ctc ttc acc     1152
Pro Gly Lys Val Asn Leu Leu His Phe Glu Phe Leu Cys Leu Phe Thr
    370                 375                 380

cga cac ctc ggc aac gag aga gga cgg cac atc ttg cca agg cgc ctt     1200
Arg His Leu Gly Asn Glu Arg Gly Arg His Ile Leu Pro Arg Arg Leu
385                 390                 395                 400

tgc tgc gat tat cct act gtg ctg ctg gca agg caa gaa cat gaa tgt     1248
Cys Cys Asp Tyr Pro Thr Val Leu Leu Ala Arg Gln Glu His Glu Cys
                405                 410                 415

gct gtg ttc tgt gga gag ttg cag tac agc aaa gca gta gtg act gcc     1296
Ala Val Phe Cys Gly Glu Leu Gln Tyr Ser Lys Ala Val Val Thr Ala
            420                 425                 430

tct gtg tct agc ggc gag tgt aca gaa acc atg ggt att agg ttt cga     1344
Ser Val Ser Ser Gly Glu Cys Thr Glu Thr Met Gly Ile Arg Phe Arg
        435                 440                 445

tgc ttt tcg atg cct gtg cga atg ctc agg gag tgg gga aca atc cgg     1392
Cys Phe Ser Met Pro Val Arg Met Leu Arg Glu Trp Gly Thr Ile Arg
    450                 455                 460

cat cct ggg aac ggg tat tgt aga att gcc tat cag tgc ggg tcc ata     1440
His Pro Gly Asn Gly Tyr Cys Arg Ile Ala Tyr Gln Cys Gly Ser Ile
465                 470                 475                 480

caa ttc tgt atc ctt ttg agg agt tct ccc atc agg acc gtt gat tgg     1488
Gln Phe Cys Ile Leu Leu Arg Ser Ser Pro Ile Arg Thr Val Asp Trp
                485                 490                 495

atg gtg gtc ttt gaa agt agg caa gga aca gga agc ttc cgt aat cgc     1536
Met Val Val Phe Glu Ser Arg Gln Gly Thr Gly Ser Phe Arg Asn Arg
            500                 505                 510

tgg cca tca cct ttt cac aaa gca aca gct tgg aag cag aca gca ggt     1584
Trp Pro Ser Pro Phe His Lys Ala Thr Ala Trp Lys Gln Thr Ala Gly
```

-continued

```
        515                 520                 525

ggg aac tac agt tct gtt tct gac agt gaa gtc agt aag gct aca ctt      1632
Gly Asn Tyr Ser Ser Val Ser Asp Ser Glu Val Ser Lys Ala Thr Leu
    530                 535                 540

aga agt tct cct aag cgg gcc ccg gca cac tac ctc tgt gtc ttc cgg      1680
Arg Ser Ser Pro Lys Arg Ala Pro Ala His Tyr Leu Cys Val Phe Arg
545                 550                 555                 560

atc acc gca gtg tgg tcc aat gac tcc agc tgc ggg gtc tct gtt aca      1728
Ile Thr Ala Val Trp Ser Asn Asp Ser Ser Cys Gly Val Ser Val Thr
                565                 570                 575

ata ctg ctc gtt ctt caa ata aat gat ctg tgg ggt gtc acc tgt cct      1776
Ile Leu Leu Val Leu Gln Ile Asn Asp Leu Trp Gly Val Thr Cys Pro
            580                 585                 590

gtg acc ctt cga cca cct gtg gga atc tgg gtc ttc atg ggt cac cgc      1824
Val Thr Leu Arg Pro Pro Val Gly Ile Trp Val Phe Met Gly His Arg
        595                 600                 605

tgt gaa acc agg gtc cga gaa aaa tgt gtc cac act ggt tta agg aag      1872
Cys Glu Thr Arg Val Arg Glu Lys Cys Val His Thr Gly Leu Arg Lys
    610                 615                 620

aga gta gag aga aga atc aag ggg gag aaa aga caa ata cag att tgg      1920
Arg Val Glu Arg Arg Ile Lys Gly Glu Lys Arg Gln Ile Gln Ile Trp
625                 630                 635                 640

tca gag tgt aca gag gga cag gtg tgc agg gcg gaa cga tgc aga ctg      1968
Ser Glu Cys Thr Glu Gly Gln Val Cys Arg Ala Glu Arg Cys Arg Leu
                645                 650                 655

gat gac aca gag gag aac agg gag cag ttt ggt cct cta cgg gaa gga      2016
Asp Asp Thr Glu Glu Asn Arg Glu Gln Phe Gly Pro Leu Arg Glu Gly
            660                 665                 670

cag tca gac aga cct act gta tgg aag gga gga aac gtc cag gag ggg      2064
Gln Ser Asp Arg Pro Thr Val Trp Lys Gly Gly Asn Val Gln Glu Gly
        675                 680                 685

cgc cgg cgc aaa caa gtc cct gcc ccc aat gcc caa gcc cag gga aga      2112
Arg Arg Arg Lys Gln Val Pro Ala Pro Asn Ala Gln Ala Gln Gly Arg
    690                 695                 700

gcc aag gta aag aag ggg gtg aac att ctg act gca cag acc agt gag      2160
Ala Lys Val Lys Lys Gly Val Asn Ile Leu Thr Ala Gln Thr Ser Glu
705                 710                 715                 720

cct cgg cag tgg gat gtg agg caa gag gtg ggc aac gga ggg aaa cac      2208
Pro Arg Gln Trp Asp Val Arg Gln Glu Val Gly Asn Gly Gly Lys His
                725                 730                 735

acc acc acc tcc gtg tcc tgc cag cgc ctg ggc cct ggg gca cga aat      2256
Thr Thr Thr Ser Val Ser Cys Gln Arg Leu Gly Pro Gly Ala Arg Asn
            740                 745                 750

agg tca act gca tca gca tcc ata gcc tta gca gag aag ctc ccc aga      2304
Arg Ser Thr Ala Ser Ala Ser Ile Ala Leu Ala Glu Lys Leu Pro Arg
        755                 760                 765

cct ctg agg aag act gac agt tat agc tct ccc atg cct gaa gct tcc      2352
Pro Leu Arg Lys Thr Asp Ser Tyr Ser Ser Pro Met Pro Glu Ala Ser
    770                 775                 780

ccg ggc atg ggc acg gga gct ggc ctc cct gcc aac cgg gaa gaa gca      2400
Pro Gly Met Gly Thr Gly Ala Gly Leu Pro Ala Asn Arg Glu Glu Ala
785                 790                 795                 800

gac agc cct tat cag gat atg tgt acc aag cat tct tgc ttc aag gac      2448
Asp Ser Pro Tyr Gln Asp Met Cys Thr Lys His Ser Cys Phe Lys Asp
                805                 810                 815

aac ctc agt caa tta tct aag gat tct att ggc aca gac ccc cgc ccc      2496
Asn Leu Ser Gln Leu Ser Lys Asp Ser Ile Gly Thr Asp Pro Arg Pro
            820                 825                 830

cat ctt cgt gat ttg tgg ctg cct gca gga gcc tct ctg tgg gat gct      2544
His Leu Arg Asp Leu Trp Leu Pro Ala Gly Ala Ser Leu Trp Asp Ala
```

```
        835                 840                 845

ggc tgg tgg cag ttg gag aca cgg aga gtg ctt tgc gtc ttg cct ttg      2592
Gly Trp Trp Gln Leu Glu Thr Arg Arg Val Leu Cys Val Leu Pro Leu
    850                 855                 860

gct ctt gca gtg tcc ctc ggt ctg gcg gtg ggt aat tgt tta agg cag      2640
Ala Leu Ala Val Ser Leu Gly Leu Ala Val Gly Asn Cys Leu Arg Gln
865                 870                 875                 880

ctg ata cct tca aag ctg gga aat ctg gtg tca gaa cac agg gat gtt      2688
Leu Ile Pro Ser Lys Leu Gly Asn Leu Val Ser Glu His Arg Asp Val
                885                 890                 895

tgc cgt tca ggg att atg ctg tgg ctc tct gga gac ctg aga ggc aga      2736
Cys Arg Ser Gly Ile Met Leu Trp Leu Ser Gly Asp Leu Arg Gly Arg
            900                 905                 910

gac ttc ttc cca aag tca ctt cac cag act cca gct tac cgt tgt gtt      2784
Asp Phe Phe Pro Lys Ser Leu His Gln Thr Pro Ala Tyr Arg Cys Val
        915                 920                 925

cct gtc aga agc agc aat tta ttc aat gag gtc atg cag atg aat ttc      2832
Pro Val Arg Ser Ser Asn Leu Phe Asn Glu Val Met Gln Met Asn Phe
    930                 935                 940

gaa atc gcc agc ttc agc agc ctc tca ggg aca cag ccc atc acc tgg      2880
Glu Ile Ala Ser Phe Ser Ser Leu Ser Gly Thr Gln Pro Ile Thr Trp
945                 950                 955                 960

cag gtg gag tac ccg agg aag ggg acc aca gac atc gcc gtg tct gag      2928
Gln Val Glu Tyr Pro Arg Lys Gly Thr Thr Asp Ile Ala Val Ser Glu
                965                 970                 975

atc ttc atc agc cag aag gac ctg gtc gcc atc gtc ccc ctc gct atg      2976
Ile Phe Ile Ser Gln Lys Asp Leu Val Ala Ile Val Pro Leu Ala Met
            980                 985                 990

gac act gaa ctc ctg aac aca gcc  atc ctc acg ggg aag  acg gtg gcc    3024
Asp Thr Glu Leu Leu Asn Thr Ala  Ile Leu Thr Gly Lys  Thr Val Ala
        995                 1000                1005

atg ccc  gtg agg gtg gtg tcg  gtg gag gag aac tgc  acc gtg aga      3069
Met Pro  Val Arg Val Val Ser  Val Glu Glu Asn Cys  Thr Val Arg
    1010                1015                1020

gac atc  tca gag ctg gcg gag  tgc aaa gcc atg gat  gag aat gtc      3114
Asp Ile  Ser Glu Leu Ala Glu  Cys Lys Ala Met Asp  Glu Asn Val
    1025                1030                1035

atc aag  gtc tca gac cac tgt  gac tat gtc ttt gtc  aac ggt aaa      3159
Ile Lys  Val Ser Asp His Cys  Asp Tyr Val Phe Val  Asn Gly Lys
    1040                1045                1050

gag atc  aag ggc aag gtg gac  tcg gtg gtg aat ttc  acc tac cag      3204
Glu Ile  Lys Gly Lys Val Asp  Ser Val Val Asn Phe  Thr Tyr Gln
    1055                1060                1065

cac ctg  agc gca ctg ctg cat  gtc acc gtg tgg gtg  cca cgg ctt      3249
His Leu  Ser Ala Leu Leu His  Val Thr Val Trp Val  Pro Arg Leu
    1070                1075                1080

ccc ctg  cag atc gag gtc tct  gac acg gaa ctg agc  cag att aag      3294
Pro Leu  Gln Ile Glu Val Ser  Asp Thr Glu Leu Ser  Gln Ile Lys
    1085                1090                1095

ggc tgg  cga gtc ccc atc gtg  gcc agc aag agg ccc  act cgg gac      3339
Gly Trp  Arg Val Pro Ile Val  Ala Ser Lys Arg Pro  Thr Arg Asp
    1100                1105                1110

agt gag  gag gaa gaa gag gaa  gaa cag aga ggc cgg  ggt tgt gcc      3384
Ser Glu  Glu Glu Glu Glu Glu  Glu Gln Arg Gly Arg  Gly Cys Ala
    1115                1120                1125

ctg cag  ttc cag cat gcc aca  gtg cgc gtc ctc acc  cag ttt gta      3429
Leu Gln  Phe Gln His Ala Thr  Val Arg Val Leu Thr  Gln Phe Val
    1130                1135                1140

tca gaa  agt gct ggg ccc tgg  ggc cag ttg agc cac  ctt ctc agt      3474
Ser Glu  Ser Ala Gly Pro Trp  Gly Gln Leu Ser His  Leu Leu Ser
```

-continued

```
    1145                1150                1155

cca gac  tgg cag ttt gac atc  acc cac ttg gtg gct  gac ttc atg      3519
Pro Asp  Trp Gln Phe Asp Ile  Thr His Leu Val Ala  Asp Phe Met
    1160                1165                1170

aag ctg  gag tcc cca cac atc  gcc acc ttg cag gat  agc agg gtc      3564
Lys Leu  Glu Ser Pro His Ile  Ala Thr Leu Gln Asp  Ser Arg Val
    1175                1180                1185

ttg gtt  ggg cgg gaa gtc gga  atg acc act atc cag  gtg ctg tcg      3609
Leu Val  Gly Arg Glu Val Gly  Met Thr Thr Ile Gln  Val Leu Ser
    1190                1195                1200

ccc ctg  tcc gac tcc atc ttg  gcc gag aag aca gta  act gtg ctg      3654
Pro Leu  Ser Asp Ser Ile Leu  Ala Glu Lys Thr Val  Thr Val Leu
    1205                1210                1215

gac gac  aaa gtg tcc gtg aca  gac ttg gct gtg cag  gtg gtg gct      3699
Asp Asp  Lys Val Ser Val Thr  Asp Leu Ala Val Gln  Val Val Ala
    1220                1225                1230

ggg ctg  tcc atc acc ctg cac  ccc atc tca gag aac  aac aag gcc      3744
Gly Leu  Ser Ile Thr Leu His  Pro Ile Ser Glu Asn  Asn Lys Ala
    1235                1240                1245

acc tca  gcc gta gcc aca gca  gag gaa ctg ctg cgt  gcc ccc aaa      3789
Thr Ser  Ala Val Ala Thr Ala  Glu Glu Leu Leu Arg  Ala Pro Lys
    1250                1255                1260

cag gtc  ctg atg gcc gtc agt  tcc cct ttc ccc tac  ttc ccc act      3834
Gln Val  Leu Met Ala Val Ser  Ser Pro Phe Pro Tyr  Phe Pro Thr
    1265                1270                1275

ctc tcc  cac aca cat agc ctg  cct cat gct cat cca  cca cca gca      3879
Leu Ser  His Thr His Ser Leu  Pro His Ala His Pro  Pro Pro Ala
    1280                1285                1290

gga gga  atc aac gac cct aaa  gga ggt tgt aac ttc  atc acc agc      3924
Gly Gly  Ile Asn Asp Pro Lys  Gly Gly Cys Asn Phe  Ile Thr Ser
    1295                1300                1305

ccc ctg  cta gga gag gtt cct  gga gat aag gca cct  ccc atg tgg      3969
Pro Leu  Leu Gly Glu Val Pro  Gly Asp Lys Ala Pro  Pro Met Trp
    1310                1315                1320

ttc tta  cag tct ctc tcc ctg  cag gaa gct ata atc  agc aca tgg      4014
Phe Leu  Gln Ser Leu Ser Leu  Gln Glu Ala Ile Ile  Ser Thr Trp
    1325                1330                1335

ctc cag  ttc agt gat ggc tca  gtg aca ccc ctg gac  atc tat gac      4059
Leu Gln  Phe Ser Asp Gly Ser  Val Thr Pro Leu Asp  Ile Tyr Asp
    1340                1345                1350

acc aag  gac ttc tcc ttg act  gcc atc tct ttg gac  gag gct gtc      4104
Thr Lys  Asp Phe Ser Leu Thr  Ala Ile Ser Leu Asp  Glu Ala Val
    1355                1360                1365

atc tcc  atc cca caa ccc ctc  tcg cct tgg tgg ccc  act gtg gta      4149
Ile Ser  Ile Pro Gln Pro Leu  Ser Pro Trp Trp Pro  Thr Val Val
    1370                1375                1380

gct gaa  gga gag ggt cag ggc  cca ctg ctc cgg gtc  gat atg tcc      4194
Ala Glu  Gly Glu Gly Gln Gly  Pro Leu Leu Arg Val  Asp Met Ser
    1385                1390                1395

atc gct  gag gcc tgt cag aaa  tcc aag cgc aag agc  gtg ctg gct      4239
Ile Ala  Glu Ala Cys Gln Lys  Ser Lys Arg Lys Ser  Val Leu Ala
    1400                1405                1410

gtt ggc  att ggc cac gtg ggg  gtc aag ttt ggg tgg  gaa gat gct      4284
Val Gly  Ile Gly His Val Gly  Val Lys Phe Gly Trp  Glu Asp Ala
    1415                1420                1425

gac tcc  ggc cag act gga gaa  aag gat gag gag gag  atc aag aac      4329
Asp Ser  Gly Gln Thr Gly Glu  Lys Asp Glu Glu Glu  Ile Lys Asn
    1430                1435                1440

cat gcc  agc gat cgt cgg cag  aag att cag gac ctg  gaa cgc cca      4374
His Ala  Ser Asp Arg Arg Gln  Lys Ile Gln Asp Leu  Glu Arg Pro
```

-continued 1445 1450 1455 ggg cca gat gaa cta cac cat ggc aac ttt ccc cgg gga tcg gaa 4419
Gly Pro Asp Glu Leu His His Gly Asn Phe Pro Arg Gly Ser Glu
1460 1465 1470 ggg ggg acc ggg gcc agg cta cac agc atc ccc ata gac ttc acc 4464
Gly Gly Thr Gly Ala Arg Leu His Ser Ile Pro Ile Asp Phe Thr
1475 1480 1485 aac ttc ccg gcc cat gtg gac ctc ccc aag gcc aag gcc ggg ggc 4509
Asn Phe Pro Ala His Val Asp Leu Pro Lys Ala Lys Ala Gly Gly
1490 1495 1500 aca ctg gag gag aat ggt ctg atg cag aca gcc cat ggc ctg agt 4554
Thr Leu Glu Glu Asn Gly Leu Met Gln Thr Ala His Gly Leu Ser
1505 1510 1515 gat cta gag att ggg atg tat gcc ctc ctg ggt gtt ttc tgc ctg 4599
Asp Leu Glu Ile Gly Met Tyr Ala Leu Leu Gly Val Phe Cys Leu
1520 1525 1530 gcc atc ctt gtc ttt ctc atc aac tgc gcc acc ttt gcc ttc aaa 4644
Ala Ile Leu Val Phe Leu Ile Asn Cys Ala Thr Phe Ala Phe Lys
1535 1540 1545 tac agg cac aaa cag gta cct cta gaa ggt cag gca tcc atg acc 4689
Tyr Arg His Lys Gln Val Pro Leu Glu Gly Gln Ala Ser Met Thr
1550 1555 1560 cac tct cat gac tgg gtc tgg ctg ggc aat gag gcg gag ctc ttg 4734
His Ser His Asp Trp Val Trp Leu Gly Asn Glu Ala Glu Leu Leu
1565 1570 1575 gag aac att ggg gac ttg tcc cca ccc caa gac gag cac acg acc 4779
Glu Asn Ile Gly Asp Leu Ser Pro Pro Gln Asp Glu His Thr Thr
1580 1585 1590 atc ata gac cga ggg ctg gga ggc ttc gag gag aac aac cac ttg 4824
Ile Ile Asp Arg Gly Leu Gly Gly Phe Glu Glu Asn Asn His Leu
1595 1600 1605 ttt ctc aat ggc ggc tcc caa aag cac atg cag agc cag gtc cac 4869
Phe Leu Asn Gly Gly Ser Gln Lys His Met Gln Ser Gln Val His
1610 1615 1620 agg cca cca gat tct ggg ggg tgg cag acc agg gag ccc agg cag 4914
Arg Pro Pro Asp Ser Gly Gly Trp Gln Thr Arg Glu Pro Arg Gln
1625 1630 1635 gaa cct gcg aac tcg ccc acc tcc aag atg aag aag gta aag ttt 4959
Glu Pro Ala Asn Ser Pro Thr Ser Lys Met Lys Lys Val Lys Phe
1640 1645 1650 gcc aca ttc acc atc cca cct gag gac agc tgc ccc aca gtg aac 5004
Ala Thr Phe Thr Ile Pro Pro Glu Asp Ser Cys Pro Thr Val Asn
1655 1660 1665 tcc atc cta agt ggg gaa gac gac gtc aag tgg gtt tgt caa gac 5049
Ser Ile Leu Ser Gly Glu Asp Asp Val Lys Trp Val Cys Gln Asp
1670 1675 1680 cta gac gtg ggc gca ccc aag gag ctc aga acc tac ctg gag aaa 5094
Leu Asp Val Gly Ala Pro Lys Glu Leu Arg Thr Tyr Leu Glu Lys
1685 1690 1695 ttc caa gac agc gtg tag 5112
Phe Gln Asp Ser Val
1700

<210> SEQ ID NO 22
<211> LENGTH: 1703
<212> TYPE: PRT
<213> ORGANISM: Rattus norvegicus

<400> SEQUENCE: 22

Met Arg Arg Leu Asn Cys Leu Met Thr Leu Asp Leu Gly Leu Leu Thr
1 5 10 15

-continued

```
Leu Ser Pro Ser Arg Gly Ser Ser Arg Gln Phe Phe Gln Ala Ala Asp
            20                  25                  30

Ala Glu Ser Lys Tyr Pro Asp Val His His Pro Pro Ser Leu Ile Leu
        35                  40                  45

Cys Gln Leu Trp Thr Asn Pro His Pro Ala Val Ser Ile Leu Thr Ala
    50                  55                  60

Leu Arg Val Ile Glu Ser Arg Gly Val Met Asp Asn Ala Gln Arg Phe
65                  70                  75                  80

Ser Ser Leu Pro Pro Tyr Leu Pro Val Ser Phe Arg Val Leu Arg Ala
                85                  90                  95

Glu Thr Ala Phe Phe Leu Arg Glu Ala Asn Pro Asp Pro Leu Arg Asn
            100                 105                 110

Ala Ser Leu Gln Ser Arg Thr Glu Ser Phe Phe Thr Tyr Lys Ala Glu
        115                 120                 125

Gln Pro Pro Ile Leu Asn Val Ser Tyr Gly Pro Tyr Ser Ala Glu Lys
    130                 135                 140

Val Met Pro Leu Asp Leu Met Leu Asn Pro Asn Phe Leu Gly Pro Thr
145                 150                 155                 160

Asn Lys Phe Pro Phe Asp Trp Arg Leu Lys Ala Tyr Ile Leu Gln Glu
                165                 170                 175

Lys Val Tyr Pro Ser His Pro Lys Val Gln Val Leu Phe His Ile Val
            180                 185                 190

Gly Arg Asp Trp Asp Asn His Arg Asp Glu Lys Leu Pro Cys Leu Arg
        195                 200                 205

Ile Phe Ala Phe Arg Asp Thr Arg Glu Val Arg Gly Ser Cys Arg Leu
    210                 215                 220

Gly Gly Ala Leu Gly Leu Cys Val Ala Gln Leu Glu Met Leu Pro Gly
225                 230                 235                 240

Trp Phe Asn Pro Pro Pro Val Val Ser Gly Arg Arg Arg Pro Thr Glu
                245                 250                 255

Gln Ser Glu Gly Ser Pro Val Glu Leu Tyr Tyr Ser Val Gln Pro Gly
            260                 265                 270

Asp Glu Arg Gly Asp Cys Thr Gly Gly Asp Thr Arg Lys Asp Asn Ala
        275                 280                 285

Ile Arg Pro Gly Lys Asp Gly Gln Glu Asp Arg Thr Ser His Leu Gln
    290                 295                 300

Lys Ile Gly Ser Ile Ser Leu Tyr Arg Thr Gln Asp Ser Thr Gln Leu
305                 310                 315                 320

Ser Glu Leu Arg Leu Asp Gly Asn Val Val Ile Trp Leu Pro Ser Gln
                325                 330                 335

Pro Val Lys Gln Gly Asp Ile Val Thr Ala Ser Val Thr Ile Ala Asn
            340                 345                 350

Asn Ser Thr Val Asp His Phe Ile Leu Ser Thr Phe Gly Phe Leu Val
        355                 360                 365

Pro Gly Lys Val Asn Leu Leu His Phe Glu Phe Leu Cys Leu Phe Thr
    370                 375                 380

Arg His Leu Gly Asn Glu Arg Gly Arg His Ile Leu Pro Arg Arg Leu
385                 390                 395                 400

Cys Cys Asp Tyr Pro Thr Val Leu Leu Ala Arg Gln Glu His Glu Cys
                405                 410                 415

Ala Val Phe Cys Gly Glu Leu Gln Tyr Ser Lys Ala Val Val Thr Ala
            420                 425                 430

Ser Val Ser Ser Gly Glu Cys Thr Glu Thr Met Gly Ile Arg Phe Arg
```

-continued

```
        435                 440                 445

Cys Phe Ser Met Pro Val Arg Met Leu Arg Glu Trp Gly Thr Ile Arg
    450                 455                 460

His Pro Gly Asn Gly Tyr Cys Arg Ile Ala Tyr Gln Cys Gly Ser Ile
465                 470                 475                 480

Gln Phe Cys Ile Leu Leu Arg Ser Ser Pro Ile Arg Thr Val Asp Trp
                485                 490                 495

Met Val Val Phe Glu Ser Arg Gln Gly Thr Gly Ser Phe Arg Asn Arg
            500                 505                 510

Trp Pro Ser Pro Phe His Lys Ala Thr Ala Trp Lys Gln Thr Ala Gly
        515                 520                 525

Gly Asn Tyr Ser Ser Val Ser Asp Ser Glu Val Ser Lys Ala Thr Leu
    530                 535                 540

Arg Ser Ser Pro Lys Arg Ala Pro Ala His Tyr Leu Cys Val Phe Arg
545                 550                 555                 560

Ile Thr Ala Val Trp Ser Asn Asp Ser Ser Cys Gly Val Ser Val Thr
                565                 570                 575

Ile Leu Leu Val Leu Gln Ile Asn Asp Leu Trp Gly Val Thr Cys Pro
            580                 585                 590

Val Thr Leu Arg Pro Pro Val Gly Ile Trp Val Phe Met Gly His Arg
        595                 600                 605

Cys Glu Thr Arg Val Arg Glu Lys Cys Val His Thr Gly Leu Arg Lys
    610                 615                 620

Arg Val Glu Arg Arg Ile Lys Gly Glu Lys Arg Gln Ile Gln Ile Trp
625                 630                 635                 640

Ser Glu Cys Thr Glu Gly Gln Val Cys Arg Ala Glu Arg Cys Arg Leu
                645                 650                 655

Asp Asp Thr Glu Glu Asn Arg Glu Gln Phe Gly Pro Leu Arg Glu Gly
            660                 665                 670

Gln Ser Asp Arg Pro Thr Val Trp Lys Gly Gly Asn Val Gln Glu Gly
        675                 680                 685

Arg Arg Arg Lys Gln Val Pro Ala Pro Asn Ala Gln Ala Gln Gly Arg
    690                 695                 700

Ala Lys Val Lys Lys Gly Val Asn Ile Leu Thr Ala Gln Thr Ser Glu
705                 710                 715                 720

Pro Arg Gln Trp Asp Val Arg Gln Glu Val Gly Asn Gly Gly Lys His
                725                 730                 735

Thr Thr Thr Ser Val Ser Cys Gln Arg Leu Gly Pro Gly Ala Arg Asn
            740                 745                 750

Arg Ser Thr Ala Ser Ala Ser Ile Ala Leu Ala Glu Lys Leu Pro Arg
        755                 760                 765

Pro Leu Arg Lys Thr Asp Ser Tyr Ser Ser Pro Met Pro Glu Ala Ser
    770                 775                 780

Pro Gly Met Gly Thr Gly Ala Gly Leu Pro Ala Asn Arg Glu Glu Ala
785                 790                 795                 800

Asp Ser Pro Tyr Gln Asp Met Cys Thr Lys His Ser Cys Phe Lys Asp
                805                 810                 815

Asn Leu Ser Gln Leu Ser Lys Asp Ser Ile Gly Thr Asp Pro Arg Pro
            820                 825                 830

His Leu Arg Asp Leu Trp Leu Pro Ala Gly Ala Ser Leu Trp Asp Ala
        835                 840                 845

Gly Trp Trp Gln Leu Glu Thr Arg Arg Val Leu Cys Val Leu Pro Leu
    850                 855                 860
```

-continued

```
Ala Leu Ala Val Ser Leu Gly Leu Ala Val Gly Asn Cys Leu Arg Gln
865                 870                 875                 880

Leu Ile Pro Ser Lys Leu Gly Asn Leu Val Ser Glu His Arg Asp Val
                885                 890                 895

Cys Arg Ser Gly Ile Met Leu Trp Leu Ser Gly Asp Leu Arg Gly Arg
            900                 905                 910

Asp Phe Phe Pro Lys Ser Leu His Gln Thr Pro Ala Tyr Arg Cys Val
        915                 920                 925

Pro Val Arg Ser Ser Asn Leu Phe Asn Glu Val Met Gln Met Asn Phe
    930                 935                 940

Glu Ile Ala Ser Phe Ser Ser Leu Ser Gly Thr Gln Pro Ile Thr Trp
945                 950                 955                 960

Gln Val Glu Tyr Pro Arg Lys Gly Thr Thr Asp Ile Ala Val Ser Glu
                965                 970                 975

Ile Phe Ile Ser Gln Lys Asp Leu Val Ala Ile Val Pro Leu Ala Met
            980                 985                 990

Asp Thr Glu Leu Leu Asn Thr Ala  Ile Leu Thr Gly Lys  Thr Val Ala
        995                 1000                1005

Met Pro  Val Arg Val Val Ser  Val Glu Glu Asn Cys  Thr Val Arg
    1010                1015                1020

Asp Ile  Ser Glu Leu Ala Glu  Cys Lys Ala Met Asp  Glu Asn Val
    1025                1030                1035

Ile Lys  Val Ser Asp His Cys  Asp Tyr Val Phe Val  Asn Gly Lys
    1040                1045                1050

Glu Ile  Lys Gly Lys Val Asp  Ser Val Val Asn Phe  Thr Tyr Gln
    1055                1060                1065

His Leu  Ser Ala Leu Leu His  Val Thr Val Trp Val  Pro Arg Leu
    1070                1075                1080

Pro Leu  Gln Ile Glu Val Ser  Asp Thr Glu Leu Ser  Gln Ile Lys
    1085                1090                1095

Gly Trp  Arg Val Pro Ile Val  Ala Ser Lys Arg Pro  Thr Arg Asp
    1100                1105                1110

Ser Glu  Glu Glu Glu Glu Glu  Glu Gln Arg Gly Arg  Gly Cys Ala
    1115                1120                1125

Leu Gln  Phe Gln His Ala Thr  Val Arg Val Leu Thr  Gln Phe Val
    1130                1135                1140

Ser Glu  Ser Ala Gly Pro Trp  Gly Gln Leu Ser His  Leu Leu Ser
    1145                1150                1155

Pro Asp  Trp Gln Phe Asp Ile  Thr His Leu Val Ala  Asp Phe Met
    1160                1165                1170

Lys Leu  Glu Ser Pro His Ile  Ala Thr Leu Gln Asp  Ser Arg Val
    1175                1180                1185

Leu Val  Gly Arg Glu Val Gly  Met Thr Thr Ile Gln  Val Leu Ser
    1190                1195                1200

Pro Leu  Ser Asp Ser Ile Leu  Ala Glu Lys Thr Val  Thr Val Leu
    1205                1210                1215

Asp Asp  Lys Val Ser Val Thr  Asp Leu Ala Val Gln  Val Val Ala
    1220                1225                1230

Gly Leu  Ser Ile Thr Leu His  Pro Ile Ser Glu Asn  Asn Lys Ala
    1235                1240                1245

Thr Ser  Ala Val Ala Thr Ala  Glu Glu Leu Leu Arg  Ala Pro Lys
    1250                1255                1260

Gln Val  Leu Met Ala Val Ser  Ser Pro Phe Pro Tyr  Phe Pro Thr
    1265                1270                1275
```

```
Leu Ser His Thr His Ser Leu Pro His Ala His Pro Pro Pro Ala
    1280                1285                1290

Gly Gly Ile Asn Asp Pro Lys Gly Gly Cys Asn Phe Ile Thr Ser
    1295                1300                1305

Pro Leu Leu Gly Glu Val Pro Gly Asp Lys Ala Pro Pro Met Trp
    1310                1315                1320

Phe Leu Gln Ser Leu Ser Leu Gln Glu Ala Ile Ile Ser Thr Trp
    1325                1330                1335

Leu Gln Phe Ser Asp Gly Ser Val Thr Pro Leu Asp Ile Tyr Asp
    1340                1345                1350

Thr Lys Asp Phe Ser Leu Thr Ala Ile Ser Leu Asp Glu Ala Val
    1355                1360                1365

Ile Ser Ile Pro Gln Pro Leu Ser Pro Trp Trp Pro Thr Val Val
    1370                1375                1380

Ala Glu Gly Glu Gly Gln Gly Pro Leu Leu Arg Val Asp Met Ser
    1385                1390                1395

Ile Ala Glu Ala Cys Gln Lys Ser Lys Arg Lys Ser Val Leu Ala
    1400                1405                1410

Val Gly Ile Gly His Val Gly Val Lys Phe Gly Trp Glu Asp Ala
    1415                1420                1425

Asp Ser Gly Gln Thr Gly Glu Lys Asp Glu Glu Glu Ile Lys Asn
    1430                1435                1440

His Ala Ser Asp Arg Arg Gln Lys Ile Gln Asp Leu Glu Arg Pro
    1445                1450                1455

Gly Pro Asp Glu Leu His His Gly Asn Phe Pro Arg Gly Ser Glu
    1460                1465                1470

Gly Gly Thr Gly Ala Arg Leu His Ser Ile Pro Ile Asp Phe Thr
    1475                1480                1485

Asn Phe Pro Ala His Val Asp Leu Pro Lys Ala Lys Ala Gly Gly
    1490                1495                1500

Thr Leu Glu Glu Asn Gly Leu Met Gln Thr Ala His Gly Leu Ser
    1505                1510                1515

Asp Leu Glu Ile Gly Met Tyr Ala Leu Leu Gly Val Phe Cys Leu
    1520                1525                1530

Ala Ile Leu Val Phe Leu Ile Asn Cys Ala Thr Phe Ala Phe Lys
    1535                1540                1545

Tyr Arg His Lys Gln Val Pro Leu Glu Gly Gln Ala Ser Met Thr
    1550                1555                1560

His Ser His Asp Trp Val Trp Leu Gly Asn Glu Ala Glu Leu Leu
    1565                1570                1575

Glu Asn Ile Gly Asp Leu Ser Pro Pro Gln Asp Glu His Thr Thr
    1580                1585                1590

Ile Ile Asp Arg Gly Leu Gly Gly Phe Glu Glu Asn Asn His Leu
    1595                1600                1605

Phe Leu Asn Gly Gly Ser Gln Lys His Met Gln Ser Gln Val His
    1610                1615                1620

Arg Pro Pro Asp Ser Gly Gly Trp Gln Thr Arg Glu Pro Arg Gln
    1625                1630                1635

Glu Pro Ala Asn Ser Pro Thr Ser Lys Met Lys Lys Val Lys Phe
    1640                1645                1650

Ala Thr Phe Thr Ile Pro Pro Glu Asp Ser Cys Pro Thr Val Asn
    1655                1660                1665

Ser Ile Leu Ser Gly Glu Asp Asp Val Lys Trp Val Cys Gln Asp
```

```
    1670                1675                1680

Leu Asp  Val Gly Ala Pro Lys  Glu Leu Arg Thr Tyr  Leu Glu Lys
    1685                1690                1695

Phe Gln  Asp Ser Val
    1700


<210> SEQ ID NO 23
<211> LENGTH: 3908
<212> TYPE: DNA
<213> ORGANISM: Bos taurus
<220> FEATURE:
<221> NAME/KEY: CDS
<222> LOCATION: (1)..(3600)
<223> OTHER INFORMATION:

<400> SEQUENCE: 23

atg tgt gtt acc aac ttc tgg aga gtg ggc ttt gat gcc tta cag caa       48
Met Cys Val Thr Asn Phe Trp Arg Val Gly Phe Asp Ala Leu Gln Gln
1               5                   10                  15

cgg atc tca agg ctg gtc cca gac cac cag cag cag cat ccc ctg atc       96
Arg Ile Ser Arg Leu Val Pro Asp His Gln Gln Gln His Pro Leu Ile
            20                  25                  30

tcg gga gag ctt gtt aga aat ggg cat gct cca ccc tgc cct cta gac      144
Ser Gly Glu Leu Val Arg Asn Gly His Ala Pro Pro Cys Pro Leu Asp
        35                  40                  45

tct gga gaa agg gcg gca gtc cta tgt gca gaa gcc atc gtc aga aca      192
Ser Gly Glu Arg Ala Ala Val Leu Cys Ala Glu Ala Ile Val Arg Thr
    50                  55                  60

tct gag cca gcc cag gtc tgt tct gac acc cag agc ctg gaa ttc tgc      240
Ser Glu Pro Ala Gln Val Cys Ser Asp Thr Gln Ser Leu Glu Phe Cys
65                  70                  75                  80

tgt gca cgt gat ctg agg cag cca gcc agc cgg gtg gct ttt agg aag      288
Cys Ala Arg Asp Leu Arg Gln Pro Ala Ser Arg Val Ala Phe Arg Lys
                85                  90                  95

aat ctc aaa aac tca att tcc ggc agc ggc ttt gca gga gag ttc tct      336
Asn Leu Lys Asn Ser Ile Ser Gly Ser Gly Phe Ala Gly Glu Phe Ser
            100                 105                 110

gat gaa cag ctg atg gag gac aca ata tcc cca aca ctg aca gtg atc      384
Asp Glu Gln Leu Met Glu Asp Thr Ile Ser Pro Thr Leu Thr Val Ile
        115                 120                 125

gag ggc cgt ggg ctc aca gac aac atc cag cga ttt tcc tcc ctg ccc      432
Glu Gly Arg Gly Leu Thr Asp Asn Ile Gln Arg Phe Ser Ser Leu Pro
    130                 135                 140

cct tac ctg cct gtg acc tat cag gtg ctc aga gcc gag act tcc ttc      480
Pro Tyr Leu Pro Val Thr Tyr Gln Val Leu Arg Ala Glu Thr Ser Phe
145                 150                 155                 160

ttc ctg aag gaa acc aac cag gac ttg aca cgc aac tcc agc ctg cag      528
Phe Leu Lys Glu Thr Asn Gln Asp Leu Thr Arg Asn Ser Ser Leu Gln
                165                 170                 175

tcc cgg gtc gag tcc ttc ttc ctc tac aaa gcc aga cag ccg cca atc      576
Ser Arg Val Glu Ser Phe Phe Leu Tyr Lys Ala Arg Gln Pro Pro Ile
            180                 185                 190

tta aat gcc agc tat ggg cct ttc tcg gtg caa aag gtc gtg ccc ctg      624
Leu Asn Ala Ser Tyr Gly Pro Phe Ser Val Gln Lys Val Val Pro Leu
        195                 200                 205

gaa ttg atg tcg act tcc aac ttt tta ggt ccc acc gac aaa gtg agt      672
Glu Leu Met Ser Thr Ser Asn Phe Leu Gly Pro Thr Asp Lys Val Ser
    210                 215                 220

ttc aac tgg aag ctg aag gcg cac atc ctg cgg gac aag atc tac ctg      720
Phe Asn Trp Lys Leu Lys Ala His Ile Leu Arg Asp Lys Ile Tyr Leu
225                 230                 235                 240
```

-continued

```
agc cgg ccc cgc gtg cag gtg ctg ttc cac ctg gtg ggc cgg gac tgg       768
Ser Arg Pro Arg Val Gln Val Leu Phe His Leu Val Gly Arg Asp Trp
                245                 250                 255

gac gac ccc agc ccc gcg cag agc ctg ccc tgc ctg cgt gtg ttc gcc       816
Asp Asp Pro Ser Pro Ala Gln Ser Leu Pro Cys Leu Arg Val Phe Ala
            260                 265                 270

ttc cgg gag acc cgg gag gtg cgg ggc agc tgc cgg ctt cgg ggg gcc       864
Phe Arg Glu Thr Arg Glu Val Arg Gly Ser Cys Arg Leu Arg Gly Ala
        275                 280                 285

ctg ggg ctg tgc gtg gca cag ctg gag ctc cca gcc agc tgg ttt ggc       912
Leu Gly Leu Cys Val Ala Gln Leu Glu Leu Pro Ala Ser Trp Phe Gly
    290                 295                 300

acc ccc acc gtg gtg gcc ggg agg aag aag gcg ccg gag ccc ccc gag       960
Thr Pro Thr Val Val Ala Gly Arg Lys Lys Ala Pro Glu Pro Pro Glu
305                 310                 315                 320

ggc agc ccc gtg gag ctc tac tac gcc gtg cag ccc ggg gac gag cgt      1008
Gly Ser Pro Val Glu Leu Tyr Tyr Ala Val Gln Pro Gly Asp Glu Arg
                325                 330                 335

gga gac tgt tcc ggg ggc gat gtc cgc aag ggc aat gcc atc cgc ccc      1056
Gly Asp Cys Ser Gly Gly Asp Val Arg Lys Gly Asn Ala Ile Arg Pro
            340                 345                 350

ggc aag gat gga ctg cag gag agc acg tcc cac ctg cag agg atc agc      1104
Gly Lys Asp Gly Leu Gln Glu Ser Thr Ser His Leu Gln Arg Ile Ser
        355                 360                 365

gcc gtg ggc ctc tac cgc gct cag gac agc gcc cag ctc agc gag ctg      1152
Ala Val Gly Leu Tyr Arg Ala Gln Asp Ser Ala Gln Leu Ser Glu Leu
    370                 375                 380

cgt cta gac ggc aac gtg gcc atc tgg ctg ccc tcc agg ccc gtc aag      1200
Arg Leu Asp Gly Asn Val Ala Ile Trp Leu Pro Ser Arg Pro Val Lys
385                 390                 395                 400

cag gga gat gtg gtc act gcc tat gtc acc gtg gcc agc aat tcc acc      1248
Gln Gly Asp Val Val Thr Ala Tyr Val Thr Val Ala Ser Asn Ser Thr
                405                 410                 415

gtg gac ttc ttc atc ttg aga gcc aag gtg aag aag ggg gtg aac atc      1296
Val Asp Phe Phe Ile Leu Arg Ala Lys Val Lys Lys Gly Val Asn Ile
            420                 425                 430

ctg agc acg cgg acc agc gag cct cgg cag tgg gac gtc aag cag gag      1344
Leu Ser Thr Arg Thr Ser Glu Pro Arg Gln Trp Asp Val Lys Gln Glu
        435                 440                 445

atg ggg aac gga ggc aaa cac gcc acc acc gct gtg gtg tgc cag cga      1392
Met Gly Asn Gly Gly Lys His Ala Thr Thr Ala Val Val Cys Gln Arg
    450                 455                 460

ctg gcg cca ggc gcg cgc aac aga agc agc agt tta ttc aat gag gtt      1440
Leu Ala Pro Gly Ala Arg Asn Arg Ser Ser Ser Leu Phe Asn Glu Val
465                 470                 475                 480

gtg cag atg aac ttt gaa atc gcc agc ttc agc agc ctc tca ggg agc      1488
Val Gln Met Asn Phe Glu Ile Ala Ser Phe Ser Ser Leu Ser Gly Ser
                485                 490                 495

cag ccc atc acc tgg caa gtg gaa tac cca cgg agg ggg acc acg gac      1536
Gln Pro Ile Thr Trp Gln Val Glu Tyr Pro Arg Arg Gly Thr Thr Asp
            500                 505                 510

atc gca gtg tca gag atc ttc atc agc cag aag gac ctg gtt ggc atc      1584
Ile Ala Val Ser Glu Ile Phe Ile Ser Gln Lys Asp Leu Val Gly Ile
        515                 520                 525

gtg ccc ttg gcc atg gac act gag atc ctg aac acc gcc atc ctc acg      1632
Val Pro Leu Ala Met Asp Thr Glu Ile Leu Asn Thr Ala Ile Leu Thr
    530                 535                 540

gga aag aca gtt gcc atg ccc atc aag gtg gtc acc gtg gag gag aac      1680
Gly Lys Thr Val Ala Met Pro Ile Lys Val Val Thr Val Glu Glu Asn
545                 550                 555                 560
```

```
agt atc gtg aca gat atc tcg gag tcc gtg gaa tgc aag tcc aca gat      1728
Ser Ile Val Thr Asp Ile Ser Glu Ser Val Glu Cys Lys Ser Thr Asp
                565                 570                 575

gag gag gtc atc aaa gtg tcc gat cat tgt gac tat gtc ttt gtc aac      1776
Glu Glu Val Ile Lys Val Ser Asp His Cys Asp Tyr Val Phe Val Asn
            580                 585                 590

ggc aaa gag atg aaa ggc aag gtg gat gtg gtg gtg aac ttc acg tac      1824
Gly Lys Glu Met Lys Gly Lys Val Asp Val Val Val Asn Phe Thr Tyr
        595                 600                 605

cag cac cta agc gcc ccc ctg cat gtc act gta tgg gtg ccc cga ctg      1872
Gln His Leu Ser Ala Pro Leu His Val Thr Val Trp Val Pro Arg Leu
    610                 615                 620

ccc ctg cag atc gag gtc tct gac acg gag ctg agc cag att aaa ggc      1920
Pro Leu Gln Ile Glu Val Ser Asp Thr Glu Leu Ser Gln Ile Lys Gly
625                 630                 635                 640

tgg agg gtg ccc atc gtg gcc agc aag agg ccc aca cga gac agc gag      1968
Trp Arg Val Pro Ile Val Ala Ser Lys Arg Pro Thr Arg Asp Ser Glu
                645                 650                 655

gat gag gac gag gag gag cgg cgg ggc cgg ggc tgc gcc ctc cag tac      2016
Asp Glu Asp Glu Glu Glu Arg Arg Gly Arg Gly Cys Ala Leu Gln Tyr
            660                 665                 670

cag cac gcc atg gtg cgg gtc ctc acc cag ttt gtg tcc gag ggg gct      2064
Gln His Ala Met Val Arg Val Leu Thr Gln Phe Val Ser Glu Gly Ala
        675                 680                 685

ggc ccc tgg ggc cag cca agc cac ctg ctc agt cca gac tgg cag ttc      2112
Gly Pro Trp Gly Gln Pro Ser His Leu Leu Ser Pro Asp Trp Gln Phe
    690                 695                 700

gac atc acc cac ctg gtt gct gac ttc atg aag ctg gag gaa cca cat      2160
Asp Ile Thr His Leu Val Ala Asp Phe Met Lys Leu Glu Glu Pro His
705                 710                 715                 720

gtg gcc act ctc cag gac agc agg atc ctg gtc ggg cgg gaa gtt ggc      2208
Val Ala Thr Leu Gln Asp Ser Arg Ile Leu Val Gly Arg Glu Val Gly
                725                 730                 735

atg aca acc atc cag gtg ctc tcc cct ctg tct gac tcc atc ctg gct      2256
Met Thr Thr Ile Gln Val Leu Ser Pro Leu Ser Asp Ser Ile Leu Ala
            740                 745                 750

gag aag acg gtc act gtg ttg gac gac aaa gtt gcg gtg tca gac ctg      2304
Glu Lys Thr Val Thr Val Leu Asp Asp Lys Val Ala Val Ser Asp Leu
        755                 760                 765

gcc atc cag ctc gtg gct ggg ctg tct gtc acc ctc cac ccc agc acg      2352
Ala Ile Gln Leu Val Ala Gly Leu Ser Val Thr Leu His Pro Ser Thr
    770                 775                 780

gag aac agc agg gct atc aca gct gtg gcc aca gct gag gag ctg ctg      2400
Glu Asn Ser Arg Ala Ile Thr Ala Val Ala Thr Ala Glu Glu Leu Leu
785                 790                 795                 800

cgg gcc cct aaa cag gaa gct gtg gtc agc act tgg ctc cag ttc agc      2448
Arg Ala Pro Lys Gln Glu Ala Val Val Ser Thr Trp Leu Gln Phe Ser
                805                 810                 815

gat ggc tct gtg acg ccc ctg gac atc tac gac acc aag gac ttc acc      2496
Asp Gly Ser Val Thr Pro Leu Asp Ile Tyr Asp Thr Lys Asp Phe Thr
            820                 825                 830

ctg aca gcc acc tcc ctg gac gag gcc atc gtg tcc gtc ccc cag ccc      2544
Leu Thr Ala Thr Ser Leu Asp Glu Ala Ile Val Ser Val Pro Gln Pro
        835                 840                 845

cgc tcg ccc agg tgg ccc act gtg atg gct gaa ggt gaa ggc cag gga      2592
Arg Ser Pro Arg Trp Pro Thr Val Met Ala Glu Gly Glu Gly Gln Gly
    850                 855                 860

ccc ctg gtc cga gtg gat ctg acc atc gca gag gcc tgc caa aaa tcc      2640
Pro Leu Val Arg Val Asp Leu Thr Ile Ala Glu Ala Cys Gln Lys Ser
865                 870                 875                 880
```

-continued

```
aaa cgc aag agc gtc ctg gca gtc ggc gtg ggg agc gtc agg gtc aag      2688
Lys Arg Lys Ser Val Leu Ala Val Gly Val Gly Ser Val Arg Val Lys
                885                 890                 895

ttc ggg cag aac gac gcg aac tcc agc cca ggt gtg gac tac gag gag      2736
Phe Gly Gln Asn Asp Ala Asn Ser Ser Pro Gly Val Asp Tyr Glu Glu
            900                 905                 910

ggt gag atc aag aac cac gcc agc gac cgg cgc cag aag gcc cag gaa      2784
Gly Glu Ile Lys Asn His Ala Ser Asp Arg Arg Gln Lys Ala Gln Glu
        915                 920                 925

gga ccc ttc tat ggc agc tcc tcc gcg gaa cgc gag gaa ggg gtc ctc      2832
Gly Pro Phe Tyr Gly Ser Ser Ser Ala Glu Arg Glu Glu Gly Val Leu
    930                 935                 940

cgg agg ggc aac ccc acg gcc aag tca ctg ctg gac aac aag gtg ggc      2880
Arg Arg Gly Asn Pro Thr Ala Lys Ser Leu Leu Asp Asn Lys Val Gly
945                 950                 955                 960

aag aac agc cgg ctg gac ggg ggc cgg ctg gcg ggg gag ggt cag ctg      2928
Lys Asn Ser Arg Leu Asp Gly Gly Arg Leu Ala Gly Glu Gly Gln Leu
                965                 970                 975

cag acc atc ccc atc gat ttc gcc aac ttc cca gca cag gtg gac ctg      2976
Gln Thr Ile Pro Ile Asp Phe Ala Asn Phe Pro Ala Gln Val Asp Leu
            980                 985                 990

ccc cag gcg ggg agc ggg cgc ggg  gcc agc gac ctg gtg  cag act ccc    3024
Pro Gln Ala Gly Ser Gly Arg Gly  Ala Ser Asp Leu Val  Gln Thr Pro
        995                 1000                1005

cgc ggc  ctg agt gat ctg gag  atc ggc atg tat gcc  ctc ctg ggg      3069
Arg Gly  Leu Ser Asp Leu Glu  Ile Gly Met Tyr Ala  Leu Leu Gly
    1010                1015                1020

gtc ttc  tgc ctg gcc atc ctc  gtc ttc ctc atc aac  tgc gcc acc      3114
Val Phe  Cys Leu Ala Ile Leu  Val Phe Leu Ile Asn  Cys Ala Thr
    1025                1030                1035

ttc gcc  ctc aag tac agg cat  aag cag gtg ccc ctg  gaa ggc cag      3159
Phe Ala  Leu Lys Tyr Arg His  Lys Gln Val Pro Leu  Glu Gly Gln
    1040                1045                1050

gcc tcc  gtg acc cac tcg cat  gac tgg gtg tgg ctg  ggc aac gag      3204
Ala Ser  Val Thr His Ser His  Asp Trp Val Trp Leu  Gly Asn Glu
    1055                1060                1065

gcg gag  ctc ctg gag aac gtg  ggc gac agc tct ccg  ccg cag gac      3249
Ala Glu  Leu Leu Glu Asn Val  Gly Asp Ser Ser Pro  Pro Gln Asp
    1070                1075                1080

gag cac  acg acc atc ata gac  cgc ggg cca ggg ggc  ttc gag gag      3294
Glu His  Thr Thr Ile Ile Asp  Arg Gly Pro Gly Gly  Phe Glu Glu
    1085                1090                1095

agc aac  cgc ctc ctg ctc aac  gga ggt tcc caa aag  cag ggg cag      3339
Ser Asn  Arg Leu Leu Leu Asn  Gly Gly Ser Gln Lys  Gln Gly Gln
    1100                1105                1110

agc cag  atc ccc agg ccg gcc  gac tct ggg ggc aag  cag ggc agg      3384
Ser Gln  Ile Pro Arg Pro Ala  Asp Ser Gly Gly Lys  Gln Gly Arg
    1115                1120                1125

gac cag  aaa cac gag ccc ctg  cac tcg ccc acc tcc  aag agg aaa      3429
Asp Gln  Lys His Glu Pro Leu  His Ser Pro Thr Ser  Lys Arg Lys
    1130                1135                1140

aag gtg  aaa ttc acc acc ttc  acc acc atc ccc gcc  gac gac ggc      3474
Lys Val  Lys Phe Thr Thr Phe  Thr Thr Ile Pro Ala  Asp Asp Gly
    1145                1150                1155

tgc ccc  acc gtc aac tcc att  ctg ggc ggg aca gag  gag gac atc      3519
Cys Pro  Thr Val Asn Ser Ile  Leu Gly Gly Thr Glu  Glu Asp Ile
    1160                1165                1170

aaa tgg  gtg tgc cag gac gtg  ggc gtg ggt gcc ccc  aaa gaa ctc      3564
Lys Trp  Val Cys Gln Asp Val  Gly Val Gly Ala Pro  Lys Glu Leu
    1175                1180                1185
```

-continued

```
aga gac  tat ctg gag aag ttc  aag gac aac gtg tag gcccctctgg        3610
Arg Asp  Tyr Leu Glu Lys Phe  Lys Asp Asn Val
    1190                 1195

tcgaaggacc agcgcctgga caccctcctt cagctccacg gtagatctgg ggctcaacag   3670

ggactctatg gggcccatct ttgaaactat tcatagttgg aagttctgaa gccggaaagg   3730

gacagttttg tgatcagagg ttgatgatgg cagactttct caagtcggaa ggaaaaaact   3790

ctgggaacgg agctgatgga gacattttaa ctgcgcaagg ccaaattagg aaggttattt   3850

tatgagtcaa aatataaccc agacaagcta ccaaaaagta tttgttaaaa aaaaaaaa     3908


<210> SEQ ID NO 24
<211> LENGTH: 1199
<212> TYPE: PRT
<213> ORGANISM: Bos taurus

<400> SEQUENCE: 24

Met Cys Val Thr Asn Phe Trp Arg Val Gly Phe Asp Ala Leu Gln Gln
1               5                   10                  15

Arg Ile Ser Arg Leu Val Pro Asp His Gln Gln Gln His Pro Leu Ile
            20                  25                  30

Ser Gly Glu Leu Val Arg Asn Gly His Ala Pro Pro Cys Pro Leu Asp
        35                  40                  45

Ser Gly Glu Arg Ala Ala Val Leu Cys Ala Glu Ala Ile Val Arg Thr
    50                  55                  60

Ser Glu Pro Ala Gln Val Cys Ser Asp Thr Gln Ser Leu Glu Phe Cys
65                  70                  75                  80

Cys Ala Arg Asp Leu Arg Gln Pro Ala Ser Arg Val Ala Phe Arg Lys
                85                  90                  95

Asn Leu Lys Asn Ser Ile Ser Gly Ser Gly Phe Ala Gly Glu Phe Ser
            100                 105                 110

Asp Glu Gln Leu Met Glu Asp Thr Ile Ser Pro Thr Leu Thr Val Ile
        115                 120                 125

Glu Gly Arg Gly Leu Thr Asp Asn Ile Gln Arg Phe Ser Ser Leu Pro
    130                 135                 140

Pro Tyr Leu Pro Val Thr Tyr Gln Val Leu Arg Ala Glu Thr Ser Phe
145                 150                 155                 160

Phe Leu Lys Glu Thr Asn Gln Asp Leu Thr Arg Asn Ser Ser Leu Gln
                165                 170                 175

Ser Arg Val Glu Ser Phe Phe Leu Tyr Lys Ala Arg Gln Pro Pro Ile
            180                 185                 190

Leu Asn Ala Ser Tyr Gly Pro Phe Ser Val Gln Lys Val Val Pro Leu
        195                 200                 205

Glu Leu Met Ser Thr Ser Asn Phe Leu Gly Pro Thr Asp Lys Val Ser
    210                 215                 220

Phe Asn Trp Lys Leu Lys Ala His Ile Leu Arg Asp Lys Ile Tyr Leu
225                 230                 235                 240

Ser Arg Pro Arg Val Gln Val Leu Phe His Leu Val Gly Arg Asp Trp
                245                 250                 255

Asp Asp Pro Ser Pro Ala Gln Ser Leu Pro Cys Leu Arg Val Phe Ala
            260                 265                 270

Phe Arg Glu Thr Arg Glu Val Arg Gly Ser Cys Arg Leu Arg Gly Ala
        275                 280                 285

Leu Gly Leu Cys Val Ala Gln Leu Glu Leu Pro Ala Ser Trp Phe Gly
    290                 295                 300

Thr Pro Thr Val Val Ala Gly Arg Lys Lys Ala Pro Glu Pro Pro Glu
```

-continued

```
305                 310                 315                 320

Gly Ser Pro Val Glu Leu Tyr Tyr Ala Val Gln Pro Gly Asp Glu Arg
                325                 330                 335

Gly Asp Cys Ser Gly Gly Asp Val Arg Lys Gly Asn Ala Ile Arg Pro
            340                 345                 350

Gly Lys Asp Gly Leu Gln Glu Ser Thr Ser His Leu Gln Arg Ile Ser
        355                 360                 365

Ala Val Gly Leu Tyr Arg Ala Gln Asp Ser Ala Gln Leu Ser Glu Leu
    370                 375                 380

Arg Leu Asp Gly Asn Val Ala Ile Trp Leu Pro Ser Arg Pro Val Lys
385                 390                 395                 400

Gln Gly Asp Val Val Thr Ala Tyr Val Thr Val Ala Ser Asn Ser Thr
                405                 410                 415

Val Asp Phe Phe Ile Leu Arg Ala Lys Val Lys Lys Gly Val Asn Ile
            420                 425                 430

Leu Ser Thr Arg Thr Ser Glu Pro Arg Gln Trp Asp Val Lys Gln Glu
        435                 440                 445

Met Gly Asn Gly Gly Lys His Ala Thr Thr Ala Val Val Cys Gln Arg
    450                 455                 460

Leu Ala Pro Gly Ala Arg Asn Arg Ser Ser Ser Leu Phe Asn Glu Val
465                 470                 475                 480

Val Gln Met Asn Phe Glu Ile Ala Ser Phe Ser Ser Leu Ser Gly Ser
                485                 490                 495

Gln Pro Ile Thr Trp Gln Val Glu Tyr Pro Arg Arg Gly Thr Thr Asp
            500                 505                 510

Ile Ala Val Ser Glu Ile Phe Ile Ser Gln Lys Asp Leu Val Gly Ile
        515                 520                 525

Val Pro Leu Ala Met Asp Thr Glu Ile Leu Asn Thr Ala Ile Leu Thr
    530                 535                 540

Gly Lys Thr Val Ala Met Pro Ile Lys Val Val Thr Val Glu Glu Asn
545                 550                 555                 560

Ser Ile Val Thr Asp Ile Ser Glu Ser Val Glu Cys Lys Ser Thr Asp
                565                 570                 575

Glu Glu Val Ile Lys Val Ser Asp His Cys Asp Tyr Val Phe Val Asn
            580                 585                 590

Gly Lys Glu Met Lys Gly Lys Val Asp Val Val Val Asn Phe Thr Tyr
        595                 600                 605

Gln His Leu Ser Ala Pro Leu His Val Thr Val Trp Val Pro Arg Leu
    610                 615                 620

Pro Leu Gln Ile Glu Val Ser Asp Thr Glu Leu Ser Gln Ile Lys Gly
625                 630                 635                 640

Trp Arg Val Pro Ile Val Ala Ser Lys Arg Pro Thr Arg Asp Ser Glu
                645                 650                 655

Asp Glu Asp Glu Glu Glu Arg Arg Gly Arg Gly Cys Ala Leu Gln Tyr
            660                 665                 670

Gln His Ala Met Val Arg Val Leu Thr Gln Phe Val Ser Glu Gly Ala
        675                 680                 685

Gly Pro Trp Gly Gln Pro Ser His Leu Leu Ser Pro Asp Trp Gln Phe
    690                 695                 700

Asp Ile Thr His Leu Val Ala Asp Phe Met Lys Leu Glu Glu Pro His
705                 710                 715                 720

Val Ala Thr Leu Gln Asp Ser Arg Ile Leu Val Gly Arg Glu Val Gly
                725                 730                 735
```

-continued

```
Met Thr Thr Ile Gln Val Leu Ser Pro Leu Ser Asp Ser Ile Leu Ala
            740                 745                 750

Glu Lys Thr Val Thr Val Leu Asp Asp Lys Val Ala Val Ser Asp Leu
        755                 760                 765

Ala Ile Gln Leu Val Ala Gly Leu Ser Val Thr Leu His Pro Ser Thr
    770                 775                 780

Glu Asn Ser Arg Ala Ile Thr Ala Val Ala Thr Ala Glu Glu Leu Leu
785                 790                 795                 800

Arg Ala Pro Lys Gln Glu Ala Val Val Ser Thr Trp Leu Gln Phe Ser
                805                 810                 815

Asp Gly Ser Val Thr Pro Leu Asp Ile Tyr Asp Thr Lys Asp Phe Thr
            820                 825                 830

Leu Thr Ala Thr Ser Leu Asp Glu Ala Ile Val Ser Val Pro Gln Pro
        835                 840                 845

Arg Ser Pro Arg Trp Pro Thr Val Met Ala Glu Gly Glu Gly Gln Gly
    850                 855                 860

Pro Leu Val Arg Val Asp Leu Thr Ile Ala Glu Ala Cys Gln Lys Ser
865                 870                 875                 880

Lys Arg Lys Ser Val Leu Ala Val Gly Val Gly Ser Val Arg Val Lys
                885                 890                 895

Phe Gly Gln Asn Asp Ala Asn Ser Ser Pro Gly Val Asp Tyr Glu Glu
            900                 905                 910

Gly Glu Ile Lys Asn His Ala Ser Asp Arg Arg Gln Lys Ala Gln Glu
        915                 920                 925

Gly Pro Phe Tyr Gly Ser Ser Ser Ala Glu Arg Glu Glu Gly Val Leu
    930                 935                 940

Arg Arg Gly Asn Pro Thr Ala Lys Ser Leu Leu Asp Asn Lys Val Gly
945                 950                 955                 960

Lys Asn Ser Arg Leu Asp Gly Gly Arg Leu Ala Gly Glu Gly Gln Leu
                965                 970                 975

Gln Thr Ile Pro Ile Asp Phe Ala Asn Phe Pro Ala Gln Val Asp Leu
            980                 985                 990

Pro Gln Ala Gly Ser Gly Arg Gly  Ala Ser Asp Leu Val  Gln Thr Pro
        995                 1000                1005

Arg Gly  Leu Ser Asp Leu Glu  Ile Gly Met Tyr Ala  Leu Leu Gly
    1010                 1015                 1020

Val Phe  Cys Leu Ala Ile Leu  Val Phe Leu Ile Asn  Cys Ala Thr
    1025                 1030                 1035

Phe Ala  Leu Lys Tyr Arg His  Lys Gln Val Pro Leu  Glu Gly Gln
    1040                 1045                 1050

Ala Ser  Val Thr His Ser His  Asp Trp Val Trp Leu  Gly Asn Glu
    1055                 1060                 1065

Ala Glu  Leu Leu Glu Asn Val  Gly Asp Ser Ser Pro  Pro Gln Asp
    1070                 1075                 1080

Glu His  Thr Thr Ile Ile Asp  Arg Gly Pro Gly Gly  Phe Glu Glu
    1085                 1090                 1095

Ser Asn  Arg Leu Leu Leu Asn  Gly Gly Ser Gln Lys  Gln Gly Gln
    1100                 1105                 1110

Ser Gln  Ile Pro Arg Pro Ala  Asp Ser Gly Gly Lys  Gln Gly Arg
    1115                 1120                 1125

Asp Gln  Lys His Glu Pro Leu  His Ser Pro Thr Ser  Lys Arg Lys
    1130                 1135                 1140

Lys Val  Lys Phe Thr Thr Phe  Thr Thr Ile Pro Ala  Asp Asp Gly
    1145                 1150                 1155
```

```
Cys Pro  Thr Val Asn Ser Ile  Leu Gly Gly Thr Glu  Glu Asp Ile
    1160                 1165                 1170

Lys Trp  Val Cys Gln Asp Val  Gly Val Gly Ala Pro  Lys Glu Leu
    1175                 1180                 1185

Arg Asp  Tyr Leu Glu Lys Phe  Lys Asp Asn Val
    1190                 1195


<210> SEQ ID NO 25
<211> LENGTH: 3527
<212> TYPE: DNA
<213> ORGANISM: Canis familiaris
<220> FEATURE:
<221> NAME/KEY: CDS
<222> LOCATION: (1)..(3270)
<223> OTHER INFORMATION:

<400> SEQUENCE: 25

atg gcc acc atg cta ttc gcc aag ctc aac ttc agg aac ttg atc gag       48
Met Ala Thr Met Leu Phe Ala Lys Leu Asn Phe Arg Asn Leu Ile Glu
1               5                   10                  15

ggc cgg ggg atc aca gat aat gtg cca cgg ttc tct tct ctg cca ccc       96
Gly Arg Gly Ile Thr Asp Asn Val Pro Arg Phe Ser Ser Leu Pro Pro
            20                  25                  30

ttc ctg cct gtg agc tac cac atc ctt gga gca gag acc tcc ttc ttc      144
Phe Leu Pro Val Ser Tyr His Ile Leu Gly Ala Glu Thr Ser Phe Phe
        35                  40                  45

ctg aag gag gcc aac cag gac gtc ctg cgc aac tcc agc ctg cac acc      192
Leu Lys Glu Ala Asn Gln Asp Val Leu Arg Asn Ser Ser Leu His Thr
    50                  55                  60

agg gtg gag tcc ttc ttc acc tac aag gcc aac cgg ccc cca gtg ctc      240
Arg Val Glu Ser Phe Phe Thr Tyr Lys Ala Asn Arg Pro Pro Val Leu
65                  70                  75                  80

aac gcc agc tac ggg ccc ttc tcc atc gag cag gtg gtg cct cag gac      288
Asn Ala Ser Tyr Gly Pro Phe Ser Ile Glu Gln Val Val Pro Gln Asp
                85                  90                  95

ctc ctg ctg ccc tcc agc ccc ttc gga gcc acc agc aag ctc tcc ctc      336
Leu Leu Leu Pro Ser Ser Pro Phe Gly Ala Thr Ser Lys Leu Ser Leu
            100                 105                 110

aac tgg agg ctg agg gcg cac atc ctg cgg gac aag gtg tac ctg agc      384
Asn Trp Arg Leu Arg Ala His Ile Leu Arg Asp Lys Val Tyr Leu Ser
        115                 120                 125

cgg ccc cgg gtg cag gtg ctc ttc cac ctg ctg ggc cgg gac tgg gcg      432
Arg Pro Arg Val Gln Val Leu Phe His Leu Leu Gly Arg Asp Trp Ala
    130                 135                 140

gca cag agc cct ggc gag cgg ctg ccc tgc ctg cgg ctg ttc gcc ttc      480
Ala Gln Ser Pro Gly Glu Arg Leu Pro Cys Leu Arg Leu Phe Ala Phe
145                 150                 155                 160

cgg gag acc cgg gag gtg cgg gcc ggc tgc cgg ctg cag ggc gcc ctg      528
Arg Glu Thr Arg Glu Val Arg Ala Gly Cys Arg Leu Gln Gly Ala Leu
                165                 170                 175

ggg ctg tgc gtg gcc gaa ctg gag ctg ctg gcc gcc tgg ttc ggg ccc      576
Gly Leu Cys Val Ala Glu Leu Glu Leu Leu Ala Ala Trp Phe Gly Pro
            180                 185                 190

ccc acc gtg gtg gcc ggg agg aag cgg gcg cct ggg ccg ccc gag ggg      624
Pro Thr Val Val Ala Gly Arg Lys Arg Ala Pro Gly Pro Pro Glu Gly
        195                 200                 205

agc ccc gtg gag ctc tac tac tcc gtg cag ccg ggg gat gcg cgc ggg      672
Ser Pro Val Glu Leu Tyr Tyr Ser Val Gln Pro Gly Asp Ala Arg Gly
    210                 215                 220

gac tgt gcg ggc ggc ggc ggc gac gtc agg aag ggc aac gcc atc cgg      720
Asp Cys Ala Gly Gly Gly Gly Asp Val Arg Lys Gly Asn Ala Ile Arg
```

-continued

```
225                 230                 235                 240

cct ggg aag gac ggg ctg gat gag gcc gtg ccc cac ctg cag agg atc      768
Pro Gly Lys Asp Gly Leu Asp Glu Ala Val Pro His Leu Gln Arg Ile
                245                 250                 255

ggc gcc gtc agc ctc tac cgg gcc cag gac agc acc cag ctc agc gag      816
Gly Ala Val Ser Leu Tyr Arg Ala Gln Asp Ser Thr Gln Leu Ser Glu
            260                 265                 270

ctg cgt ttg gac agc aac gtg gtc atc tgg ctg ccc tcc cgg ccc gtc      864
Leu Arg Leu Asp Ser Asn Val Val Ile Trp Leu Pro Ser Arg Pro Val
        275                 280                 285

aag caa gga gat gtg gtc acc gcc tac gtc acc atc gcc agc aac tcc      912
Lys Gln Gly Asp Val Val Thr Ala Tyr Val Thr Ile Ala Ser Asn Ser
    290                 295                 300

act gtg gac ctt ttc atc ctg aga gcc aag gtg aag aag ggg gtg aac      960
Thr Val Asp Leu Phe Ile Leu Arg Ala Lys Val Lys Lys Gly Val Asn
305                 310                 315                 320

atc ctg ggc act cag acc agc gag ccc cgg cag tgg gat gtc aaa cag     1008
Ile Leu Gly Thr Gln Thr Ser Glu Pro Arg Gln Trp Asp Val Lys Gln
                325                 330                 335

gag atg ggg aat ggc gga aag cat gct acc acc acc gtg ctg tgc cag     1056
Glu Met Gly Asn Gly Gly Lys His Ala Thr Thr Thr Val Leu Cys Gln
            340                 345                 350

cgc ctg ggg tcc agc aca cgt aac aga agc agc agc ctg ttc agt gag     1104
Arg Leu Gly Ser Ser Thr Arg Asn Arg Ser Ser Ser Leu Phe Ser Glu
        355                 360                 365

gtt atg cag atg aac ttt gaa ata gcc agc ttc agt agc ctc tcg ggg     1152
Val Met Gln Met Asn Phe Glu Ile Ala Ser Phe Ser Ser Leu Ser Gly
    370                 375                 380

act cag ccc atc gcc tgg cag gtg gaa tat cca cgg aga gcg acc acc     1200
Thr Gln Pro Ile Ala Trp Gln Val Glu Tyr Pro Arg Arg Ala Thr Thr
385                 390                 395                 400

gac acc gct gtg tcc gag atc ttc atc agc cag aag gac ctg gct ggc     1248
Asp Thr Ala Val Ser Glu Ile Phe Ile Ser Gln Lys Asp Leu Ala Gly
                405                 410                 415

atc gtt cct cta gcc acg gac acg gaa att ctg aac act gcc atc ctc     1296
Ile Val Pro Leu Ala Thr Asp Thr Glu Ile Leu Asn Thr Ala Ile Leu
            420                 425                 430

acg gga aag aca gtg gtc ctg ccc atc aag gtg gtc tct gtg gag gag     1344
Thr Gly Lys Thr Val Val Leu Pro Ile Lys Val Val Ser Val Glu Glu
        435                 440                 445

aac agt gcc gtg atg gat atc tcc gag tcg gtg gag tgc aag tcc aca     1392
Asn Ser Ala Val Met Asp Ile Ser Glu Ser Val Glu Cys Lys Ser Thr
    450                 455                 460

gac gag gat gtc atc aag gtg tct gaa aga tgt gac tac gtc ttt gtc     1440
Asp Glu Asp Val Ile Lys Val Ser Glu Arg Cys Asp Tyr Val Phe Val
465                 470                 475                 480

aat ggc aaa gag atg aag ggc aag gtg gat gcg gtg gtg aac ttc acc     1488
Asn Gly Lys Glu Met Lys Gly Lys Val Asp Ala Val Val Asn Phe Thr
                485                 490                 495

tac cag cac ctg agt gcc tcc ctg cac atc acc gtg tgg gtg ccc cgg     1536
Tyr Gln His Leu Ser Ala Ser Leu His Ile Thr Val Trp Val Pro Arg
            500                 505                 510

cta ccc cta cag att gag gtc tct gac aca gag ctg agc cag atc aaa     1584
Leu Pro Leu Gln Ile Glu Val Ser Asp Thr Glu Leu Ser Gln Ile Lys
        515                 520                 525

ggc tgg agg gtc ccc att gtg tcc agt aag agg ccc act cga gag agc     1632
Gly Trp Arg Val Pro Ile Val Ser Ser Lys Arg Pro Thr Arg Glu Ser
    530                 535                 540

gag gat gaa gac gag gag gag cgg cgg ggc cga ggc tgt gcc ctg cag     1680
Glu Asp Glu Asp Glu Glu Glu Arg Arg Gly Arg Gly Cys Ala Leu Gln
```

-continued

```
545                 550                 555                 560

tac cag cac gcc acg gtg cgg gtc ctc acc cag ttc gtg tcg gag ggc      1728
Tyr Gln His Ala Thr Val Arg Val Leu Thr Gln Phe Val Ser Glu Gly
                565                 570                 575

gct ggc ccg tgg ggc cag ccg agc cac ctt ctc agt ccc gac tgg caa      1776
Ala Gly Pro Trp Gly Gln Pro Ser His Leu Leu Ser Pro Asp Trp Gln
            580                 585                 590

gtc gac atc acc cac ctg gtt gca gac ttc atg aag ctg gag gaa cct      1824
Val Asp Ile Thr His Leu Val Ala Asp Phe Met Lys Leu Glu Glu Pro
        595                 600                 605

cac gtg gcc aca ctc cag gac agc agg atc ctg gtc ggg cgg gag gtt      1872
His Val Ala Thr Leu Gln Asp Ser Arg Ile Leu Val Gly Arg Glu Val
    610                 615                 620

ggg atg acc acc atc cag gtg ttg tct cca ctc tct gac tcc atc ctg      1920
Gly Met Thr Thr Ile Gln Val Leu Ser Pro Leu Ser Asp Ser Ile Leu
625                 630                 635                 640

gca gag aag acg gtg acc gtg tta gat gac aag gta tcg gtg aca gac      1968
Ala Glu Lys Thr Val Thr Val Leu Asp Asp Lys Val Ser Val Thr Asp
                645                 650                 655

ttg gcc atc cag ctc gtg gct ggg ctg tct gtc acc ctc cac ccc agc      2016
Leu Ala Ile Gln Leu Val Ala Gly Leu Ser Val Thr Leu His Pro Ser
            660                 665                 670

acg gag aac agc aag gcc atc act gct gtg gcc aca gct gag gag ctg      2064
Thr Glu Asn Ser Lys Ala Ile Thr Ala Val Ala Thr Ala Glu Glu Leu
        675                 680                 685

ctg cgg acc ccc aaa cag gag gcc gtg gtc agc act tgg ctc cag ctc      2112
Leu Arg Thr Pro Lys Gln Glu Ala Val Val Ser Thr Trp Leu Gln Leu
    690                 695                 700

agc gac ggc tcc gcc acc ccc ctg gac atc tac gac acc aag gac ttc      2160
Ser Asp Gly Ser Ala Thr Pro Leu Asp Ile Tyr Asp Thr Lys Asp Phe
705                 710                 715                 720

acc ctg acc gcc acc tcc ctg aac gag gcc gtc gtg tcc acc ccc cag      2208
Thr Leu Thr Ala Thr Ser Leu Asn Glu Ala Val Val Ser Thr Pro Gln
                725                 730                 735

gcc cgc tct ccc aga tgg ccg gtg gtg atg gcc gaa ggg gaa ggc cag      2256
Ala Arg Ser Pro Arg Trp Pro Val Val Met Ala Glu Gly Glu Gly Gln
            740                 745                 750

ggg ccg ctg gtg cga gtg gac atg tcc atc gcc gag gcc tgc cag aag      2304
Gly Pro Leu Val Arg Val Asp Met Ser Ile Ala Glu Ala Cys Gln Lys
        755                 760                 765

tcc aag cgc aag agc gtc ctg gcc gtg ggt gtg ggc agc gtc agg gtc      2352
Ser Lys Arg Lys Ser Val Leu Ala Val Gly Val Gly Ser Val Arg Val
    770                 775                 780

aag ttt ggc cag ggc aac gcc gac tcc agc cgc ggc gcg gac ggc gac      2400
Lys Phe Gly Gln Gly Asn Ala Asp Ser Ser Arg Gly Ala Asp Gly Asp
785                 790                 795                 800

agt ggc gag atc aag aac cac gcc agc gac cgc cgg cag aag agc cag      2448
Ser Gly Glu Ile Lys Asn His Ala Ser Asp Arg Arg Gln Lys Ser Gln
                805                 810                 815

gag ccc gag ggg cac ctc caa ggc agc ccg ggg gag cgc gag gac ggc      2496
Glu Pro Glu Gly His Leu Gln Gly Ser Pro Gly Glu Arg Glu Asp Gly
            820                 825                 830

gcc ctg cag aga ggc gac agc acg gcc agg ccg ctc ctg gac aac agg      2544
Ala Leu Gln Arg Gly Asp Ser Thr Ala Arg Pro Leu Leu Asp Asn Arg
        835                 840                 845

gtg gtg aag agc ggc cgg ccg gac gcg ggc agg ccg tcc ggg ggg gac      2592
Val Val Lys Ser Gly Arg Pro Asp Ala Gly Arg Pro Ser Gly Gly Asp
    850                 855                 860

cag ctg cag aac atc ccc ctg gac ttc gcc aac ttc ccg gcg cag gtg      2640
Gln Leu Gln Asn Ile Pro Leu Asp Phe Ala Asn Phe Pro Ala Gln Val
```

```
865                 870                 875                 880

gag ctg ccc cgg gcg ggg ggc ggc ctg ggg gcc agc gac ctg gtg cag      2688
Glu Leu Pro Arg Ala Gly Gly Gly Leu Gly Ala Ser Asp Leu Val Gln
                885                 890                 895

acg ccc cgg ggc ctg agc gac ctg gag atc ggc atg tac gcc ctg ctc      2736
Thr Pro Arg Gly Leu Ser Asp Leu Glu Ile Gly Met Tyr Ala Leu Leu
            900                 905                 910

ggc gtc ttc tgc ttg gcc atc ctt gtc ttc ctc atc aac tgc gcc acc      2784
Gly Val Phe Cys Leu Ala Ile Leu Val Phe Leu Ile Asn Cys Ala Thr
        915                 920                 925

ttc gcc ctc agg tac cgc cac aag cag gtg ccc ctg gaa ggc cag gcc      2832
Phe Ala Leu Arg Tyr Arg His Lys Gln Val Pro Leu Glu Gly Gln Ala
    930                 935                 940

tct gtg acc cac tcg cac gac tgg gtg tgg ctg ggc aac gag gcg gag      2880
Ser Val Thr His Ser His Asp Trp Val Trp Leu Gly Asn Glu Ala Glu
945                 950                 955                 960

ctc ctg gag cac gcg ggc gag ggg tcg cca ccg cag gac gag cac acg      2928
Leu Leu Glu His Ala Gly Glu Gly Ser Pro Pro Gln Asp Glu His Thr
                965                 970                 975

act gtc ctg gac cgc ggg ccg ggc ggc agc gac gac ggc agc cgg ctg      2976
Thr Val Leu Asp Arg Gly Pro Gly Gly Ser Asp Asp Gly Ser Arg Leu
            980                 985                 990

ctg ctc aac ggc ggc gcc cgg cag  cac gtg cag ggc cag  gtg cac cgg    3024
Leu Leu Asn Gly Gly Ala Arg Gln  His Val Gln Gly Gln  Val His Arg
        995                 1000                1005

gcg ggc  tcg gcg ggc agg ccg  gcc agg gac ccg aag  ctc gag ccc      3069
Ala Gly  Ser Ala Gly Arg Pro  Ala Arg Asp Pro Lys  Leu Glu Pro
    1010                1015                1020

ctg cat  tcg ccc acc tcc aaa  agg aag aaa gtg aag  ttc acc acc      3114
Leu His  Ser Pro Thr Ser Lys  Arg Lys Lys Val Lys  Phe Thr Thr
    1025                1030                1035

ttc acc  acc atc ccg ccc gac  gac ggc tgc ccc acc  gtg aac tcc      3159
Phe Thr  Thr Ile Pro Pro Asp  Asp Gly Cys Pro Thr  Val Asn Ser
    1040                1045                1050

atc ctg  ggg ggc ggc ggc ggc  gag gac atc aag tgg  gtg tgc cag      3204
Ile Leu  Gly Gly Gly Gly Gly  Glu Asp Ile Lys Trp  Val Cys Gln
    1055                1060                1065

gac gtg  tcc ccg ggc gcc ccc  aag gag ctc aga aac  tac ctg gag      3249
Asp Val  Ser Pro Gly Ala Pro  Lys Glu Leu Arg Asn  Tyr Leu Glu
    1070                1075                1080

aaa ttc  aag gac ccg gcc tag gcccccgcgg ggcctggctc ctcgctcggc      3300
Lys Phe  Lys Asp Pro Ala
    1085

tccagagtgg gctggccggg gcgtcggagg gtctggccga gcgggacgca ccggggccgg   3360

cggaccgcgg aggcctccga gccgggaagg gctgtgtgcc tcttttgcag cagcgggttt   3420

agcagccggt gacggtggag ttcccagtca gcggagcaaa ctccggcctg caccgtcgga   3480

aagtgagtct atgagtcaaa atagaacaga caagctacca aaaatta                 3527


<210> SEQ ID NO 26
<211> LENGTH: 1089
<212> TYPE: PRT
<213> ORGANISM: Canis familiaris

<400> SEQUENCE: 26

Met Ala Thr Met Leu Phe Ala Lys Leu Asn Phe Arg Asn Leu Ile Glu
1               5                   10                  15

Gly Arg Gly Ile Thr Asp Asn Val Pro Arg Phe Ser Ser Leu Pro Pro
            20                  25                  30
```

-continued

```
Phe Leu Pro Val Ser Tyr His Ile Leu Gly Ala Glu Thr Ser Phe Phe
        35                  40                  45

Leu Lys Glu Ala Asn Gln Asp Val Leu Arg Asn Ser Ser Leu His Thr
    50                  55                  60

Arg Val Glu Ser Phe Phe Thr Tyr Lys Ala Asn Arg Pro Pro Val Leu
65                  70                  75                  80

Asn Ala Ser Tyr Gly Pro Phe Ser Ile Glu Gln Val Val Pro Gln Asp
                85                  90                  95

Leu Leu Leu Pro Ser Ser Pro Phe Gly Ala Thr Ser Lys Leu Ser Leu
            100                 105                 110

Asn Trp Arg Leu Arg Ala His Ile Leu Arg Asp Lys Val Tyr Leu Ser
        115                 120                 125

Arg Pro Arg Val Gln Val Leu Phe His Leu Leu Gly Arg Asp Trp Ala
    130                 135                 140

Ala Gln Ser Pro Gly Glu Arg Leu Pro Cys Leu Arg Leu Phe Ala Phe
145                 150                 155                 160

Arg Glu Thr Arg Glu Val Arg Ala Gly Cys Arg Leu Gln Gly Ala Leu
                165                 170                 175

Gly Leu Cys Val Ala Glu Leu Glu Leu Leu Ala Ala Trp Phe Gly Pro
            180                 185                 190

Pro Thr Val Val Ala Gly Arg Lys Arg Ala Pro Gly Pro Pro Glu Gly
        195                 200                 205

Ser Pro Val Glu Leu Tyr Tyr Ser Val Gln Pro Gly Asp Ala Arg Gly
    210                 215                 220

Asp Cys Ala Gly Gly Gly Gly Asp Val Arg Lys Gly Asn Ala Ile Arg
225                 230                 235                 240

Pro Gly Lys Asp Gly Leu Asp Glu Ala Val Pro His Leu Gln Arg Ile
                245                 250                 255

Gly Ala Val Ser Leu Tyr Arg Ala Gln Asp Ser Thr Gln Leu Ser Glu
            260                 265                 270

Leu Arg Leu Asp Ser Asn Val Val Ile Trp Leu Pro Ser Arg Pro Val
        275                 280                 285

Lys Gln Gly Asp Val Val Thr Ala Tyr Val Thr Ile Ala Ser Asn Ser
    290                 295                 300

Thr Val Asp Leu Phe Ile Leu Arg Ala Lys Val Lys Lys Gly Val Asn
305                 310                 315                 320

Ile Leu Gly Thr Gln Thr Ser Glu Pro Arg Gln Trp Asp Val Lys Gln
                325                 330                 335

Glu Met Gly Asn Gly Gly Lys His Ala Thr Thr Thr Val Leu Cys Gln
            340                 345                 350

Arg Leu Gly Ser Ser Thr Arg Asn Arg Ser Ser Ser Leu Phe Ser Glu
        355                 360                 365

Val Met Gln Met Asn Phe Glu Ile Ala Ser Phe Ser Ser Leu Ser Gly
    370                 375                 380

Thr Gln Pro Ile Ala Trp Gln Val Glu Tyr Pro Arg Arg Ala Thr Thr
385                 390                 395                 400

Asp Thr Ala Val Ser Glu Ile Phe Ile Ser Gln Lys Asp Leu Ala Gly
                405                 410                 415

Ile Val Pro Leu Ala Thr Asp Thr Glu Ile Leu Asn Thr Ala Ile Leu
            420                 425                 430

Thr Gly Lys Thr Val Val Leu Pro Ile Lys Val Val Ser Val Glu Glu
        435                 440                 445

Asn Ser Ala Val Met Asp Ile Ser Glu Ser Val Glu Cys Lys Ser Thr
    450                 455                 460
```

```
Asp Glu Asp Val Ile Lys Val Ser Glu Arg Cys Asp Tyr Val Phe Val
465                 470                 475                 480

Asn Gly Lys Glu Met Lys Gly Lys Val Asp Ala Val Val Asn Phe Thr
                485                 490                 495

Tyr Gln His Leu Ser Ala Ser Leu His Ile Thr Val Trp Val Pro Arg
            500                 505                 510

Leu Pro Leu Gln Ile Glu Val Ser Asp Thr Glu Leu Ser Gln Ile Lys
        515                 520                 525

Gly Trp Arg Val Pro Ile Val Ser Ser Lys Arg Pro Thr Arg Glu Ser
    530                 535                 540

Glu Asp Glu Asp Glu Glu Glu Arg Arg Gly Arg Gly Cys Ala Leu Gln
545                 550                 555                 560

Tyr Gln His Ala Thr Val Arg Val Leu Thr Gln Phe Val Ser Glu Gly
                565                 570                 575

Ala Gly Pro Trp Gly Gln Pro Ser His Leu Leu Ser Pro Asp Trp Gln
            580                 585                 590

Val Asp Ile Thr His Leu Val Ala Asp Phe Met Lys Leu Glu Glu Pro
        595                 600                 605

His Val Ala Thr Leu Gln Asp Ser Arg Ile Leu Val Gly Arg Glu Val
    610                 615                 620

Gly Met Thr Thr Ile Gln Val Leu Ser Pro Leu Ser Asp Ser Ile Leu
625                 630                 635                 640

Ala Glu Lys Thr Val Thr Val Leu Asp Asp Lys Val Ser Val Thr Asp
                645                 650                 655

Leu Ala Ile Gln Leu Val Ala Gly Leu Ser Val Thr Leu His Pro Ser
            660                 665                 670

Thr Glu Asn Ser Lys Ala Ile Thr Ala Val Ala Thr Ala Glu Glu Leu
        675                 680                 685

Leu Arg Thr Pro Lys Gln Glu Ala Val Val Ser Thr Trp Leu Gln Leu
    690                 695                 700

Ser Asp Gly Ser Ala Thr Pro Leu Asp Ile Tyr Asp Thr Lys Asp Phe
705                 710                 715                 720

Thr Leu Thr Ala Thr Ser Leu Asn Glu Ala Val Val Ser Thr Pro Gln
                725                 730                 735

Ala Arg Ser Pro Arg Trp Pro Val Val Met Ala Glu Gly Glu Gly Gln
            740                 745                 750

Gly Pro Leu Val Arg Val Asp Met Ser Ile Ala Glu Ala Cys Gln Lys
        755                 760                 765

Ser Lys Arg Lys Ser Val Leu Ala Val Gly Val Gly Ser Val Arg Val
    770                 775                 780

Lys Phe Gly Gln Gly Asn Ala Asp Ser Ser Arg Gly Ala Asp Gly Asp
785                 790                 795                 800

Ser Gly Glu Ile Lys Asn His Ala Ser Asp Arg Arg Gln Lys Ser Gln
                805                 810                 815

Glu Pro Glu Gly His Leu Gln Gly Ser Pro Gly Glu Arg Glu Asp Gly
            820                 825                 830

Ala Leu Gln Arg Gly Asp Ser Thr Ala Arg Pro Leu Leu Asp Asn Arg
        835                 840                 845

Val Val Lys Ser Gly Arg Pro Asp Ala Gly Arg Pro Ser Gly Gly Asp
    850                 855                 860

Gln Leu Gln Asn Ile Pro Leu Asp Phe Ala Asn Phe Pro Ala Gln Val
865                 870                 875                 880

Glu Leu Pro Arg Ala Gly Gly Gly Leu Gly Ala Ser Asp Leu Val Gln
```

```
                885                 890                 895

Thr Pro Arg Gly Leu Ser Asp Leu Glu Ile Gly Met Tyr Ala Leu Leu
            900                 905                 910

Gly Val Phe Cys Leu Ala Ile Leu Val Phe Leu Ile Asn Cys Ala Thr
        915                 920                 925

Phe Ala Leu Arg Tyr Arg His Lys Gln Val Pro Leu Glu Gly Gln Ala
    930                 935                 940

Ser Val Thr His Ser His Asp Trp Val Trp Leu Gly Asn Glu Ala Glu
945                 950                 955                 960

Leu Leu Glu His Ala Gly Glu Gly Ser Pro Pro Gln Asp Glu His Thr
                965                 970                 975

Thr Val Leu Asp Arg Gly Pro Gly Gly Ser Asp Asp Gly Ser Arg Leu
            980                 985                 990

Leu Leu Asn Gly Gly Ala Arg Gln  His Val Gln Gly Gln  Val His Arg
        995                 1000                1005

Ala Gly  Ser Ala Gly Arg Pro  Ala Arg Asp Pro Lys  Leu Glu Pro
    1010                 1015                1020

Leu His  Ser Pro Thr Ser Lys  Arg Lys Lys Val Lys  Phe Thr Thr
    1025                 1030                1035

Phe Thr  Thr Ile Pro Pro Asp  Asp Gly Cys Pro Thr  Val Asn Ser
    1040                 1045                1050

Ile Leu  Gly Gly Gly Gly Gly  Glu Asp Ile Lys Trp  Val Cys Gln
    1055                 1060                1065

Asp Val  Ser Pro Gly Ala Pro  Lys Glu Leu Arg Asn  Tyr Leu Glu
    1070                 1075                1080

Lys Phe  Lys Asp Pro Ala
    1085


<210> SEQ ID NO 27
<211> LENGTH: 3144
<212> TYPE: DNA
<213> ORGANISM: Pan troglodytes
<220> FEATURE:
<221> NAME/KEY: CDS
<222> LOCATION: (1)..(3144)
<223> OTHER INFORMATION:

<400> SEQUENCE: 27

atg cag ctc ctg gac agc agc agt acc ggt acc cag tgg cag ata agg       48
Met Gln Leu Leu Asp Ser Ser Ser Thr Gly Thr Gln Trp Gln Ile Arg
1               5                   10                  15

aga atc agg agc agc agt tta ttc aat gag gtt gtg cag atg aac ttt       96
Arg Ile Arg Ser Ser Ser Leu Phe Asn Glu Val Val Gln Met Asn Phe
            20                  25                  30

gaa ata gcc agt ttc agc agc ctt tca ggg act cag ccc atc aca tgg      144
Glu Ile Ala Ser Phe Ser Ser Leu Ser Gly Thr Gln Pro Ile Thr Trp
        35                  40                  45

cag gtg gag tac cca cgg aag ggg acc aca gac atc gcc gtg tcc gag      192
Gln Val Glu Tyr Pro Arg Lys Gly Thr Thr Asp Ile Ala Val Ser Glu
    50                  55                  60

atc ttt gtc agc cag aag gac ctg gtg ggc atc gtt ccc ttg gct atg      240
Ile Phe Val Ser Gln Lys Asp Leu Val Gly Ile Val Pro Leu Ala Met
65                  70                  75                  80

cac cgg cat ccc agg cat tat ctt gtg aac att aat cct gtg acc atc      288
His Arg His Pro Arg His Tyr Leu Val Asn Ile Asn Pro Val Thr Ile
                85                  90                  95

att cgg aaa gcc cct gtg agc cct ggg tcc cct gtc ctg ctg cct tca      336
Ile Arg Lys Ala Pro Val Ser Pro Gly Ser Pro Val Leu Leu Pro Ser
            100                 105                 110
```

-continued

```
acc caa gac agc agt ctc atc tct gcc aga cac gat gct atc tgt gca      384
Thr Gln Asp Ser Ser Leu Ile Ser Ala Arg His Asp Ala Ile Cys Ala
        115                 120                 125

gtc agc ctc tcc atc gcc cat gct ccc tct ggg cgg tca tgc cca gag      432
Val Ser Leu Ser Ile Ala His Ala Pro Ser Gly Arg Ser Cys Pro Glu
    130                 135                 140

gct cgg gaa ctt ggc tgt gtc cac tcc cta gtc ccc acc ttc cag atc      480
Ala Arg Glu Leu Gly Cys Val His Ser Leu Val Pro Thr Phe Gln Ile
145                 150                 155                 160

act gct caa tat cta gtc gat ggc caa aac ata tct aca ttg aat aaa      528
Thr Ala Gln Tyr Leu Val Asp Gly Gln Asn Ile Ser Thr Leu Asn Lys
                165                 170                 175

tcc atg tcc agc atc tcc ctc aat aac act aag aca aca act gca gac      576
Ser Met Ser Ser Ile Ser Leu Asn Asn Thr Lys Thr Thr Thr Ala Asp
            180                 185                 190

atg tcc tcc cag tgt ccc tgt gag atc tgg agt gcg ttg ggt tgt gtc      624
Met Ser Ser Gln Cys Pro Cys Glu Ile Trp Ser Ala Leu Gly Cys Val
        195                 200                 205

cct caa aga gat ccc atc agt gtt gga tgt gag tgt gtt tac tgg agt      672
Pro Gln Arg Asp Pro Ile Ser Val Gly Cys Glu Cys Val Tyr Trp Ser
    210                 215                 220

cca tca gcg ctg gat gtg agt gtg ttt act gga gtc cat cag cgt tgg      720
Pro Ser Ala Leu Asp Val Ser Val Phe Thr Gly Val His Gln Arg Trp
225                 230                 235                 240

atg agt gtg ttt act gga gtc cat cag cgt tgg atg agt gtg ttt act      768
Met Ser Val Phe Thr Gly Val His Gln Arg Trp Met Ser Val Phe Thr
                245                 250                 255

gga gtc cat cag cgc tgg atg tac ccc aag aag acc cat gaa cac ctc      816
Gly Val His Gln Arg Trp Met Tyr Pro Lys Lys Thr His Glu His Leu
            260                 265                 270

ata gtc tct tca cat ctg cag ttg tct gca gcc caa gca cag ggc cct      864
Ile Val Ser Ser His Leu Gln Leu Ser Ala Ala Gln Ala Gln Gly Pro
        275                 280                 285

ggc ctc atc tcc aag gct ggc tct tca gac aac gac tcc atc cag ggt      912
Gly Leu Ile Ser Lys Ala Gly Ser Ser Asp Asn Asp Ser Ile Gln Gly
    290                 295                 300

cct gat gct cgg aac aca gag ttc tcg gag cca caa gga gca gga ttc      960
Pro Asp Ala Arg Asn Thr Glu Phe Ser Glu Pro Gln Gly Ala Gly Phe
305                 310                 315                 320

aca gaa gac aga gga caa tgc ctc cac gtg cgt ata agt gga gcg tgc     1008
Thr Glu Asp Arg Gly Gln Cys Leu His Val Arg Ile Ser Gly Ala Cys
                325                 330                 335

tcc ggg aaa cag ggg ccc agg aca gga ggc ctg cct ggt ggc cag cat     1056
Ser Gly Lys Gln Gly Pro Arg Thr Gly Gly Leu Pro Gly Gly Gln His
            340                 345                 350

ggc cac act tcc cag ccc ctg acc cgg gac act gaa att ctg aac acc     1104
Gly His Thr Ser Gln Pro Leu Thr Arg Asp Thr Glu Ile Leu Asn Thr
        355                 360                 365

gcc ata ctc aca gga aag aca gtt gcc atg cct atc aag gtg gtc tct     1152
Ala Ile Leu Thr Gly Lys Thr Val Ala Met Pro Ile Lys Val Val Ser
    370                 375                 380

gtg gag gag aac agt gcc gtg atg gac atc tca gag tcg gtg gag tgc     1200
Val Glu Glu Asn Ser Ala Val Met Asp Ile Ser Glu Ser Val Glu Cys
385                 390                 395                 400

aag tcc aca gac gag gac gtt atc aaa gtg tct gac cgc tgt gac tac     1248
Lys Ser Thr Asp Glu Asp Val Ile Lys Val Ser Asp Arg Cys Asp Tyr
                405                 410                 415

atc ttt gtc aat ggc aaa gag atc aaa gga aag atg gat gcg gtg gtg     1296
Ile Phe Val Asn Gly Lys Glu Ile Lys Gly Lys Met Asp Ala Val Val
            420                 425                 430
```

-continued

```
aac ttc aca tac cag tac ctg agc gcc ccc ctg cgt gtc acc gtg tgg      1344
Asn Phe Thr Tyr Gln Tyr Leu Ser Ala Pro Leu Arg Val Thr Val Trp
        435                 440                 445

gtg ccc cgg ctg ccc ctg cag atc gag gtc tct gac acg gag ctc agc      1392
Val Pro Arg Leu Pro Leu Gln Ile Glu Val Ser Asp Thr Glu Leu Ser
    450                 455                 460

cag ata aag ggc tgg agg gtc ccc att gtg acc aat aag agg cct act      1440
Gln Ile Lys Gly Trp Arg Val Pro Ile Val Thr Asn Lys Arg Pro Thr
465                 470                 475                 480

cgt gag agc gag gat gag gac gag gag gag cgg cgg ggc cgg ggc tgc      1488
Arg Glu Ser Glu Asp Glu Asp Glu Glu Glu Arg Arg Gly Arg Gly Cys
                485                 490                 495

gcg ctg cag tac cag cac gcc acc gtg cgg gtc ctc acc cag ttt gtg      1536
Ala Leu Gln Tyr Gln His Ala Thr Val Arg Val Leu Thr Gln Phe Val
            500                 505                 510

tcc gag ggc gcc ggt ccg tgg ggc cag ccg aac tac ctg ctt agt cct      1584
Ser Glu Gly Ala Gly Pro Trp Gly Gln Pro Asn Tyr Leu Leu Ser Pro
        515                 520                 525

aac tgg cag ttc gac atc act cac ctg gtg gca gac ttc atg aag ctg      1632
Asn Trp Gln Phe Asp Ile Thr His Leu Val Ala Asp Phe Met Lys Leu
    530                 535                 540

gag gaa cct cac gtg gcc acc ctc cag gac agc cgg gtc ctg gtt ggg      1680
Glu Glu Pro His Val Ala Thr Leu Gln Asp Ser Arg Val Leu Val Gly
545                 550                 555                 560

cga gag gtt ggg atg acg acc atc cag gtg ttg tct cca ctg tct gac      1728
Arg Glu Val Gly Met Thr Thr Ile Gln Val Leu Ser Pro Leu Ser Asp
                565                 570                 575

tcc atc ctg gca gag aag aca ata acc gtg cta gat gac aaa gtg tcg      1776
Ser Ile Leu Ala Glu Lys Thr Ile Thr Val Leu Asp Asp Lys Val Ser
            580                 585                 590

gtg aca gac ttg gcc atc cag ctc gtg gct ggg ctg tct gtt gcc ctt      1824
Val Thr Asp Leu Ala Ile Gln Leu Val Ala Gly Leu Ser Val Ala Leu
        595                 600                 605

tac ccc aac gca gaa aac agc aag gcc ata aca gct gtg gtc aca gct      1872
Tyr Pro Asn Ala Glu Asn Ser Lys Ala Ile Thr Ala Val Val Thr Ala
    610                 615                 620

gag gag gtg ctg cgg acc ccc aaa cag gca aag ctt aat tca ctg ggg      1920
Glu Glu Val Leu Arg Thr Pro Lys Gln Ala Lys Leu Asn Ser Leu Gly
625                 630                 635                 640

gca gtg cag gca gaa gag ggg agg ttc ctt tct gat gtc att ggt tct      1968
Ala Val Gln Ala Glu Glu Gly Arg Phe Leu Ser Asp Val Ile Gly Ser
                645                 650                 655

gac agt gtt tcc tgc cca tca acc ttt gtc atc agg ctg gat aca gac      2016
Asp Ser Val Ser Cys Pro Ser Thr Phe Val Ile Arg Leu Asp Thr Asp
            660                 665                 670

aac agc tca gcc acc tct cag gac gag gct gtc gtg tcc gtc ccc cag      2064
Asn Ser Ser Ala Thr Ser Gln Asp Glu Ala Val Val Ser Val Pro Gln
        675                 680                 685

ccc cgc tct ccc agg tgg ccc gtt gtg gtg gcc gaa ggg gaa ggc cag      2112
Pro Arg Ser Pro Arg Trp Pro Val Val Val Ala Glu Gly Glu Gly Gln
    690                 695                 700

ggc cca ctg atc cga gtg gac atg acg atc gcc gag gcc tgc cag aaa      2160
Gly Pro Leu Ile Arg Val Asp Met Thr Ile Ala Glu Ala Cys Gln Lys
705                 710                 715                 720

tcc aaa cgc aag agc atc ctg gct gtg ggc gtc ggc aac gtc agg gtc      2208
Ser Lys Arg Lys Ser Ile Leu Ala Val Gly Val Gly Asn Val Arg Val
                725                 730                 735

aag ttc gga cag aac gat gct gac tcc agc ccc ggc agg gac tat gag      2256
Lys Phe Gly Gln Asn Asp Ala Asp Ser Ser Pro Gly Arg Asp Tyr Glu
            740                 745                 750
```

```
gaa gat gag atc aag aac cac gcc agc gac cgc cgg cag aag ggc cag     2304
Glu Asp Glu Ile Lys Asn His Ala Ser Asp Arg Arg Gln Lys Gly Gln
        755                 760                 765

cac cat gag cgc aca ggc cag gat ggg cac ctc tat ggc agc tct ccc     2352
His His Glu Arg Thr Gly Gln Asp Gly His Leu Tyr Gly Ser Ser Pro
    770                 775                 780

gtg gag cgt gag gaa ggg gct ctc cga aga gcc act acc acg gcc agg     2400
Val Glu Arg Glu Glu Gly Ala Leu Arg Arg Ala Thr Thr Thr Ala Arg
785                 790                 795                 800

tcc ctg ctg gac aac aaa gtg gtg aag aac agt cgg gca gac ggg ggc     2448
Ser Leu Leu Asp Asn Lys Val Val Lys Asn Ser Arg Ala Asp Gly Gly
                805                 810                 815

agg ctg gca gga gag ggg cag ctg cag aac atc ccc att gac ttc acc     2496
Arg Leu Ala Gly Glu Gly Gln Leu Gln Asn Ile Pro Ile Asp Phe Thr
            820                 825                 830

aac ttc ccg gcc cac gtg gac ctc ccc aag gcc ggg agt ggg ctg gag     2544
Asn Phe Pro Ala His Val Asp Leu Pro Lys Ala Gly Ser Gly Leu Glu
        835                 840                 845

gaa aac gac ctg gtg cag act ccg cgg ggc ctg agt gat ctg gag ata     2592
Glu Asn Asp Leu Val Gln Thr Pro Arg Gly Leu Ser Asp Leu Glu Ile
    850                 855                 860

ggg atg tac gcc ctc ctg ggg gtg ttc tgc ctg gcc atc ctc gtc ttc     2640
Gly Met Tyr Ala Leu Leu Gly Val Phe Cys Leu Ala Ile Leu Val Phe
865                 870                 875                 880

ctg atc aac tgc gcc acc ttt gcc ctg aag tac agg cac aag caa gtg     2688
Leu Ile Asn Cys Ala Thr Phe Ala Leu Lys Tyr Arg His Lys Gln Val
                885                 890                 895

ccc ctg gaa ggt cag gcc tcc atg acc cac tct cac gac tgg gtg tgg     2736
Pro Leu Glu Gly Gln Ala Ser Met Thr His Ser His Asp Trp Val Trp
            900                 905                 910

ctt ggc aat gag gcc gaa ctc ctg gag agc atg ggg gac gcg cca ccg     2784
Leu Gly Asn Glu Ala Glu Leu Leu Glu Ser Met Gly Asp Ala Pro Pro
        915                 920                 925

ccc cag gac gag cac acc acc atc ata gac cgc gga ccg ggg gcc tgc     2832
Pro Gln Asp Glu His Thr Thr Ile Ile Asp Arg Gly Pro Gly Ala Cys
    930                 935                 940

gag gag agc aac cat ctc ctg ctc aat ggt ggc tcc cac aag cac gtg     2880
Glu Glu Ser Asn His Leu Leu Leu Asn Gly Gly Ser His Lys His Val
945                 950                 955                 960

cag agc cag att cac agg tca gcc gac tcc ggg ggg cgg cag ggc aga     2928
Gln Ser Gln Ile His Arg Ser Ala Asp Ser Gly Gly Arg Gln Gly Arg
                965                 970                 975

gaa cag aag cag gac ccc ctg cac tcg ccc acc tcc aag agg aag aag     2976
Glu Gln Lys Gln Asp Pro Leu His Ser Pro Thr Ser Lys Arg Lys Lys
            980                 985                 990

gtg aaa ttc acc acc ttt acc acc  atc ccc ccg gac gac  agc tgc ccc   3024
Val Lys Phe Thr Thr Phe Thr Thr  Ile Pro Pro Asp Asp  Ser Cys Pro
        995                 1000                 1005

aca gtg  aac tcc atc gtc agc  agc aat gat gag gac  atc aaa tgg      3069
Thr Val  Asn Ser Ile Val Ser  Ser Asn Asp Glu Asp  Ile Lys Trp
    1010                 1015                 1020

gtg tgt  caa gac atg gct gtg  ggt gcc ccc aag gaa  ctt aga aac      3114
Val Cys  Gln Asp Met Ala Val  Gly Ala Pro Lys Glu  Leu Arg Asn
    1025                 1030                 1035

tat ctg  gag aaa ctc aaa gat  aag gct tag                          3144
Tyr Leu  Glu Lys Leu Lys Asp  Lys Ala
    1040                 1045
```

<210> SEQ ID NO 28
<211> LENGTH: 1047

<212> TYPE: PRT
<213> ORGANISM: Pan troglodytes

<400> SEQUENCE: 28

```
Met Gln Leu Leu Asp Ser Ser Ser Thr Gly Thr Gln Trp Gln Ile Arg
1               5                   10                  15

Arg Ile Arg Ser Ser Ser Leu Phe Asn Glu Val Val Gln Met Asn Phe
            20                  25                  30

Glu Ile Ala Ser Phe Ser Ser Leu Ser Gly Thr Gln Pro Ile Thr Trp
        35                  40                  45

Gln Val Glu Tyr Pro Arg Lys Gly Thr Thr Asp Ile Ala Val Ser Glu
    50                  55                  60

Ile Phe Val Ser Gln Lys Asp Leu Val Gly Ile Val Pro Leu Ala Met
65                  70                  75                  80

His Arg His Pro Arg His Tyr Leu Val Asn Ile Asn Pro Val Thr Ile
                85                  90                  95

Ile Arg Lys Ala Pro Val Ser Pro Gly Ser Pro Val Leu Leu Pro Ser
            100                 105                 110

Thr Gln Asp Ser Ser Leu Ile Ser Ala Arg His Asp Ala Ile Cys Ala
        115                 120                 125

Val Ser Leu Ser Ile Ala His Ala Pro Ser Gly Arg Ser Cys Pro Glu
    130                 135                 140

Ala Arg Glu Leu Gly Cys Val His Ser Leu Val Pro Thr Phe Gln Ile
145                 150                 155                 160

Thr Ala Gln Tyr Leu Val Asp Gly Gln Asn Ile Ser Thr Leu Asn Lys
                165                 170                 175

Ser Met Ser Ser Ile Ser Leu Asn Asn Thr Lys Thr Thr Thr Ala Asp
            180                 185                 190

Met Ser Ser Gln Cys Pro Cys Glu Ile Trp Ser Ala Leu Gly Cys Val
        195                 200                 205

Pro Gln Arg Asp Pro Ile Ser Val Gly Cys Glu Cys Val Tyr Trp Ser
    210                 215                 220

Pro Ser Ala Leu Asp Val Ser Val Phe Thr Gly Val His Gln Arg Trp
225                 230                 235                 240

Met Ser Val Phe Thr Gly Val His Gln Arg Trp Met Ser Val Phe Thr
                245                 250                 255

Gly Val His Gln Arg Trp Met Tyr Pro Lys Lys Thr His Glu His Leu
            260                 265                 270

Ile Val Ser Ser His Leu Gln Leu Ser Ala Ala Gln Ala Gln Gly Pro
        275                 280                 285

Gly Leu Ile Ser Lys Ala Gly Ser Ser Asp Asn Asp Ser Ile Gln Gly
    290                 295                 300

Pro Asp Ala Arg Asn Thr Glu Phe Ser Glu Pro Gln Gly Ala Gly Phe
305                 310                 315                 320

Thr Glu Asp Arg Gly Gln Cys Leu His Val Arg Ile Ser Gly Ala Cys
                325                 330                 335

Ser Gly Lys Gln Gly Pro Arg Thr Gly Gly Leu Pro Gly Gly Gln His
            340                 345                 350

Gly His Thr Ser Gln Pro Leu Thr Arg Asp Thr Glu Ile Leu Asn Thr
        355                 360                 365

Ala Ile Leu Thr Gly Lys Thr Val Ala Met Pro Ile Lys Val Val Ser
    370                 375                 380

Val Glu Glu Asn Ser Ala Val Met Asp Ile Ser Glu Ser Val Glu Cys
385                 390                 395                 400
```

-continued

```
Lys Ser Thr Asp Glu Asp Val Ile Lys Val Ser Asp Arg Cys Asp Tyr
                405                 410                 415

Ile Phe Val Asn Gly Lys Glu Ile Lys Gly Lys Met Asp Ala Val Val
            420                 425                 430

Asn Phe Thr Tyr Gln Tyr Leu Ser Ala Pro Leu Arg Val Thr Val Trp
        435                 440                 445

Val Pro Arg Leu Pro Leu Gln Ile Glu Val Ser Asp Thr Glu Leu Ser
    450                 455                 460

Gln Ile Lys Gly Trp Arg Val Pro Ile Val Thr Asn Lys Arg Pro Thr
465                 470                 475                 480

Arg Glu Ser Glu Asp Glu Asp Glu Glu Glu Arg Arg Gly Arg Gly Cys
                485                 490                 495

Ala Leu Gln Tyr Gln His Ala Thr Val Arg Val Leu Thr Gln Phe Val
            500                 505                 510

Ser Glu Gly Ala Gly Pro Trp Gly Gln Pro Asn Tyr Leu Leu Ser Pro
        515                 520                 525

Asn Trp Gln Phe Asp Ile Thr His Leu Val Ala Asp Phe Met Lys Leu
    530                 535                 540

Glu Glu Pro His Val Ala Thr Leu Gln Asp Ser Arg Val Leu Val Gly
545                 550                 555                 560

Arg Glu Val Gly Met Thr Thr Ile Gln Val Leu Ser Pro Leu Ser Asp
                565                 570                 575

Ser Ile Leu Ala Glu Lys Thr Ile Thr Val Leu Asp Asp Lys Val Ser
            580                 585                 590

Val Thr Asp Leu Ala Ile Gln Leu Val Ala Gly Leu Ser Val Ala Leu
        595                 600                 605

Tyr Pro Asn Ala Glu Asn Ser Lys Ala Ile Thr Ala Val Val Thr Ala
    610                 615                 620

Glu Glu Val Leu Arg Thr Pro Lys Gln Ala Lys Leu Asn Ser Leu Gly
625                 630                 635                 640

Ala Val Gln Ala Glu Glu Gly Arg Phe Leu Ser Asp Val Ile Gly Ser
                645                 650                 655

Asp Ser Val Ser Cys Pro Ser Thr Phe Val Ile Arg Leu Asp Thr Asp
            660                 665                 670

Asn Ser Ser Ala Thr Ser Gln Asp Glu Ala Val Val Ser Val Pro Gln
        675                 680                 685

Pro Arg Ser Pro Arg Trp Pro Val Val Val Ala Glu Gly Glu Gly Gln
    690                 695                 700

Gly Pro Leu Ile Arg Val Asp Met Thr Ile Ala Glu Ala Cys Gln Lys
705                 710                 715                 720

Ser Lys Arg Lys Ser Ile Leu Ala Val Gly Val Gly Asn Val Arg Val
                725                 730                 735

Lys Phe Gly Gln Asn Asp Ala Asp Ser Ser Pro Gly Arg Asp Tyr Glu
            740                 745                 750

Glu Asp Glu Ile Lys Asn His Ala Ser Asp Arg Arg Gln Lys Gly Gln
        755                 760                 765

His His Glu Arg Thr Gly Gln Asp Gly His Leu Tyr Gly Ser Ser Pro
    770                 775                 780

Val Glu Arg Glu Glu Gly Ala Leu Arg Arg Ala Thr Thr Thr Ala Arg
785                 790                 795                 800

Ser Leu Leu Asp Asn Lys Val Val Lys Asn Ser Arg Ala Asp Gly Gly
                805                 810                 815

Arg Leu Ala Gly Glu Gly Gln Leu Gln Asn Ile Pro Ile Asp Phe Thr
            820                 825                 830
```

```
Asn Phe Pro Ala His Val Asp Leu Pro Lys Ala Gly Ser Gly Leu Glu
        835                 840                 845

Glu Asn Asp Leu Val Gln Thr Pro Arg Gly Leu Ser Asp Leu Glu Ile
    850                 855                 860

Gly Met Tyr Ala Leu Leu Gly Val Phe Cys Leu Ala Ile Leu Val Phe
865                 870                 875                 880

Leu Ile Asn Cys Ala Thr Phe Ala Leu Lys Tyr Arg His Lys Gln Val
                885                 890                 895

Pro Leu Glu Gly Gln Ala Ser Met Thr His Ser His Asp Trp Val Trp
            900                 905                 910

Leu Gly Asn Glu Ala Glu Leu Leu Glu Ser Met Gly Asp Ala Pro Pro
        915                 920                 925

Pro Gln Asp Glu His Thr Thr Ile Ile Asp Arg Gly Pro Gly Ala Cys
    930                 935                 940

Glu Glu Ser Asn His Leu Leu Leu Asn Gly Gly Ser His Lys His Val
945                 950                 955                 960

Gln Ser Gln Ile His Arg Ser Ala Asp Ser Gly Gly Arg Gln Gly Arg
                965                 970                 975

Glu Gln Lys Gln Asp Pro Leu His Ser Pro Thr Ser Lys Arg Lys Lys
            980                 985                 990

Val Lys Phe Thr Thr Phe Thr Thr  Ile Pro Pro Asp Asp  Ser Cys Pro
        995                 1000                 1005

Thr Val  Asn Ser Ile Val Ser  Ser Asn Asp Glu Asp  Ile Lys Trp
    1010                 1015                 1020

Val Cys  Gln Asp Met Ala Val  Gly Ala Pro Lys Glu  Leu Arg Asn
    1025                 1030                 1035

Tyr Leu  Glu Lys Leu Lys Asp  Lys Ala
    1040                 1045
```

<210> SEQ ID NO 29
<211> LENGTH: 26
<212> TYPE: DNA
<213> ORGANISM: Artificial
<220> FEATURE:
<223> OTHER INFORMATION: primer

<400> SEQUENCE: 29
cagctccaca acctacatca ttccgt 26

<210> SEQ ID NO 30
<211> LENGTH: 12
<212> TYPE: DNA
<213> ORGANISM: Artificial
<220> FEATURE:
<223> OTHER INFORMATION: primer

<400> SEQUENCE: 30
acggaatgat gt 12

<210> SEQ ID NO 31
<211> LENGTH: 26
<212> TYPE: DNA
<213> ORGANISM: Artificial
<220> FEATURE:
<223> OTHER INFORMATION: primer

<400> SEQUENCE: 31
tagtctacca ctgctcgact gtaacg 26

<210> SEQ ID NO 32
<211> LENGTH: 26
<212> TYPE: DNA
<213> ORGANISM: Artificial
<220> FEATURE:
<223> OTHER INFORMATION: primer

<400> SEQUENCE: 32
cagagtgaac ccagtggaca tatctg 26

<210> SEQ ID NO 33
<211> LENGTH: 26
<212> TYPE: DNA
<213> ORGANISM: Artificial
<220> FEATURE:
<223> OTHER INFORMATION: primer

<400> SEQUENCE: 33
tggttcaggt gtggttccag aaccag 26

<210> SEQ ID NO 34
<211> LENGTH: 26
<212> TYPE: DNA
<213> ORGANISM: Artificial
<220> FEATURE:
<223> OTHER INFORMATION: primer

<400> SEQUENCE: 34
gagttgtaga cgctctgttc aatggc 26

<210> SEQ ID NO 35
<211> LENGTH: 26
<212> TYPE: DNA
<213> ORGANISM: Artificial
<220> FEATURE:
<223> OTHER INFORMATION: primer

<400> SEQUENCE: 35
accaggaagg acaatgccat tcgtcc 26

<210> SEQ ID NO 36
<211> LENGTH: 26
<212> TYPE: DNA
<213> ORGANISM: Artificial
<220> FEATURE:
<223> OTHER INFORMATION: primer

<400> SEQUENCE: 36
ccttcttcac cttggctctt aggatg 26

<210> SEQ ID NO 37
<211> LENGTH: 12
<212> TYPE: DNA
<213> ORGANISM: Artificial
<220> FEATURE:
<223> OTHER INFORMATION: primer

<400> SEQUENCE: 37
catcccagtc tc 12

<210> SEQ ID NO 38
<211> LENGTH: 26
<212> TYPE: DNA
<213> ORGANISM: Artificial
<220> FEATURE:
<223> OTHER INFORMATION: primer

<400> SEQUENCE: 38
tggagaaggt tgtgcctctg gacttg 26

<210> SEQ ID NO 39
<211> LENGTH: 26
<212> TYPE: DNA
<213> ORGANISM: Artificial
<220> FEATURE:
<223> OTHER INFORMATION: primer

<400> SEQUENCE: 39
ctggttggct tccttgagga agaagg 26

<210> SEQ ID NO 40
<211> LENGTH: 26
<212> TYPE: DNA
<213> ORGANISM: Artificial
<220> FEATURE:
<223> OTHER INFORMATION: primer

<400> SEQUENCE: 40
tcctgcggga caaagtctac ctgagc 26

<210> SEQ ID NO 41
<211> LENGTH: 26
<212> TYPE: DNA
<213> ORGANISM: Artificial
<220> FEATURE:
<223> OTHER INFORMATION: primer

<400> SEQUENCE: 41
ctgaggatgt ggtagctcac aggtag 26

<210> SEQ ID NO 42
<211> LENGTH: 39
<212> TYPE: DNA
<213> ORGANISM: Artificial
<220> FEATURE:
<223> OTHER INFORMATION: primer

<400> SEQUENCE: 42
gaggtcgacg ccaccatgcg ctccgagggt gcggccccc 39

<210> SEQ ID NO 43
<211> LENGTH: 26
<212> TYPE: DNA
<213> ORGANISM: Artificial
<220> FEATURE:
<223> OTHER INFORMATION: primer

<400> SEQUENCE: 43
gggtccatag ctggcattga gcactg 26

<210> SEQ ID NO 44
<211> LENGTH: 26
<212> TYPE: DNA
<213> ORGANISM: Artificial
<220> FEATURE:
<223> OTHER INFORMATION: primer

<400> SEQUENCE: 44
ctacctgtga gctaccacat cctcag 26

<210> SEQ ID NO 45
<211> LENGTH: 26
<212> TYPE: DNA
<213> ORGANISM: Artificial

<220> FEATURE:
<223> OTHER INFORMATION: primer

<400> SEQUENCE: 45
ttctctgcca ggatggagtc agacag 26

<210> SEQ ID NO 46
<211> LENGTH: 26
<212> TYPE: DNA
<213> ORGANISM: Artificial
<220> FEATURE:
<223> OTHER INFORMATION: primer

<400> SEQUENCE: 46
actggcagtt cgacatcact cacctg 26

<210> SEQ ID NO 47
<211> LENGTH: 35
<212> TYPE: DNA
<213> ORGANISM: Artificial
<220> FEATURE:
<223> OTHER INFORMATION: primer

<400> SEQUENCE: 47
gaggaattcc agtacaagga aggcatctgg gcagg 35

<210> SEQ ID NO 48
<211> LENGTH: 26
<212> TYPE: DNA
<213> ORGANISM: Artificial
<220> FEATURE:
<223> OTHER INFORMATION: primer

<400> SEQUENCE: 48
agctgagcca ccttctcagt ccagac 26

<210> SEQ ID NO 49
<211> LENGTH: 26
<212> TYPE: DNA
<213> ORGANISM: Artificial
<220> FEATURE:
<223> OTHER INFORMATION: primer

<400> SEQUENCE: 49
ccacgtccag gtcttgacaa acccac 26

<210> SEQ ID NO 50
<211> LENGTH: 26
<212> TYPE: DNA
<213> ORGANISM: Artificial
<220> FEATURE:
<223> OTHER INFORMATION: primer

<400> SEQUENCE: 50
gacagtgaac ctttggtcac tgatgg 26

<210> SEQ ID NO 51
<211> LENGTH: 26
<212> TYPE: DNA
<213> ORGANISM: Artificial
<220> FEATURE:
<223> OTHER INFORMATION: primer

<400> SEQUENCE: 51
gccttcctgt cctgggatca gcttgg 26

```
<210> SEQ ID NO 52
<211> LENGTH: 26
<212> TYPE: DNA
<213> ORGANISM: Artificial
<220> FEATURE:
<223> OTHER INFORMATION: primer

<400> SEQUENCE: 52

tctgaggttg ccaggaagca gtctcc                                          26
```

DOPAMINERGIC NEURON PROGENITOR CELL MARKER 187A5

CROSS REFERENCE TO RELATED APPLICATIONS

This application is a U.S. National Phase of PCT/JP2007/058009, filed Apr. 11, 2007, which claims priority to Japanese Patent Application No. 2006-108786, filed Apr. 11, 2006. The contents of all of the aforementioned applications are herein incorporated by reference in their entirety.

TECHNICAL FIELD

The present invention relates to a 187A5 gene, which is a dopaminergic neuron progenitor cell marker. More particularly, the present invention relates to a means for detecting a dopaminergic neuron progenitor cell, a method for detecting the cell, and a kit for detecting the cell.

BACKGROUND ART

The dopamine system is a very important system involved in movement control, hormone secretion control, affectivity control, and so forth, which are important in the mammalian brain. Therefore, abnormalities in dopaminergic neurotransmission cause various disorders of the neural system. For example, the Parkinson's disease is a neurodegenerative disease of the extrapyramidal system which is caused by specific degeneration of dopaminergic neurons in the mesencephalon substantia nigra (HARRISON'S PRINCIPLES OF INTERNAL MEDICINE Vol. 2 $23^{rd}$ ed., Isselbacher et al. edited by McGraw-Hill Inc., NY (1994) pp. 2275-7).

As a method for treating the Parkinson's disease, a method of orally administering L-DOPA (3,4-dihydroxy-phenylalanine) has been mainly adopted for compensating the decrease in the amount of the produced dopamine, but it is known that the duration of the effect is not good.

Accordingly, as a method for compensating the loss of dopaminergic neurons, recently, there has been attempted a therapeutic method of transplanting a mesencephalon ventral region of a 6-9 week aborted fetus containing dopaminergic neuron precursors (U.S. Pat. No. 5,690,927; Spencer et al. (1992) N. Engl. J. Med. 327:1541-8; Freed et al. (1992) N. Engl. J. Med. 327:1549-55; Widner et al. (1992) N. Engl. J. Med. 327:1556-63; Kordower et al. (1995) N. Engl. J. Med. 332:1118-24; Defer et al. (1996) Brain 119:41-50; and Lopez-Lozano et al. (1997) Transp. Proc. 29:977-80). However, at the present time, in addition to cell supply and ethical issues (Rosenstain (1995) Exp. Neurol. 33:106; Turner et al. (1993) Neurosurg. 33:1031-7), various other problems have been indicated, for example, risk of infectious contamination, immunologic transplant rejection (Lopez-Lozano et al. (1997) Transp. Proc. 29:977-80 and Widner and Brudin (1988) Brain Res. Rev. 13:287-324), low survival rate due to the fetus tissue's mainly dependence on lipid metabolism rather than glycolysis (Rosenstein (1995) Exp. Neurol. 33:106), and so forth.

As a method for solving the problem of the ethical issues or supply shortage, for example, a method by using a cortex, a striatum, and mesencephalon cells, derived from a pig, and so forth have been proposed (for example, Japanese Patent Laid-Open Publication No. 10-508487, No. 10-508488, and No. 10-509034). However, in this method, a complex procedure for modifying an antigen on the cell surface (MHC class I antigen) is required to suppress rejection. As a method for solving the transplant rejection, for example, a method involving local immunosuppression by simultaneously transplanting Sertoli cells has been proposed (Japanese Patent Laid-Open Publication No. 11-509170 and No. 11-501818; and Selawly and Cameron (1993) Cell Transplant 2:123-9). It is possible that transplant cells are obtained from a relative whose MHC matches, bone marrow of another person, a bone marrow bank, a cord blood bank, and so forth. However, if patient's own cells can be used, the problems of rejection can be solved without extra procedures and trouble.

Accordingly, it has been expected that, instead of cells derived from an aborted fetus, a differentiation system of dopaminergic neurons in vitro from non-neural cells such as embryo-stem (ES) cell and bone marrow stromal cells are utilized as a transplant material. Actually, it is confirmed that a dopaminergic neuron derived from ES cell is functional for transplantation into lesion striatum of a rat Parkinson's disease model (Kim et al. (2002) Nature 418:50-56). It is thought that in the future, importance of regenerative medicine from ES cells or the patient's own neural stem cells will increase.

On the other hand, in the treatment of damage of neural tissue, restructuring of brain function is required, and for forming appropriate linkage with surrounding cells (network formation), not mature cells but progenitor cells that can differentiate into neurons in vivo are required to be transplanted. However, in the transplantation of neuron progenitor cells, in addition to the above-described problem regarding supply, there is a problem that the progenitor cells can differentiate into a nonuniform cell population. For example, in the treatment of the Parkinson's disease, it is necessary that dopaminergic neurons are selectively transplanted among catecholamine-containing neurons. Before now, as transplant cells for use in the treatment of the Parkinson's disease, there has been proposed a striatum (Lindvall et al. (1989) Arch. Neurol. 46:615-31 and Widner et al. (1992) N. Engl. J. Med. 327:1556-63), an immortalized cell line derived from human embryonic nerve (Japanese Patent Laid-Open Publication No. 8-509215, No. 11-506930, and No. 2002-522070), a post-mitotic human neuron of NT2Z cells (Japanese Patent Laid-Open Publication No. 9-5050554), a neuron primordial cell (Japanese Patent Laid-Open Publication No. 11-509729), a cell transfected with an exogenous gene so as to produce catecholamine such as dopamine, a bone marrow stromal cell (Japanese Patent Laid-Open Publication No. 2002-504503 and No. 2002-513545), an ES cell in which a gene is modified (Kim et al. (2002) Nature 418:50-56), and so forth. However, none of these contain only dopaminergic neurons or cells to differentiate into dopaminergic neurons.

As a method for selectively condensing or isolating dopaminergic neurons from undifferentiated cell population, there has been proposed a method of, introducing a reporter gene expressing a fluorescent protein under control of promoter/enhancer of a gene such as tyrosine hydroxylase (TH) expressed in dopaminergic neurons into each cell of the cell population, isolating the cells emitting fluorescence, and thereby visualizing the alive dopaminergic neurons to condense, segregate or identify (Japanese Patent Laid-Open Publication No. 2002-51775). However, this method requires a complex step of introduction of an exogenous gene, and furthermore, when used in gene treatment, the existence of the reporter gene causes problem of toxicity and immunogenicity.

As described above, now, one of the largest problems in transplantation treatment for the Parkinson's disease is that the either dopaminergic neuron progenitor cells derived from the mesencephalon ventral region of aborted fetus or induced to differentiate are a mixture of various cells. It is desirable that only a desired cell species is isolated and used, considering safety in neural network formation. Furthermore, considering survival or ability for correctly forming a network in a brain in which the cells are transplanted, it can be said that it is desirable from the treatment effect that earlier proliferative progenitor cells are isolated and transplanted.

Before now, as a gene that is expressed in the dopaminergic neuron proliferative progenitor cells, Lrp4 (WO 2004/065599) has been reported. Additionally, some markers of dopaminergic neuron progenitor cells have been reported (WO 2004/038018 and WO 2004/052190).

SUMMARY OF THE INVENTION

In order to isolate a gene selectively expressed in dopaminergic neuron progenitor cells, and preferably dopaminergic neuron proliferative progenitor cells, the present inventors have separated cells positive for an Lrp4 protein, a dopaminergic neuron proliferative progenitor cell marker gene, from the mesencephalon and metencephalon ventral regions of a 13.5-day rat embryo, and have searched a gene specific for the Lrp4-positive cells in the mesencephalon by a subtraction (N-RDA) method. The present inventors have consequently found a gene selectively expressed in dopaminergic neuron proliferative progenitor cells (187A5 gene (hereinafter, occasionally referred to as "187A5")) (Example 2). The present invention is based on this finding.

An object of the present invention is to provide a means for detecting a dopaminergic neuron progenitor cell (preferably, a dopaminergic neuron proliferative progenitor cell), a method for detecting a dopaminergic neuron progenitor cell (preferably, a dopaminergic neuron proliferative progenitor cell), and a kit for detecting a dopaminergic neuron progenitor cell (preferably, a dopaminergic neuron proliferative progenitor cell).

Further, an object of the present invention is to provide a method for screening for an effective substance for inducing differentiation into a dopaminergic neuron progenitor cell (preferably, a dopaminergic neuron proliferative progenitor cell).

Furthermore, an object of the present invention is to provide a method for producing a dopaminergic neuron progenitor cell (preferably, a dopaminergic neuron proliferative progenitor cell) for use in the treatment of the Parkinson's disease.

The present invention provides a polynucleotide selected from the following (i), (ii), (iii) and (iv) (hereinafter, occasionally referred to as a "187A5 gene"):

(i) a polynucleotide comprising the nucleotide sequence of SEQ ID NO: 1;

(ii) a polynucleotide encoding a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii) a polynucleotide which hybridizes under stringent conditions to a polynucleotide consisting of the nucleotide sequence of SEQ ID NO: 1, and which encodes a protein functionally equivalent to a protein consisting of the amino acid sequence of SEQ ID NO: 2; and (iv) a polynucleotide which has 70% or more identity with a polynucleotide consisting of the nucleotide sequence of SEQ ID NO: 1, and which encodes a protein functionally equivalent to a protein consisting of the amino acid sequence of SEQ ID NO: 2.

The present invention also provides a protein selected from the following (v), (vi), (vii) and (viii) (hereinafter, occasionally referred to as a "187A5 protein"):

(v) a protein comprising the amino acid sequence of SEQ ID NO: 2;

(vi) a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;

(vii) a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and (viii) a protein which consists of an amino acid sequence having 70% or more identity with the amino acid sequence of SEQ ID NO: 2, and which is functionally equivalent to a protein consisting of the amino acid sequence of SEQ ID NO: 2.

The present invention provides a probe or primer for use in the detection or selection of a dopaminergic neuron progenitor cell (preferably, a dopaminergic neuron proliferative progenitor cell), which can hybridize to a nucleotide sequence of a 187A5 gene, or a complementary sequence thereto (hereinafter, occasionally referred to as a "probe according to the present invention" and a "primer according to the present invention", respectively).

The present invention provides an antibody for use in the detection or selection of a dopaminergic neuron progenitor cell (preferably, a dopaminergic neuron proliferative progenitor cell), which is capable of binding to a 187A5 protein (hereinafter, occasionally referred to as an "antibody according to the present invention").

The present invention provides a method for detecting or selecting a dopaminergic neuron progenitor cell (preferably, a dopaminergic neuron proliferative progenitor cell), comprising the step of detecting expression of a 187A5 gene, or a 187A5 protein (hereinafter, occasionally referred to as a "detection method according to the present invention").

The present invention provides a kit for detecting or selecting a dopaminergic neuron progenitor cell (preferably, a dopaminergic neuron proliferative progenitor cell), comprising at least a probe according to the present invention, a primer according to the present invention, a primer set according to the present invention, or an antibody according to the present invention (hereinafter, occasionally referred to as a "detection kit according to the present invention").

The present invention provides an agent for detecting or selecting a dopaminergic neuron progenitor cell (preferably, a dopaminergic neuron proliferative progenitor cell), comprising at least a probe according to the present invention, a primer according to the present invention, a primer set according to the present invention, or an antibody according to the present invention (hereinafter, occasionally referred to as an "agent for detection according to the present invention").

The present invention provides a method for screening for an effective substance for inducing differentiation into a dopaminergic neuron progenitor cell (preferably, a dopaminergic neuron proliferative progenitor cell), comprising the step of detecting expression of a 187A5 gene, or a 187A5 protein.

The present invention provides a method for producing a dopaminergic neuron progenitor cell (preferably, a dopaminergic neuron proliferative progenitor cell) for use in the treatment of the Parkinson's disease.

The probe according to the present invention, the primer according to the present invention, the primer set according to the present invention and the antibody according to the present invention can be used as markers specific for dopaminergic neuron progenitor cells, and preferably dopaminergic neuron proliferative progenitor cells in the mesencephalon. Accordingly, the present invention is extremely useful in a purity test of a transplant material and development of a method for inducing differentiation into a dopaminergic neuron progenitor cell, and preferably a dopaminergic neuron proliferative progenitor cell in vitro, or the like, and largely contributes to the promotion of practical application of regenerative medicine. Moreover, the protein according to the present invention is not merely expressed but has a region expressed in the extracellular space. Accordingly, the extracellular region of the protein according to the present invention can be used as an index for detecting live cells with reliability and for separating and obtaining the cells. Therefore, the present invention is expected to largely contribute to the practical application of regenerative medicine.

BRIEF DESCRIPTION OF THE DRAWINGS

FIG. 15 schematically shows the structure of a DNA construct that can be used for selecting dopaminergic neuron progenitor cells.

DETAILED DESCRIPTION OF THE INVENTION

Figure 1:
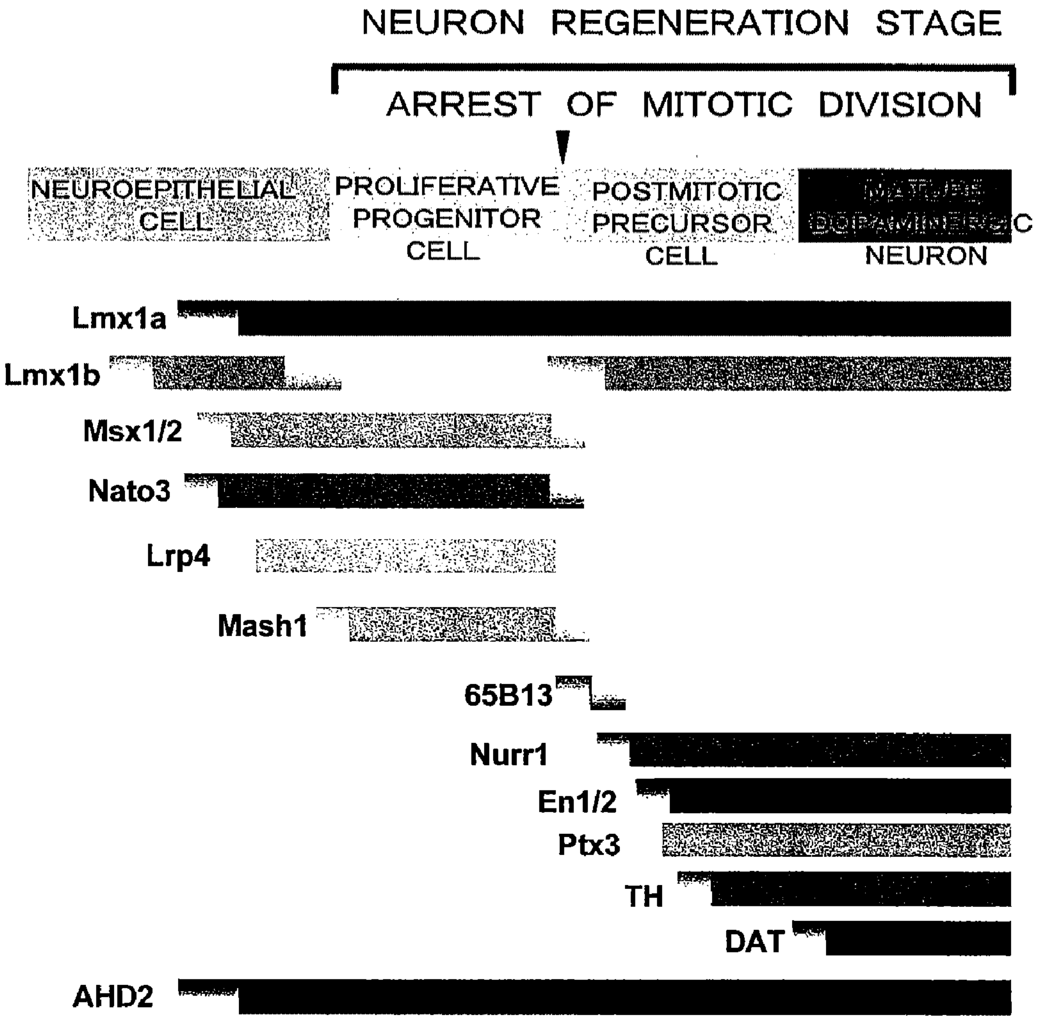
FIG. 1 shows an expression period of dopaminergic neuron-related marker genes.

Hereinafter, the present invention will be explained in detail. The following description is an example for explaining the present invention, and the present invention is not limited to the embodiments to be described. All technical terms, scientific terms and terminologies used in the present specification have the same meanings as those that are generally understood by those ordinary skilled in the art in the technical fields to which the present invention belongs, and are used merely for the purpose of explaining a specific embodiment but are not intended to make limitation. The present invention can be carried out in various embodiments as long as not departing from the spirit thereof. All the prior art documents, published publications, patent publications and other patent documents cited in the present specification are incorporated into the present specification as references, and can be used for carrying out the present invention.

[Dopaminergic Neuron Progenitor Cell]

The "dopaminergic neuron progenitor cell", which is an object to be detected or selected in the present invention, means premature dopaminergic neuron cells.

The "dopaminergic neuron proliferative progenitor cell", which is also an object to be detected or selected in the present invention, means dopaminergic neuron progenitor cells before arrest of mitotic division.

Dopaminergic neurons differentiate from neuroepithelial cells, through the differentiation stages of proliferative progenitor cells and postmitotic precursor cells, into mature dopaminergic neurons. The dopaminergic neuron progenitor cells are progenitor cells in the dopaminergic neurons. Among them, the dopaminergic neuron proliferative progenitor cell is the earliest progenitor cell in the dopaminergic neurons, and therefore, high survival rate and high ability of network formation in the brain to which the cell is transplanted can be expected. Therefore, the dopaminergic neuron progenitor cell, particularly, the dopaminergic neuron proliferative progenitor cell is useful for the transplantation treatment of diseases caused by decrease in dopamine due to degeneration of the dopaminergic neurons, such as the Parkinson's disease.

The cells selected by using the probe according to the present invention, the primer according to the present invention, the primer set according to the present invention or the antibody according to the present invention as an index are dopaminergic neuron progenitor cells, and therefore, are preferable for the transplantation treatment of neurodegenerative diseases such as the Parkinson's disease in the aspects of safety, survival rate and network formation ability, compared to a conventional mixed cell population or dopaminergic neuron progenitor cells in which an exogenous gene is introduced. Particularly, when the cells detected or selected by using the probe according to the present invention, the primer according to the present invention, the primer set according to the present invention or the antibody according to the present invention are dopaminergic neuron progenitor cells before arrest of mitotic division, namely, dopaminergic neuron progenitor cells in proliferation, the cells have the possibility of differentiating to mature in the most appropriate place in the brain, and also, the dopaminergic neuron progenitor cells have the possibility of proliferating in vivo. Therefore, a longer effect of the treatment can be expected. Therefore, it can be said that the present invention paves the way to the practical application of the effective transplantation treatment of neurodegenerative diseases such as the Parkinson's disease.

[187A5 Gene and Protein]

In the present invention, the "187A5 gene" means those encoding a 187A5 protein and includes not only cDNA but also genomic DNA. It also includes RNA corresponding thereto.

In the present invention, the "187A5 gene", which is an index for the existence of dopaminergic neuron progenitor cells, has been registered in database as a functionally unknown sequence in mice. However, in humans, rats, bovines, dogs, chimpanzees, and so forth, only predicted sequences of 187A5 genes have been obtained. GenBank Accession Numbers disclosing the respective sequences are as follows.

Human: XM_044062 (SEQ ID NO: 3 (base sequence), SEQ ID NO: 4 (amino acid sequence), hereinafter, representation will be in the same order), AK126715 (SEQ ID NO: 5, SEQ ID NO: 6), HSM803256 (SEQ ID NO: 7, SEQ ID NO: 8), HSM803467 (SEQ ID NO: 9, SEQ ID NO: 10)

Mouse: AK028289 (SEQ ID NO: 11, SEQ ID NO: 12), AK157823 (SEQ ID NO: 13 (base sequence)), AK028541 (SEQ ID NO: 14, SEQ ID NO: 15), AK035053 (SEQ ID NO: 16, SEQ ID NO: 17), XM_485684 (SEQ ID NO: 18, SEQ ID NO: 19), AK163356 (SEQ ID NO: 20 (base sequence))

Rat: XM_344107 (SEQ ID NO: 21, SEQ ID NO: 22)

Bovine: XM_590147 (SEQ ID NO: 23, SEQ ID NO: 24)

Dog: XM_543360 (SEQ ID NO: 25, SEQ ID NO: 26)

Chimpanzee: XM_522557 (SEQ ID NO: 27, SEQ ID NO: 28)

In the present invention, a cDNA sequence (SEQ ID NO: 1) of a human 187A5 gene as a gene selectively expressed in dopaminergic neuron progenitor cells (preferably, dopaminergic neuron proliferative progenitor cells) in a mesencephalon site as well as an amino acid sequence (SEQ ID NO: 2) of a human 187A5 protein (polypeptide) as a protein (polypeptide) selectively expressed in dopaminergic neuron progenitor cells (preferably, dopaminergic neuron proliferative progenitor cells) were determined.

Those skilled in the art can specify a nucleotide sequence of a 187A5 gene or an amino acid sequence of a 187A5 protein inherent in various animals based on the nucleotide sequence of the 187A5 gene of SEQ ID NO: 1 and the amino acid sequence of the 187A5 protein of SEQ ID NO: 2. For example, by homology search based on the human or mouse 187A5 gene or 187A5 protein, a 187A5 gene or a 187A5 protein of the animal can be searched and identified. In the homology search, BLAST to be described later or the like can be used. Therefore, in the present invention, the "187A5 gene" and the "187A5 protein" used is meant to include, in addition to a human-derived 187A5 gene or a human-derived 187A5 protein, a 187A5 gene or a 187A5 protein inherent in various animals (preferably, mammals).

The 187A5 gene includes:

a polynucleotide encoding a human 187A5 protein comprising the amino acid sequence of SEQ ID NO: 2, SEQ ID NO: 4, SEQ ID NO: 6, SEQ ID NO: 8 or SEQ ID NO: 10;

a polynucleotide encoding a mouse 187A5 protein comprising the amino acid sequence of SEQ ID NO: 12, SEQ ID NO: 15, SEQ ID NO: 17 or SEQ ID NO: 19;

a polynucleotide encoding a rat 187A5 protein comprising the amino acid sequence of SEQ ID NO: 22;

a polynucleotide encoding a bovine 187A5 protein comprising the amino acid sequence of SEQ ID NO: 24;

a polynucleotide encoding a dog 187A5 protein comprising the amino acid sequence of SEQ ID NO: 26; and a polynucleotide encoding a chimpanzee 187A5 protein comprising the amino acid sequence of SEQ ID NO: 28.

Moreover, the 187A5 gene includes:

a polynucleotide comprising the human 187A5 gene nucleotide sequence of SEQ ID NO: 1, SEQ ID NO: 3, SEQ ID NO: 5, SEQ ID NO: 7 or SEQ ID NO: 9;

a polynucleotide comprising the mouse 187A5 gene nucleotide sequence of SEQ ID NO: 11, SEQ ID NO: 13, SEQ ID NO: 14, SEQ ID NO: 16, SEQ ID NO: 18 or SEQ ID NO: 20;

a polynucleotide comprising the rat 187A5 gene nucleotide sequence of SEQ ID NO: 21;

a polynucleotide comprising the bovine 187A5 gene nucleotide sequence of SEQ ID NO: 23; a polynucleotide comprising the dog 187A5 gene nucleotide sequence of SEQ ID NO: 25; and a polynucleotide comprising the chimpanzee 187A5 gene nucleotide sequence of SEQ ID NO: 27.

The 187A5 gene includes a polynucleotide selected from the following (i'), (ii'), (iii') and (iv'):

(i') a polynucleotide comprising the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27;

(ii') a polynucleotide encoding a protein which consists of an amino acid sequence encoded by a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii') a polynucleotide which hybridizes under stringent conditions to a polynucleotide consisting of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27, and which encodes a protein functionally equivalent to a protein consisting of the amino acid sequence of SEQ ID NO: 2; and (iv') a polynucleotide which has 70% or more identity with a polynucleotide consisting of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27, and which encodes a protein functionally equivalent to a protein consisting of the amino acid sequence of SEQ ID NO: 2.

Moreover, the 187A5 gene includes a polynucleotide encoding a protein selected from the following (v'), (vi'), (vii') and (viii'):

(v') a protein comprising the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28;

(vi') a protein which consists of an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28 in which one or more amino acids are inserted, substituted and/or deleted, and/or one or more amino acids are added to one or both of ends, and which is functionally equivalent to a protein consisting of the amino acid sequence of SEQ ID NO: 2;

(vii') a protein which is encoded by a polynucleotide which hybridizes under stringent conditions to a polynucleotide which encodes the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28, and which is functionally equivalent to a protein consisting of the amino acid sequence of SEQ ID NO: 2; and (viii') a protein which consists of an amino acid sequence having 70% or more identity with the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28, and which is functionally equivalent to a protein consisting of the amino acid sequence of SEQ ID NO: 2.

According to the present invention, preferably, there is provided a polynucleotide selected from the following (i"), (ii"), (iii") and (iv"):

(i") a polynucleotide comprising the nucleotide sequence of SEQ ID NO: 1;

(ii") a polynucleotide encoding a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii") a polynucleotide which hybridizes under stringent conditions to a polynucleotide consisting of the nucleotide sequence of SEQ ID NO: 1, and which encodes a protein functionally equivalent to a protein consisting of the amino acid sequence of SEQ ID NO: 2; and (iv") a polynucleotide which has 70% or more identity with a polynucleotide consisting of the nucleotide sequence of SEQ ID NO: 1, and which encodes a protein functionally equivalent to a protein consisting of the amino acid sequence of SEQ ID NO: 2.

According to the present invention, preferably, there is also provided a polynucleotide encoding a protein selected from the following (v"), (vi"), (vii") and (viii"):

(v") a protein comprising the amino acid sequence of SEQ ID NO: 2;

(vi") a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;

(vii") a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and (viii") a protein which consists of an amino acid sequence having 70% or more identity with the amino acid sequence of SEQ ID NO: 2, and which is functionally equivalent to a protein consisting of the amino acid sequence of SEQ ID NO: 2.

According to the present invention, more preferably, there is provided a human-derived polynucleotide selected from the following (i'"), (ii'"), (iii'") and (iv'"):

(i'") a polynucleotide comprising the nucleotide sequence of SEQ ID NO: 1;

(ii'") a polynucleotide encoding a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii'") a polynucleotide which hybridizes under stringent conditions to a polynucleotide consisting of the nucleotide sequence of SEQ ID NO: 1, and which encodes a protein functionally equivalent to a protein consisting of the amino acid sequence of SEQ ID NO: 2; and (iv'") a polynucleotide which has 95% or more identity with a polynucleotide consisting of the nucleotide sequence of SEQ ID NO: 1, and which encodes a protein functionally equivalent to a protein consisting of the amino acid sequence of SEQ ID NO: 2.

According to the present invention, more preferably, there is also provided a polynucleotide encoding a human-derived protein selected from the following (v'"), (vi'"), (vii'") and (viii'"):

(v'") a protein comprising the amino acid sequence of SEQ ID NO: 2;

(vi'") a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;

(vii'") a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and (viii'") a protein which consists of an amino acid sequence having 95% or more identity with the amino acid sequence of SEQ ID NO: 2, and which is functionally equivalent to a protein consisting of the amino acid sequence of SEQ ID NO: 2.

According to the present invention, further preferably, there is provided a human-derived polynucleotide comprising the nucleotide sequence of SEQ ID NO: 1.

According to the present invention, further preferably, there is also provided a polynucleotide encoding a human-derived protein comprising the amino acid sequence of SEQ ID NO: 2.

The 187A5 protein (polypeptide) includes:

a human 187A5 protein comprising the amino acid sequence of SEQ ID NO: 2, SEQ ID NO: 4, SEQ ID NO: 6, SEQ ID NO: 8 or SEQ ID NO: 10;

a mouse 187A5 protein comprising the amino acid sequence of SEQ ID NO: 12, SEQ ID NO: 15, SEQ ID NO: 17 or SEQ ID NO: 19, a rat 187A5 protein comprising the amino acid sequence of SEQ ID NO: 22;

a bovine 187A5 protein comprising the amino acid sequence of SEQ ID NO: 24;

a dog 187A5 protein comprising the amino acid sequence of SEQ ID NO: 26; and a chimpanzee 187A5 protein comprising the amino acid sequence of SEQ ID NO: 28.

Moreover, the 187A5 protein (polypeptide) includes:

a protein which is encoded by a nucleotide sequence comprising the human 187A5 gene nucleotide sequence of SEQ ID NO: 1, SEQ ID NO: 3, SEQ ID NO: 5, SEQ ID NO: 7 or SEQ ID NO: 9, a protein which is encoded by a nucleotide sequence comprising the mouse 187A5 gene nucleotide sequence of SEQ ID NO: 11, SEQ ID NO: 13, SEQ ID NO: 14, SEQ ID NO: 16, SEQ ID NO: 18 or SEQ ID NO: 20;

a protein which is encoded by a nucleotide sequence comprising the rat 187A5 gene nucleotide sequence of SEQ ID NO: 21;

a protein which is encoded by a nucleotide sequence comprising the bovine 187A5 gene nucleotide sequence of SEQ ID NO: 23;

a protein which is encoded by a nucleotide sequence comprising the dog 187A5 gene nucleotide sequence of SEQ ID NO: 25; and a protein which is encoded by a nucleotide sequence comprising the chimpanzee 187A5 gene nucleotide sequence of SEQ ID NO: 27.

The 187A5 protein (polypeptide) includes a protein selected from the following (i'), (ii'), (iii') and (iv'):

(i') a protein which is encoded by the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27;

(ii') a protein which consists of an amino acid sequence encoded by a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii') a protein which is encoded by a polynucleotide which hybridizes under stringent conditions to a polynucleotide consisting of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27, and which is functionally equivalent to a protein consisting of the amino acid sequence of SEQ ID NO: 2; and (iv') a protein which is encoded by a polynucleotide which has 70% or more identity with a polynucleotide consisting of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27, and which is functionally equivalent to a protein consisting of the amino acid sequence of SEQ ID NO: 2.

Moreover, the 187A5 protein (polypeptide) includes a protein selected from the following (v'), (vi'), (vii') and (viii'):

(v') a protein comprising the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28;

(vi') a protein which consists of an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28 in which one or more amino acids are inserted, substituted and/or deleted, and/or one or more amino acids are added to one or both of ends, and which is functionally equivalent to a protein consisting of the amino acid sequence of SEQ ID NO: 2;

(vii') a protein which is encoded by a polynucleotide which hybridizes under stringent conditions to a polynucleotide which encodes the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28, and which is functionally equivalent to a protein consisting of the amino acid sequence of SEQ ID NO: 2; and (viii') a protein which consists of an amino acid sequence having 70% or more identity with the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28, and which is functionally equivalent to a protein consisting of the amino acid sequence of SEQ ID NO: 2.

According to the present invention, preferably, there is provided a protein (polypeptide) selected from the following (i"), (ii"), (iii") and (iv"):

(i") a protein which is encoded by the nucleotide sequence of SEQ ID NO: 1;

(ii") a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii") a protein which is encoded by a polynucleotide which hybridizes under stringent conditions to a polynucleotide consisting of the nucleotide sequence of SEQ ID NO: 1, and which is functionally equivalent to a protein consisting of the amino acid sequence of SEQ ID NO: 2; and (iv") a protein which is encoded by a polynucleotide which has 70% or more identity with a polynucleotide consisting of the nucleotide sequence of SEQ ID NO: 1, and which is functionally equivalent to a protein consisting of the amino acid sequence of SEQ ID NO: 2.

According to the present invention, preferably, there is also provided a protein (polypeptide) selected from the following (v"), (vi"), (vii") and (viii"):

(v") a protein comprising the amino acid sequence of SEQ ID NO: 2;

(vi") a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;

(vii") a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and (viii") a protein which consists of an amino acid sequence having 70% or more identity with the amino acid sequence of SEQ ID NO: 2, and which is functionally equivalent to a protein consisting of the amino acid sequence of SEQ ID NO: 2.

According to the present invention, more preferably, there is provided a human-derived protein (polypeptide) selected from the following (i'''), (ii'''), (iii''') and (iv'''):

(i''') a protein which is encoded by the nucleotide sequence of SEQ ID NO: 1;

(ii''') a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii''') a protein which is encoded by a polynucleotide which hybridizes under stringent conditions to a polynucleotide consisting of the nucleotide sequence of SEQ ID NO: 1, and which is functionally equivalent to a protein consisting of the amino acid sequence of SEQ ID NO: 2; and (iv''') a protein which is encoded by a polynucleotide which has 95% or more identity with a polynucleotide consisting of the nucleotide sequence of SEQ ID NO: 1, and which is functionally equivalent to a protein consisting of the amino acid sequence of SEQ ID NO: 2.

According to the present invention, more preferably, there is also provided a human-derived protein (polypeptide) selected from the following (v'''), (vi'''), (vii''') and (viii'''):

(v''') a protein comprising the amino acid sequence of SEQ ID NO: 2;

(vi''') a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;

(vii''') a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and (viii''') a protein which consists of an amino acid sequence having 95% or more identity with the amino acid sequence of SEQ ID NO: 2, and which is functionally equivalent to a protein consisting of the amino acid sequence of SEQ ID NO: 2.

According to the present invention, further preferably, there is provided a human-derived protein encoded by the nucleotide sequence of SEQ ID NO: 1.

According to the present invention, further preferably, there is also provided a human-derived protein comprising the amino acid sequence of SEQ ID NO: 2.

In the present specification, "a polynucleotide in which one or more nucleotides are inserted, substituted and/or deleted, and/or one or more nucleotides are added to one or both of ends" or "an amino acid sequence in which one or more amino acids are inserted, substituted and/or deleted, and/or one or more amino acids are added to one or both of ends" means that the modification is performed by a well-known technical method such as site-directed mutagenesis or by substitution of a plurality of nucleotides or amino acids to an extent of being naturally generated, or the like. In the case of the polynucleotide, the term is meant to include single nucleotide polymorphisms (SNPs). The number of nucleotide or amino acid modifications can be insertion, substitution, deletion, and/or addition to one or both of ends, of, for example, 1 to 30, preferably 1 to 20, more preferably 1 to 10, further preferably one to several (for example, 9 or less), particularly preferably 1 to 4, and most preferably 1 or 2 nucleotides or amino acids.

The modified nucleotide sequence can be preferably a nucleotide sequence of SEQ ID NO: 1 having one or more (for example, one or several, or 1, 2, 3 or 4) mutations without affecting the functions of a protein consisting of the amino acid sequence of SEQ ID NO: 2.

The modified amino acid sequence can be preferably an amino acid sequence of SEQ ID NO: 2 having one or more (for example, one or several, or 1, 2, 3 or 4) conservative substitutions.

The number of insertion, substitution, deletion or addition introduced into the nucleotide sequence in (ii), (ii'), (ii'') or (ii''') can be preferably one or several (for example, 9 or less), more preferably 1 to 6, particularly preferably 1 to 4, most preferably 1 or 2.

The number of insertion, substitution, deletion or addition introduced into the amino acid sequence in (vi), (vi'), (vi'') or (vi''') can be preferably one or several (for example, 9 or less), more preferably 1 to 6, particularly preferably 1 to 4, most preferably 1 or 2.

In the present specification, the "conservative substitutions" mean that one or more amino acid residues are substituted with other chemically analogous amino acid residues so as not to substantially change protein functions. For example, the case that a certain hydrophobic residue is substituted with another hydrophobic residue and the case that a certain polar residue is substituted with another polar residue having the same charge can be exemplified. Functionally analogous amino acids which can be substituted in such a manner are known in the technical field, with respect to every amino acid. To give specific examples, non-polar (hydrophobic) amino acids include alanine, valine, isoleucine, leucine, proline, tryptophan, phenylalanine and methionine. Polar (neutral) amino acids include glycine, serine, threonine, tyrosine, glutamine, asparagine and cysteine. Positively charged (basic) amino acids include arginine, histidine and lysine. Negatively charged (acidic) amino acids include aspartic acid and glutamic acid.

The modified nucleotide sequence includes a nucleotide sequence having substitution of guanine to adenine at nucleotide 512 of SEQ ID NO: 1, substitution of guanine to adenine at nucleotide 844 of SEQ ID NO: 1, substitution of guanine to adenine at nucleotide 1360 of SEQ ID NO: 1, substitution of adenine to guanine at nucleotide 2458 of SEQ ID NO: 1 or substitution of adenine to guanine at nucleotide 2991 of SEQ ID NO: 1. The modified nucleotide sequence may have all or some of these substitutions in combination.

The modified amino acid sequence includes an amino acid sequence having substitution of arginine to histidine at amino acid 161 of SEQ ID NO: 2, substitution of valine to isoleucine at amino acid 272 of SEQ ID NO: 2, substitution of valine to isoleucine at amino acid 444 of SEQ ID NO: 2 or substitution of arginine to glycine at amino acid 810 of SEQ ID NO: 2. The modified amino acid sequence may have all or some of these substitutions in combination.

In the present specification, "hybridize under stringent conditions" means hybridization to a target polynucleotide under stringent conditions. Specifically, there can be exemplified a polynucleotide having at least 70% or more, preferably 80% or more, more preferably 85% or more, further preferably 90% or more, further more preferably 95% or more, particularly preferably 98% or more, and most preferably 99% or more identity, with the target nucleotide sequence when calculation is performed using a parameter of default (initial setting) with homology search software such as FASTA, BLAST or Smith-Waterman (Meth. Enzym., 164, 765 (1988)). Moreover, the "stringent conditions" can be performed according to a method of performing reaction in a hybridization buffer that can be generally used by those skilled in the art so that the temperature is 40 to 70° C., and preferably 60 to 65° C., and performing rinsing in a rinse solution whose salt concentration is 15 to 300 mmol/L, and preferably 15 to 60 mmol/L. The temperature and the salt concentration can be appropriately adjusted according to a length of the probe to be used. Furthermore, the condition when the hybridized nucleotide is rinsed can be 0.2 or 2×SSC, 0.1% SDS, and a temperature of 20 to 68° C. As to control of stringent (high stringency) or mild (low stringency) conditions, the difference can be provided by a salt concentration or a temperature in rinsing. When the difference of the hybridization is provided by a salt concentration, a stringent wash buffer (high stringency wash buffer) of 0.2×SSC, 0.1% SDS, or a mild wash buffer (low stringency wash buffer) of 2×SSC, 0.1% SDS can be used. Alternatively, when the difference of the hybridization is provided by a temperature, the temperature is 68° C. in the stringent case, 42° C. in the case of moderate stringency, and room temperature (20 to 25° C.) in the mild case, and every case thereof may be performed under 0.2×SSC, 0.1% SDS.

In general, prehybridization is performed under the same conditions as the hybridization. However, hybridization and preliminary rinsing are not limited to be performed under the same conditions.

The hybridization can be performed according to a known method. Moreover, in the case of using a commercially available library, the hybridization can be performed according to the method described in the appended instruction for use.

In the present specification, the "identity" (occasionally referred to as homology) with respect to amino acid sequences means the degree of identity of the amino acid residues of the respective sequences between the sequences to be compared. In this case, existence of a gap and properties of the amino acids are considered (Wilbur, Natl. Acad. Sci. U.S.A. 80: 726-730 (1983)). For calculation of the homology, commercially available software BLAST (Altschul: J. Mol. Biol. 215: 403-410 (1990)), FASTA (Peasron: Methods in Enzymology 183: 63-69 (1990)), or the like can be used.

The "identity" may be a value calculated by using a homology search program known by those skilled in the art and can be calculated, for example, by using a parameter of default (initial setting) in the homology algorithm BLAST (Basic local alignment search tool) http://www.ncbi.nlm.nih.gov/BLAST/in NCBI (National Center for Biotechnology Information).

The nucleotide sequence having at least 70% or more identity with the nucleotide sequence of SEQ ID NO: 1 can be a nucleotide sequence having preferably 80% or more, more preferably 90% or more, further preferably 90% or more, further more preferably 95% or more, particularly preferably 98% or more, and most preferably 99% or more identity.

The amino acid sequence having at least 70% or more identity with the amino acid sequence of SEQ ID NO: 2 can be an amino acid sequence having preferably 80% or more, more preferably 90% or more, further preferably 90% or more, further more preferably 95% or more, particularly preferably 98% or more, and most preferably 99% or more identity.

In the present invention, if the amino acid sequence of SEQ ID NO: 2 is given, a nucleotide sequence encoding it can be easily determined, and thereby, various nucleotide sequences encoding the amino acid sequence of SEQ ID NO: 2 can be selected. Thus, a polynucleotide encoding a protein consisting of the amino acid sequence of SEQ ID NO: 2 means not only a part or all of a cDNA sequence of SEQ ID NO: 1 but also a cDNA sequence encoding the same amino acids, which has a codon having a degeneracy relationship therewith as a cDNA sequence. Furthermore, the polynucleotide encoding a protein consisting of the amino acid sequence of SEQ ID NO: 2 means even a genomic DNA sequence also containing introns or noncoding regions. In the present invention, it further includes an RNA sequence corresponding thereto.

In the present specification, whether or not to be "functionally equivalent to a protein consisting of the amino acid sequence of SEQ ID NO: 2" can be determined by evaluating a biological phenomenon or functions associated with the expression of the 187A5 gene. For example, it can be determined by evaluating whether or not to be selectively expressed in dopaminergic neuron progenitor cells, and preferably dopaminergic neuron proliferative progenitor cells in the mesencephalon.

The present invention provides a protein comprising a polypeptide consisting of at least 5 amino acid residues (preferably, at least 6 amino acid residues) or all of an amino acid sequence of amino acids 248-397 or 792-877 of SEQ ID NO: 2. This protein corresponds to a high discrimination part in the amino acid sequence of the 187A5 protein, and therefore, can be used as an antigen against an antibody that can discriminate the 187A5 protein with higher accuracy.

The 187A5 protein is a type I single transmembrane protein that is expressed on the cell surface in a direction wherein the N-terminal side thereof can be located in the extracellular space. Thus, by flow cytometry using an antibody capable of binding to the protein, live cells in which the protein is expressed can be separated.

The present invention provides a protein comprising a polypeptide consisting of at least 5 amino acid residues (preferably, at least 6 amino acid residues) or all of an amino acid sequence of amino acids 28 to 927 of SEQ ID NO: 2, amino acids 16 to 1267 of SEQ ID NO: 4, amino acids 1 to 550 of SEQ ID NO: 6, amino acids 1 to 542 of SEQ ID NO: 8, amino acids 1 to 418 of SEQ ID NO: 10, amino acids 76 to 964 of SEQ ID NO: 12, amino acids 40 to 928 of SEQ ID NO: 15, amino acids 1 to 540 of SEQ ID NO: 17, amino acids 40 to 1106 of SEQ ID NO: 19, amino acids 24 to 1524 of SEQ ID NO: 22, amino acids 43 to 1018 of SEQ ID NO: 24, amino acids 43 to 908 of SEQ ID NO: 26 or amino acids 1 to 866 of SEQ ID NO: 28. This protein corresponds to the extracellular region in the amino acid sequence of the 187A5 protein, and therefore, can be used as an antigen for preparing an antibody that can detect live cells as an object to be detected.

The present invention provides use of the protein according to the present invention as an index for detecting or selecting a dopaminergic neuron progenitor cell, and preferably a dopaminergic neuron proliferative progenitor cell.

[Probe, Primer and Primer Set]

The probe or primer according to the present invention for use in the detection or selection of a dopaminergic neuron progenitor cell, and preferably a dopaminergic neuron proliferative progenitor cell can specifically hybridize to a 187A5 gene. According to Example 2, in a 12.5-day mouse embryo which is in the period of generating dopaminergic neurons, mRNA of 187A5 is selectively expressed in the mesencephalon most ventral ventricular zone (ventricular zone; VZ) and the mesencephalon most dorsal roof plate zone in which Lrp4-positive dopaminergic neuron progenitor cells exist, but is not expressed in metencephalon floor plate cells positive for Lrp4. Therefore, it became revealed that mRNA of 187A5 is selectively expressed in dopaminergic neuron proliferative progenitor cells. Accordingly, the expression of the 187A5 gene is useful as an index for dopaminergic neuron progenitor cells. Therefore, the probe, the primer and the primer set according to the present invention can be used as a marker for detecting dopaminergic neuron progenitor cells, and preferably dopaminergic neuron proliferative progenitor cells.

The probe and the primer according to the present invention can be used for detecting expression of a 187A5 gene, and corresponds to a polymer consisting of a plurality of bases or base pairs such as deoxyribonucleic acid (DNA) or ribonucleic acid (RNA). It is known that double-strand cDNA can also be used in tissue in situ hybridization, and such double-strand cDNA is also included in the probe and the primer according to the present invention. As a particularly preferable probe and primer in the detection of RNA in tissue, an RNA probe (riboprobe) can be exemplified.

The probe and the primer according to the present invention include those comprising a nucleotide sequence consisting of at least 10, preferably at least 15 contiguous nucleotides of a nucleotide sequence of a 187A5 gene, or a complementary sequence thereto. Also, the probe and the primer according to the present invention include those comprising a nucleotide sequence consisting of preferably 10 to 50 or 10 to 30, more preferably 15 to 50 or 15 to 30, further preferably 20 to 50 or 20 to 30, further more preferably 25 to 50 or 25 to 30, and most preferably 26 to 39 or 26 to 35 nucleotides.

The probe and the primer according to the present invention can be at least 10 base length, preferably at least 15 base length, more preferably at least 20 base length, and further preferably at least 25 base length. The probe and the primer according to the present invention can also be preferably 10 to 50 base length or 10 to 30 base length, more preferably 15 to 50 base length or 15 to 30 base length, further preferably 20 to 50 base length or 20 to 30 base length, further more preferably 25 to 50 base length or 25 to 30 base length, and most preferably 26 to 39 base length or 26 to 35 base length.

According to preferable embodiments of the probe and the primer according to the present invention, there is provided a polynucleotide for use in the detection or selection of a dopaminergic neuron progenitor cell, and preferably a dopaminergic neuron proliferative progenitor cell in the mesencephalon, comprising a nucleotide sequence consisting of at least 10 (more preferably, at least 15) contiguous nucleotides of a nucleotide sequence of a 187A5 gene, or a complementary sequence thereto and having 15 to 50 base length or 15 to 30 base length, more preferably 25 to 50 base length or 25 to 30 base length, and most preferably 26 to 39 base length or 26 to 35 base length, which can hybridize with a 187A5 gene.

According to preferable embodiments of the probe according to the present invention, there is also provided a polynucleotide that can hybridize to a high discrimination part in the nucleotide sequence of the 187A5 gene. By using such a polynucleotide, it becomes possible to detect the progenitor cells, and preferably the proliferative progenitor cells with higher accuracy. Such a polynucleotide includes a polynucleotide that hybridizes to a nucleotide sequence comprising a part or all of a nucleotide sequence of nucleotides 774 to 1221 or 2403 to 2666 of SEQ ID NO: 1

According to preferable embodiments of the primer according to the present invention, there is also provided those that can amplify a high discrimination part in the nucleotide sequence of the 187A5 gene by a nucleic acid amplification method, and a polynucleotide that can hybridize to the high discrimination part. By using such a polynucleotide, it becomes possible to detect the progenitor cells, and preferably the proliferative progenitor cells with higher accuracy. Such a polynucleotide includes a polynucleotide that can amplify, by a nucleic acid amplification method, a nucleotide sequence comprising a part or all of a nucleotide sequence of nucleotides 774 to 1221 or 2403 to 2666 of SEQ ID NO: 1.

The probe according to the present invention can be used as a probe according to the general methods in known methods for detecting a gene of interest, such as a northern blotting method, a southern blotting method or in situ hybridization method.

The probe according to the present invention can be chemically synthesized based on the nucleotide sequences disclosed in the present specification. The preparation of the probe is well-known and can be performed, for example, according to "Molecular Cloning, A Laboratory Manual $2^{nd}$ ed." (Cold Spring Harbor Press (1989)) or "Current Protocols in Molecular Biology" (John Wiley & Sons (1987-1997)).

The primer according to the present invention can also be used as a primer set consisting of two or more primers according to the present invention.

The primer and the primer set according to the present invention can be used as a primer and a primer set according to the general methods in known methods for detecting a gene of interest by using a nucleic acid amplification method such as a PCR method, a RT-PCR method, a real-time PCR method or in situ PCR.

The primer set according to the present invention can be selected so that the nucleotide sequence of the 187A5 gene can be amplified by a nucleic acid amplification method such as a PCR method. The nucleic acid amplification method is well-known, and selection of the primer set in the nucleic acid amplification method is understood by those skilled in the art. For example, in the PCR method, primers can be selected so that one of two primers (primer pair) is paired with the plus strand of the double-strand DNA of the 187A5 gene while the other primer is paired with the minus strand of the double-strand DNA, and with a strand extended by one primer, the other primer can be paired. Moreover, in the LAMP method (WO 00/28082), with respect to the target gene, three regions F3c, F2c and F1c and three regions B1, B2 and B3 are defined from the 3' end side and from the 5' end side, respectively, and by using these six regions, four primers can be designed.

The primer according to the present invention can be chemically synthesized based on the nucleotide sequences disclosed in the present specification. The preparation of the primer is well-known and can be performed, for example, according to "Molecular Cloning, A Laboratory Manual $2^{nd}$ ed." (Cold Spring Harbor Press (1989)) or "Current Protocols in Molecular Biology" (John Wiley & Sons (1987-1997)).

[Antibody]

The antibody according to the present invention can specifically recognize a 187A5 protein. According to Example 5, it was confirmed that the 187A5 protein exists in dopaminergic neuron progenitor cells. Accordingly, the existence of the 187A5 protein is useful as an index for dopaminergic neuron progenitor cells including dopaminergic neuron proliferative progenitor cells. Therefore, the antibody according to the present invention can be used as a marker for detecting dopaminergic neuron progenitor cells, and preferably dopaminergic neuron progenitor cells.

The 187A5 protein is expressed on the cell surface in a direction wherein the N-terminal side thereof can be located in the extracellular space (Example 4). Therefore, the antibody according to the present invention has the advantage that the dopaminergic neuron progenitor cells can be detected or selected as live cells (Example 6). Moreover, the antibody according to the present invention has the advantage that ES cell-derived cells can also be detected or selected (Example 7).

The 187A5 protein for obtaining the antibody according to the present invention may have antigenicity of 187A5 and includes the above-described protein. Moreover, it includes a protein having an amino acid sequence of the 187A5 protein in which one or more amino acid residues are deleted, inserted, substituted or added. It is known that in such a protein, the same biological activity as the original protein is maintained (Mark et al. (1984) Proc. Natl. Acad. Sci. USA 81: 5662-6; Zoller and Smith (1982) Nucleic Acids Res. 10: 6487-500; Wang et al. (1984) Science 224: 1431-3; and Dalbadie-McFarland et al. (1982) Proc. Natl. Acad. Sci. USA 79: 6409-13). A method by which in a protein, one or more amino acid residues are deleted, inserted, substituted or added in the state of maintaining the antigenicity of the original protein is known. For example, a polynucleotide encoding a mutant protein can be prepared by site-directed mutagenesis and can be appropriately expressed to obtain the protein (Molecular Cloning, A Laboratory Manual $2^{nd}$ ed., Cold Spring Harbor Press (1989); Current Protocols in Molecular Biology, John Wiley & Sons, (1987-1997), Section 8.1-8.5; Hashimoto-Goto et al. (1995) Gene 152: 271-5; Kinkel (1985) Proc. Natl. Acad. Sci. USA 82: 488-92; Kramer and Fritz (1987) Method. Enzymol 154: 350-67; and Kunkel (1988) Method. Enzymol. 85: 2763-6).

The antibody according to the present invention also includes an antibody specific for a part of a 187A5 protein. Specifically, the 187A5 protein for obtaining the antibody of the present invention includes a polypeptide having the full-length amino acid sequence of the 187A5 protein as well as a polypeptide fragment having a sequence of at least 6 amino acid residues or more (for example, 8, 10, 12 or 15 amino acid residues or more) of the 187A5 protein. The polypeptide fragment of the 187A5 protein in the present specification may be any fragment as long as having the 187A5 protein or antigenicity thereof.

Preferable fragments can include polypeptide fragments such as the amino terminal of the 187A5 protein. The antigenic determinant site of the polypeptide is estimated by a method of analyzing hydrophobicity/hydrophilicity of the amino acid sequence of the protein (Kyte-Doolittle (1982) J. Mol. Biol. 157: 105-22) or a method of analyzing the secondary structure (Chou-Fasman (1978) Ann. Rev. Biochem. 47: 251-76), and furthermore, can be confirmed by a computer program (Anal. Biochem. 151: 540-6 (1985)) or a technique such as a PEPSCAN method (Japanese Patent Laid-Open Publication No. 60-500684) of synthesizing a short peptide and confirming its antigenicity.

The antibody capable of binding to the 187A5 protein includes:

an antibody capable of binding to a protein consisting of the amino acid sequence of SEQ ID NO: 2, SEQ ID NO: 4, SEQ ID NO: 6, SEQ ID NO: 8 or SEQ ID NO: 10, or a part thereof;

an antibody capable of binding to a protein consisting of the amino acid sequence of SEQ ID NO: 12, SEQ ID NO: 15, SEQ ID NO: 17 or SEQ ID NO: 19 or, or a part thereof;

an antibody capable of binding to a protein consisting of the amino acid sequence of SEQ ID NO: 22, or a part thereof;

an antibody capable of binding to a protein consisting of the amino acid sequence of SEQ ID NO: 24, or a part thereof;

an antibody capable of binding to a protein consisting of the amino acid sequence of SEQ ID NO: 26, or a part thereof; and an antibody capable of binding to a protein consisting of the amino acid sequence of SEQ ID NO: 28, or a part thereof.

According to preferable embodiments of the antibody according to the present invention, there is provided an antibody that recognizes a high discrimination polypeptide region in the 187A5 protein. By using such an antibody, it becomes possible to detect the progenitor cells, and preferably the proliferative progenitor cells with higher accuracy. Such an antibody includes an antibody capable of binding to a protein comprising a polypeptide consisting of at least 5 amino acid residues (preferably, at least 6 amino acid residues) or all of an amino acid sequence of amino acids 248 to 397 or 792 to 877 of SEQ ID NO: 2.

According to preferable embodiments of the antibody according to the present invention, there is also provided an antibody that recognizes a polypeptide region expressed in the extracellular space of the 187A5 protein. By using such an antibody, it becomes possible to detect the progenitor cells, and preferably the proliferative progenitor cells as live cells. Such an antibody includes an antibody capable of binding to the polypeptide region expressed in the extracellular space of the 187A5 protein, for example, an antibody capable of binding to a protein comprising a polypeptide consisting of at least 5 amino acid residues (preferably, at least 6 amino acid residues) or all of an amino acid sequence of amino acids 28 to 927 of SEQ ID NO: 2, amino acids 16 to 1267 of SEQ ID NO: 4, amino acids 1 to 550 of SEQ ID NO: 6, amino acids 1 to 542 of SEQ ID NO: 8, amino acids 1 to 418 of SEQ ID NO: 10, amino acids 76 to 964 of SEQ ID NO: 12, amino acids 40 to 928 of SEQ ID NO: 15, amino acids 1 to 540 of SEQ ID NO: 17, amino acids 40 to 1106 of SEQ ID NO: 19, amino acids 24 to 1524 of SEQ ID NO: 22, amino acids 43 to 1018 of SEQ ID NO: 24, amino acids 43 to 908 of SEQ ID NO: 26 or amino acids 1 to 866 of SEQ ID NO: 28.

The antibody according to the present invention can be obtained by using a well-known method for those skilled in the art (for example, "Current Protocols in Molecular Biology" (John Wiley & Sons (1987)) and Antibodies: A Laboratory Manual, Ed. Harlow and David Lane, Cold Spring Harbor Laboratory (1988)).

The antibody according to the present invention includes a polyclonal antibody, a monoclonal antibody, a chimeric antibody, a single-strand antibody (scFv), a humanized antibody, a polyspecific antibody and antibody fragments such as Fab, Fab', $F(ab')_2$, Fc and Fv.

In the case of the polyclonal antibody, the blood of a mammal in which an antigen is sensitized is extracted, and serum can be segregated as polyclonal antibody-containing serum from the blood by a known method.

According to need, fractions containing the polyclonal antibody can also be further isolated from this serum.

In the case of the monoclonal antibody, antibody-producing cells obtained from the spleen or lymph node of the above-described mammal in which an antigen is sensitized are extracted and cell-fused with myeloma cells or the like. The obtained hybridomas (fused cells) are cloned, and antibodies can be collected as the monoclonal antibody from the cultures thereof.

A fragment of the 187A5 protein can be used as the immunizing antigen. Alternatively, those synthesized based on the above-described amino acid sequence can be used. The antigen may be used as a complex with a carrier protein. For preparation of the complex of the antigen and the carrier protein, various condensation agents such as glutaraldehyde, carbodiimide or maleimide-activated ester can be used. The carrier protein may be one generally used such as bovine serum albumin, thyroglobulin or hemocyanin, and a method for coupling at a ratio of 1 to 5 is generally used.

The animal to be immunized includes a mouse, a rat, a hamster, a guinea pig, a rabbit, a cat, a dog, a pig, a goat, a horse and a bovine, and, preferably, includes a mouse, a rat, a rabbit, a guinea pig and a hamster. The injection method includes subcutaneous, muscular or intraperitoneal administration. In the administration, the antigen may be mixed with complete Freund's adjuvant or incomplete Freund's adjuvant. The administration is generally performed once per 2 to 5 weeks.

The antibody-producing cells obtained from the spleen or lymph node of the immunized animal are cell-fused with myeloma cells and isolated as hybridomas. The myeloma cells to be used are derived from a mouse, a rat, a human, or the like, and preferably, derived from the same species as the antibody-producing cells, but cells between different species are occasionally possible.

Operation of the hybridomas (cell fusion) can be performed according to a previously known method, for example, the method disclosed in Nature, 256, 495, 1975. Fusion accelerators include polyethylene glycol and Sendai virus. In general, the cell fusion can be performed by reaction for approximately 1 to 10 minutes so that the ratio between the number of the antibody-producing cells and the number of the myeloma cells is generally approximately 1:1 to 10:1, under a temperature of 20 to 40° C., and preferably 30 to 37° C. by using polyethylene glycol (average molecular weight 1000 to 4000) having a concentration of approximately 20 to 50%.

For screening of the antibody-producing hybridomas, various immunochemical methods can be used, which include an ELISA method by using a microplate coated with the 187A5 protein, an EIA method by using a microplate coated with an anti-immunoglobulin antibody, and an immunoblotting method by using a nitrocellulose transfer membrane after electrophoresing samples containing the 187A5 protein.

From such wells, cloning is further performed, for example, by a limiting dilution method, and thereby, clones can be obtained. Selection and culture of the hybridomas are generally performed in a medium for animal cells (for example, RPMI1640) containing 10 to 20% fetal bovine serum to which HAT (hypoxanthine, aminopterin and thymidine) is added. The clones obtained as described above are transplanted into the peritoneal cavity of an SCID mouse to which pristine is preliminarily administered, and ascitic fluid containing the monoclonal antibody at a high concentration is collected after 10 to 14 days, and can be used as a material for antibody purification. Also, the clones can be cultured, and the cultures thereof can also be used as a material for antibody purification.

For the purification of the monoclonal antibody, a previously known method as an immunoglobulin purification method may be used, and the purification can be easily achieved, for example, by a means such as an ammonium sulfate fraction method, a PEG fraction method, an ethanol fraction method, use of an anion exchanger, or affinity chromatography using the 187A5 protein.

The purification of the polyclonal antibody from the serum can be similarly performed.

[Detection Method]

The expression of the 187A5 gene serves as an index for the existence of dopaminergic neuron progenitor cells, and preferably dopaminergic neuron proliferative progenitor cells, as described above. Therefore, according to the present invention, the dopaminergic neuron progenitor cells, and preferably the dopaminergic neuron proliferative progenitor cells can be detected or selected by detecting expression of a 187A5 gene.

The method for "detecting expression of a 187A5 gene" used herein is not particularly limited as long as being capable of detecting the expression of the 187A5 gene in cell samples to be tested, and can be performed, for example, by the following steps of:

(a) contacting a cell sample to be tested, with the probe, the primer or the primer set according to the present invention; and (b) detecting the presence or absence of reactivity.

The method for "detecting the presence or absence of reactivity" used herein, for example, includes hybridization methods and nucleic acid amplification methods.

The "cell sample to be tested" used herein may be cell samples that are thought to contain the dopaminergic neuron progenitor cells, and preferably the dopaminergic neuron proliferative progenitor cells, and, preferably, cells in the mesencephalon ventral region can be used. The cells in the mesencephalon ventral region can be obtained by a known method (Studer, L., et al. Nature Neurosci (1998) 1: 290-295). For example, fetus's (preferably, human aborted fetus's) or patient's own cells of the mesencephalon ventral region can be used as the cell sample to be tested. Moreover, culture cells containing dopaminergic neuron progenitor cells, and preferably dopaminergic neuron proliferative progenitor cells induced to differentiate in vitro can be used. The induction to differentiate into the dopaminergic neuron progenitor cells or the dopaminergic neuron proliferative progenitor cells in vitro can be performed by differentiation treatment by a known method such as an SDIA method (Kawasaki et al. Neuron (2000) 28 (1): 31-40) or a 5-stage method (Lee, S H., et al. Nature Biotech (2000) 18: 675-579) using, as a starting material, cells such as known ES cells (Kawasaki et al. Neuron (2000) 28 (1): 31-40) and Lee, S H., et al. Nature Biotech (2000) 18: 675-579), bone marrow stromal cells, nerve-derived immortalized cell lines (Japanese Patent Laid-Open Publication No. 8-509215, No. 11-506930 and No. 2002-522070) or neuron primordial cells (Japanese Patent Laid-Open Publication No. 11-509729). Preferably, ES cells subjected to the differentiation treatment by the SDIA method can be used as the cell sample to be tested.

The "SDIA method" used herein can be performed by co-culturing ES cells and the stromal cell line PA6 in a serum-free medium (Kawasaki et. al. Neuron. 2000 28 (1): 31-40). Moreover, the "5-stage method" can be performed as follows. ES cells are cultured on a non-adherent culture plate in the presence of serum, and thereby, an embryoid body (EB) is formed. Sequentially, the EB is attached onto an adherent culture plate, and thereby, neuron progenitor cells are selected. Finally, a growth factor such as Shh, FGF2 or FGF8 is added thereto, and thereby, dopaminergic neuron progenitor cells are induced (Lee, S H., et al. Nature Biotech (2000) 18: 675-579).

According to the first embodiment of the detection method according to the present invention, using the probe according to the present invention, the polynucleotide for detection hybridizes to a nucleic acid sample (mRNA or a transcript thereof), and the hybridization complex, namely, the nucleotide double strand, is detected. Thus, the expression of the 187A5 gene can be detected in the cell sample.

For the detailed procedure of the hybridization method, there can be referred to "Molecular Cloning, A Laboratory Manual $2^{nd}$ ed." (Cold Spring Harbor Press (1989), particularly, Sections 9.47-9.58), "Current Protocols in Molecular Biology" (John Wiley & Sons (1987-1997), particularly, Sections 6.3-6.4), and "DNA Cloning 1: Core Techniques, A Practical Approach $2^{nd}$ ed." (Oxford University (1995), particularly, Section 2.10 for the conditions).

The detection of expression of a 187A5 gene by using the hybridization method can be performed, for example, by the following steps of:

(a-1) contacting a polynucleotide derived from a cell sample to be tested, with the probe according to the present invention; and (b-1) detecting a hybridization complex.

In step (a-1), mRNA prepared from the cell sample that is thought to contain dopaminergic neuron progenitor cells, and preferably dopaminergic neuron proliferative progenitor cells, or a complementary DNA (cDNA) transcribed from the mRNA can be contacted, as the polynucleotide derived from the cell sample to be tested, with the probe.

In the detection method by using the probe, the probe can be labeled. The label includes a label by using radioactivity (such as $^{32}P$, $^{14}C$ and $^{35}S$), fluorescence (such as FITC and europium), an enzyme (such as peroxidase or alkaline phosphatase) reaction such as chemical coloring, or the like.

The detection of the hybridization product can be performed by using a well-known method such as northern hybridization, southern hybridization or colony hybridization.

The cells in which the hybridization complex is detected are those expressing a 187A5 gene, and therefore, can be determined as the dopaminergic neuron progenitor cells, and preferably the dopaminergic neuron proliferative progenitor cells.

According to the second embodiment of the detection method according to the present invention, using the primer or the primer set according to the present invention, a nucleic acid sample (mRNA or a transcript thereof) is amplified by a nucleic acid amplification method, and the amplification product is detected. Thus, the expression of the 187A5 gene can be detected in the cell sample.

The detection of expression of a 187A5 gene by using the nucleic acid amplification method can be performed, for example, by the following steps of:

(a-2) performing a nucleic acid amplification method by using a polynucleotide derived from a cell sample to be tested as a template and the primer or the primer set according to the present invention; and (b-2) detecting a formed amplification product.

In step (a-2), mRNA prepared from the sample that is thought to contain dopaminergic neuron progenitor cells, and preferably dopaminergic neuron proliferative progenitor cells, or a complementary DNA (cDNA) transcribed from the mRNA can be used as the template.

The detection of the amplification product can be performed by using a nucleic acid amplification method such as a PCR method, a RT-PCR method, a real-time PCR method or a LAMP method.

The cells in which the amplification product is detected are those expressing a 187A5 gene, and therefore, can be determined as the dopaminergic neuron progenitor cells, and preferably the dopaminergic neuron proliferative progenitor cells.

The 187A5 protein serves as an index for the existence of dopaminergic neuron progenitor cells, and preferably dopaminergic neuron proliferative progenitor cells, as described above. Therefore, according to the present invention, the dopaminergic neuron progenitor cells, and preferably the dopaminergic neuron proliferative progenitor cells can be detected or selected by detecting a 187A5 protein.

The method for "detecting a 187A5 protein" used herein is not particularly limited as long as being capable of detecting the 187A5 protein in cell samples to be tested, and, for example, includes antigen-antibody reaction methods.

According to the third embodiment of the detection method according to the present invention, the antibody according to the present invention and the cell sample are contacted, and the antigen-antibody reaction is detected. Thus, the 187A5 protein can be detected in the cell sample.

The detection of a 187A5 protein by using the antigen-antibody reaction can be performed, for example, by the following steps of:

(c) contacting a protein derived from a cell sample to be tested, with the antibody according to the present invention; and (d) detecting the presence or absence of reactivity.

The method for "detecting the presence or absence of reactivity" used herein, for example, includes antigen-antibody reaction methods.

The "cell sample to be tested" used herein can be cell samples to be tested that are thought to contain the dopaminergic neuron progenitor cells, and preferably the dopaminergic neuron proliferative progenitor cells, and are preferably cells in the mesencephalon ventral region or culture cells containing dopaminergic neuron progenitor cells, and preferably dopaminergic neuron proliferative progenitor cells induced to differentiate in vitro. For example, those derived from an embryonic mesencephalon can be used as the cell sample to be tested. The method for obtaining the cell sample to be tested is as described above.

The detection of a 187A5 protein by using the antigen-antibody reaction method can be performed, for example, by the following steps of:

(c-1) contacting a protein derived from a cell sample to be tested, with the antibody according to the present invention; and (d-1) detecting an antigen-antibody complex.

The method for detecting the antigen-antibody reaction is well-known for those skilled in the art, and, for example, a 187A5 protein can be detected in the cell sample to be tested that is thought to contain dopaminergic neuron progenitor cells, and preferably dopaminergic neuron proliferative progenitor cells, by an immunological method. For the immunological method, a previously known method such as an immunohistologic staining method, an enzyme-linked immunosorbent assay, a western blotting method, an agglutination method, a competition method or a sandwich method, can be applied to the cell sample subjected to appropriate treatment according to need, such as cell separation or extraction operation. The immunohistologic staining method can be performed by, for example, a direct method by using a labeled antibody or an indirect method by using a labeled antibody capable of binding to the antibody. For the labeling agent, a known labeling substance such as a fluorescent substance, a radioactive substance, an enzyme, a metal or a pigment can be used.

The protein derived from a cell sample to be tested is preferably a polypeptide comprising the extracellular region (namely, the N-terminal region).

The cells in which the antigen-antibody complex is detected are those expressing a 187A5 protein, and therefore, can be determined as the dopaminergic neuron progenitor cells, and preferably the dopaminergic neuron proliferative progenitor cells.

For use in the treatment of the Parkinson's disease, it is desirable that the purity of the dopaminergic neuron progenitor cells, and preferably the dopaminergic neuron proliferative progenitor cells is high.

The accuracy of the detection or selection of the dopaminergic neuron progenitor cells, and preferably the dopaminergic neuron proliferative progenitor cells can be enhanced by performing each of the above-described detection steps not only once but repeatedly.

Therefore, according to the detection method according to the present invention, the dopaminergic neuron progenitor cells, and preferably the dopaminergic neuron proliferative progenitor cells can be detected or selected with higher accuracy by performing the above-described step twice or more.

Moreover, the accuracy of the detection or selection of the dopaminergic neuron progenitor cells, and preferably the dopaminergic neuron proliferative progenitor cells can be further enhanced by using together other marker genes, preferably a dopaminergic neuron proliferative progenitor cell marker gene other than the 187A5 gene.

Therefore, according to the detection method according to the present invention, the dopaminergic neuron progenitor cells, and preferably the dopaminergic neuron proliferative progenitor cells can be detected or selected with higher accuracy by using together a dopaminergic neuron proliferative progenitor cell marker gene other than the 187A5 gene or a protein thereof, a postmitotic dopaminergic neuron precursor cell marker gene or a protein thereof, a dopaminergic neuron progenitor cell marker gene other than the 187A5 gene or a protein thereof, or a mature dopaminergic neuron cell marker gene or a protein thereof, and detecting not only expression of the 187A5 gene, or a protein thereof but also expression of the above-described other marker genes, or the proteins thereof.

Dopaminergic neuron-related marker genes selectively expressed in each of differentiation stages are shown in FIG. 1.

In the detection method characterized in that the expression of the 187A5 gene is detected, the dopaminergic neuron progenitor cells, and preferably the dopaminergic neuron proliferative progenitor cells can be detected or selected with high accuracy by using together a dopaminergic neuron proliferative progenitor cell marker gene other than the 187A5 gene or a protein thereof, and detecting not only the 187A5 gene but also expression of the dopaminergic neuron proliferative progenitor cell marker gene other than the 187A5 gene, or the protein thereof.

Specifically, in step (a), the dopaminergic neuron progenitor cells, and preferably the dopaminergic neuron proliferative progenitor cells can be detected or selected with high accuracy by using, as the cell sample to be tested, the cells in which the expression of the dopaminergic neuron proliferative progenitor cell marker gene other than the 187A5 gene, or the protein thereof is detected. In this case, the cells in which reactivity is detected (for example, the cells in which the hybridization complex or the amplification product is detected) in step (b) are those which express the 187A5 gene, and which express the dopaminergic neuron proliferative progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-1) detecting expression of a dopaminergic neuron proliferative progenitor cell marker gene other than the 187A5 gene, or a protein thereof, with respect to the cells in which reactivity is detected (for example, the cells in which the hybridization complex or the amplification product is detected) in step (b). In this case, in step (e-1), the cells in which the expression of the dopaminergic neuron proliferative progenitor cell marker gene other than the 187A5 gene, or the protein thereof is detected are those which express the 187A5 gene, and which express the dopaminergic neuron proliferative progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the expression of the 187A5 gene is detected, by using together a postmitotic dopaminergic neuron precursor cell marker gene or a protein thereof, it can be confirmed that the 187A5 gene is expressed but the expression of the postmitotic dopaminergic neuron precursor cell marker gene, or the protein thereof is not detected. Thus, the dopaminergic neuron progenitor cells, and preferably the dopaminergic neuron proliferative progenitor cells can be detected or selected with high accuracy.

Specifically, in step (a), the dopaminergic neuron progenitor cells, and preferably the dopaminergic neuron proliferative progenitor cells can be detected or selected with high accuracy by using, as the cell sample to be tested, the cells in which the expression of the postmitotic dopaminergic neuron precursor cell marker gene, or the protein thereof is not detected. In this case, the cells in which reactivity is detected (for example, the cells in which the hybridization complex or the amplification product is detected) in step (b) are those which express the 187A5 gene, which do not express the postmitotic dopaminergic neuron precursor cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-2) detecting expression of a postmitotic dopaminergic neuron precursor cell marker gene, or a protein thereof, with respect to the cells in which reactivity is detected (for example, the cells in which the hybridization complex or the amplification product is detected) in step (b). In this case, in step (e-2), the cells in which the expression of the postmitotic dopaminergic neuron precursor cell marker gene, or the protein thereof is not detected are those which express the 187A5 gene, which do not express the postmitotic dopaminergic neuron precursor cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the expression of the 187A5 gene is detected, the dopaminergic neuron progenitor cells, and preferably the dopaminergic neuron proliferative progenitor cells can be detected or selected with high accuracy by using together a dopaminergic neuron progenitor cell marker gene other than the 187A5 gene or a protein thereof, and detecting not only the 187A5 gene but also expression of the dopaminergic neuron progenitor cell marker gene other than the 187A5 gene, or the protein thereof.

Specifically, in step (a), the dopaminergic neuron progenitor cells, and preferably the dopaminergic neuron proliferative progenitor cells can be detected or selected with high accuracy by using, as the cell sample to be tested, the cells in which the expression of the dopaminergic neuron progenitor cell marker gene other than the 187A5 gene, or the protein thereof is detected. In this case, the cells in which reactivity is detected (for example, the cells in which the hybridization complex or the amplification product is detected) in step (b) are those which express the 187A5 gene, and which express the dopaminergic neuron progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-3) detecting expression of a dopaminergic neuron progenitor cell marker gene other than the 187A5 gene, or a protein thereof, with respect to the cells in which reactivity is detected (for example, the cells in which the hybridization complex or the amplification product is detected) in step (b). In this case, in step (e-3), the cells in which the expression of the dopaminergic neuron progenitor cell marker gene other than the 187A5 gene, or the protein thereof is detected are those which express the 187A5 gene, and which express the dopaminergic neuron progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the expression of the 187A5 gene is detected, by using together a mature dopaminergic neuron cell marker gene or a protein thereof, it can be confirmed that the 187A5 gene is expressed but the expression of the mature dopaminergic neuron cell marker gene, or the protein thereof is not detected. Thus, the dopaminergic neuron progenitor cells, and preferably the dopaminergic neuron proliferative progenitor cells can be detected or selected with high accuracy.

Specifically, in step (a), the dopaminergic neuron progenitor cells, and preferably the dopaminergic neuron proliferative progenitor cells can be detected or selected with high accuracy by using, as the cell sample to be tested, the cells in which the expression of the mature dopaminergic neuron cell marker gene, or the protein thereof is not detected. In this case, the cells in which reactivity is detected (for example, the cells in which the hybridization complex or the amplification product is detected) in step (b) are those which express the 187A5 gene, which do not express the mature dopaminergic neuron cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-4) detecting expression of a mature dopaminergic neuron cell marker gene, or a protein thereof, with respect to the cells in which reactivity is detected (for example, the cells in which the hybridization complex or the amplification product is detected) in step (b). In this case, in step (e-4), the cells in which the expression of the mature dopaminergic neuron cell marker gene, or the protein thereof is not detected are those which express the 187A5 gene, which do not express the mature dopaminergic neuron cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the 187A5 protein is detected, the dopaminergic neuron progenitor cells, and preferably the dopaminergic neuron proliferative progenitor cells can be detected or selected with high accuracy by using together a dopaminergic neuron proliferative progenitor cell marker gene other than the 187A5 gene or a protein thereof, and detecting not only the 187A5 protein but also expression of the dopaminergic neuron proliferative progenitor cell marker gene other than the 187A5 gene, or the protein thereof.

Specifically, in step (c), the dopaminergic neuron progenitor cells, and preferably the dopaminergic neuron proliferative progenitor cells can be detected or selected with high accuracy by using, as the cell sample to be tested, the cells in which the expression of the dopaminergic neuron proliferative progenitor cell marker gene other than the 187A5 gene, or the protein thereof is detected. In this case, the cells in which reactivity is detected (for example, the cells in which the antigen-antibody complex is detected) in step (d) are those which have the existence of the 187A5 protein, and which express the dopaminergic neuron proliferative progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-1) detecting expression of a dopaminergic neuron proliferative progenitor cell marker gene other than the 187A5 gene, or a protein thereof, with respect to the cells in which reactivity is detected (for example, the cells in which the antigen-antibody complex is detected) in step (d). In this case, in step (e-1), the cells in which the expression of the dopaminergic neuron proliferative progenitor cell marker gene other than the 187A5 gene, or the protein thereof is detected are those which have the existence of the 187A5 protein, and which express the dopaminergic neuron proliferative progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the 187A5 protein is detected, by using together a postmitotic dopaminergic neuron precursor cell marker gene or a protein thereof, it can be confirmed that the 187A5 protein is expressed but the expression of the postmitotic dopaminergic neuron precursor cell marker gene, or the protein thereof is not detected. Thus, the dopaminergic neuron progenitor cells, and preferably the dopaminergic neuron proliferative progenitor cells can be detected or selected with high accuracy.

Specifically, in step (c), the dopaminergic neuron progenitor cells, and preferably the dopaminergic neuron proliferative progenitor cells can be detected or selected with high accuracy by using, as the cell sample to be tested, the cells in which the expression of the postmitotic dopaminergic neuron precursor cell marker gene, or the protein thereof is not detected. In this case, the cells in which reactivity is detected (for example, the cells in which the antigen-antibody complex is detected) in step (d) are those which have the existence of the 187A5 protein, which do not express the postmitotic dopaminergic neuron precursor cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-2) detecting expression of a postmitotic dopaminergic neuron precursor cell marker gene, or a protein thereof, with respect to the cells in which reactivity is detected (for example, the cells in which the antigen-antibody complex is detected) in step (d). In this case, in step (e-2), the cells in which the expression of the postmitotic dopaminergic neuron precursor cell marker gene, or the protein thereof is not detected are those which have the existence of the 187A5 protein, which do not express the postmitotic dopaminergic neuron precursor cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the 187A5 protein is detected, the dopaminergic neuron progenitor cells, and preferably the dopaminergic neuron proliferative progenitor cells can be detected or selected with high accuracy by using together a dopaminergic neuron progenitor cell marker gene other than the 187A5 gene or a protein thereof, and detecting not only the 187A5 protein but also expression of the dopaminergic neuron progenitor cell marker gene other than the 187A5 gene, or the protein thereof.

Specifically, in step (c), the dopaminergic neuron progenitor cells, and preferably the dopaminergic neuron proliferative progenitor cells can be detected or selected with high accuracy by using, as the cell sample to be tested, the cells in which the dopaminergic neuron progenitor cell marker gene other than the 187A5 gene, or the protein thereof is detected. In this case, the cells in which reactivity is detected (for example, the cells in which the antigen-antibody complex is detected) in step (d) are those which have the existence of the 187A5 protein, and which express the dopaminergic neuron progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-3) detecting expression of a dopaminergic neuron progenitor cell marker gene other than the 187A5 gene, or a protein thereof, with respect to the cells in which reactivity is detected (for example, the cells in which the antigen-antibody complex is detected) in step (d). In this case, in step (e-3), the cells in which the expression of the dopaminergic neuron progenitor cell marker gene other than the 187A5 gene, or the protein thereof is detected are those which have the existence of the 187A5 protein, and which express the dopaminergic neuron progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the 187A5 protein is detected, by using together a mature dopaminergic neuron cell marker gene or a protein thereof, it can be confirmed that the 187A5 protein is expressed but the expression of the mature dopaminergic neuron cell marker gene, or the protein thereof is not detected. Thus, the dopaminergic neuron progenitor cells, and preferably the dopaminergic neuron proliferative progenitor cells can be detected or selected with high accuracy.

Specifically, in step (c), the dopaminergic neuron progenitor cells, and preferably the dopaminergic neuron proliferative progenitor cells can be detected or selected with high accuracy by using, as the cell sample to be tested, the cells in which the expression of the mature dopaminergic neuron cell marker gene, or the protein thereof is not detected. In this case, the cells in which reactivity is detected (for example, the cells in which the antigen-antibody complex is detected) in step (d) are those which have the existence of the 187A5 protein, which do not express the mature dopaminergic neuron cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-4) detecting expression of a mature dopaminergic neuron cell marker gene, or a protein thereof, with respect to the cells in which reactivity is detected (for example, the cells in which the antigen-antibody complex is detected) in step (d). In this case, in step (e-4), the cells in which the expression of the mature dopaminergic neuron cell marker gene, or the protein thereof is not detected are those which have the existence of the 187A5 protein, which do not express the mature dopaminergic neuron cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

"The dopaminergic neuron proliferative progenitor cell marker gene other than the 187A5 gene or the protein thereof" is a "dopaminergic neuron proliferative progenitor cell marker gene other than the 187A5 gene" or a "dopaminergic neuron proliferative progenitor cell marker protein other than the 187A5 protein".

"The dopaminergic neuron proliferative progenitor cell marker gene other than the 187A5 gene" includes a dopaminergic neuron proliferative progenitor cell marker gene other than the 187A5 gene which is expressed in the mesencephalon most ventral ventricular zone (VZ region), and includes an Lrp4 gene, a Nato3 gene, an Msx1 gene, an Msx2 gene and a Mash1 gene.

The Lrp4 gene is described in WO 2004/065599. The Nato3 gene is described in WO 2007/021003. The Msx1 gene and the Msx2 gene are described in WO 2007/021004. The Mash1 gene is described in Kele J, Simplicio N, Ferri A L, Mira H, Guillemot F, Arenas E, Ang S L. Neurogenin 2 is required for the development of ventral mesencephalon dopaminergic neurons. Development. 2006 February; 133 (3): 495-505.

The detection of the dopaminergic neuron proliferative progenitor cell marker gene other than the 187A5 gene is not particularly limited as long as using a method by which expression of the known gene can be detected, and, for example, includes the hybridization method and the nucleic acid amplification method, as described above.

"The dopaminergic neuron proliferative progenitor cell marker protein other than the 187A5 protein" includes a dopaminergic neuron proliferative progenitor cell marker protein other than the 187A5 protein which is expressed in the mesencephalon most ventral ventricular zone (VZ region), and, preferably, includes a protein detected only in dopaminergic neuron proliferative progenitor cells.

Such a protein includes proteins of an Lrp4 gene, a Nato3 gene, an Msx1 gene, an Msx2 gene and a Mash1 gene.

The detection of the dopaminergic neuron proliferative progenitor cell marker protein other than the 187A5 protein is not particularly limited as long as using a method by which expression of the known protein can be detected, and, for example, includes the antigen-antibody reaction method, as described above.

"The postmitotic dopaminergic neuron precursor cell marker gene or the protein thereof" includes a gene expressed in the mesencephalon most ventral mantle layer (ML region) or a protein thereof, and includes a Nurr1 gene, an En1 gene, an En2 gene, a Ptx3 gene and a TH gene. Moreover, the marker gene includes a gene expressed in the mesencephalon most ventral ventricular zone (VZ region) or a protein thereof, and includes a 65B13 gene.

The Nurr1 gene is described in Science. 1997 11; 276 (5310): 248-50. The En1 gene is described in J. Neurosci. 2001 21 (9): 3126-34. The En2 gene is described in J. Neurosci. 2001 21 (9): 3126-34. The Ptx3 gene is described in Proc. Natl. Acad. Sci. 1997 94: 13305-10. The TH gene is described in Science. 1997 11; 276 (5310): 248-50. The 65B13 gene is described in WO 2004/038018.

The detection of the postmitotic dopaminergic neuron precursor cell marker gene or the protein thereof is not particularly limited as long as using a method by which expression of the known gene or the protein thereof can be detected, and, for example, includes the hybridization method, the nucleic acid amplification method and the antigen-antibody reaction method, as described above.

"The dopaminergic neuron progenitor cell marker gene other than the 187A5 gene or the protein thereof" is a "dopaminergic neuron progenitor cell marker gene other than the 187A5 gene" or a "dopaminergic neuron progenitor cell marker protein other than the 187A5 protein".

"The dopaminergic neuron progenitor cell marker gene other than the 187A5 gene" includes a dopaminergic neuron progenitor cell marker gene other than the 187A5 gene which is expressed in the mesencephalon most ventral region, and includes an Lmx1a gene.

The Lmx1a gene is described in WO 2005/052190.

The detection of the dopaminergic neuron progenitor cell marker gene other than the 187A5 gene is not particularly limited as using a method by which expression of the known gene can be detected, and, for example, includes the hybridization method and the nucleic acid amplification method, as described above.

"The dopaminergic neuron progenitor cell marker protein other than the 187A5 protein" includes a dopaminergic neuron progenitor cell marker protein other than the 187A5 protein which is expressed in the mesencephalon most ventral region. Such a protein includes a protein of an Lmx1a gene.

The detection of the dopaminergic neuron progenitor cell marker protein other than the 187A5 protein is not particularly limited as long as using a method by which expression of the known protein can be detected, and, for example, includes the antigen-antibody reaction method, as described above.

"The mature dopaminergic neuron cell marker gene" includes a DAT gene.

The DAT gene is described in Development 2003 131: 1145-55.

The detection of the mature dopaminergic neuron cell marker gene or the protein thereof is not particularly limited as long as using a method by which expression of the known gene or the protein thereof can be detected, and, for example, includes the hybridization method, the nucleic acid amplification method and the antigen-antibody reaction method, as described above.

Moreover, the accuracy of the detection or selection of the dopaminergic neuron progenitor cells, and preferably the dopaminergic neuron proliferative progenitor cells can be further enhanced by using together a vector comprising a gene construct in which a promoter of the 187A5 gene is operably linked to a marker gene.

Therefore, according to the detection method according to the present invention, the dopaminergic neuron progenitor cells, and preferably the dopaminergic neuron proliferative progenitor cells can be detected or selected with higher accuracy by using together a gene construct in which a promoter of the 187A5 gene is operably linked to a marker gene, and detecting not only expression of the 187A5 gene, or the protein thereof but also expression of the marker gene.

The detection of the dopaminergic neuron progenitor cells by using the vector comprising a gene construct in which a promoter of the 187A5 gene is operably linked to a marker gene can be performed, for example, according to Japanese Patent Laid-Open Publication No. 2002-51775.

A marker gene that can be detected under the control of a promoter/enhancer of the 187A5 gene expressed in dopaminergic neuron progenitor cells is introduced into each cell in a cell population, and the expression of the marker gene is detected. Thus, the dopaminergic neuron progenitor cells can be detected.

Specifically, the dopaminergic neuron progenitor cells can be detected or selected by performing the steps of transforming the cell sample to be tested, with a vector comprising a gene construct in which a promoter of the gene according to the present invention is operably linked to a marker gene, and detecting expression of the marker gene in the cell sample to be tested. In this case, in the step, the cells in which the expression of the marker gene is detected can be determined as the detected or selected dopaminergic neuron progenitor cells, and preferably the detected or selected dopaminergic neuron proliferative progenitor cell with high accuracy.

The nucleotide sequence of the "promoter of the gene according to the present invention" used herein includes a nucleotide sequence of a promoter region obtained by expression region analysis of the 187A5 gene to be described later, and also includes a modified sequence thereof having approximately equivalent promoter activity.

The "marker gene" used herein may be a marker gene that can be detected under the control of a promoter/enhancer of the 187A5 gene, and includes GFP.

The "gene construct" used herein may have a structure in which the 187A5 gene is linked upstream or downstream of the marker gene under the control of an expression control sequence (including a promoter, an enhancer, or the like) of the 187A5 gene. In addition, a gene encoding the maker can be knocked in to the 187A5 gene locus. As preferable embodiments of the gene construct, constructs having structures schematically described in 2 to 4 in FIG. 15 can be exemplified.

[Detection Kit]

The present invention provides a detection kit for performing the detection method according to the present invention.

The first embodiment of the detection kit according to the present invention includes a detection kit for performing the first embodiment of the detection method according to the present invention, and specifically, includes a kit for detecting expression of a 187A5 gene, comprising at least the probe according to the present invention. This probe may be labeled. The detection kit detects the expression of the 187A5 gene by a hybrid formation method. Therefore, the detection kit of the first embodiment can optionally further include various reagents for performing the hybrid formation method, for example, a substrate compound for use in the detection of a label, a hybridization buffer, instructions, equipment, and/or so forth.

Moreover, a detection kit for performing the detection with high accuracy includes the kit further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the detection kit further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

The second embodiment of the detection kit according to the present invention includes a detection kit for performing the second embodiment of the detection method according to the present invention, and specifically, includes a kit for detecting expression of a 187A5 gene, comprising at least the primer according to the present invention or the primer set according to the present invention. The detection kit detects the expression of the 187A5 gene by the nucleic acid amplification method. Therefore, the detection kit of the second embodiment can optionally further include various reagents for performing the nucleic acid amplification method, for example, a buffer, an internal standard indicating that the amplification reaction can normally progress, instructions, equipment, and/or so forth.

Moreover, a detection kit for performing the detection with high accuracy includes the kit further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the detection kit further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

The third embodiment of the detection kit according to the present invention includes a detection kit for performing the third embodiment of the detection method according to the present invention, and specifically, includes a kit for detecting a 187A5 protein, comprising at least the antibody according to the present invention. This antibody may be labeled. The detection kit detects the expression of the 187A5 protein by detecting the antigen-antibody reaction. Therefore, the detection kit of the third embodiment can optionally further include various reagents for performing the antigen-antibody reaction, for example, a secondary antibody for use in an ELISA method or the like, a coloring reagent, a buffer, instructions, equipment, and/or so forth.

Moreover, a detection kit for performing the detection with high accuracy includes the kit further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the detection kit further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

Furthermore, a detection kit for performing the detection with high accuracy includes the detection kits of the first to third embodiment according to the present invention, further comprising a vector comprising a gene construct in which a promoter of the 187A5 gene is operably linked to a marker gene.

[Agent for Detection]

The present invention provides an agent for detection for performing the detection method according to the present invention.

The first embodiment of the agent for detection according to the present invention includes an agent for detection for performing the first embodiment of the detection method according to the present invention, and specifically, includes an agent for detecting expression of a 187A5 gene, comprising at least the probe according to the present invention. This probe may be labeled. The agent for detection detects the expression of the 187A5 gene by a hybrid formation method. Therefore, the agent for detection of the first embodiment can optionally further includes various reagents for performing the hybrid formation method, for example, a substrate compound for use in the detection of a label, a hybridization buffer, instructions, equipment, and/or so forth.

Moreover, an agent for detection for performing the detection with high accuracy includes the agent for detection further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the agent for detection further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

The second embodiment of the agent for detection according to the present invention includes an agent for detection for performing the second embodiment of the detection method according to the present invention, and specifically, includes an agent for detecting expression of a 187A5 gene, comprising at least the primer according to the present invention or the primer set according to the present invention. The agent for detection detects the expression of the 187A5 gene by the nucleic acid amplification method. Therefore, the agent for detection of the second embodiment can optionally further include various reagents for performing the nucleic acid amplification method, for example, a buffer, an internal standard indicating that the amplification reaction can normally progress, instructions, equipment, and/or so forth Moreover, an agent for detection for performing the detection with high accuracy includes the agent for detection further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the agent for detection further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

The third embodiment of the agent for detection according to the present invention includes an agent for detection for performing the third embodiment of the detection method according to the present invention, and specifically, includes a agent for detecting a 187A5 protein, comprising at least the antibody according to the present invention. This antibody may be labeled. The agent for detection detects the expression of the 187A5 protein by detecting the antigen-antibody reaction. Therefore, the agent for detection of the third embodiment can optionally further include various reagents for performing the antigen-antibody reaction, for example, a secondary antibody for use in an ELISA method or the like, a coloring reagent, a buffer, instructions, equipment, and/or so forth.

Moreover, an agent for detection for performing the detection with high accuracy includes the agent for detection further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the agent for detection further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

Furthermore, an agent for detection for performing the detection with high accuracy includes the agents for detection of the first to third embodiment according to the present invention, further comprising a vector comprising a gene construct in which a promoter of the 187A5 gene is operably linked to a marker gene.

[Screening Method]

The detection method according to the present invention can be applied to screening for an effective substance for inducing differentiation into a dopaminergic neuron progenitor cell. Specifically, whether or not the addition of a candidate substance has induced the differentiation into a dopaminergic neuron progenitor cell, and preferably a dopaminergic neuron proliferative progenitor cell is determined by using expression of a 187A5 gene, or a protein thereof as an index, and thereby, the effective substance for inducing differentiation into a dopaminergic neuron progenitor cell can be screened for.

Therefore, the present invention provides a method for screening for an effective substance for inducing differentiation into a dopaminergic neuron progenitor cell, comprising the following steps of:

(i) contacting a cell that can differentiate into a dopaminergic neuron progenitor cell, with a substance to be tested; and (ii) detecting expression of a 187A5 gene, or a protein thereof in the cell that has been contacted with the substance to be tested.

The cell that can differentiate into a dopaminergic neuron progenitor cell in step (i) is preferably a cell that can differentiate into a dopaminergic neuron proliferative progenitor cell, and can be preferably collected from an embryonic mesencephalon or from culture cells containing neuron progenitor cells induced to differentiate from ES cells.

"Contacting with a substance to be tested" in step (i) can be performed, for example, by adding the substance to be tested to culture cells containing the cell that can differentiate into a dopaminergic neuron progenitor cell, and preferably a dopaminergic neuron proliferative progenitor cell.

The "substance to be tested" includes a synthesized low-molecular compound, a protein, a synthesized peptide, a purified or partially purified polypeptide, an antibody, a bacterium-releasing material (including bacterial metabolites) and a nucleic acid (such as antisense, ribozyme and RNAi), and is preferably a compound or a salt thereof, or a solvate thereof (for example, a hydrate), but is not limited thereto. The "substance to be tested" may be a novel substance or a known substance.

In step (ii), according to the detection method according to the present invention, the expression of the 187A5 gene, or the protein thereof can be detected.

Specifically, steps (a-1) and (b-1) are performed for the detection by using the hybridization method. Steps (a-2) and (b-2) are performed for the detection by using the nucleic acid amplification method. Steps (c-1) and (d-1) are performed for the detection by using the antigen-antibody reaction method. Thus, the expression of the 187A5 gene, or the protein thereof can be detected.

In step (ii), when the expression of the 187A5 gene, or the protein thereof is detected in the cell sample to be tested by contacting the substance to be tested, the substance can be determined as the effective substance for inducing differentiation into a dopaminergic neuron progenitor cell, and preferably a dopaminergic neuron proliferative progenitor cell.

The substance specified by the screening method according to the present invention can be used as the effective substance for inducing differentiation into a dopaminergic neuron progenitor cell, and preferably a dopaminergic neuron proliferative progenitor cell.

The present invention provides the method for screening for an effective substance for inducing differentiation into a dopaminergic neuron progenitor cell, further comprising the following step of:

(iii-1) detecting expression of a dopaminergic neuron proliferative progenitor cell marker gene other than the 187A5 gene, or a protein thereof in the cell that has been contacted with the substance to be tested.

When the expression of the 187A5 gene, or the protein thereof is detected in step (ii), and the expression of the dopaminergic neuron proliferative progenitor cell marker gene other than the 187A5 gene, or the protein thereof is detected in step (iii-1), the substance can be determined as the effective substance for inducing differentiation into a dopaminergic neuron progenitor cell, and preferably a dopaminergic neuron proliferative progenitor cell, with high accuracy.

Step (iii-1) may be performed after step (i) and may be performed before or after step (ii).

The present invention provides the method for screening for an effective substance for inducing differentiation into a dopaminergic neuron progenitor cell, further comprising the following step of:

(iii-2) detecting expression of a postmitotic dopaminergic neuron precursor cell marker gene, or a protein thereof in the cell that has been contacted with the substance to be tested.

When the expression of the 187A5 gene, or the protein thereof is detected in step (ii), but the postmitotic dopaminergic neuron precursor cell marker gene or the protein thereof is not detected in step (iii-2), the substance can be determined as the effective substance for inducing differentiation into a dopaminergic neuron progenitor cell, and preferably a dopaminergic neuron proliferative progenitor cell, with high accuracy.

Step (iii-2) may be performed after step (i) and may be performed before or after step (ii).

"The dopaminergic neuron proliferative progenitor cell marker gene other than the 187A5 gene or the protein thereof" is a "dopaminergic neuron proliferative progenitor cell marker gene other than the 187A5 gene" or a "dopaminergic neuron proliferative progenitor cell marker protein other than the 187A5 protein".

"The dopaminergic neuron proliferative progenitor cell marker gene other than the 187A5 gene" includes a dopaminergic neuron proliferative progenitor cell marker gene other than the 187A5 gene which is expressed in the mesencephalon most ventral ventricular zone (VZ region), and includes an Lrp4 gene, a Nato3 gene, an Msx1 gene, an Msx2 gene and a Mash1 gene.

The detection of the dopaminergic neuron proliferative progenitor cell marker gene other than the 187A5 gene is not particularly limited as long as using a method by which the expression of the known gene can be detected, and, for example, includes the hybridization method and the nucleic acid amplification method.

"The dopaminergic neuron proliferative progenitor cell marker protein other than the 187A5 protein" includes a dopaminergic neuron proliferative progenitor cell marker protein other than the 187A5 protein which is expressed in the mesencephalon most ventral ventricular zone (VZ region), and, preferably, includes a protein detected only in dopaminergic neuron proliferative progenitor cells.

Such a protein includes proteins of an Lrp4 gene, a Nato3 gene, an Msx1 gene, an Msx2 gene and a Mash1 gene.

The detection of the dopaminergic neuron proliferative progenitor cell marker protein other than the 187A5 protein is not particularly limited as long as using a method by which the expression of the known protein can be detected, and, for example, includes the antigen-antibody reaction method.

"The postmitotic dopaminergic neuron precursor cell marker gene or the protein thereof" includes a gene expressed in the mesencephalon most ventral mantle layer (ML region) or a protein thereof, and includes a Nurr1 gene, an En1 gene, an En2 gene, a Ptx3 gene and a TH gene. Moreover, the marker gene or the protein thereof includes a gene expressed in the mesencephalon most ventral ventricular zone (VZ region) or a protein thereof, and includes a 65B13 gene.

The detection of the postmitotic dopaminergic neuron precursor cell marker gene or the protein thereof is not particularly limited as long as using a method by which the expression of the known gene or the protein thereof can be detected, and, for example, includes the hybridization method, the nucleic acid amplification method and the antigen-antibody reaction method.

The present invention provides the method for screening for an effective substance for inducing differentiation into a dopaminergic neuron progenitor cell, further comprising the following step of:

(iii-3) transforming the cell that has been contacted with the substance to be tested, with a vector comprising a gene construct in which a promoter of the 187A5 gene is operably linked to a marker gene, and detecting expression of the marker gene in the cell.

When the expression of the 187A5 gene, or the protein thereof is detected in step (ii), and the expression of the marker gene is detected in step (iii-3), the substance can be determined as the effective substance for inducing differentiation into a dopaminergic neuron progenitor cell, and preferably a dopaminergic neuron proliferative progenitor cell, with high accuracy.

Step (iii-3) may be performed after step (i) and may be performed before or after step (ii). Furthermore, step (iii-3) may be performed after step (iii-1) or (iii-2).

[Production Method]

The detection method according to the present invention can detect or select dopaminergic neuron progenitor cells. The dopaminergic neuron progenitor cells can be used in the treatment of the Parkinson's disease. Therefore, the dopaminergic neuron progenitor cells for use in the treatment of the Parkinson's disease can be produced from dopaminergic neuron progenitor cells detected or selected by using expression of a 187A5 gene, or a protein as an index.

The dopaminergic neuron progenitor cells used herein are preferably dopaminergic neuron proliferative progenitor cells.

The present invention provides a method for producing a dopaminergic neuron progenitor cell, comprising the following steps of:

(i) obtaining cells that can contain a dopaminergic neuron progenitor cell;

(ii) detecting or selecting the dopaminergic neuron progenitor cell by using the detection method according to the present invention; and (iii) culturing the cell obtained in step (ii).

The present invention provides a therapeutic agent for the Parkinson's disease, comprising dopaminergic neuron progenitor cells, and preferably dopaminergic neuron proliferative progenitor cells detected or selected by the detection method according to the present invention.

The present invention provides use of dopaminergic neuron progenitor cells, and preferably dopaminergic neuron proliferative progenitor cells detected or selected by the detection method according to the present invention, for the production of a drug for use in the treatment of the Parkinson's disease.

The present invention provides a method for treating the Parkinson's disease, comprising transplanting dopaminergic neuron progenitor cells, and preferably dopaminergic neuron proliferative progenitor cells detected or selected by the detection method according to the present invention, into the brain of a mammal including a human.

In the present specification, the "detection" also includes "discrimination". Moreover, the "detection" includes not only the case that cells as an object are discriminated as being cells of a particular kind but also the case that cells as an object are discriminated as not being cells of a particular kind.

EXAMPLES

Example 1

Isolation and Sequence Analysis of Dopaminergic Neuron Progenitor Cell-Selective Gene An Lrp4 gene has been identified as a cell surface marker for separating dopaminergic neuron proliferative progenitor cells (WO 2004/065599). By using an anti-Lrp4 antibody, it becomes possible to separate dopaminergic neuron proliferative progenitor cells derived from ES cells. Thus, hereinafter, the isolation and sequence analysis of a gene selective for dopaminergic neuron proliferative progenitor cells will be described.

(1) Isolation of Lrp4-Positive Cell

Figure 2:
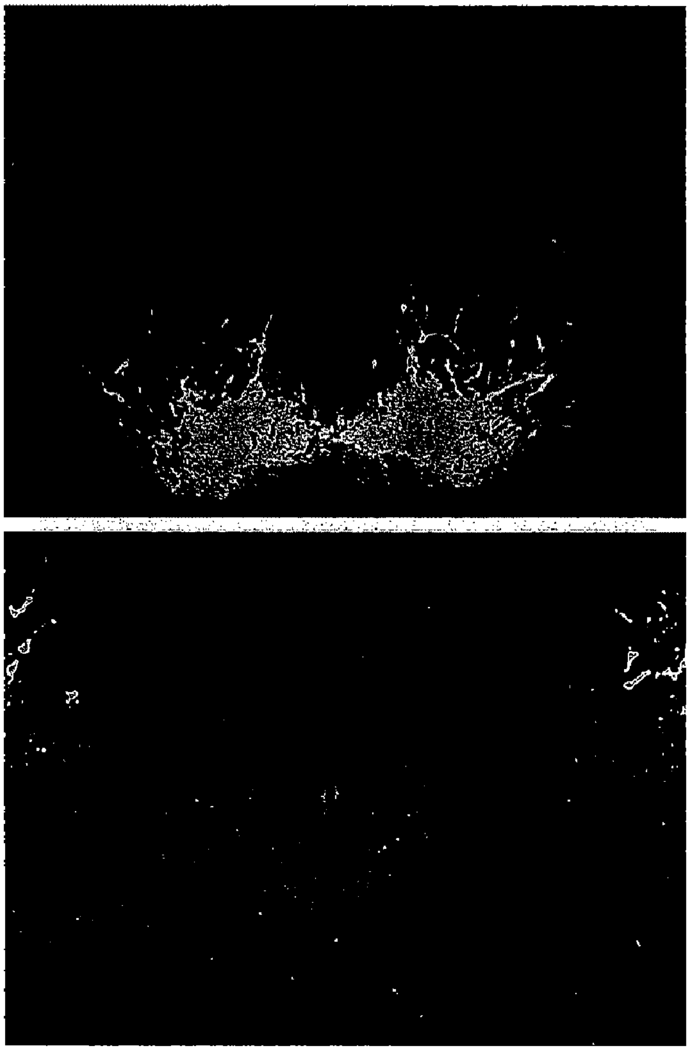
FIG. 2 shows the results of analyzing, by an immunostaining method, protein expressions of Lrp4 and TH in the mesencephalon and metencephalon of a 14.5-day rat embryo.

First, the mesencephalon and metencephalon ventral regions of a 13.5-day rat embryo were dispersed by using the accumax (MS Techno Systems), and then, without being subjected to fixation and permeabilization treatments, the cells were stained for 30 minutes at 4° C. by using an anti-Lrp4 monoclonal antibody (obtained from hybridomas (Deposition No. FERM BP-10315 and No. FERM BP-10316), diluted to 1/10, 1% fetal bovine serum (JRH), 5% fetal rat serum (JRH), 1 mM EDTA (Invitrogen)/PBS (Sigma)). Then, by using an FACS buffer (PBS+1% fetal bovine serum (JRH)+1 mM EDTA), rinsing was performed for 3 minutes at 4° C. three times, and the cells were stained for 20 minutes at 4° C. by using a PE-labeled anti-hamster IgG antibody (Becton Dickinson, 8 μg/ml, 1% fetal bovine serum, 5% fetal rat serum, 1 mM EDTA/PBS). Then, rinsing was performed in the same manner. After the staining, Lrp4-positive cells were separated by a cell sorter (FACS vantage SE, Becton Dickinson) (FIG. 2). The total RNA was prepared from the cells immediately after the separation by using the RNeasy mini kit (Qiagen), and double-strand cDNA was synthesized by using the cDNA synthesis kit (TAKARA). Next, the synthesized cDNA was digested with the restriction enzyme RsaI (TAKARA), and then, ad2 was added thereto. The cDNA was amplified by PCR using ad2S as a primer.

The amplification was carried out under the conditions that incubation was performed for 5 minutes at 72° C., then, reactions for 30 seconds at 94° C., for 30 seconds at 65° C. and for 2 minutes at 72° C. were performed at 20 cycles, and finally, incubation was performed for 2 minutes at 72° C.

```
                                    (SEQ ID NO: 29)
ad2S: CAGCTCCACAACCTACATCATTCCGT

                                    (SEQ ID NO: 30)
ad2A: ACGGAATGATGT
```

PCR was performed by using a reaction solution with the following composition.

| | |
|---|---|
| 10xExTaq | 5 μl |
| 2.5 mM dNTP | 4 μl |
| ExTaq | 0.25 μl |
| 100 μM primer | 0.5 μl |
| cDNA | 2 μl |
| Distilled water | 38.25 μl |

Next, by using the cDNAs corresponding to the amplified cDNA of 4 ng, 0.4 ng and 0.04 ng as templates, PCR was performed in the following reaction system.

| | |
|---|---|
| 10xExTaq | 1 μl |
| 2.5 mM dNTP | 0.8 μl |
| ExTaq | 0.05 μl |
| 100 μM primer | 0.1 μl for each |
| cDNA | 1 μl |
| Distilled water | 6.95 μl |

After Incubation for 2 minutes at 94° C., the amplification reactions were performed for 30 seconds at 94° C., for 30 seconds at 65° C. and for 2 minutes at 72° C., and finally, incubation was performed for 2 minutes at 72° C. The amplifications of PCR were performed at 26 cycles.

The following primers were used in the PCR.

```
                                    (SEQ ID NO: 31)
Lrp4: TAGTCTACCACTGCTCGACTGTAACG

                                    (SEQ ID NO: 32)
CAGAGTGAACCCAGTGGACATATCTG

                                    (SEQ ID NO: 33)
Lmx1a: TGGTTCAGGTGTGGTTCCAGAACCAG

                                    (SEQ ID NO: 34)
GAGTTGTAGACGCTCTGTTCAATGGC
```

Figure 3:
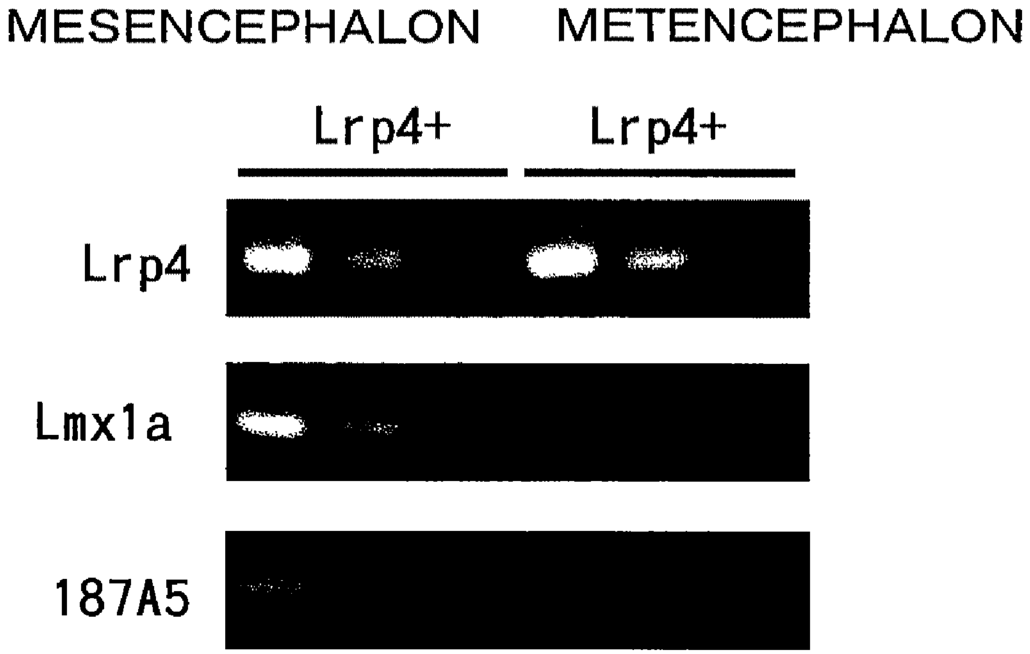
FIG. 3 shows the results of analyzing, by a RT-PCR method, mRNA expressions of 187A5, Lmx1a and Lrp4 in mesencephalon and metencephalon Lrp4-positive cells.

As a result, the Lrp4 gene is expressed at the approximately equal level in any of the mesencephalon and metencephalon Lrp4-positive cells. However, it was confirmed that an Lmx1a gene (WO 2005/052190), which is a marker gene of dopaminergic neurons and dopaminergic neuron progenitor cells, is strongly expressed only in the mesencephalon Lrp4-positive cells (FIG. 3). Therefore, it is thought that the mesencephalon Lrp4-positive cells contain the dopaminergic neuron proliferative progenitor cells, but the metencephalon Lrp4-positive cells do not contain the dopaminergic neuron proliferative progenitor cells.

Thus, next, by using this sample, a gene specific for the Lrp4-positive cells in the mesencephalon was searched by a subtraction (N-RDA) method (described in WO 2004/065599). As a result, one (187A5) of the isolated cDNA fragments was a fragment encoding a functionally unknown gene. Next, expression of this gene was confirmed by the above-described RT-PCR method using the following primers.

```
                                    (SEQ ID NO: 35)
187A5: ACCAGGAAGGACAATGCCATTCGTCC

                                    (SEQ ID NO: 36)
CCTTCTTCACCTTGGCTCTTAGGATG
```

As a result, it was confirmed that the 187A5 gene is specifically expressed in the Lrp4-positive cells in the mesencephalon in the same manner as the Lmx1a gene (FIG. 3).

(2) Sequence Analysis

As a result of database search, rat and mouse cDNA sequences that are thought to be the full length of this gene were obtained (for example, Sequence Number: Mouse 187A5 AK028289, Mouse 187A5 AK157823 (frame shift), Mouse 187A5 AK028541, Mouse 187A5 XM_485684 (alternative), Mouse 187A5 AK163356 (frame shift), Rat 187A5 XM_344107 (predicted)). A partial sequence (SEQ ID NO: 1) that is thought to be a human homologous gene was also obtained, but the full length could not be obtained. Thus, homology search was performed with respect to the human genomic sequence, and a human cDNA sequence was predicted. However, for the neighborhood of the 5' end, a region having high homology could not be found. Therefore, sequence determination was performed by using a 5' RACE method.

From 1 μg of human embryonic brain mRNA (Clontech), cDNA was amplified by using the 5' RACE core kit (TAKARA), and self-ligation was performed. By using the following primers, the cDNA 5' end was amplified. The obtained fragments were cloned into pCRII (Invitrogen), and sequence determination was performed.

```
                                    (SEQ ID NO: 37)
RT Reaction: CATCCCAGTCTC

                                    (SEQ ID NO: 38)
Primary PCR: TGGAGAAGGTTGTGCCTCTGGACTTG

                                    (SEQ ID NO: 39)
CTGGTTGGCTTCCTTGAGGAAGAAGG

                                    (SEQ ID NO: 40)
Secondary PCR: TCCTGCGGGACAAAGTCTACCTGAGC

                                    (SEQ ID NO: 41)
CTGAGGATGTGGTAGCTCACAGGTAG
```

The PCR reaction was performed with the following composition.

| | | |
|---|---|---|
| 10xExTaq | 5 | μl |
| 2.5 mM dNTP | 4 | μl |
| ExTaq | 0.25 | μl |
| 100 μM primer | 0.5 | μl for each |
| Template | 1 | μl |
| DMSO | 1.5 | μl |
| Distilled water | 37.25 | μl |

After incubation for 2 minutes at 94° C., the amplification reactions were performed for 30 seconds at 94° C., for 30 seconds at 65° C. and for 2 minutes at 72° C., and finally, incubation was performed for 2 minutes at 72° C. The amplifications of PCR were performed at 35 cycles for primary PCR, and secondary PCR was performed by using the primary PCR products diluted 10-fold as templates and performing amplifications at 20 cycles.

Next, in order to confirm that the predicted sequence is correct, each of three divided regions thereof was amplified by RT-PCR. The PCR products were cloned into pCRII (Invitrogen), and sequence determination was performed.

From 0.5 μg of human embryonic brain mRNA (Clontech), cDNA was amplified by using the RNA PCR kit (TAKARA). By using the cDNA as a template, PCR was performed.

The neighborhood of the 5' end was amplified by using the following primers.

```
                                    (SEQ ID NO: 42)
Human 187A5 F4: GAGGTCGACGCCACCATGCGCTCCGAGGGTGCGG
CCCCC

                                    (SEQ ID NO: 43)
Human 187a5 R1: GGGTCCATAGCTGGCATTGAGCACTG
```

The PCR reaction was performed with the following composition.

| | | |
|---|---|---|
| 10xLATaq | 5 | μl |
| $MgCl_2$ | 5 | μl |
| 2.5 mM dNTP | 8 | μl |
| LATaq | 0.5 | μl |
| 100 μM primer | 0.5 | μl for each |
| cDNA | 1 | μl |
| DMSO | 1.5 | μl |
| Distilled water | 28 | μl |

After incubation for 2 minutes at 94° C., the amplification reactions for 30 seconds at 94° C., for 30 seconds at 65° C. and for 3.5 minutes at 72° C. were performed at 35 cycles, and finally, incubation was performed for 2 minutes at 72° C.

The remaining regions were amplified by using the following primers F12 and R5 as well as F13 and R4 in combination.

(SEQ ID NO: 44)
Human 187A5 F12: CTACCTGTGAGCTACCACATCCTCAG (SEQ ID NO: 45)
Human 187A5 R5: TTCTCTGCCAGGATGGAGTCAGACAG (SEQ ID NO: 46)
Human 187A5 F13: ACTGGCAGTTCGACATCACTCACCTG (SEQ ID NO: 47)
Human 187A5 R4: GAGGAATTCCAGTACAAGGAAGGCATCTGGGC
AGG As a result of sequence determination, a protein encoding this human gene exhibited a high homology to the mouse 187A5 protein over the whole region and had 77% amino acid identity and 87% amino acid homology. Therefore, this gene is thought to be a human 187A5 homologous gene (SEQ ID NO: 1).

Example 2

Expression Analysis by In Situ Hybridization of 187A5 Gene

In order to investigate the expression pattern of the 187A5 gene in detail in the cells of dopaminergic neuron lineage, expression analysis of mRNAs of 187A5 and Lrp4 was performed by in situ hybridization according to the following protocol.

First, a DIG-probe was produced by the following method. From a 12.5-day mouse (obtained from SLC) embryo, the mesencephalon metencephalon region was cut out. The total RNA was prepared by using the RNeasy mini kit (Qiagen), and double-strand cDNA was synthesized by using the cDNA synthesis kit (TAKARA). Next, by using the synthesized cDNA as a template, cDNAs of 187A5 and Lrp4 were amplified in the following reaction system.

| | |
|---|---|
| 10xExTaq | 5 μl |
| 2.5 mM dNTP | 4 μl |
| ExTaq | 0.25 μl |
| 100 μM primer | 0.5 μl for each |
| cDNA | 1 μl |
| DMSO | 1.5 μl |
| Distilled water | 37.25 μl |

The amplification was carried out under the conditions that incubation was performed for 5 minutes at 94° C., then reactions for 30 seconds at 94° C., for 30 seconds at 65° C. and for 2 minutes at 72° C. were performed at 35 cycles, and finally, incubation was performed for 2 minutes at 72° C.

The following primers were used in the PCR.

(SEQ ID NO: 48)
187A5: AGCTGAGCCACCTTCTCAGTCCAGAC (SEQ ID NO: 49)
CCACGTCCAGGTCTTGACAAACCCAC (SEQ ID NO: 50)
Lrp4: GACAGTGAACCTTTGGTCACTGATGG (SEQ ID NO: 51)
GCCTTCCTGTCCTGGGATCAGCTTGG

The amplified cDNA fragments were cloned into pCRII (Invitrogen) and used as templates, and thereby, DIG-probes were synthesized in the following reaction system (all of the reagents were purchased from Roche).

| | |
|---|---|
| RNA Polymerase Buffer | 2 μl |
| NTP Labeling Mix | 2 μl |
| RNase Inhibitor | 1 μl |
| RNA polymerase (T7 or SP6) | 2 μl |
| Template DNA | 1 μg |
| Distilled water | Total 20 μl |

After 2 hours at 37° C., DNaseI (Roche) treatment was performed for 15 minutes at 37° C., and the DIG-RNA probe was collected by ethanol precipitation.

Next, a 12.5-day mouse embryo was excised and fixed for 2 hours at 4° C. by using 4% PFA (WAKO)/PBS. Then, the solution was replaced at 4° C. overnight by 20% sucrose (WAKO)/PBS, and then, the embryo was embedded with OCT (Sakura Seiki Co., Ltd.). Sections of 12 μm thickness were prepared, dried on slide glasses, and then fixed again for 30 minutes at room temperature by using 4% PFA. After rinsing with PBS, hybridization (1 μg/ml DIG-RNA probe, 50% formamide (Nacalai Tesque, Inc.), 5×SSC, 1% SDS, 50 μg/ml yeast RNA (Sigma), 50 μg/ml heparin) was performed for 40 hours at 68° C. Then, rinsing (50% formamide, 5×SSC, 1% SDS) was performed at 68° C., and further rinsing (50% formamide, 5×SSC) was performed at 68° C. After rinsing with 1×TBST at room temperature, blocking (blocking agent: Roche) was performed. An alkaline phosphatase-labeled anti-DIG antibody (DAKO) was reacted therewith at 4° C. overnight, and after rinsing (1×TBST, 2 mM levamisole), NBT/BCIP (DAKO) was used as the substrate for coloring.

Figure 4:
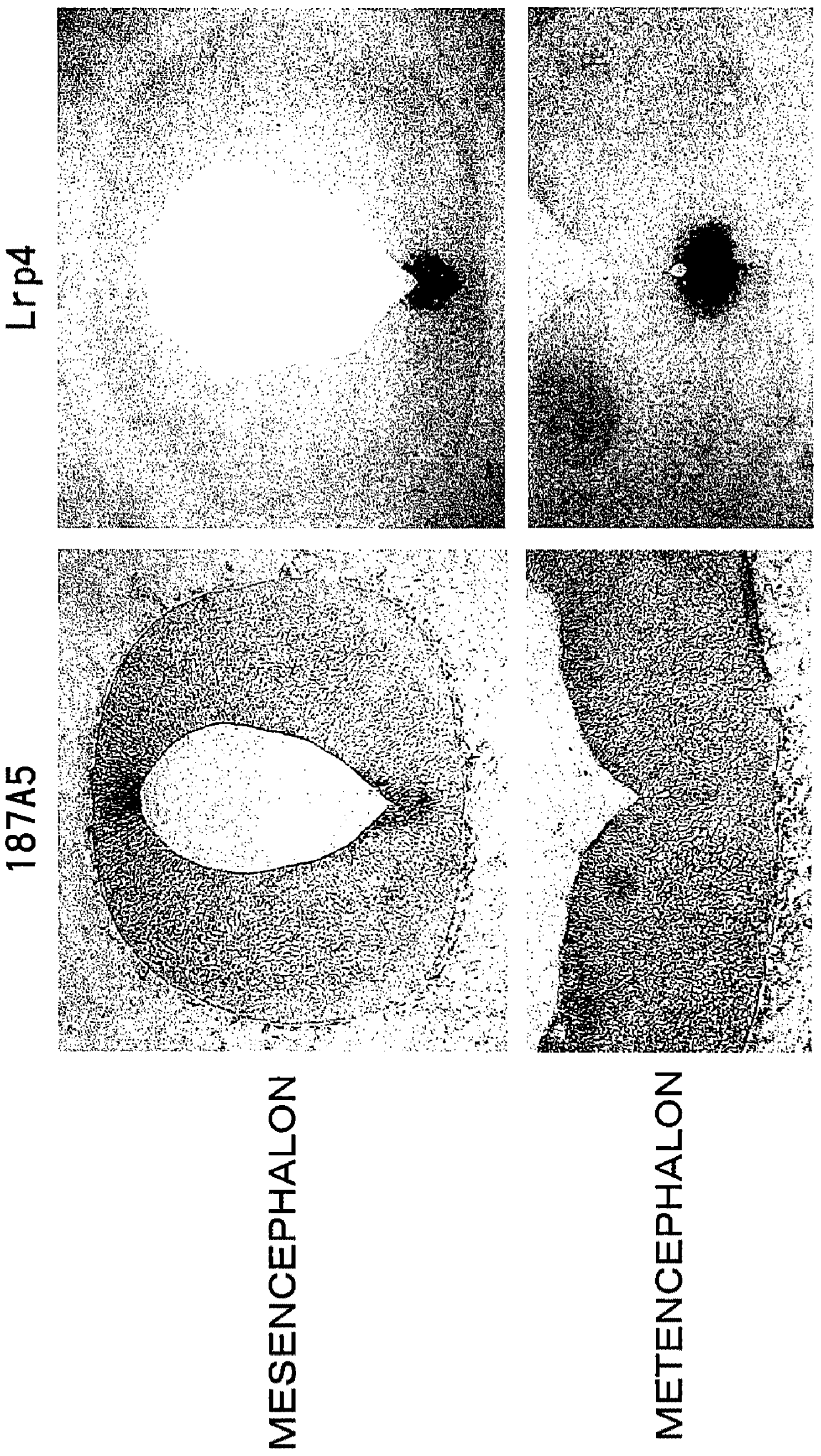
FIG. 4 shows the results of analyzing, by in situ hybridization, mRNA expressions of 187A5 and Lrp4 in the mesencephalon and metencephalon of a 12.5-day mouse embryo.

As a result, in the 12.5-day mouse embryo which is in the period of generating dopaminergic neurons, it became revealed that mRNA of 187A5 is selectively expressed in the mesencephalon most ventral ventricular zone (ventricular zone: VZ) in which the Lrp4-positive dopaminergic neuron progenitor cells exist and the mesencephalon most dorsal roof plate region (FIG. 4). On the other hand, the expression was not recognized in the metencephalon ventral region. Therefore, it was confirmed that mRNA of 187A5 is not expressed in the metencephalon floor plate cells positive for Lrp4.

From the above-described results, it became revealed that mRNA of 187A5 is selectively expressed in the dopaminergic neuron proliferative progenitor cells. Cells simultaneously expressing both of the Lrp4 and 187A5 genes are limited to the dopaminergic neuron proliferative progenitor cells that exist in the mesencephalon most ventral ventricular zone. Therefore, it is thought that the dopaminergic neuron proliferative progenitor cells can be discriminated with higher accuracy by using these markers in combination.

Example 3

Expression of 187A5 Gene in Dopaminergic Neurons Induced to Differentiate from ES Cells Whether or not the 187A5 gene is expressed when ES cells are induced to differentiate into dopaminergic neurons in vitro was studied.

First, according to the SDIA method (Kawasaki et al. Neuron. 2000 October; 28 (1): 31-40), ES cells (mouse-derived CCE strain provided from Mr. Nishikawa in Riken CDB, Kawasaki et al. Neuron. 2000 28 (1): 31-40.) were induced to differentiate into dopaminergic neurons. Lrp4-positive and Lrp4-negative cells were separated from the cells in the sixth day after the induction (Example 5 of WO 2004/065599), and the total RNA was prepared from the cells immediately after the separation. By using this total RNA as a template, cDNA was synthesized and amplified.

Moreover, according to the 5-stage method (Lee et al. (2000) Nat. Biotech. 18: 675-679, mouse dopaminergic neuron differentiation kit (R & D Systems)), ES cells (CCE) were induced to differentiate into dopaminergic neurons. Lrp4-positive and Lrp4-negative cells were separated from the cells in the seventh day of stage 4 (Example 8 of WO 2004/065599), and the total RNA was prepared from the cells immediately after the separation. By using this total RNA as a template, cDNA was synthesized and amplified.

Next, by using the cDNAs corresponding to the amplified cDNA of 4 ng, 0.4 ng and 0.04 ng as templates, PCR was performed in the following reaction system.

| | |
|---|---|
| 10xExTaq | 1 μl |
| 2.5 mM dNTP | 0.8 μl |
| ExTaq | 0.05 μl |
| 100 μM primer | 0.1 μl for each |
| cDNA | 1 μl |
| DMSO | 0.3 μl |
| Distilled water | 6.65 μl |

After incubation for 2 minutes at 94° C., the amplification reactions were performed for 30 seconds at 94° C., for 30 seconds at 65° C. and for 2 minutes at 72° C., and finally, incubation was performed for 2 minutes at 72° C. The amplifications of PCR were performed at 26 cycles.

The following primers were used in the PCR.

```
                                        (SEQ ID NO: 33)
Lmx1a: TGGTTCAGGTGTGGTTCCAGAACCAG

                                        (SEQ ID NO: 52)
TCTGAGGTTGCCAGGAAGCAGTCTCC
```

In addition, for Lrp4 and 187A5, the primers of Example 1 were used.

Figure 5:
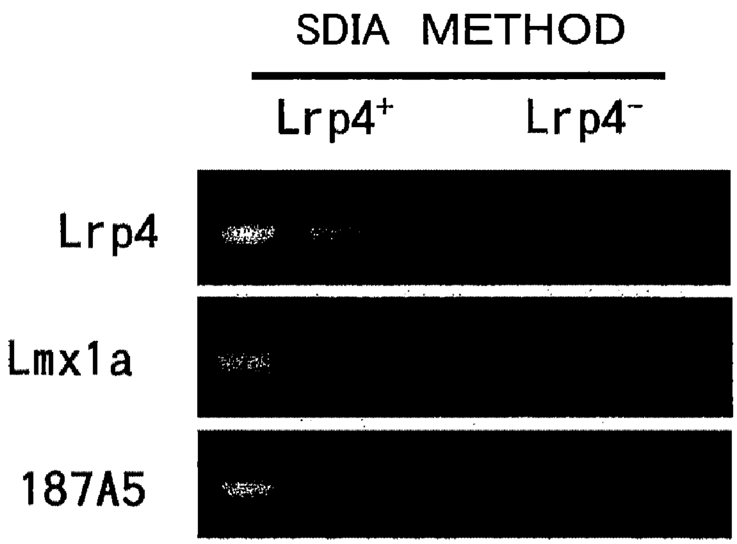
FIG. 5 shows the results of analyzing, by a RT-PCR method, mRNA expressions of 187A5, Lmx1a and Lrp4 in dopaminergic neuron proliferative progenitor cells induced to differentiate from ES cells by an SDIA method.
Figure 6:
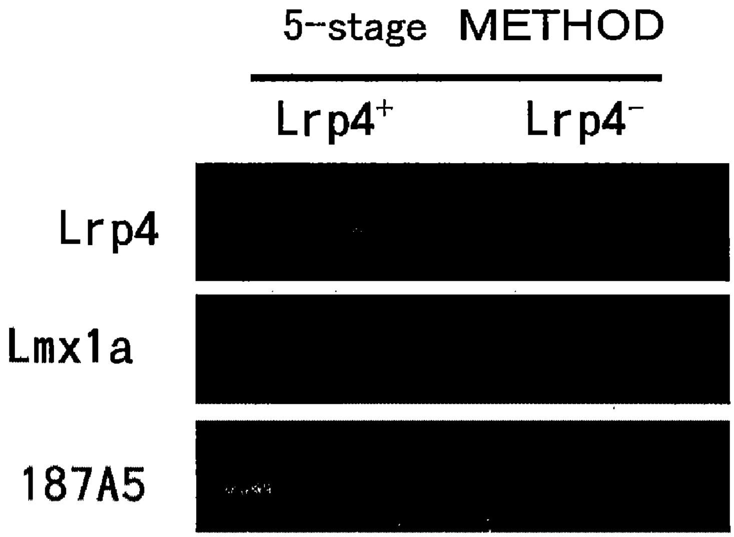
FIG. 6 shows the results of analyzing, by a RT-PCR method, mRNA expressions of 187A5, Lmx1a and Lrp4 in dopaminergic neuron progenitor cells induced to differentiate from ES cells by a 5-stage method.

As a result, it was confirmed that the 187A5 gene is expressed in the differentiation induction by any of the methods, and strongly expressed, particularly, in the Lrp4-positive cells (FIGS. 5 and 6). Therefore, it became revealed that mRNA of 187A5 is expressed in the dopaminergic neuron progenitor cells not only in the cells derived from the mouse and rat embryonic mesencephalons but also in the cells induced to differentiate by any of the SDIA method and the 5-stage method. Specifically, it became revealed that the 187A5 gene serves as a useful marker for discriminating not only the dopaminergic neuron progenitor cells derived from the embryonic mesencephalon but also the dopaminergic neuron progenitor cells induced to differentiate from ES cells in vitro.

Example 4

Expression of 187A5 Protein on Cell Surface

In the 187A5 protein, a sequence that is thought to be a transmembrane region exists at one site. If the 187A5 protein is expressed on the cell surface, 187A5-positive live cells can be separated by flow cytometry using an antibody capable of binding to the 187A5 protein and are expected to be useful in preparation of a transplant material for the Parkinson's disease or the like. Therefore, the intracellular localization of the 187A5 protein was studied.

(1) Analysis of Signal Sequence

In the case of a type I transmembrane protein, a signal sequence generally exists in the neighborhood of the N-terminal and is cleaved off immediately after the signal sequence, and thereby, the protein can be expressed on the membrane. As a result of computer search (PSORT II, http://psort.ims.u-tokyo.ac.jp/form2.html), a sequence that is predicted to be a signal sequence was not found in the mouse 187A5 gene. On the other hand, a signal sequence-like sequence existed in the neighborhood of the N-terminal of the human 187A5 gene. Therefore, whether a functional signal sequence exists in the 187A5 gene was studied.

Figure 7:
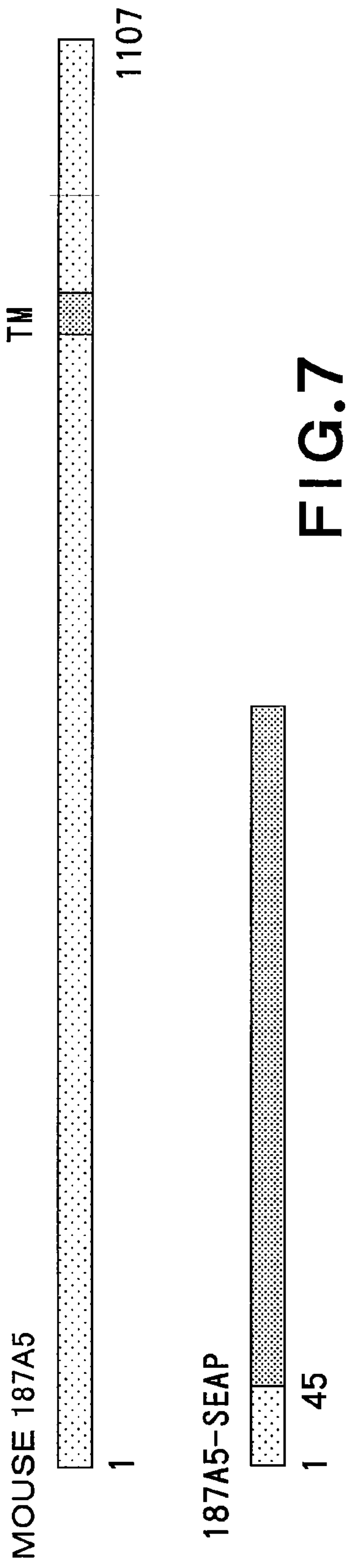
FIG. 7 shows mouse 187A5 and 187A5-SEAP.

A construct in which a region encoding the amino acids from the N-terminal to amino acid 45 in mouse cDNA was linked to signal sequence-deficient secreted alkaline phosphatase cDNA was prepared and transfected into 293E cells. A culture supernatant in the fourth day of culture was collected, and alkaline phosphatase activity was measured by using the Aurora kit (ICN) (FIG. 7).

Figure 8:
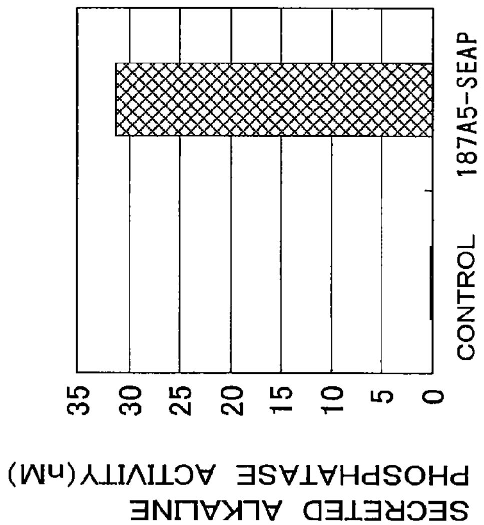
FIG. 8 shows the results of analyzing signal sequence activity of 187A5.

As a result, when signal sequence-deficient secreted alkaline phosphatase (control) is expressed, this protein is not secreted. Therefore, alkaline phosphatase activity is not recognized in the supernatant. By contrast, in the case of the fusion protein in which the N-terminal sequence was linked, strong activity was recognized in the supernatant. Therefore, it became revealed that the fusion protein is efficiently secreted by the N-terminal sequence of 187A5 (FIG. 8). Therefore, it became revealed that a functional signal sequence exists in the neighborhood of the N-terminal of 187A5. This indicates that the 187A5 protein is a type I single transmembrane molecule.

(2) Expression of 187A5 on Cell Surface (Biotinylation Method)

In order to confirm whether or not the 187A5 protein is expressed on the cell surface, whether the 187A5 protein is biotinylated when only proteins on the cell surface are biotin-labeled was studied.

A construct in which an HA tag was added to the C-terminal of 187A5 was transfected into NS20Y cells. After 2 days, the cells were rinsed with cold PBS twice, and then, 5 ml of 0.5 mg/ml EZ-link Sulfo-NHS-SS-Biotin (PIERCE) (dissolved in PBS+1 mM $CaCl_2$, 0.5 mM $MgCl_2$) was added thereto. The reaction was performed for 30 minutes at room temperature. After rinsing with cold PBS twice, the cells were collected, then suspended in 600 μl of a dissolution buffer (1% SDS, 10 mM Tris-Cl, 100 mM NaCl, 1 mM EDTA), and subjected to ultrasonication. After centrifugation for 3 minutes at 14000 rpm, the supernatant was collected. 20 μl of streptavidin beads (PIERCE) was added thereto, and after rotation for 1 hour at room temperature, rinsing was performed with a dissolution buffer twice. To the beads, 75 μl of SDS-PAGE sample buffer was added, and after 3 minutes at 100° C., the bound proteins were collected by centrifugation. The 187A5 protein was detected by western blotting using an anti-HA antibody (Roche).

Figure 9:
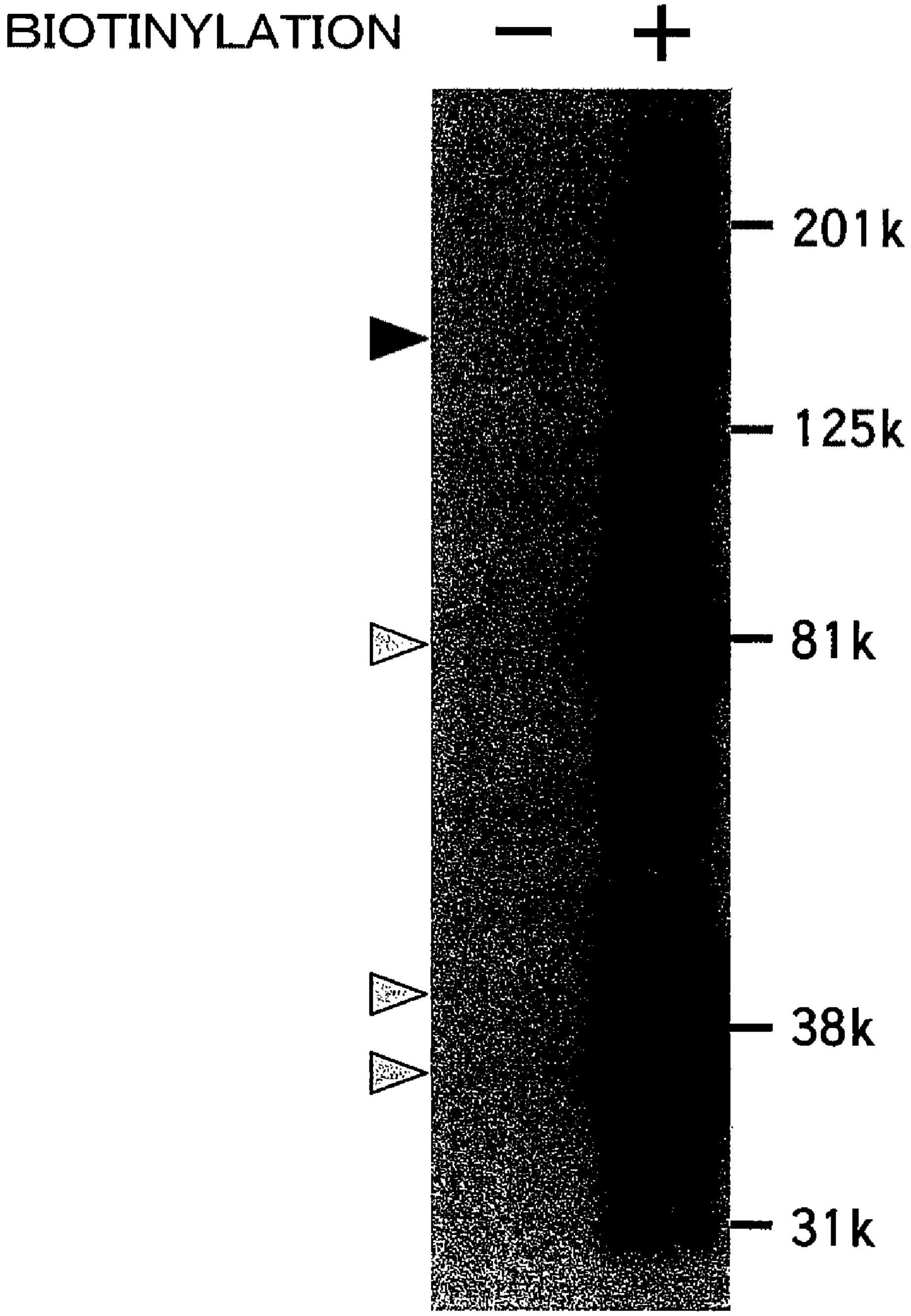
FIG. 9 shows the results of analyzing expression of a 187A5 protein on the cell surface by a biotinylation method of cell surface proteins.

As a result, it became revealed that the 187A5 protein is biotinylated with high efficiency (FIG. 9). Therefore, it is thought that the 187A5 protein is expressed on the cell surface.

(3) Expression of 187A5 on Cell Surface (FACS Analysis)

Whether the 187A5 protein can be detected by a FACS method was studied. A construct in which cDNA encoding the C-terminal side from the predicted cleavage site (amino acid 39) of 187A5 was linked immediately after a signal sequence of Preprotrypsin and a sequence encoding a FLAG tag was prepared. By expressing this construct, 187A5 in which the FLAG tag is added to the N-terminal can be expressed after the cleavage of the signal sequence. This construct was stably introduced into B300.19 cells through retrovirus vectors. The parent cells and transformants were rinsed with a FACS buffer (PBS+1% fetal bovine serum (JRH)+1 mM EDTA). Then, reaction with 10 μg/ml anti-FLAG antibody (SIGMA) was performed for 30 minutes on ice, and rinsing was performed with a FACS buffer. Sequentially, reaction with a PE-labeled anti-mouse IgG antibody (Jackson) (diluted to 1/200) was performed for 30 minutes on ice, and rinsing was performed with a FACS buffer. After staining, analysis was performed by flow cytometry (FACS calibur, Becton Dickinson).

Figure 10:
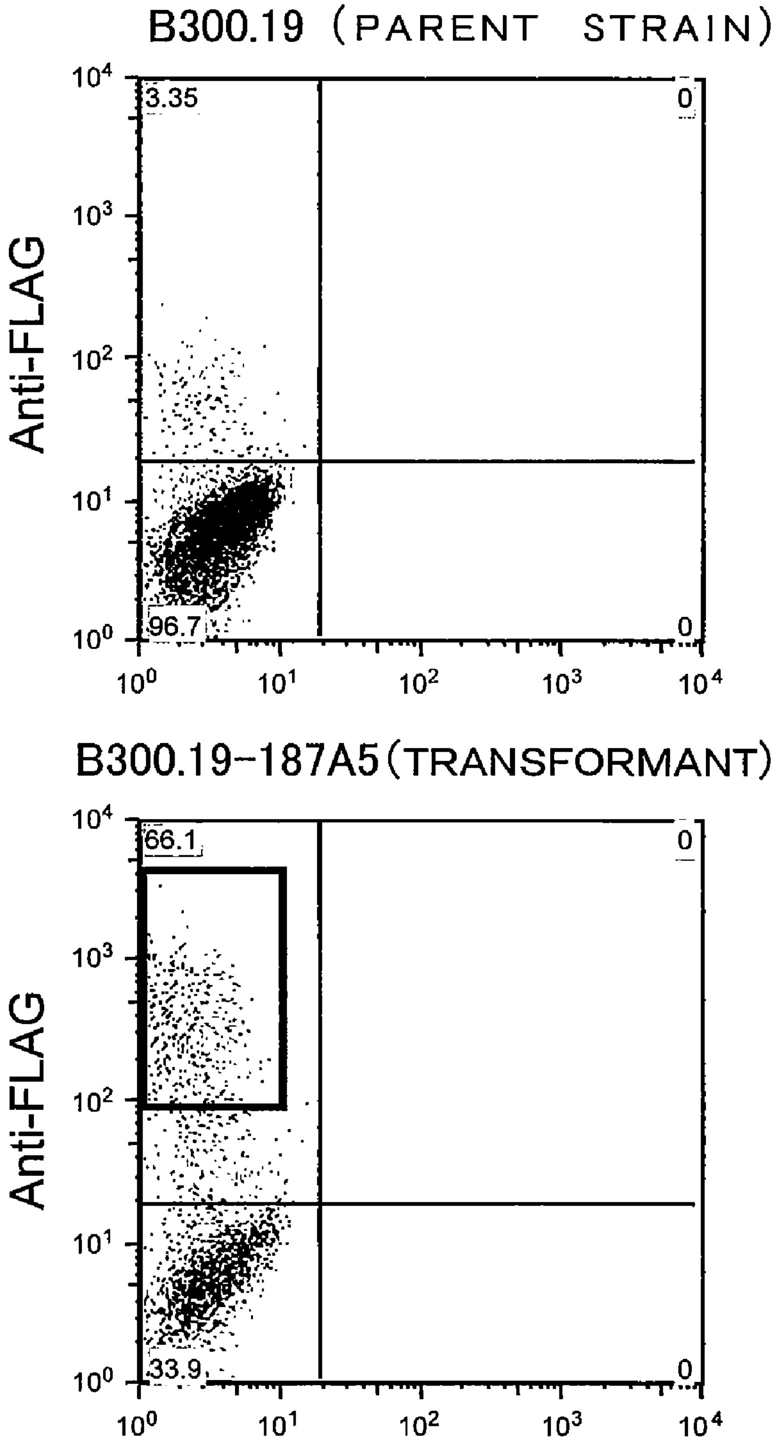
FIG. 10 shows the results of investigating expression of a 187A5 protein on the cell surface by FACS analysis. In the drawing, a boxed area represents 187A5-expressing cells.

As a result, unlike the parent strains, a population that strongly reacts with the FLAG antibody was detected in the stable transformants (FIG. 10). Therefore, it became revealed that 187A5 is expressed on the cell surface in a direction wherein the N-terminal side thereof can be located in the extracellular space, and can be detected by FACS using an antibody. Specifically, it is thought that 187A5 is useful as a marker for separating dopaminergic neuron progenitor cells as live cells.

Example 5

Expression Analysis of 187A5 Protein

By using a gene sequence encoding the extracellular region in the 187A5 gene, an anti-187A5 antibody was produced according to the following protocol, and expression analysis was performed by immunohistologic staining.

First, a gene sequence encoding the extracellular region (amino acids 1 to 919 of SEQ ID NO: 15) in the mouse 187A5 gene was gene-transfected into 293E cells, and the extracellular region of the 187A5 protein was expressed and collected. A rat was immunized with the collected protein, and then, lymphocytic cells were extracted and cell-fused with myeloma cells. From the fused cell population, a clone capable of reacting with 187A5 was selected. An anti-187A5 monoclonal antibody was purified from a culture supernatant of this clone. Next, an 11.5-day mouse embryo was fixed for 2 hours at 4° C. by using 4% PFA/PBS (−). Then, the solution was replaced at 4° C. overnight by 20% sucrose/PBS (−), and then, the embryo was embedded with OCT. Sections of 12 μm thickness were prepared, mounted on slide glasses, then dried for 30 minutes at room temperature, and moistened again with PBS (−). Then, blocking (25% Blockace (Dainippon Sumitomo Pharma Co., Ltd.)) was performed for 30 minutes at room temperature. The prepared anti-187A5 monoclonal antibody (culture supernatant diluted 2-fold, 2.5% Blockace/PBS) was reacted therewith for 2.5 hours at room temperature, and then, rinsing was performed for 10 minutes at room temperature four times by using 0.01% Triton X-100/PBS (−). A Cy3-labeled anti-rat IgG antibody (Jackson, 10 μg/ml, 2.5% Blockace/PBS) was reacted therewith for 1 hour at room temperature, and rinsing was performed in the same manner. Then, rinsing with PBS (−) was performed for 5 minutes at room temperature, and sealing was performed.

Figure 11:
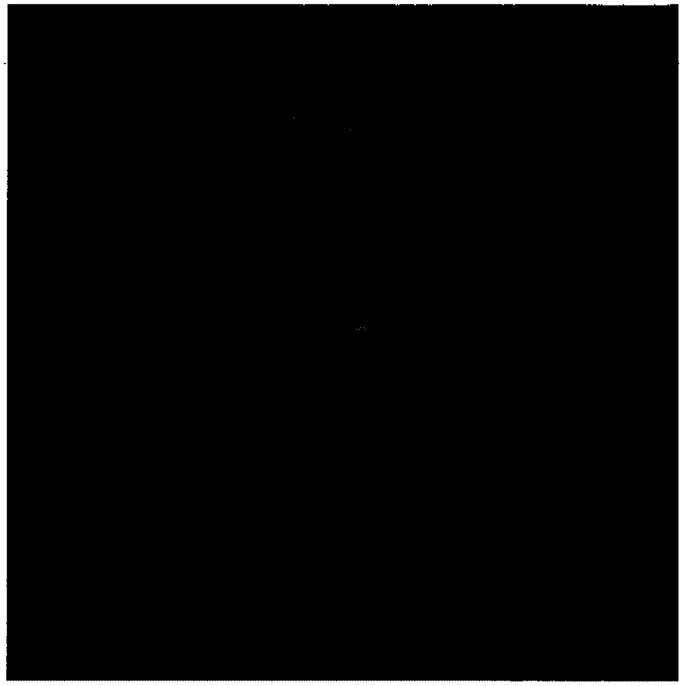
FIG. 11 shows the results of analyzing, by an immunostaining method, expression of a 187A5 protein in the mesencephalon and metencephalon ventral regions of an 11.5-day mouse embryo.
Figure 11:
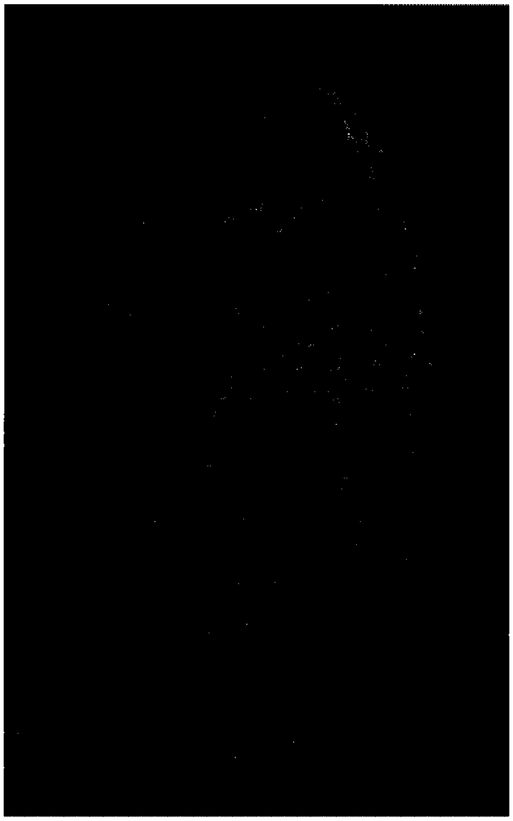

As a result of expression analysis by immunohistologic staining using the prepared anti-187A5 monoclonal antibody, as with the results of Example 2, the existence of the 187A5 protein was recognized in the mesencephalon ventral region of E11.5 which is in the period of generating dopaminergic neurons, and was not recognized in the metencephalon ventral region in which dopaminergic neurons are not generated (FIG. 11).

From these results, it was confirmed that the 187A5 protein exists in dopaminergic neuron progenitor cells.

Example 6

Detection of Cell in which 187A5 Protein Exists

By using the anti-187A5 monoclonal antibody prepared in Example 5, cells in which the 187A5 protein exists were detected by flow cytometry.

First, the mesencephalon and metencephalon ventral regions of a mouse E12.5 embryo were dispersed by using the cell dissociation buffer (Invitrogen), and then, without being subjected to fixation and permeabilization treatments, the cells were stained for 20 minutes at 4° C. by using the anti-187A5 monoclonal antibody (purified antibody diluted to 1/10, 1% fetal bovine serum, 1 mM EDTA/PBS) and an anti-Lrp4 antibody (culture supernatant diluted to 1/2, 1% fetal bovine serum, 1 mM EDTA/PBS). Then, by using 1% fetal bovine serum and 1 mM EDTA/PBS-, rinsing was performed for 3 minutes at 4° C. three times. The cells were stained for 20 minutes at 4° C. by using a biotin-labeled anti-Armenian hamster IgG antibody (Jackson, 10 μg/ml, 1% fetal bovine serum, 1 mM EDTA/PBS), and rinsing was performed in the same manner. Then, the cells were stained for 20 minutes at 4° C. by using APC-labeled streptavidin (Pharmingen, 8 μg/ml, 1% fetal bovine serum, 1 mM EDTA/PBS) and a PE-labeled anti-rat IgG antibody (Jackson, 20 μg/ml, 1% fetal bovine serum, 1 mM EDTA/PBS), and rinsing was performed in the same manner. After the staining, detection was performed by using a flow cytometer.

Figure 12:
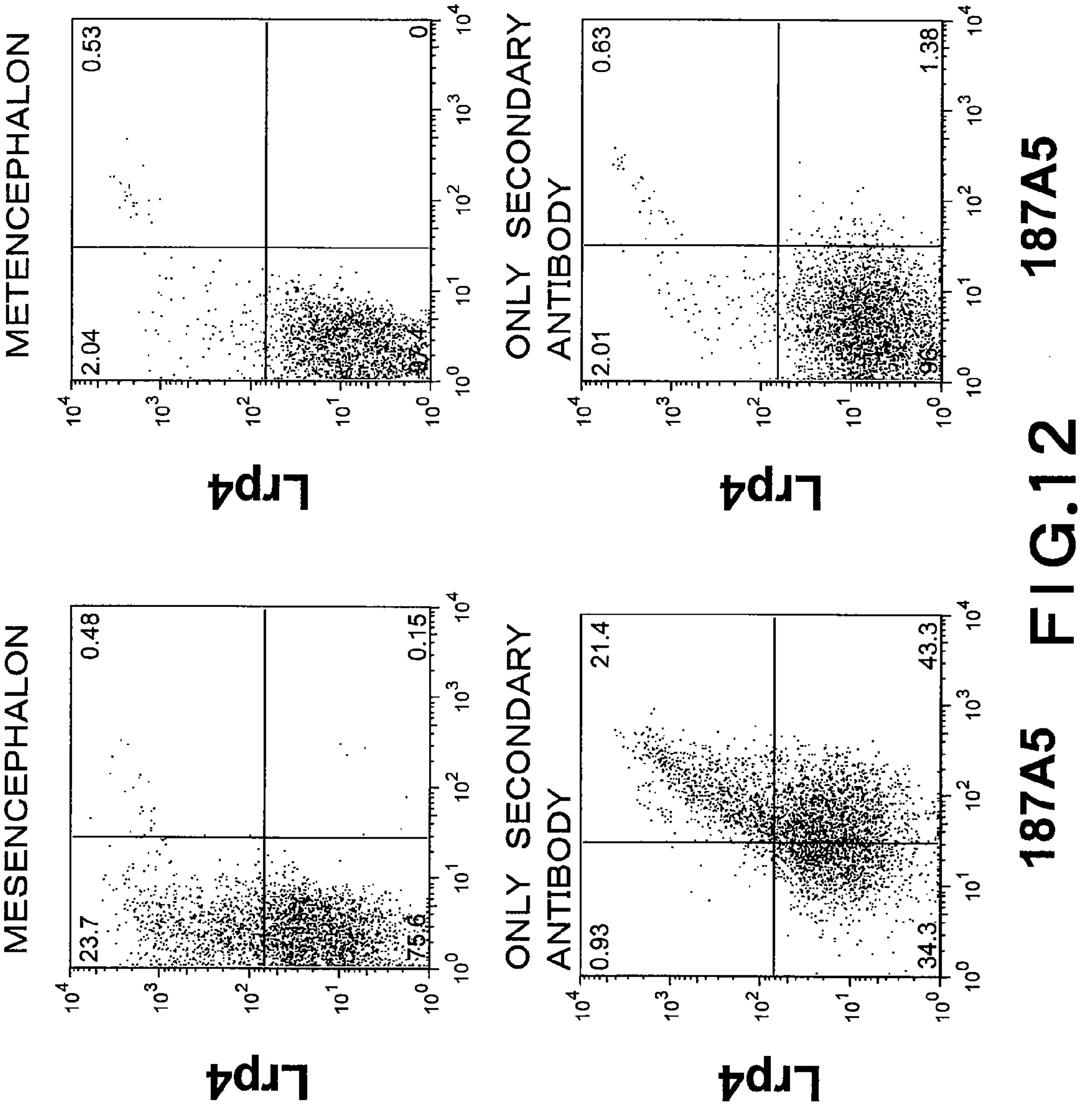
FIG. 12 shows the results of investigating, by FACS analysis, expressions of 187A5 and Lrp4 proteins in the mesencephalon and metencephalon ventral regions of a 12.5-day mouse embryo.

As a result of flow cytometry by using the prepared anti-187A5 monoclonal antibody, a cell population in which the 187A5 protein exists was detected (FIG. 12). Here, the cells in which the 187A5 protein exists can be detected without being subjected to fixation and permeabilization treatments. Therefore, it was suggested that the cells in which the 187A5 protein exists can be separated as live cells by using a flow cytometer equipped with a cell sorter. Moreover, it was confirmed that the 187A5 protein exists in all of the mesencephalon Lrp4-positive cells, namely, the dopaminergic neuron progenitor cells. On the other hand, it was confirmed that the 187A5 protein does not exist in the metencephalon Lrp4-positive cells which do not contain dopaminergic neuron progenitor cells (FIG. 12).

From these results, it was shown that the 187A5 antibody is useful for separating dopaminergic neuron progenitor cells.

Example 7

Expression of 187A5 Protein in Dopaminergic Neurons Induced to Differentiate from ES Cells The group of the cells containing the dopaminergic neuron progenitor cells induced to differentiate from ES cells in vitro by the SDIA method was dispersed by using the cell dissociation buffer (Invitrogen), and then, without being subjected to fixation and permeabilization treatments, the cells were stained for 20 minutes at 4° C. by using the anti-187A5 monoclonal antibody (purified antibody diluted to 1/10, 10% knockout serum replacement, 1% fetal bovine serum, 1 mM EDTA/SDIA differentiation medium) prepared in Example 5 and an anti-Lrp4 antibody (culture supernatant diluted to 1/2, 10% knockout serum replacement, 1% fetal bovine serum, 1 mM EDTA/SDIA differentiation medium). Then, by using 10% knockout serum replacement, 1% fetal bovine serum and 1 mM EDTA/SDIA differentiation medium, rinsing was performed for 3 minutes at 4° C. three times. The cells were stained for 20 minutes at 4° C. by using a biotin-labeled anti-Armenian hamster IgG antibody (Jackson, 10 μg/ml, 10% knockout serum replacement, 1% fetal bovine serum, 1 mM EDTA/SDIA differentiation medium), and rinsing was performed in the same manner. Then, the cells were stained for 20 minutes at 4° C. by using APC-labeled streptavidin (Pharmingen, 8 μg/ml, 10% knockout serum replacement, 1% fetal bovine serum, 1 mM EDTA/SDIA differentiation medium) and a PE-labeled anti-rat IgG antibody (Jackson, 20 μg/ml, 10% knockout serum replacement, 1% fetal bovine serum, 1 mM EDTA/SDIA differentiation medium), and rinsing was performed in the same manner. After the staining, 187A5- and Lrp4-expressing cells were detected by using a flow cytometer.

Figure 13:
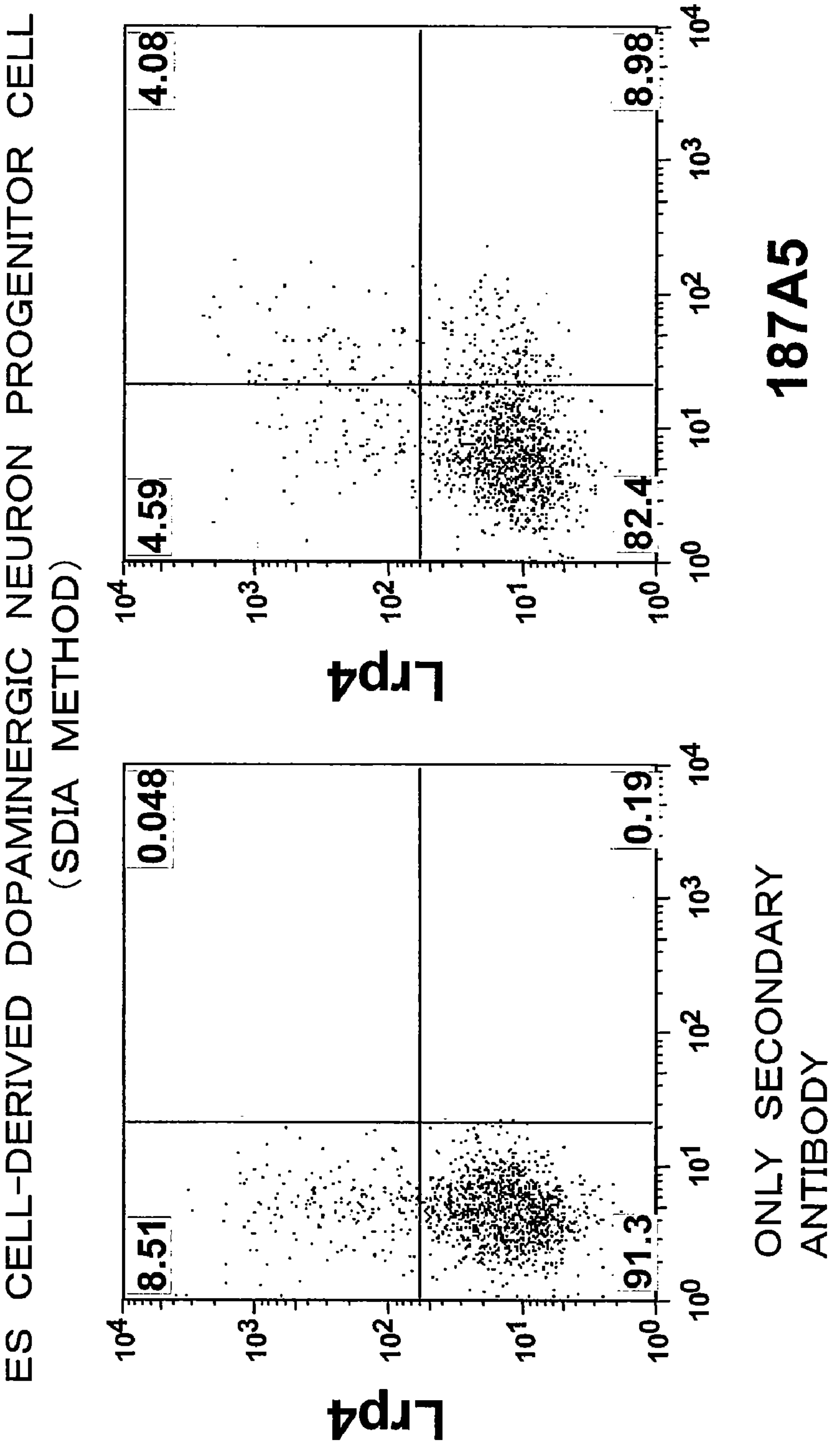
FIG. 13 shows the results of investigating, by FACS analysis, expressions of 187A5 and Lrp4 proteins in dopaminergic neuron proliferative progenitor cells induced to differentiate from ES cells by an SDIA method.

As a result of flow cytometry, a cell population in which the 187A5 and Lrp4 proteins exist was detected in the same manner as the mouse embryonic mesencephalon (FIG. 13).

From these results, it was shown that the 187A5 antibody is also useful for separating dopaminergic neuron progenitor cells derived from ES cells.

Example 8

Separation of Lrp4-Expressing Cell by Using Antibody

In order to confirm that the separated 187A5/Lrp4-copositive cells differentiate into dopaminergic neurons, the following experiment was performed by using Nurr1, a postmitotic dopaminergic neuron precursor cell marker.

The cells separated after being induced to differentiate from ES cells in vitro by the SDIA method were inoculated onto a slide glass coated with poly-L-ornithine (Sigma, 0.002% in PBS), laminin (Invitrogen, 2.5 μg/ml in PBS) and fibronectin (Sigma, 5 μg/ml in PBS), and cultured for 6 days at 37° C. in N2 (Invitrogen, 1×), B27 (Invitrogen, 1×), ascorbic acid (Sigma, 200 uM) BDNF (Invitrogen, 20 ng/ml) and 10% knockout serum replacement (Invitrogen)/SDIA differentiation medium. The cultured cells were fixed for 20 minutes at 4° C. by using 2% PFA/PBS, and rinsing with PBS was performed for 10 minutes at 4° C. twice. Then, permeabilization treatment with 0.3% Triton X-100/PBS was performed for 30 minutes at room temperature, and blocking was performed for 20 minutes at room temperature with 10% normal donkey serum/Blockace. Sequentially, reaction with an anti-Nurr1 antibody (in house culture supernatant diluted to 1/1000, 10% normal donkey serum, 2.5% Blockace, 0.1% Triton X-100/PBS) and an anti-HuC/D antibody (Molecular Probe, 1/50, 4 μg/ml, 10% normal donkey serum, 2.5% Blockace, 0.1% Triton X-100/PBS) was performed for 1 hour at room temperature, and sequentially, the reaction was performed overnight at 4° C. On the next day, by using 0.1% Triton X-100/PBS, rinsing was performed for 10 minutes at room temperature four times. Then, reaction with an FITC-labeled anti-mouse IgG antibody and a Cy3-labeled anti-rat IgG antibody (all Jackson, 3 μg/ml, 10% normal donkey serum, 2.5% Blockace, 0.1% Triton X-100/PBS) was performed for 1 hour at room temperature. Then, rinsing was performed in the same manner, and rinsing with PBS was performed for 5 minutes at room temperature. After sealing, the cells were observed.

Figure 14:
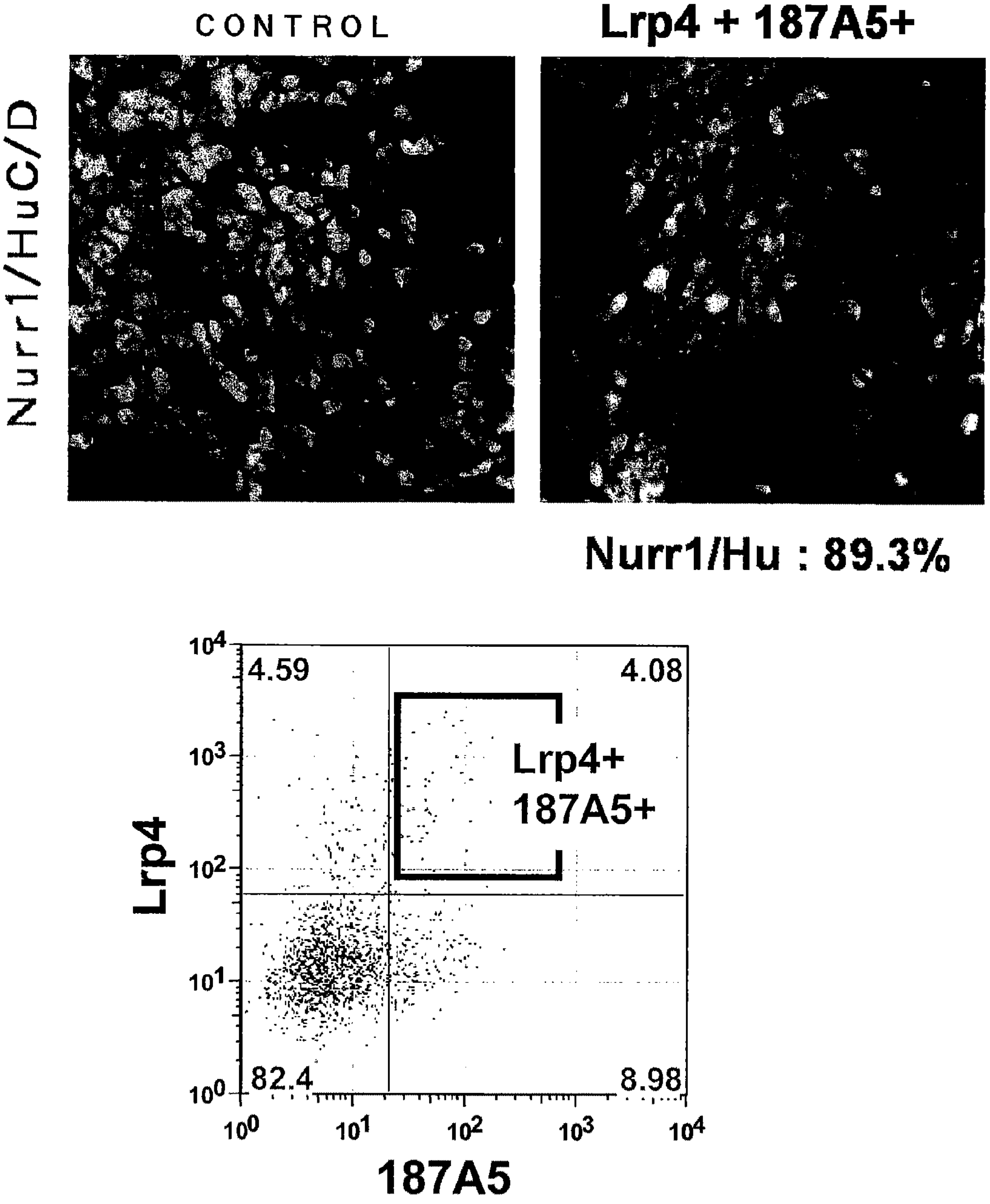
FIG. 14 shows the results of separating 187A5/Lrp4-copositive cells induced to differentiate from ES cells by an SDIA method, and culturing.

As a result of culturing the cells separated by flow cytometry for 6 days in vitro, evidently many Nurr1-positive dopaminergic neurons were induced, compared to unseparated cells as controls (FIG. 14).

From these results, it became revealed that the 187A5/Lrp4-copositive cells were certainly progenitor cells of dopaminergic neuron lineage and can be matured in vitro.

The invention claimed is:

1. An antibody bound to a protein on a dopaminergic neuron progenitor cell wherein the protein is selected from the following (i), (ii), and (iii):

(i) a protein comprising the amino acid sequence of SEQ ID NO: 2;

(ii) a protein which is encoded by a polynucleotide which hybridizes under stringent conditions to a polynucleotide consisting of a complementary sequence of a nucleotide sequence of a polynucleotide encoding the amino acid sequence of SEQ ID NO: 2, wherein said stringent conditions comprise hybridization at 65 to 68° C. and washing in 0.2×SSC, 0.1% SDS; and (iii) a protein which consists of an amino acid sequence having 70% or more identity with the amino acid sequence of SEQ ID NO: 2.

2. The antibody of claim 1, wherein the dopaminergic neuron progenitor cell is a dopaminergic neuron proliferative progenitor cell.

* * * * *